US012286653B2

(12) United States Patent
Voladri et al.

(10) Patent No.: US 12,286,653 B2
(45) Date of Patent: Apr. 29, 2025

(54) CARBOXYESTERASE POLYPEPTIDES FOR AMIDE COUPLING

(71) Applicant: Codexis, Inc., Redwood City, CA (US)

(72) Inventors: Rama Voladri, Pleasanton, CA (US); David Entwistle, San Carlos, CA (US); Christopher Michael Micklitsch, Philadelphia, PA (US); Vesna Mitchell, Santa Clara, CA (US); Nikki Dellas, San Carlos, CA (US); Xiyun Zhang, Fremont, CA (US); Antoinette Sero, Foster City, CA (US); Brent Dorr, King of Prussia, PA (US); Douglas E. Fuerst, King of Prussia, PA (US)

(73) Assignee: Codexis, Inc., Redwood City, CA (US)

( * ) Notice: Subject to any disclaimer, the term of this patent is extended or adjusted under 35 U.S.C. 154(b) by 718 days.

(21) Appl. No.: 17/236,928

(22) Filed: Apr. 21, 2021

(65) Prior Publication Data

US 2021/0238565 A1 Aug. 5, 2021

Related U.S. Application Data

(62) Division of application No. 16/218,003, filed on Dec. 12, 2018, now Pat. No. 11,015,180.

(60) Provisional application No. 62/598,189, filed on Dec. 13, 2017.

(51) Int. Cl.
*C12N 9/18* (2006.01)

(52) U.S. Cl.
CPC ........ *C12N 9/18* (2013.01); *C12Y 301/01001* (2013.01)

(58) Field of Classification Search
CPC .......................... C12N 9/18; C12Y 301/01001
See application file for complete search history.

(56) References Cited

U.S. PATENT DOCUMENTS

| | | | |
|---|---|---|---|
| 5,605,793 | A | 2/1997 | Stemmer |
| 5,811,238 | A | 9/1998 | Stemmer et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 5,928,905 | A | 7/1999 | Stemmer et al. |

(Continued)

FOREIGN PATENT DOCUMENTS

| | | | |
|---|---|---|---|
| WO | 95/22625 | A1 | 8/1995 |
| WO | 95/33836 | A1 | 12/1995 |

(Continued)

OTHER PUBLICATIONS

EMBL BAR42294.1; https://www.ebi.ac.uk/ena/browser/view/BAR42294.1; accessed Dec. 14, 2023 (Year: 2007).*

(Continued)

*Primary Examiner* — Louise W Humphrey
*Assistant Examiner* — Candice Lee Swift

(57) ABSTRACT

The present invention provides engineered carboxyesterase enzymes having improved properties as compared to a naturally occurring wild-type carboxyesterase enzymes, as well as polynucleotides encoding the engineered carboxyesterase enzymes, host cells capable of expressing the engineered carboxyesterase enzymes, and methods of using the engineered carboxyesterase enzymes in amidation reactions.

18 Claims, 30 Drawing Sheets

Specification includes a Sequence Listing.

Pairwise alignment of the Polynucleotide Sequence Encoding the *E. coli* codon optimized for the Wild-Type Carboxyesterase Enzyme, *Thermobifida fusca* (*T. fusca*) (SEQ ID NO: 1) against the polynucleotide sequences of *T. fusca* variants

(56) References Cited

U.S. PATENT DOCUMENTS 6,096,548 A 8/2000 Stemmer
6,117,679 A 9/2000 Stemmer
6,132,970 A 10/2000 Stemmer
6,165,793 A 12/2000 Stemmer
6,180,406 B1 1/2001 Stemmer
6,251,674 B1 6/2001 Tobin et al.
6,265,201 B1 7/2001 Wackett et al.
6,277,638 B1 8/2001 Stemmer
6,287,861 B1 9/2001 Stemmer et al.
6,287,862 B1 9/2001 delCardayre et al.
6,291,242 B1 9/2001 Stemmer
6,294,328 B1 * 9/2001 Fleischmann .......... C12Q 1/689 435/6.15
6,297,053 B1 10/2001 Stemmer
6,303,344 B1 10/2001 Patten et al.
6,309,883 B1 10/2001 Minshull et al.
6,319,713 B1 11/2001 Patten et al.
6,319,714 B1 11/2001 Crameri et al.
6,323,030 B1 11/2001 Stemmer
6,326,204 B1 12/2001 delCardayre et al.
6,335,160 B1 1/2002 Patten et al.
6,335,198 B1 1/2002 delCardayre et al.
6,337,186 B1 1/2002 Krebber
6,344,356 B1 2/2002 Stemmer
6,352,859 B1 3/2002 delCardayre et al.
6,355,484 B1 3/2002 Patten et al.
6,358,740 B1 3/2002 Patten et al.
6,358,742 B1 3/2002 Stemmer
6,365,377 B1 4/2002 Patten et al.
6,365,408 B1 4/2002 Stemmer
6,368,861 B1 4/2002 Crameri et al.
6,372,497 B1 4/2002 Stemmer
6,376,246 B1 4/2002 Crameri et al.
6,379,964 B1 4/2002 delCardayre et al.
6,387,702 B1 5/2002 Stemmer
6,391,552 B2 5/2002 Stemmer
6,391,640 B1 5/2002 Minshull et al.
6,395,547 B1 5/2002 Stemmer
6,406,855 B1 6/2002 Patten et al.
6,406,910 B1 6/2002 Patten et al.
6,413,745 B1 7/2002 Patten et al.
6,413,774 B1 7/2002 Stemmer
6,420,175 B1 7/2002 Stemmer
6,423,542 B1 7/2002 Crameri et al.
6,426,224 B1 7/2002 Crameri et al.
6,436,675 B1 8/2002 Welch et al.
6,444,468 B1 9/2002 Stemmer et al.
6,455,253 B1 9/2002 Patten et al.
6,479,652 B1 11/2002 Crameri et al.
6,482,647 B1 11/2002 Stemmer
6,483,011 B1 11/2002 Stemmer et al.
6,484,105 B2 11/2002 Zhang
6,489,146 B2 12/2002 Stemmer et al.
6,500,617 B1 12/2002 Stemmer et al.
6,500,639 B2 12/2002 Subramanian
6,506,602 B1 1/2003 Stemmer
6,506,603 B1 1/2003 Stemmer
6,518,065 B1 2/2003 Stemmer
6,519,065 B1 2/2003 Colbourne et al.
6,521,453 B1 2/2003 Crameri et al.
6,528,311 B1 3/2003 delCardayre et al.
6,537,746 B2 3/2003 Arnold et al.
6,573,098 B1 6/2003 Stemmer
6,576,467 B1 6/2003 Stemmer
6,579,678 B1 6/2003 Patten et al.
6,586,182 B1 7/2003 Patten et al.
6,602,986 B1 8/2003 Stemmer et al.
6,605,430 B1 8/2003 Affholter et al.
6,613,514 B2 9/2003 Patten et al.
6,653,072 B1 11/2003 Patten et al.
6,686,515 B1 2/2004 Lassner et al.
6,703,240 B1 3/2004 Stemmer et al.
6,716,631 B1 4/2004 delCardayre et al.
6,825,001 B2 11/2004 Wackett et al.
6,902,922 B2 6/2005 Ness et al.
6,917,882 B2 7/2005 Selfinov et al.
6,946,296 B2 9/2005 Patten et al.
6,961,664 B2 11/2005 Selfinov et al.
6,995,017 B1 2/2006 Stemmer
7,024,312 B1 4/2006 Selfinov et al.
7,058,515 B1 6/2006 Selfinov et al.
7,105,297 B2 9/2006 Minshull et al.
7,148,054 B2 12/2006 delCardayre et al.
7,220,566 B2 5/2007 Ness et al.
7,288,375 B2 10/2007 Stemmer et al.
7,384,387 B1 6/2008 Raillard et al.
7,421,347 B2 9/2008 Selfinov et al.
7,430,477 B2 9/2008 Selfinov et al.
7,462,469 B2 12/2008 Bass et al.
7,534,564 B2 5/2009 Patten et al.
7,620,500 B2 11/2009 Mundorff et al.
7,620,502 B2 11/2009 Selfinov et al.
7,629,170 B2 12/2009 delCardayre et al.
7,702,464 B1 4/2010 Emig et al.
7,747,391 B2 6/2010 Gustafsson et al.
7,747,393 B2 6/2010 Fox
7,751,986 B2 7/2010 Gustafsson et al.
7,776,598 B2 8/2010 Patten et al.
7,783,428 B2 8/2010 Gustafsson et al.
7,795,030 B2 9/2010 Minshull et al.
7,853,410 B2 12/2010 Selfinov et al.
7,868,138 B2 1/2011 Stemmer et al.
7,873,477 B1 1/2011 Gustafsson et al.
7,873,499 B2 1/2011 Selfinov et al.
7,904,249 B2 3/2011 Selfinov et al.
7,957,912 B2 6/2011 Selfinov et al.
7,981,614 B2 7/2011 Stemmer et al.
8,014,961 B2 9/2011 Bass et al.
8,029,988 B2 10/2011 Crameri et al.
8,048,674 B2 11/2011 Minshull et al.
8,058,001 B2 11/2011 Crameri et al.
8,076,138 B2 12/2011 delCardayre et al.
8,108,150 B2 1/2012 Mundorff et al.
8,170,806 B2 5/2012 Selfinov et al.
8,224,580 B2 7/2012 Mundorff et al.
8,377,681 B2 2/2013 delCardayre et al.
8,383,346 B2 2/2013 Colbeck et al.
8,457,903 B1 6/2013 Emig et al.
8,504,498 B2 8/2013 Fox
8,589,085 B2 11/2013 Selfinov et al.
8,762,066 B2 6/2014 Fox
8,768,871 B2 7/2014 Fox
9,593,326 B2 3/2017 Clark et al.
9,665,694 B2 5/2017 Cope
9,684,771 B2 6/2017 Cope et al.
9,714,437 B2 7/2017 Chan et al.
11,015,180 B2 5/2021 Rama et al.
2006/0195947 A1 8/2006 Davis et al.
2007/0015909 A1 1/2007 Cash et al.
2008/0220990 A1 9/2008 Fox
2009/0312196 A1 12/2009 Colbeck et al.
2011/0137002 A1 6/2011 Hauer et al.
2011/0212504 A1 * 9/2011 Liu ....................... C12N 15/80 435/197

FOREIGN PATENT DOCUMENTS

WO 96/00787 A1 1/1996
WO 97/0078 A1 1/1997
WO 97/35966 A1 10/1997
WO 98/27230 A1 6/1998
WO 2000/42651 A1 7/2000
WO 2001/75767 A2 10/2001
WO 2005/045016 A2 5/2005
WO 2007/128441 A2 11/2007
WO 2009/008908 A1 1/2009
WO 2009/152336 12/2009

OTHER PUBLICATIONS

Oeser, Thorsten, et al. "High level expression of a hydrophobic poly (ethylene terephthalate)-hydrolyzing carboxylesterase from Thermobifida fusca KW3 in *Escherichia coli* BL21 (DE3)." Journal of biotechnology 146.3 (2010): 100-104. (Year: 2010).*

(56) References Cited

OTHER PUBLICATIONS

Gopal, Gopal Jee, and Awanish Kumar. "Strategies for the production of recombinant protein in *Escherichia coli*." The protein journal 32 (2013): 419-425. (Year: 2013).*
Sockolosky JT, Szoka FC. Periplasmic production via the pET expression system of soluble, bioactive human growth hormone. Protein Expr Purif. Feb. 2013;87(2):129-35. doi: 10.1016/j.pep.2012.11.002. Epub Nov. 17, 2012. PMID: 23168094; PMCID: PMC3537859. (Year: 2013).*
GenBank CAZ65068.1; https://www.ncbi.nlm.nih.gov/protein/CAZ65068.1; accessed Apr. 19, 2024 (Year: 2010).*
WP_068758395.1; https://www.ncbi.nlm.nih.gov/protein/WP_068758395.1?report=genbank&log$=protalign&blast_rank=10&RID=1UE2EZFB013 accessed Apr. 15, 2024 (Year: 2017).*
UniProt Accession No. A0A0E4FHY0 dated Jun. 24, 2015.
UniProt Accession No. A0A147Kl12 dated Jun. 8, 2016.
Supplementary European Search Report from corresponding European Application No. 18887373.1 dated Oct. 25, 2021.
Altschul, S., et al., "Basic local alignment search tool," J. Mol. Biol., 215: 403-410 [1990].
Altschul, S.F., et al., "Gapped BLAST and PSI-BLAST: a new generation of protein database search programs," Nucleic Acids Res., 25(17):3389-3402 [1997].
Beaucage, S.L., et al., "Deoxynucleoside phosphoamidites—A new class of key intermediates for deoxypolynucleotide synthesis," Tetrahedron Letters, 22(20):1859-62 [1981].
Botstein, D., et al., "Strategies and applications of in vitro mutagenesis," Science, 229(4719):1193-1201 [1985].
Carter, P., "Site-directed mutagenesis," Biochem. J., 237:1-7 [1986].
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Ehrlich, S.D., "DNA cloning in Bacillus subtilis," Proc. Natl. Acad. Sci. USA, 75(3):1433-1436 [1978].
El-Faham, A., et al., "Peptide Coupling Reagents, More than a Letter Soup," Chem. Rev., 111(11): 6557-6602 [2011].
Guo, Z., et al., "3'-End-Forming Signals of Yeast mRNA," Mol. Cell. Biol., 15(11):5983-5990 [1995].
Guzman, F., et al., "Peptide synthesis: chemical or enzymatic," Elec. J. Biotech., 10(2):279-314 [2007].
Henikoff, S.,et al., "Amino acid substitution matrices from protein blocks," Proc. Natl. Acad. Sci., 89:10915-10919 (1992).
Koszelewski, D., et al., "Immobilization of omega-transaminases by encapsulation in a sol-gel/celite matrix," J. Mol. Cat. B: Enz., 63: 39-44 [2010].
Kramer, B., et al., "Different base/base mismatches are corrected with different efficiencies by the methyl-directed DNA mismatch-repair system of *E. coli*," Cell, 38(3):879-887, 1984.
Lathe, R., et al., "Plasmid and bacteriolphage vecotrs for excision of intact inserts," Gene, 57:193-201 [1987].
Ling, M., et al., "Approaches to DNA Mutagenesis:An Overview," Anal. Biochem., 254:157-78 (1997).
Lundberg, H., et al., "Catalytic amide formation from non-activated carboxylic acids and amines," Chem. Soc. Rev., 43: 2714-2742 [2014].
Martin, A.R., et al., "Characterization of free and immobilized (S)-aminotransferase for acetophenone production," Appl. Microbiol. Biotechnol., 76: 843-851 [2007].
Mateo, C., et al., "Epoxy Sepabeads: A Novel Epoxy Support for Stabilization of Industrial Enzymes via Very Intense Multipoint Covalent Attachment," Biotechnol. Prog., 18:629-34 [2002].
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pattabiraman, V.R., et al., "Rethinking amide bond synthesis," Nature, 480: 471-479 [2011].
Pearson, W.R., "Improved tools for biological sequence comparison," Proc. Nat'l. Acad. Sci. USA, 85:2444-2448 (1988).
Rauwerdink, A., et al., "How the Same Core Catalytic Machinery Catalyzes 17 Different Reactions: the Serine-Histidine-Aspartate Catalytic Triad of α/β-Hydrolase Fold Enzymes," ACS Cat., 5(10): 6153-6176 [2015].
Romanos, M.A., et al., "Foreign gene expression in yeast: a review," Yeast 8:423-488 [1992].
Roughley, S.D., et al., "The Medicinal Chemist's Toolbox: An Analysis of Reactions Used in the Pursuit of Drug Candidates," J. Med. Chem., 54(10): 3451-3479 [2011].
Sharma, J., et al., "Enzymatic chemoselective synthesis of secondary-amide surfactant from N-methylethanol amine," J. Biosci. Bioeng., 100(6):662-666 [2005].
Simonen, M., et al., "Protein Secretion in Bacillus Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Truppo, M.D., et al., "Development of an Improved Immobilized CAL-B for the Enzymatic Resolution of a Key Intermediate to Odanacatib," Org. Proc. Res. Develop., 15:1033-1035 [2011].
Varma, R., et al., "Lipase Catalysed Enantioselective Amidation of α-phenylethylamine," Asian J. Biochem., 2(4):279-283 [2007].
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Yi, S., et al., "Covalent immobilization of w-transaminase from Vibrio fluvialis JS17 on chitosan beads," Proc. Biochem., 42: 895-898 [2007].
Zhang, J-H., et al., "Directed evolution of a fucosidase from a galactosidase by DNA shuffling and screening ," Proc. Nat. Acad. Sci., U.S.A., 94:4504-4509 (1997).
GenBank Accession No. WP_003407276 dated Dec. 26, 2018.
GenBank Accession No. WP_011292850.1 dated Apr. 23, 2018.
GenBank Accession No. WP_033015113 dated May 15, 2017.
Billig, S., et al., "Hydrolysis of cyclic poly(ethylene terephthalate) trimers by a carboxylesterase from Thermobifida fusca KW3," Applied Microbiology and Biotechnology, 87(5):1753-1764 [2010].
Oeser, T., et al., "High level expression of a hydrophobic poly(ethylene terephthalate)-hydrolyzing carboxylesterase from Thermobifida fusca KW3 in *Escherichia coli* BL21(DE3)," Journal of Biotechnology, 146(3):100-104 [2010].
GenBank Accession No. CAZ65068.1 dated May 21, 2010.
Whisstock, J. C. et al. "Prediction of protein function from protein sequence and structure", Quarterly Reviews of Biophysics 36(3):307-340 [2003].

(56) References Cited

OTHER PUBLICATIONS

Witkowski, A. et al. "Conversion of a Beta-Ketoacyl Synthase to a Malonyl Decarboxylase by Replacement of the Active-Site Cysteine with Glutamine", Biochemistry, 38:11643-11650 [1999].
Seffernick, J. L. et al. "Melamine Deaminase and Atrazine Chlorohydrolase: 98 Percent Identical but Functionally Different", Journal of Bacteriology, 183(8):2405-2410 [2001].
Thumarat, U. "Carboxylic ester hydrolase". 2015. Database: EMBL. Accession No. A0A0E4FHY0. Retrieved from the Internet: URL:https://www.uniprot.org/uniprotkb/A0A0E4FHY0/entry.
https://www.uniprot.org/uniprot/A0A147KI12.txt., retrieved on Oct. 15, 2021.
Toth, A., et al., "Plant polysaccharide degrading enzyme system of Thermobifida cellulosilytica TB100T revealed by de novo genome project data," Acta Alimentaria, 46(3):323-335 [2017].
"UniProtKB", https://www.uniprot.org/help/uniprotkb, 2023.
Andrievsky et al., "Ontogenetic features of the expression of carboxyesterases in *Drosophila melanogaster*", Vestnik ONU, vol. 10, n. 5. 2005, Biology [in Russian].
NCBI Accession No. P86325 dated Nov. 30, 2016.
Kitadokoro, K., et al., "Structural insights into the unique polylactate-degrading mechanism of Thermobifida alba cutinase," FEBS J, 286(11):2087-2098 [2019].
Thumarat, U., et al., "Biochemical and genetic analysis of a cutinase-type polyesterase from a thermophilic Thermobifida alba AHK119," Appl Microbiol Biotechnol., 95(2):419-30 [2012].
Thumarat, U., et al., "Comparison of genetic structures and biochemical properties of tandem cutinase-type polyesterases from Thermobifida alba AHK119," J Biosci Bioeng., 120(5):491-7 [2015].
Hu, X., et al., "Diversity of polyester-degrading bacteria in compost and molecular analysis of a thermoactive esterase from Thermobifida alba AHK119," Appl Microbiol Biotechnol., 87(2):771-9 [2010].

* cited by examiner

**Figure 1. Pairwise alignment of the Polynucleotide Sequence Encoding the *E. coli* codon optimized for the Wild-Type Carboxyesterase Enzyme, *Thermobifida fusca* (*T. fusca*) (SEQ ID NO: 1) against the polynucleotide sequences of *T. fusca* variants**

```
                          10         20         30         40         50         60         70
                  ....|....| ....|....| ....|....| ....|....| ....|....| ....|....| ....|....|
SEQIDNO:1     1   atggagatcg tgattcgcac gggcagcgga gatgtgcgtg gtagtaaaga gaacggcatt gcagtgtttc  70
SEQIDNO:3     1   .......... .......... .......... .......... .......... .......... ..........  70
SEQIDNO:5     1   .......... .......... .......... .......... .......... .......... ..........  70
SEQIDNO:7     1   .......... .......... .......... .......... .......... .......... ..........  70
SEQIDNO:9     1   .......... .......... .......... .......... .......... .......... ..........  70
SEQIDNO:11    1   .......... .......... .......... .......... .......... .......... ..........  70
SEQIDNO:13    1   .......... .......... .......... .......... .......... .......... ..........  70
SEQIDNO:15    1   .......... .......... .......... .......... .......... .......... ..........  70
SEQIDNO:17    1   .......... .......... .......... .......... .......... .......... ..........  70
SEQIDNO:19    1   .......... .......... .......... .......... .......... .......... ..........  70
SEQIDNO:21    1   .......... .......... .......... .......... .......... .......... ..........  70
SEQIDNO:23    1   .......... .......... .......... .......... .......... .......... ..........  70
SEQIDNO:25    1   .......... .......... .......... .......... .......... .......... ..........  70
SEQIDNO:27    1   .......... .......... .......... .......... .......... .......... ..........  70
SEQIDNO:29    1   .......... .......... .......... .......... .......... .......... ..........  70
SEQIDNO:31    1   .......... .......... .......... .......... .......... .......... ..........  70
SEQIDNO:33    1   .......... .......... .......... .......... .......... .......... ..........  70
SEQIDNO:35    1   .......... .......... .......... .......... .......... .......... ..........  70
SEQIDNO:37    1   .......... .......... .......... .......... .......... .......... ..........  70
SEQIDNO:39    1   .......... .......... .......... .......... .......... .......... ..........  70
SEQIDNO:41    1   .......... .......... .......... .......... .......... .......... ..........  70
SEQIDNO:43    1   .......... .......... .......... .......... .......... .......... ..........  70
SEQIDNO:45    1   .......... .......... .......... .......... .......... .......... ..........  70
SEQIDNO:47    1   .......... .......... .......... .......... .......... .......... ..........  70
SEQIDNO:49    1   .......... .......... .......... .......... .......... .......... ..........  70
SEQIDNO:51    1   .......... .......... .......... .......... .......... .......... ..........  70
SEQIDNO:53    1   .......... .......... .......... .......... .......... .......... ..........  70
SEQIDNO:55    1   .......... .......... .......... .......... .......... .......... ..........  70
SEQIDNO:57    1   .......... .......... .......... .......... .......... .......... ..........  70
SEQIDNO:59    1   .......... .......... .......... .......... .......... .......... ..........  70
SEQIDNO:61    1   .......... .......... .......... .......... .......... .......... ..........  70
SEQIDNO:63    1   .......... .......... .......... .......... .......... .......... ..........  70
SEQIDNO:65    1   .......... .......... .......... .......... .......... .......... ..........  70
SEQIDNO:67    1   .......... .......... .......... .......... .......... .......... ..........  70
SEQIDNO:69    1   .......... .......... .......... .......... .......... .......... ..........  70
SEQIDNO:71    1   .......... .......... .......... .......... .......... .......... ..........  70
SEQIDNO:73    1   .......... .......... .......... .......... .......... .......... ..........  70
SEQIDNO:75    1   .......... .......... .......... .......... .......... .......... ..........  70
SEQIDNO:77    1   .......... .......... .......... .......... .......... .......... ..........  70
SEQIDNO:79    1   .......... .......... .......... .......... .......... .......... ..........  70
SEQIDNO:81    1   .......... .......... .......... .......... .......... .......... ..........  70
SEQIDNO:83    1   .......... .......... .......... .......... .......... .......... ..........  70
SEQIDNO:85    1   .......... .......... .......... .......... .......... .......... ..........  70
SEQIDNO:87    1   .......... .......... .......... .......... .......... .......... ..........  70
SEQIDNO:89    1   .......... .......... .......... .......... .......... .......... ..........  70
SEQIDNO:91    1   .......... .......... .......... .......... .......... .......... ..........  70
SEQIDNO:93    1   .......... .......... .......... .......... .......... .......... ..........  70
SEQIDNO:95    1   .......... .......... .......... .......... .......... .......... ..........  70
SEQIDNO:97    1   .......... .......... .......... .......... .......... .......... ..........  70
SEQIDNO:99    1   .......... .......... .......... .......... .......... .......... ..........  70
SEQIDNO:101   1   .......... .......... .......... .......... .......... .......... ..........  70
SEQIDNO:103   1   .......... .......... .......... .......... .......... .......... ..........  70
SEQIDNO:105   1   .......... .......... .......... .......... .......... .......... ..........  70
SEQIDNO:107   1   .......... .......... .......... .......... .......... .......... ..........  70
SEQIDNO:109   1   .......... .......... .......... .......... .......... .......... ..........  70
SEQIDNO:111   1   .......... .......... .......... .......... .......... .......... ..........  70
SEQIDNO:113   1   .......... .......... .......... .......... .......... .......... ..........  70
SEQIDNO:115   1   .......... .......... .......... .......... .......... .......... ..........  70
SEQIDNO:117   1   .......... .......... .......... .......... .......... .......... ..........  70
SEQIDNO:119   1   .......... .......... .......... .......... .......... .......... ..........  70
SEQIDNO:121   1   .......... .......... .......... .......... .......... .......... ..........  70
SEQIDNO:123   1   .......... .......... .......... .......... .......... .......... ..........  70
SEQIDNO:125   1   .......... .......... .......... .......... .......... .......... ..........  70
SEQIDNO:127   1   .......... .......... .......... .......... .......... .......... ..........  70
SEQIDNO:129   1   .......... .......... .......... .......... .......... .......... ..........  70
SEQIDNO:131   1   .......... .......... .......... .......... .......... .......... ..........  70
SEQIDNO:133   1   .......... .......... .......... .......... .......... .......... ..........  70
SEQIDNO:135   1   .......... .......... .......... .......... .......... .......... ..........  70
```

Figure 1, Continued

```
                            80         90        100        110        120        130        140
                    ....|....| ....|....| ....|....| ....|....| ....|....| ....|....| ....|....|
SEQIDNO:1      71   gtggcatccc ctatgcggaa ccaccggttg gcgctcaccg ctttacggcg ccacgtccac cacgtccatg  140
SEQIDNO:3      71   .......... .......... .......... .......... .......... .......... ..........  140
SEQIDNO:5      71   .......... .......... .......... .......... .......... .......... ..........  140
SEQIDNO:7      71   .......... .......... .......... .......... .......... .......... ..........  140
SEQIDNO:9      71   .......... .......... .......... .......... .......... .......... ..........  140
SEQIDNO:11     71   .......... .......... .......... .......... .......... .......... ..........  140
SEQIDNO:13     71   .......... .......... .......... .......... .......... .......... ..........  140
SEQIDNO:15     71   .......... .......... .......... .......... .......... .......... ..........  140
SEQIDNO:17     71   .......... .......... .......... .......... .......... .......... ..........  140
SEQIDNO:19     71   .......... .......... .......... .......... .......... .......... ..........  140
SEQIDNO:21     71   .......... .......... .......... .......... .......... .......... ..........  140
SEQIDNO:23     71   .......... .......... .......... .......... .......... .......... ..........  140
SEQIDNO:25     71   .......... .......... .......... .......... .......... .......... ..........  140
SEQIDNO:27     71   .......... .......... .......... .......... .......... .......... ..........  140
SEQIDNO:29     71   .......... .......... .......... .......... .......... .......... ..........  140
SEQIDNO:31     71   .......... .......... .......... .......... .......... .......... ..........  140
SEQIDNO:33     71   .......... .......... .......... .t........ .......... .......... ..........  140
SEQIDNO:35     71   .......... .......... .......... .......... .......... .......... ..........  140
SEQIDNO:37     71   .......... .......... .......... .......... .......... .......... ..........  140
SEQIDNO:39     71   .......... .......... .......... .......... .......... .......... ..........  140
SEQIDNO:41     71   .......... .......... .......... .......... .......... .......... ..........  140
SEQIDNO:43     71   .......... .......... .......... .......... .......... .......... ..........  140
SEQIDNO:45     71   .......... .......... .......... .......... .......... .......... ..........  140
SEQIDNO:47     71   .......... .......... .......... .......... .......... .......... ..........  140
SEQIDNO:49     71   .......... .......... .......... .......... .......... .......... ..........  140
SEQIDNO:51     71   .......... .......... .......... .......... .......... .......... ..........  140
SEQIDNO:53     71   .......... .......... .......... .......... .......... .......... ..........  140
SEQIDNO:55     71   .......... .......... .......... .......... .......... .......... ..........  140
SEQIDNO:57     71   .......... .......... .......... .......... .......... .......... ..........  140
SEQIDNO:59     71   .......... .......... .......... .......... .......... .......... ..........  140
SEQIDNO:61     71   .......... .......... .......... .......... .......... .......... ..........  140
SEQIDNO:63     71   .......... .......... .......... .......... .......... .......... ..........  140
SEQIDNO:65     71   .......... .......... .......... .......... .......... .......... ..........  140
SEQIDNO:67     71   .......... .......... .......... .......... .......... .......... ..........  140
SEQIDNO:69     71   .......... .......... .......... .......... .......... .......... ..........  140
SEQIDNO:71     71   .......... .......... .......... .......... .......... .......... ..........  140
SEQIDNO:73     71   .......... .......... .......... .......... .......... .......... ..........  140
SEQIDNO:75     71   .......... .......... .......... .......... .......... .......... ..........  140
SEQIDNO:77     71   .......... .......... .......... .......... .......... .......... ..........  140
SEQIDNO:79     71   .......... .......... .......... .......... .......... .......... ..........  140
SEQIDNO:81     71   .......... .......... .......... .......... .......... .......... ..........  140
SEQIDNO:83     71   .......... .......... .......... .......... .......... .......... ..........  140
SEQIDNO:85     71   .......... .......... .......... .......... .......... .......... ..........  140
SEQIDNO:87     71   .......... .......... .......... .......... .......... .......... ..........  140
SEQIDNO:89     71   .......... .......... .......... .......... .......... .......... ..........  140
SEQIDNO:91     71   .......... .......... .......... .......... .......... .......... ..........  140
SEQIDNO:93     71   .......... .......... .......... .......... .......... .......... ..........  140
SEQIDNO:95     71   .......... .......... .......... .......... .......... .......... ..........  140
SEQIDNO:97     71   .......... .......... .......... .......... .......... .......... ..........  140
SEQIDNO:99     71   .......... .......... .......... .......... .......... .......... ..........  140
SEQIDNO:101    71   .......... .......... .......... .......... .......... .......... ..........  140
SEQIDNO:103    71   .......... .......... .......... .......... .......... .......... ..........  140
SEQIDNO:105    71   .......... .......... .......... .......... .......... .......... ..........  140
SEQIDNO:107    71   .......... .......... .......... .......... .......... .......... ..........  140
SEQIDNO:109    71   .......... .......... .......... .......... .......... .......... ..........  140
SEQIDNO:111    71   .......... .......... .......... .......... .......... .......... ..........  140
SEQIDNO:113    71   .......... .......... .......... .......... .......... .......... ..........  140
SEQIDNO:115    71   .......... .......... .......... .......... .......... .......... ..........  140
SEQIDNO:117    71   .......... .......... .......... .......... .......... .......... ..........  140
SEQIDNO:119    71   .......... .......... .......... .......... .......... .......... ..........  140
SEQIDNO:121    71   .......... .......... .......... .......... .......... .......... ..........  140
SEQIDNO:123    71   .......... .......... .......... .......... .......... .......... ..........  140
SEQIDNO:125    71   .......... .......... .......... .......... .......... .......... ..........  140
SEQIDNO:127    71   .......... .......... .......... .......... .......... .......... ..........  140
SEQIDNO:129    71   .......... .......... .......... .......... .......... .......... ..........  140
SEQIDNO:131    71   .......... .......... .......... .......... .......... .......... ..........  140
SEQIDNO:133    71   .......... .......... .......... .......... .......... .......... ..........  140
SEQIDNO:135    71   .......... .......... .......... .......... .......... .......... ..........  140
```

Figure 1, Continued

```
                               150        160        170        180        190        200        210
                         ....|....| ....|....| ....|....| ....|....| ....|....| ....|....| ....|....|
SEQIDNO:1          141   ggatggtgtt cgtgacgcta ctgaattctc ggcgactgca ccacgtccac catatccaga ggcaattggt  210
SEQIDNO:3          141   .......... .......... .......... .......... .......... .......... ..........  210
SEQIDNO:5          141   .......... .......... .......... .......... .......... .......... ..........  210
SEQIDNO:7          141   .......... .......... .......... .......... .......... .......... ..........  210
SEQIDNO:9          141   .......... .......... .......... .......... .......... .......... ..........  210
SEQIDNO:11         141   .......... .......... .......... .......... .......... .......... ..........  210
SEQIDNO:13         141   .......... .......... .......... .......... .......... .......... ..........  210
SEQIDNO:15         141   .......... .......... .......... .......... .......... .......... ..........  210
SEQIDNO:17         141   .......... .......... .......... .......... .......... .......... ..........  210
SEQIDNO:19         141   .......... .......... .......... .......... .......... .......... ..........  210
SEQIDNO:21         141   .......... .......... .......... .......... .......... .......... ..........  210
SEQIDNO:23         141   .......... .......... .......... .......... .......... .......... ..........  210
SEQIDNO:25         141   .......... .......... .......... .......... .......... .......... ..........  210
SEQIDNO:27         141   .......... .......... .......... .......... .......... .......... ..........  210
SEQIDNO:29         141   .......... .......... .......... .......... .......... .......... ..........  210
SEQIDNO:31         141   .......... .......... .......... .......... .......... .......... ..........  210
SEQIDNO:33         141   .......... .......... .......... .......... .......... .......... ..........  210
SEQIDNO:35         141   .......... .......... .......... .......... .......gg. .......... ..........  210
SEQIDNO:37         141   .......... .......... .......... .......... .......... .......... ..........  210
SEQIDNO:39         141   .......... .......... .......... .......... .......... .......... ..........  210
SEQIDNO:41         141   .......... .......... .......... .......... .......... .......... ..........  210
SEQIDNO:43         141   .......... .......... .......... .......... .......... .......... ..........  210
SEQIDNO:45         141   .......... .......... .......... .......... .......... .......... .c.t......  210
SEQIDNO:47         141   .......... .......... .......... .......... .......... .......... ..........  210
SEQIDNO:49         141   .......... .......... .......... .......... .......... .......... ..........  210
SEQIDNO:51         141   .......... .......... .......... .......... .......... .......... ..........  210
SEQIDNO:53         141   .......... .......... .......... .......... .......... .......... ..........  210
SEQIDNO:55         141   .......... .......... .......... .......... .......... .......... ..........  210
SEQIDNO:57         141   .......... .......... .......... .......... .......... .......... ..........  210
SEQIDNO:59         141   .......... .......... .......... .......... .......... .......... ..........  210
SEQIDNO:61         141   .......... .......... .......... .......... .......... .......... ..........  210
SEQIDNO:63         141   .......... .......... .......... .......... .......... .......... ..........  210
SEQIDNO:65         141   .......... .......... .......... .......... .......... .......... ..........  210
SEQIDNO:67         141   .......... .......... .......... .......... .......... ...gg..... ....c.....  210
SEQIDNO:69         141   .......... .......... .......... .......... .......... .......... .c.gc.g...  210
SEQIDNO:71         141   .......... .......... .......... .......... .......... .......... ....c.g...  210
SEQIDNO:73         141   .......... .......... .......... .......... .......... .......... ..........  210
SEQIDNO:75         141   .......... .......... .......... .......... .......gg. ....c..... ..........  210
SEQIDNO:77         141   .......... .......... .......... .......... .......... ...gg..... ......g.c.  210
SEQIDNO:79         141   .......... .......... .......... .......... .......... .......... ....tgg...  210
SEQIDNO:81         141   .......... .......... .......... .......... .......... .......... ..........  210
SEQIDNO:83         141   .......... .......... .......... .......... .......... .......... ..........  210
SEQIDNO:85         141   .......... .......... .......... .......... .......... .......... ....c.g...  210
SEQIDNO:87         141   .......... .......... .......... .......... .......... .......... ..........  210
SEQIDNO:89         141   .......... .......... .......... .......... .......gg. ..gga..... ..........  210
SEQIDNO:91         141   .......... .......... .......... .......... .......... .......... .c.g......  210
SEQIDNO:93         141   .......... .......... .......... .......... ........g. ....c..... ..........  210
SEQIDNO:95         141   .......... .......... .......... .......... .......... .......... ..........  210
SEQIDNO:97         141   .......... .......... .......... .......... .......... .......... .c.g......  210
SEQIDNO:99         141   .......... .......... .......... .......... .......... .......... ..........  210
SEQIDNO:101        141   .......... .......... .......... .......... .......... .......... ..........  210
SEQIDNO:103        141   .......... .......... .......... .......... ......a.g. .......... ..........  210
SEQIDNO:105        141   .......... .......... .......... .......... .......... .......... ....tgg...  210
SEQIDNO:107        141   .......... .......... .......... .......... ......g.g. .......... ..........  210
SEQIDNO:109        141   .......... .......... .......... .......... ......tat. .......... ..........  210
SEQIDNO:111        141   .......... .......... .......... .......... ......tat. .......... ..........  210
SEQIDNO:113        141   .......... .......... .......... .......... ......tet. .......... ..........  210
SEQIDNO:115        141   .......... .......... .......... .......... .......... .......... .c.gtgg...  210
SEQIDNO:117        141   .......... .......... .......... .......... .......... .......... ..........  210
SEQIDNO:119        141   .......... .......... .......... .......... .......... .......... ..........  210
SEQIDNO:121        141   .......... .......... .......... .......... .......... .......... ..........  210
SEQIDNO:123        141   .......... .......... .......... .......... .......... .......... ..........  210
SEQIDNO:125        141   .......... .......... .......... .......... .......... .......... ..........  210
SEQIDNO:127        141   .......... .......... .......... .......... .......... .......... ..........  210
SEQIDNO:129        141   .......... .......... .......... .......... .......... .......... ....t.....  210
SEQIDNO:131        141   .......... .......... .......... .......... .......... .......... ..........  210
SEQIDNO:133        141   .......... .......... .......... .......... .......... .......... ..........  210
SEQIDNO:135        141   .......... .......... .......... .......... .......... .......... ..........  210
```

Figure 1, Continued

```
                          220        230        240        250        260        270        280
                   ....|....| ....|....| ....|....| ....|....| ....|....| ....|....| ....|....|
SEQIDNO:1     211  gcgttgctga tcgaacgctt cattcctggc gacgattacc tgaccctgaa cgtatggact ccggacccga  280
SEQIDNO:3     211  .......... .......... .......... .......... .......... .......... ..........  280
SEQIDNO:5     211  .......... .......... .......... .......... .......... .......... ..........  280
SEQIDNO:7     211  .......... .......... .......... .......... .......... .......... ..........  280
SEQIDNO:9     211  .......... .......... .......... .......... .......... .......... ..........  280
SEQIDNO:11    211  .......... .......... .......... .......... .......... .......... ..........  280
SEQIDNO:13    211  .......... .......... .......... .......... .......... .......... ..........  280
SEQIDNO:15    211  .......... .......... .......... .......... .......... .......... ..........  280
SEQIDNO:17    211  .......... .......... .......... .......... .......... .......... ..........  280
SEQIDNO:19    211  .......... .......... .......... .......... .......... .......... ..........  280
SEQIDNO:21    211  .......... .......... .......... .......... .......... .......... ..........  280
SEQIDNO:23    211  .......... .......... .......... .......... .......... .......... ..........  280
SEQIDNO:25    211  .......... .......... .......... .......... .......... .......... ..........  280
SEQIDNO:27    211  .......... .......... .......... .......... .......... .......... ..........  280
SEQIDNO:29    211  .......... .......... .......... .......... .......... .......... ..........  280
SEQIDNO:31    211  .......... .......... .......... .......... .......... .......... ..........  280
SEQIDNO:33    211  .......... .......... .......... .......... .......... .......... ..........  280
SEQIDNO:35    211  .......... .......... .......... .......... .......... .......... ..........  280
SEQIDNO:37    211  .......... .......... .......... .......... .......... .......... ..........  280
SEQIDNO:39    211  .......... .......... .......... .......... .......... .......... ..........  280
SEQIDNO:41    211  .......... .......... .......... .......... .......... .......... ..........  280
SEQIDNO:43    211  .......... .......... .......... .......... .......... .......... ..........  280
SEQIDNO:45    211  .......... .......... .......... .......... .......... .......... ..........  280
SEQIDNO:47    211  .......... .......... .......... .......... .......... .......... ..........  280
SEQIDNO:49    211  .......... .......... .......... .......... .......... .......... ..........  280
SEQIDNO:51    211  .......... .......... .......... .......... .......... .......... ..........  280
SEQIDNO:53    211  .......... .......... .......... .......... .......... .......... ..........  280
SEQIDNO:55    211  .......... .......... .......... .......... .......... .......... ..........  280
SEQIDNO:57    211  .......... .......... .......... .......... .......... .......... ..........  280
SEQIDNO:59    211  .......... .......... .......... .......... .......... .......... ..........  280
SEQIDNO:61    211  .......... .......... .......... .......... .......... .......... ..........  280
SEQIDNO:63    211  .......... .......... .......... .......... .......... .......... ..........  280
SEQIDNO:65    211  .......... .........c .......... .......... .......... .......... ..........  280
SEQIDNO:67    211  .......... .......... .......... .......... .......... .......... ..........  280
SEQIDNO:69    211  .......... .......... .......... .......... .......... .......... ..........  280
SEQIDNO:71    211  .......... .......... .......... .......... .......... .......... ..........  280
SEQIDNO:73    211  .......... .......... .......... .......... .......... .......... ..........  280
SEQIDNO:75    211  .......... .......... .......... .......... .......... .......... ..........  280
SEQIDNO:77    211  .......... .......... .......... .......... .......... .......... ..........  280
SEQIDNO:79    211  .......... .......... .......... .......... .......... .......... ..........  280
SEQIDNO:81    211  .......... .......... .......... .......... .......... .......... ..........  280
SEQIDNO:83    211  .......... .......... .......... .......... .......... .......... ..........  280
SEQIDNO:85    211  .......... .......... .......... .......... .......... .......... ..........  280
SEQIDNO:87    211  .......... .......... .......... .......... .......... .......... ..........  280
SEQIDNO:89    211  .......... .......... .......... .......... .......... .......... ..........  280
SEQIDNO:91    211  .......... .......... .......... .......... .......... .......... ..........  280
SEQIDNO:93    211  .......... .......... .......... .......... .......... .......... ..........  280
SEQIDNO:95    211  .......... .......... .......... .......... .......... .......... ..........  280
SEQIDNO:97    211  .......... .......... .......... .......... .......... .......... ..........  280
SEQIDNO:99    211  .......... .......... .......... .......... .......... .......... ..........  280
SEQIDNO:101   211  .......... .......... .......... .......... .......... .......... ..........  280
SEQIDNO:103   211  .......... .......... .......... .......... .......... .......... ..........  280
SEQIDNO:105   211  .......... .......... .......... .......... .......... .......... ..........  280
SEQIDNO:107   211  .......... .......... .......... .......... .......... .......... ..........  280
SEQIDNO:109   211  .......... .......... .......... .......... .......... .......... ..........  280
SEQIDNO:111   211  .......... .......... .......... .......... .......... .......... ..........  280
SEQIDNO:113   211  .......... .......... .......... .......... .......... .......... ..........  280
SEQIDNO:115   211  .......... .......... .......... .......... .......... .......... ..........  280
SEQIDNO:117   211  .......... .......... .......... .......... .......... .......... ..........  280
SEQIDNO:119   211  .......... .......... .......... .......... .......... .......... ..........  280
SEQIDNO:121   211  .......... .......... .......... .......... .......... .......... ..........  280
SEQIDNO:123   211  .......... .......... .......... .......... .......... .......... ..........  280
SEQIDNO:125   211  .......... .......... .......... .......... .......... .......... ..........  280
SEQIDNO:127   211  .......... .......... .......... .......... .......... .......... ..........  280
SEQIDNO:129   211  .......... .......... .......... .......... .......... .......... ..........  280
SEQIDNO:131   211  .......... .......... .......... .......... .......... .......... ..........  280
SEQIDNO:133   211  .......... .......... .......... .......... .......... .......... ..........  280
SEQIDNO:135   211  .......... .......... .......... .......... .......... .......... ..........  280
```

Figure 1, Continued

```
                           290        300        310        320        330        340        350
                    ....|....| ....|....| ....|....| ....|....| ....|....| ....|....| ....|....|
SEQIDNO:1      281  atgcagttgg tctgccagtc atggtgtgga ttcatggtgg tgcctttact aacggtagtg gtagcgaacc  350
SEQIDNO:3      281  .......... .......... .......... .......... .......... .......... ..........  350
SEQIDNO:5      281  .......... .......... .......... .......... .......... .......... ..........  350
SEQIDNO:7      281  .......... .......... .......... .......... .......... .......... ..........  350
SEQIDNO:9      281  .......... .......... .......... .......... .......... .......... ..........  350
SEQIDNO:11     281  .......... .......... .......... .......... .......... .......... ..........  350
SEQIDNO:13     281  .......... .......... .......... .......... ..gg...... .......... ..........  350
SEQIDNO:15     281  .......... .......... .......... .......... .......... .......... ..........  350
SEQIDNO:17     281  .......... .......... .......... .......... .......... .......... ..........  350
SEQIDNO:19     281  .......... .......... .......... .......... .......... .......... ..........  350
SEQIDNO:21     281  .......... .......... .......... .......... .......... .......... ..........  350
SEQIDNO:23     281  .......... .......... .......... .......... .......... .......... ..........  350
SEQIDNO:25     281  .......... .......... .......... .......... .......... .......... ..........  350
SEQIDNO:27     281  .......... .......... .......... .......... .......... .......... ..........  350
SEQIDNO:29     281  .......... .......... .......... .......... .......... .......... ..........  350
SEQIDNO:31     281  .......... .......... .......... .......... .......... .......... ..........  350
SEQIDNO:33     281  .......... .......... .......... .......... .......... .......... ..........  350
SEQIDNO:35     281  .......... .......... .......... .......... .......... .......... ..........  350
SEQIDNO:37     281  .......... .......... .......... .......... .......... .......... ..........  350
SEQIDNO:39     281  .......... .......... .......... .......... .......... .......... ..........  350
SEQIDNO:41     281  .......... .......... .......... .......... .......... .......... ..........  350
SEQIDNO:43     281  .......... .......... .......... .......... .......... .......... ..........  350
SEQIDNO:45     281  .......... .......... .......... .......... .......... .......... ..........  350
SEQIDNO:47     281  .......... .......... .......... .......... .......... .......... ..........  350
SEQIDNO:49     281  .......... .......... .......... .......... .......... .......... ..........  350
SEQIDNO:51     281  .......... .......... .......... .......... .......... .......... ..........  350
SEQIDNO:53     281  .......... .......... .......... .......... .......... .......... ..........  350
SEQIDNO:55     281  .......... .......... .......... .......... .......... .......... ..........  350
SEQIDNO:57     281  .......... .......... .......... .......... .......... .......... ..........  350
SEQIDNO:59     281  .......... .......... .......... .......... .......... .......... ..........  350
SEQIDNO:61     281  .......... .......... .......... .......... .......... .......... ..........  350
SEQIDNO:63     281  .......... .......... .......... .......... .......... .......... ..........  350
SEQIDNO:65     281  .......... .......... .......... .......... .......... .......... ..........  350
SEQIDNO:67     281  .......... .......... .......... .......... .......... .......... ..........  350
SEQIDNO:69     281  .......... .......... .......... .......... .......... .......... ..........  350
SEQIDNO:71     281  .......... .......... .......... .......... .......... .......... ..........  350
SEQIDNO:73     281  .......... .......... .......... .......... .......... .......... ..........  350
SEQIDNO:75     281  .......... .......... .......... .......... ..g....... .......... ..........  350
SEQIDNO:77     281  .......... .......... .......... .......... .......... .......... ..........  350
SEQIDNO:79     281  .......... .......... .......... .......... .......... .......... ..........  350
SEQIDNO:81     281  .......... .......... .......... .......... .......... .......... ..........  350
SEQIDNO:83     281  .......... .......... .......... .......... .......... .......... ..........  350
SEQIDNO:85     281  .......... .......... .......... .......... .......... .......... ..........  350
SEQIDNO:87     281  .......... .......... .......... .......... .......... .......... ..........  350
SEQIDNO:89     281  .......... .......... .......... .......... ..g....... .......... ..........  350
SEQIDNO:91     281  .......... .......... .......... .......... .......... .......... ..........  350
SEQIDNO:93     281  .......... .......... .......... .......... ..g....... .......... ..........  350
SEQIDNO:95     281  .......... .......... .......... .......... ..gg...... .......... ..........  350
SEQIDNO:97     281  .......... .......... .......... .......... .......... .......... ..........  350
SEQIDNO:99     281  .......... .......... .......... .......... .......... .......... ..........  350
SEQIDNO:101    281  .......... .......... .......... .......... ...a...... .......... ..........  350
SEQIDNO:103    281  .......... .......... .......... .......... .......... .......... ..........  350
SEQIDNO:105    281  .......... .......... .......... .......... .......... .......... ..........  350
SEQIDNO:107    281  .......... .......... .......... .......... .......... .......... ..........  350
SEQIDNO:109    281  .......... .......... .......... .......... .......... .......... ..........  350
SEQIDNO:111    281  .......... .......... .......... .......... .......... .......... ..........  350
SEQIDNO:113    281  .......... .......... .......... .......... .......... .......... ..........  350
SEQIDNO:115    281  .......... .......... .......... .......... .......... .......... ..........  350
SEQIDNO:117    281  .......... .......... .......... .......... .......... .......... ..........  350
SEQIDNO:119    281  .......... .......... .......... .......... .......... .......... ..........  350
SEQIDNO:121    281  .......... .......... .......... .......... .......... .......... ..........  350
SEQIDNO:123    281  .......... .......... .......... .......... .......... .......... ..........  350
SEQIDNO:125    281  .......... .......... .......... .......... .......... .......... ..........  350
SEQIDNO:127    281  .......... .......... .......... .......... .......... .......... ..........  350
SEQIDNO:129    281  .......... .......... .......... .......... .......... .......... ..........  350
SEQIDNO:131    281  .......... .......... .......... .......... .......... .......... ..........  350
SEQIDNO:133    281  .......... .......... .......... .......... ..gg...... .......... ..........  350
SEQIDNO:135    281  .......... .......... .......... .......... .......... .......... ..........  350
```

Figure 1, Continued

```
                          360        370        380        390        400        410        420
                    ....|....| ....|....| ....|....| ....|....| ....|....| ....|....| ....|....|
SEQIDNO:1      351  ggtgtatgac ggtgcagcat ttgcacgtga tggtgtggtg tttgtgagct tcaactatcg tctgggcatc  420
SEQIDNO:3      351  .......... .......... .......... .......... .......... .......... ..........  420
SEQIDNO:5      351  .......... .......... .......... .......... .......... .......... ..........  420
SEQIDNO:7      351  .......... .......... .......... .......... .......... .......... ..........  420
SEQIDNO:9      351  .......... .......... .......... .......... .......... .......... ..........  420
SEQIDNO:11     351  .......... .......... .......... .......... .......... .......... ..........  420
SEQIDNO:13     351  .......... .......... .......... .......... .......... .......... ..........  420
SEQIDNO:15     351  .......... .......... .......... .......... .......... .......... ..........  420
SEQIDNO:17     351  .......... .......... .......... .......... .......... .......... ..........  420
SEQIDNO:19     351  .......... .......... .......... .......... .......... .......... ..........  420
SEQIDNO:21     351  .......... .......... .......... .......... .......... .......... ..........  420
SEQIDNO:23     351  .......... .......... .......... .......... .......... .......... ..........  420
SEQIDNO:25     351  .......... .......... .......... .......... .......... .......... ..........  420
SEQIDNO:27     351  .......... .......... .......... .......... .......... .......... ..........  420
SEQIDNO:29     351  .......... .......... .......... .......... .......... .......... ..........  420
SEQIDNO:31     351  .......... .......... .......... .......... .......... .......... ..........  420
SEQIDNO:33     351  .......... .......... .......... .......... .......... .......... ..........  420
SEQIDNO:35     351  .......... .......... .......... .......... .......... .......... ..........  420
SEQIDNO:37     351  .......... .......... .......... .......... .......... .......... ..........  420
SEQIDNO:39     351  .......... .......... .......... .......... .......... .......... ..........  420
SEQIDNO:41     351  .......... .......... .......... .......... .......... .......... ..........  420
SEQIDNO:43     351  .......... .......... .......... .......... .......... .......... ..........  420
SEQIDNO:45     351  .......... .......... .......... .......... .......... .......... ..........  420
SEQIDNO:47     351  .......... .......... .......... .......... .......... .......... ..........  420
SEQIDNO:49     351  .......... .......... .......... .......... .......... .......... ..........  420
SEQIDNO:51     351  .......... .......... .......... .......... .......... .......... ..........  420
SEQIDNO:53     351  .......... .......... .......... .......... .......... .......... ..........  420
SEQIDNO:55     351  .......... .......... .......... .......... .......... .......... ..........  420
SEQIDNO:57     351  .......... .......... .......... .......... .......... .......... ..........  420
SEQIDNO:59     351  .......... .......... .......... .......... .......... .......... ..........  420
SEQIDNO:61     351  .......... .......... .......... .......... .......... .......... ..........  420
SEQIDNO:63     351  .......... .......... .......... .......... .......... .......... ..........  420
SEQIDNO:65     351  .......... .......... .......... .......... .......... .......... ..........  420
SEQIDNO:67     351  .......... .......... .......... .......... .......... .......... ..........  420
SEQIDNO:69     351  .......... .......... .......... .......... .......... .......... ..........  420
SEQIDNO:71     351  .......... .......... .......... .......... .......... .......... ..........  420
SEQIDNO:73     351  .......... .......... .......... .......... .......... .......... ..........  420
SEQIDNO:75     351  .......... .......... .......... .......... .......... .......... ..........  420
SEQIDNO:77     351  .......... .......... .......... .......... .......... .......... ..........  420
SEQIDNO:79     351  .......... .......... .......... .......... .......... .......... ..........  420
SEQIDNO:81     351  .......... .......... .......c.. .......... .......... .......... ..........  420
SEQIDNO:83     351  .......... .......... .......... .......... .......... .......... ..........  420
SEQIDNO:85     351  .......... .......... .......... .......... .......... .......... ..........  420
SEQIDNO:87     351  .......... .......... .......... .......... .......... .......... ..........  420
SEQIDNO:89     351  .......... .......... .......... .......... .......... .......... ..........  420
SEQIDNO:91     351  .......... .......... .......... .......... .......... .......... ..........  420
SEQIDNO:93     351  .......... .......... .......... .......... .......... .......... ..........  420
SEQIDNO:95     351  .......... .......... .......... .......... .......... .......... ..........  420
SEQIDNO:97     351  .......... .......... .......... .......... .......... .......... ..........  420
SEQIDNO:99     351  .......... .......... .......c.. .......... .......... .......... ..........  420
SEQIDNO:101    351  .......... .......... .......... .......... .......... .......... ..........  420
SEQIDNO:103    351  .......... .......... .......... .......... .......... .......... ..........  420
SEQIDNO:105    351  .......... .......... .......... .......... .......... .......... ..........  420
SEQIDNO:107    351  .......... .......... .......... .......... .......... .......... ..........  420
SEQIDNO:109    351  .......... .......... .......... .......... .......... .......... ..........  420
SEQIDNO:111    351  .......... .......... .......... .......... .......... .......... ..........  420
SEQIDNO:113    351  .......... .......... .......... .......... .......... .......... ..........  420
SEQIDNO:115    351  .......... .......... .......... .......... .......... .......... ..........  420
SEQIDNO:117    351  .......... .......... .......... .......... .......... .......... ..........  420
SEQIDNO:119    351  .......... .......... .......... .......... .......... .......... ..........  420
SEQIDNO:121    351  .......... .......... .......... .......... .......... .......... ..........  420
SEQIDNO:123    351  .......... .......... .......... .......... .......... .......... ..........  420
SEQIDNO:125    351  .......... .......... .......... .......... .......... .......... ..........  420
SEQIDNO:127    351  .......... .......... .......... .......... .......... .......... ..........  420
SEQIDNO:129    351  .......... .......... .......... .......... .......... .......... ..........  420
SEQIDNO:131    351  .......... .......... .......... .......... .......... .......... ..........  420
SEQIDNO:133    351  .......... .......... .......... .......... .......... .......... ..........  420
SEQIDNO:135    351  .......... .......... .......... .......... .......... .......... ..........  420
```

Figure 1, Continued

```
                         430        440        450        460        470        480        490
                  ....|....| ....|....| ....|....| ....|....| ....|....| ....|....| ....|....|
SEQIDNO:1    421  attggctttg cagatctgcc agatgcacca agtaatcgcg gcctgttaga tcaaatcgcc gcactggaat  490
SEQIDNO:3    421  .......... .......... .......... .......... .......... .......... ..........  490
SEQIDNO:5    421  .......... .......... .......... .......... .......... .......... ..........  490
SEQIDNO:7    421  .......... .......... .......... .......... .......... .......... ..........  490
SEQIDNO:9    421  .......... .......... .......... .......... .......... .......... ..........  490
SEQIDNO:11   421  .......... .......... .......... .......... .......... .......... ..........  490
SEQIDNO:13   421  .......... .......... .......... .......... .......... .......... ..........  490
SEQIDNO:15   421  .......... .......... .......... .......... .......... .......... ..........  490
SEQIDNO:17   421  .......... .......... .......... .......... .......... .......... ..........  490
SEQIDNO:19   421  .......... .......... .......... .......... .......... .......... ..........  490
SEQIDNO:21   421  .......... .......... .......... .......... .......... .......... ..........  490
SEQIDNO:23   421  .......... .......... .......... .......... .......... .......... ..........  490
SEQIDNO:25   421  .......... .......... .......... .......... .......... .......... ..........  490
SEQIDNO:27   421  .......... .......... .......... .......... .......... .......... ..........  490
SEQIDNO:29   421  .......... .......... .......... .......... .......... .......... ..........  490
SEQIDNO:31   421  .......... .......... .......... .......... .......... .......... ..........  490
SEQIDNO:33   421  .......... .......... .......... .......... .......... .......... ..........  490
SEQIDNO:35   421  .......... .......... .......... .......... .......... .......... ..........  490
SEQIDNO:37   421  .......... .......... .......... .......... .......... .......... ..........  490
SEQIDNO:39   421  .......... .......... .......... .......... .......... .......... ..........  490
SEQIDNO:41   421  .......... .......... .......... .......... .......... .......... ..........  490
SEQIDNO:43   421  .......... .......... .......... .......... .......... .......... ..........  490
SEQIDNO:45   421  .......... .......... .......... .......... .......... .......... ..........  490
SEQIDNO:47   421  .......... .......... .......... .......... .......... .......... ..........  490
SEQIDNO:49   421  .......... .......... .......... .......... .......... .......... ..........  490
SEQIDNO:51   421  .......... .......... .......... .......... .......... .......... ..........  490
SEQIDNO:53   421  .......... .......... .......... .......... .......... .......... ..........  490
SEQIDNO:55   421  .......... .......... .......... .......... .......... .......... ..........  490
SEQIDNO:57   421  .......... .......... .......... .......... .......... .......... ..........  490
SEQIDNO:59   421  .......... .......... .......... .......a.. .......... .......... ..........  490
SEQIDNO:61   421  .......... .......... .......... .......... .......... .......... ..........  490
SEQIDNO:63   421  .......... .......... .......... .......... .......... .......... ..........  490
SEQIDNO:65   421  .......... .......... .......... .......... .......... .......... ..........  490
SEQIDNO:67   421  .......... .......... .......... .......... .......... .......... ..........  490
SEQIDNO:69   421  .......... .......... .......... .......... .......... .......... ..........  490
SEQIDNO:71   421  .......... .......... .......... .......... .......... .......... ..........  490
SEQIDNO:73   421  .......... .......... .......... .......... .......... .......... ..........  490
SEQIDNO:75   421  .......... .......... .......... .......... .......... .......... ..........  490
SEQIDNO:77   421  .......... .......... .......... .......... .......... .......... ..........  490
SEQIDNO:79   421  .......... .......... .......... .......... .......... .......... ..........  490
SEQIDNO:81   421  .......... .......... .......... .......... .......... .......... ..........  490
SEQIDNO:83   421  .......... .......... .......... .......... .......... .......... ..........  490
SEQIDNO:85   421  .......... .......... .......... .......... .......... .......... ..........  490
SEQIDNO:87   421  .......... .......... .......... .......... .......... .......... ..........  490
SEQIDNO:89   421  .......... .......... .......... .......... .......... .......... ..........  490
SEQIDNO:91   421  .......... .......... .......... .......... .......... .......... ..........  490
SEQIDNO:93   421  .......... .......... .......... .......... .......... .......... ..........  490
SEQIDNO:95   421  .......... .......... .......... .......... .......... .......... ..........  490
SEQIDNO:97   421  .......... .......... .......... .......... .......... .......... ..........  490
SEQIDNO:99   421  .......... .......... .......... .......... .......... .......... ..........  490
SEQIDNO:101  421  .......... .......... .......... .......... .......... .......... ..........  490
SEQIDNO:103  421  .......... .......... .......... .......... .......... .......... ..........  490
SEQIDNO:105  421  .......... .......... .......... .......... .......... .......... ..........  490
SEQIDNO:107  421  .......... .......... .......... .......... .......... .......... ..........  490
SEQIDNO:109  421  .......... .......... .......... .......... .......... .......... ..........  490
SEQIDNO:111  421  .......... .......... .......... .......... .......... .......... ..........  490
SEQIDNO:113  421  .......... .......... .......... .......... .......... .......... ..........  490
SEQIDNO:115  421  .......... .......... .......... .......... .......... .......... ..........  490
SEQIDNO:117  421  .......... .......... .......... .......... .......... .......... ..........  490
SEQIDNO:119  421  .......... .......... .......... .......... .......... .......... ..........  490
SEQIDNO:121  421  .......... .......... .......... .......... .......... .......... ..........  490
SEQIDNO:123  421  .......... .......... .......... .......... .......... .......... ..........  490
SEQIDNO:125  421  .......... .......... .......... .......... .......... .......... ..........  490
SEQIDNO:127  421  .......... .......... .......... .......... .......... .......... ..........  490
SEQIDNO:129  421  .......... .......... .......... .......... .......... .......... ..........  490
SEQIDNO:131  421  .......... .......... .......... .......... .......... .......... ..........  490
SEQIDNO:133  421  .......... .......... .......... .......... .......... .......... ..........  490
SEQIDNO:135  421  .......... .......... .......... .......... .......... .......... ..........  490
```

Figure 1, Continued

```
                          500        510        520        530        540        550        560
                  ....|....| ....|....| ....|....| ....|....| ....|....| ....|....| ....|....|
SEQIDNO:1     491 gggttcgcga caacattgca cgctttgggg gtgacccagg taatgtgacc gtgtttggcg aaagtgcggg 560
SEQIDNO:3     491 .......... .......... .......... .......... .......... .......... .......... 560
SEQIDNO:5     491 .......... .......... .......... .......... .......... .......... .......... 560
SEQIDNO:7     491 .......... .......... .......... .......... .......... .......... .......... 560
SEQIDNO:9     491 .......... .......... .......... .......... .......... .......... .......... 560
SEQIDNO:11    491 .......... .......... .......... .......... .......... .......... .......... 560
SEQIDNO:13    491 .......... .......... .......... .......... .......... .......... .......... 560
SEQIDNO:15    491 .......... .......... .......... .......... .......... .......... .......... 560
SEQIDNO:17    491 .......... .......... .......... .......... .......... .......... .......... 560
SEQIDNO:19    491 .......... .......... .......... .......... .......... .......... .......... 560
SEQIDNO:21    491 .......... .......... .......... .......... .......... .......... .......... 560
SEQIDNO:23    491 .......... .......... .......... .......... .......... .......... .......... 560
SEQIDNO:25    491 .......... .......... .......... .......... .......... .......... .......... 560
SEQIDNO:27    491 .......... .......... .......... .......... .......... .......... .......... 560
SEQIDNO:29    491 .......... .......... .......... .......... .......... .......... .......... 560
SEQIDNO:31    491 .......... .......... .......... .......... .......... .......... .......... 560
SEQIDNO:33    491 .......... .......... .......... .......... .......... .......... .......... 560
SEQIDNO:35    491 .......... .......... .......... .......... .......... .......... .......... 560
SEQIDNO:37    491 .......... .......... .......... .......... .......... .......... .......... 560
SEQIDNO:39    491 .......... .......... .......... .......... .......... .......... .......... 560
SEQIDNO:41    491 .......... .......... .......... .......... .......... .......... .......... 560
SEQIDNO:43    491 .......... .......... .......... .......... .......... .......... .......... 560
SEQIDNO:45    491 .......... .......... .......... .......... .......... .......... .......... 560
SEQIDNO:47    491 .......... .......... .......... .......... .......... .......... .......... 560
SEQIDNO:49    491 .......... .......... .......... .......... .......... .........t ct........ 560
SEQIDNO:51    491 .......... .......... .......... .......... .......... .......... .......... 560
SEQIDNO:53    491 .......... .......... .......... .......... .......... .......... .......... 560
SEQIDNO:55    491 .......... .......... .......... .......... .......... .......... .......... 560
SEQIDNO:57    491 .......... .......... .......... .......... .......... .......... gg........ 560
SEQIDNO:59    491 .......... .......... .......... .......... .......... .......... .......... 560
SEQIDNO:61    491 .......... .......... .......... .......... .......... .......... .......... 560
SEQIDNO:63    491 .......... .......... .......... .......... .......... .......... .......... 560
SEQIDNO:65    491 .......... .......... .......... .......... .......... .......... gg........ 560
SEQIDNO:67    491 .......... .......... .......... .......... .......... .......... .......... 560
SEQIDNO:69    491 .......... .......... .......... .......... .......... .......... .......... 560
SEQIDNO:71    491 .......... .......... .......... .......... .......... .......... .......... 560
SEQIDNO:73    491 .......... .......... .......... .......... .......... .......... .......... 560
SEQIDNO:75    491 .......... .......... .......... .......... .......... .......... .......... 560
SEQIDNO:77    491 .......... .......... .......... .......... .......... .......... .......... 560
SEQIDNO:79    491 .......... .......... .......... .......... .......... .......... .......... 560
SEQIDNO:81    491 .......... .......... .......... .......... .......... .......... .......... 560
SEQIDNO:83    491 .......... .......... .......... .......... .......... .......... .......... 560
SEQIDNO:85    491 .......... .......... .......... .......... .......... .......... .......... 560
SEQIDNO:87    491 .......... .......... .......... .......... .......... .......... .......... 560
SEQIDNO:89    491 .......... .......... .......... .......... .......... .......... .......... 560
SEQIDNO:91    491 .......... .......... .......... .......... .......... .......... .......... 560
SEQIDNO:93    491 .......... .......... .......... .......... .......... .......... .......... 560
SEQIDNO:95    491 .......... .......... .......... .......... .......... .......... .......... 560
SEQIDNO:97    491 .......... .......... .......... .......... .......... .......... .......... 560
SEQIDNO:99    491 .......... .......... .......... .......... .......... .......... .......... 560
SEQIDNO:101   491 .......... .......... .......... .......... .......... .......... .......... 560
SEQIDNO:103   491 .......... .......... .......... .......... .......... .......... .......... 560
SEQIDNO:105   491 .......... .......... .......... .......... .......... .......... .......... 560
SEQIDNO:107   491 .......... .......... .......... .......... .......... .......... .......... 560
SEQIDNO:109   491 .......... .......... .......... .......... .......... .......... .......... 560
SEQIDNO:111   491 .......... .......... .......... .......... .......... .......... .......... 560
SEQIDNO:113   491 .......... .......... .......... .......... .......... .......... .......... 560
SEQIDNO:115   491 .......... .......... .......... .......... .......... .......... .......... 560
SEQIDNO:117   491 .......... .......... .......... .......... .......... .......... .......... 560
SEQIDNO:119   491 .......... .......... .......... .......... .......... .......... .......... 560
SEQIDNO:121   491 .......... .......... .......... .......... .......... .......... .......... 560
SEQIDNO:123   491 .......... .......... .......... .......... .......... .......... .......... 560
SEQIDNO:125   491 .......... .......... .......... .......... .......... .......... .......... 560
SEQIDNO:127   491 .......... .......... .......... .......... .......... .......... .......... 560
SEQIDNO:129   491 .......... .......... .......... .......... .......... .......... .......... 560
SEQIDNO:131   491 .......... .......... .......... .......... .......... .......... .......... 560
SEQIDNO:133   491 .......... .......... .......... .......... .......... .......... .......... 560
SEQIDNO:135   491 .......... .......... .......... .......... .......... .......... .......... 560
```

Figure 1, Continued

```
                               570        580        590        600        610        620        630
                        ....|....| ....|....| ....|....| ....|....| ....|....| ....|....| ....|....|
SEQIDNO:1       561     cgcgatgagc gtgtgcaccc tgatggcaac cccgcgtgca cgtggtctgt ttcgtcgtgc tatcttacag  630
SEQIDNO:3       561     .......... .......... .......... .......... .......... .......... ..........  630
SEQIDNO:5       561     .......... .......... .......... .......... .......... .......... ..........  630
SEQIDNO:7       561     .......... .......... .......... .......... .......... .......... ..........  630
SEQIDNO:9       561     .......... .......... .......... .......... .......... .......... ..........  630
SEQIDNO:11      561     .......... .......... .......... .......... .......... .......... ..........  630
SEQIDNO:13      561     .......... .......... .......... .......... .......... .......... ..........  630
SEQIDNO:15      561     .......... .......... .......... .......... .......... .......... ..........  630
SEQIDNO:17      561     .......... .......... .......... .......... .......... .......... ..........  630
SEQIDNO:19      561     .......... .......... .......... .......... .......... .......... ..........  630
SEQIDNO:21      561     .......... .......... .......... .......... .......... .......... ..........  630
SEQIDNO:23      561     .......... .......... .......... .......... .......... .......... ..........  630
SEQIDNO:25      561     .......... .......... .......... .......... .......... .......... ..........  630
SEQIDNO:27      561     .......... .......... .......... .......... .......... .......... ..........  630
SEQIDNO:29      561     .......... .......... .......... .......... .......... .......... ..........  630
SEQIDNO:31      561     .......... .......... .......... .......... .......... .......... ..........  630
SEQIDNO:33      561     .......... .......... .......... .......... .......... .......... ..........  630
SEQIDNO:35      561     .......... .......... .......... .......... .......... .......... ..........  630
SEQIDNO:37      561     .......... .......... .......... .......... .......... .......... ..........  630
SEQIDNO:39      561     ........ag .......... .......... .......... .......... .......... ..........  630
SEQIDNO:41      561     .......... .......... .......... .......... .......... .......... ..........  630
SEQIDNO:43      561     .......... .......... .......... .......... .......... .......... ..........  630
SEQIDNO:45      561     .......... .......... .......... .......... .......... .......... ..........  630
SEQIDNO:47      561     .......... .......... .......... .......... .......... .......... ..........  630
SEQIDNO:49      561     .......... .......... .......... .......... .......... .......... ..........  630
SEQIDNO:51      561     .......... .......... .......... .......... .......... .......... ..........  630
SEQIDNO:53      561     .......... .......... .......... .......... .......... .......... ..........  630
SEQIDNO:55      561     .......... .......... .......... .......... .......... .......... ..........  630
SEQIDNO:57      561     .......... .......... .......... .......... .......... .......... ..........  630
SEQIDNO:59      561     .......... .......... .......... .......... .......... .......... ..........  630
SEQIDNO:61      561     .......... .......... .......... .......... .......... .......... ..........  630
SEQIDNO:63      561     .......t.g .......... .......... .......... .......... .......... ..........  630
SEQIDNO:65      561     .......... .......... .......... .......... .......... .......... ..........  630
SEQIDNO:67      561     .......... .......... .......... .......... .......... .......... ..........  630
SEQIDNO:69      561     .......... .......... .......... .......... .......... .......... ..........  630
SEQIDNO:71      561     .......... .......... .......... .......... .......... .......... ..........  630
SEQIDNO:73      561     .......... .......... .......... .......... .......... .......... ..........  630
SEQIDNO:75      561     .......... .......... .......... .......... .......... .......... ..........  630
SEQIDNO:77      561     .......tca .......... .......... .......... .......... .......... ..........  630
SEQIDNO:79      561     .......... .......... .......... .......... .......... .......... ..........  630
SEQIDNO:81      561     .......... .......... .......... .......... .......... .......... ..........  630
SEQIDNO:83      561     .......... .......... .......... .......... .......... .......... ..........  630
SEQIDNO:85      561     .......... .......... .......... .......... .......... .......... ..........  630
SEQIDNO:87      561     .......... .......... .......... .......... .......... .......... ..........  630
SEQIDNO:89      561     .......... .......... .......... .......... .......... .......... ..........  630
SEQIDNO:91      561     .......... .......... .......... .......... .......... .......... ..........  630
SEQIDNO:93      561     .......... .......... .......... .......... .......... .......... ..........  630
SEQIDNO:95      561     .......... .......... .......... .......... .......... .......... ..........  630
SEQIDNO:97      561     .......... .......... .......... .......... .......... .......... ..........  630
SEQIDNO:99      561     .......... .......... .......... .......... .......... .......... ..........  630
SEQIDNO:101     561     .......... .......... .......... .......... .......... .......... ..........  630
SEQIDNO:103     561     .......... .......... .......... .......... .......... .......... ..........  630
SEQIDNO:105     561     .......... .......... .......... .......... .......... .......... ..........  630
SEQIDNO:107     561     .......... .......... .......... .......... .......... .......... ..........  630
SEQIDNO:109     561     .......... .......... .......... .......... .......... .......... ..........  630
SEQIDNO:111     561     .......... .......... .......... .......... .......... .......... ..........  630
SEQIDNO:113     561     .......... .......... .......... .......... .......... .......... ..........  630
SEQIDNO:115     561     ......t... .......... .......... .......... .......... .......... ..........  630
SEQIDNO:117     561     .......... .......... .......... .......... .......... .......... ..........  630
SEQIDNO:119     561     .......... .......... .......... .......... .......... .......... ..........  630
SEQIDNO:121     561     ......t... .......... .......... .......... .......... .......... ..........  630
SEQIDNO:123     561     .......... .......... .......... .......... .......... .......... ..........  630
SEQIDNO:125     561     .......... .......... .......... .......... .......... .......... ..........  630
SEQIDNO:127     561     ......t... .......... .......... .......... .......... .......... ..........  630
SEQIDNO:129     561     .......... .......... .......... .......... .......... .......... ..........  630
SEQIDNO:131     561     ....ca.... .......... .......... .......... .......... .......... ..........  630
SEQIDNO:133     561     .......... .......... .......... .......... .......... .......... ..........  630
SEQIDNO:135     561     .......... .......... .......... .......... .......... .......... ..........  630
```

Figure 1, Continued

```
                               640        650        660        670        680        690        700
                         ....|....| ....|....| ....|....| ....|....| ....|....| ....|....| ....|....|
SEQIDNO:1         631    agcgggcgcag gcaacatggc agtcgctgca gaagatgcta ccacaatcgc agctgtgatt gcccatcgtt  700
SEQIDNO:3         631    .......... .......... .......... .......... .......... .......... ..........  700
SEQIDNO:5         631    .......... .......... .......... .......... .......... .......... ..........  700
SEQIDNO:7         631    .......... .......... .......... .......... .......... .......... ..........  700
SEQIDNO:9         631    .......... .......... .......... .......... .......... .......... ..........  700
SEQIDNO:11        631    .......... .......... .......... .......... .......... .......... ..........  700
SEQIDNO:13        631    .......... .......... .......... .......... .......... .......... ..........  700
SEQIDNO:15        631    .......... ...gg..... .......... .......... .......... .......... ..........  700
SEQIDNO:17        631    .......... .......... .......... .......... .......... .......... ..........  700
SEQIDNO:19        631    .......... ..tgg..... .......... .......... .......... .......... ..........  700
SEQIDNO:21        631    ...cct.... .......... .......... .......... .......... .......... ..........  700
SEQIDNO:23        631    .......... .......... .......... .......... .......... .......... ..........  700
SEQIDNO:25        631    .......... ..ccg..... .......... .......... .......... .......... ..........  700
SEQIDNO:27        631    .......... .......... .......... .......... .......... .......... ..........  700
SEQIDNO:29        631    .......... .......... .......... .......... .......... .......... ..........  700
SEQIDNO:31        631    .......... .......... .......... .......... .......... .......... ..........  700
SEQIDNO:33        631    .......... .......... .......... .......... .......... .......... ..........  700
SEQIDNO:35        631    .......... .......... .......... .......... .......... .......... ..........  700
SEQIDNO:37        631    .......... .......... .......... .......... .......... .......... ..........  700
SEQIDNO:39        631    .......... .......... .......... .......... .......... .......... ..........  700
SEQIDNO:41        631    .......... ...gg..... .......... .......... .......... .......... ..........  700
SEQIDNO:43        631    .......... .......... .......... .......... .......... .......... ..........  700
SEQIDNO:45        631    .......... .......... .......... .......... .......... .......... ..........  700
SEQIDNO:47        631    .......... .......... .......... .......... .......... .......... ..........  700
SEQIDNO:49        631    .......... .......... .......... .......... .......... .......... ..........  700
SEQIDNO:51        631    .......... .......... .......... .......... .......... .......... ..........  700
SEQIDNO:53        631    ......ctg. .......... .......... .......... .......... .......... ..........  700
SEQIDNO:55        631    .......... .......... .......... .......... .......... .......... ..........  700
SEQIDNO:57        631    .......... .......... .......... .......... .......... .......... ..........  700
SEQIDNO:59        631    .......... ..cct..... .......... .......... .......... .......... ..........  700
SEQIDNO:61        631    .........c tt........ .......... .......... .......... .......... ..........  700
SEQIDNO:63        631    .......... .......... .......... .......... .......... .......... ..........  700
SEQIDNO:65        631    .......... .......... .......... .......... .......... .......... ..........  700
SEQIDNO:67        631    .......... .......... .......... .......... .......... .......... ..........  700
SEQIDNO:69        631    .......... .......... .......... .......... .......... .......... ..........  700
SEQIDNO:71        631    .......... .......... .......... .......... .......... .......... ..........  700
SEQIDNO:73        631    .......... .......... .......... .......... .......... .......... ..........  700
SEQIDNO:75        631    .......... .......... .......... .......... .......... .......... ..........  700
SEQIDNO:77        631    .......... .......... .......... .......... .......... .......... ..........  700
SEQIDNO:79        631    .......... .......... .......... .......... .......... .......... ..........  700
SEQIDNO:81        631    .......... .......... .......... .......... .......... .......... ..........  700
SEQIDNO:83        631    .......... .......... .......... .......... .......... .......... ..........  700
SEQIDNO:85        631    .......... .......... .......... .......... .......... .......... ..........  700
SEQIDNO:87        631    .......... .......... .......... .......... .......... .......... ..........  700
SEQIDNO:89        631    .......... .......... .......... .......... .......... .......... ..........  700
SEQIDNO:91        631    .......... .......... .......... .......... .......... .......... ..........  700
SEQIDNO:93        631    .......... .......... .......... .......... .......... .......... ..........  700
SEQIDNO:95        631    .......... ....g..... .......... .......... .......... .......... ..........  700
SEQIDNO:97        631    .......... .......... .......... .......... .......... .......... ..........  700
SEQIDNO:99        631    ........g. ..cga..... .......... .......... .......... .......... ..........  700
SEQIDNO:101       631    .......... ....g..... .......... .......... .......... .......... ..........  700
SEQIDNO:103       631    .....a.... ..cg...... .......... .......... .......... .......... ..........  700
SEQIDNO:105       631    .......... ...gg..... .......... .......... .......... .......... ..........  700
SEQIDNO:107       631    .....a.... ..cg...... .......... .......... .......... .......... ..........  700
SEQIDNO:109       631    ...cc..... ..cg...... .......... .......... .......... .......... ..........  700
SEQIDNO:111       631    ...cc..... ..cg...... .......... .......... .......... .......... ..........  700
SEQIDNO:113       631    .....a.... ..cg...... .......... .......... .......... .......... ..........  700
SEQIDNO:115       631    .........c .tccg..... .......... .......... .......... .......... ..........  700
SEQIDNO:117       631    .......... ....a..... .......... .......... .......... .......... ..........  700
SEQIDNO:119       631    .......... ....g..... .......... .......... .......... .......... ..........  700
SEQIDNO:121       631    .......... .......... .......... .......... .......... .......... ..........  700
SEQIDNO:123       631    .......... ...gg..... .......... .......... .......... .......... ..........  700
SEQIDNO:125       631    .......... ..tgg..... .......... .......... .......... .......... ..........  700
SEQIDNO:127       631    .......... .......... .......... .......... .......... .......... ..........  700
SEQIDNO:129       631    .......... ....g..... .......... .......... .......... .......... ..........  700
SEQIDNO:131       631    .......... ..ccg..... .......... .......... .......... .......... ..........  700
SEQIDNO:133       631    .......... ..ccg..... .......... .......... .......... .......... ..........  700
SEQIDNO:135       631    .......... .......... .......... .......... .......... .......... ..........  700
```

Figure 1, Continued

```
                              710        720        730        740        750        760        770
                       ....|....| ....|....| ....|....| ....|....| ....|....| ....|....| ....|....|
SEQIDNO:1        701   taggtgttga gccaactgca gcagcattag cgcatgttcc agttgcacag ttactggatg ttcagcagca  770
SEQIDNO:3        701   .......... .......... .......... .......... .......... .......... ..........  770
SEQIDNO:5        701   .......... .......... .......... .......... .......... .......... ..........  770
SEQIDNO:7        701   .......... .......... .......... .......... .......... .......... ..........  770
SEQIDNO:9        701   .......... .......... .......... .......... .......... .......... ..........  770
SEQIDNO:11       701   .......... .......... .......... .......... .......... .......... ..........  770
SEQIDNO:13       701   .......... .......... .......... .......... .......... .......... ..........  770
SEQIDNO:15       701   .......... .......... .......... .......... .......... .......... ..........  770
SEQIDNO:17       701   .......... .......... .......... .......... .......... .......... ..........  770
SEQIDNO:19       701   .......... .......... .......... .......... .......... .......... ..........  770
SEQIDNO:21       701   .......... .......... .......... .......... .......... .......... ..........  770
SEQIDNO:23       701   .......... .......... .......... .......... .......... .......... ..........  770
SEQIDNO:25       701   .......... .......... .......... .......... .......... .......... ..........  770
SEQIDNO:27       701   .......... .......... .......... .......... .......... .......... ..........  770
SEQIDNO:29       701   .......... .......... .......... .......... .......... .......... ..........  770
SEQIDNO:31       701   .......... .......... .......... .......... .......... .......... ..........  770
SEQIDNO:33       701   .......... .......... .......... .......... .......... .......... ..........  770
SEQIDNO:35       701   .......... .......... .......... .......... .......... .......... ..........  770
SEQIDNO:37       701   .......... .......... .......... .......... .......... .......... ..........  770
SEQIDNO:39       701   .......... .......... .......... .......... .......... .......... ..........  770
SEQIDNO:41       701   .......... .......... .......... .......... .......... .......... ..........  770
SEQIDNO:43       701   .......... .......... .......... .......... .......... .......... ..........  770
SEQIDNO:45       701   .......... .......... .......... .......... .......... .......... ..........  770
SEQIDNO:47       701   .......... .......... .......... .......... .......... .......... ..........  770
SEQIDNO:49       701   .......... .......... .......... .......... ....a..... .......... ..........  770
SEQIDNO:51       701   .......... .......... .......... .......... .......... .......... ..........  770
SEQIDNO:53       701   .......... .......... .......... .......... .......... .......... ..........  770
SEQIDNO:55       701   .......... .......... .......... .......... .......... .......... ..........  770
SEQIDNO:57       701   .......... .......... .......... .......... .......... .......... ..........  770
SEQIDNO:59       701   .......... .......... .......... .......... .......... .......... ..........  770
SEQIDNO:61       701   .......... .......... .......... .......... .......... .......... ..........  770
SEQIDNO:63       701   .......... .......... .......... .......... .......... .......... ..........  770
SEQIDNO:65       701   .......... .......... .......... .......... .......... .......... ..........  770
SEQIDNO:67       701   .......... .......... .......... .......... .......... .......... ..........  770
SEQIDNO:69       701   .......... .......... .......... .......... .......... .......... ..........  770
SEQIDNO:71       701   .......... .......... .......... .......... .......... .......... ..........  770
SEQIDNO:73       701   .......... .......... .......... .......... .......... .......... ..........  770
SEQIDNO:75       701   .......... .......... .......... .......... .......... .......... ..........  770
SEQIDNO:77       701   .......... .......... .......... .......... .......... .......... ..........  770
SEQIDNO:79       701   .......... .......... .......... .......... .......... .......... ..........  770
SEQIDNO:81       701   .......... .......... .......... .......... ......c... .......... ..........  770
SEQIDNO:83       701   .......... .......... .......... .......... .......... .......... ..........  770
SEQIDNO:85       701   .......... .......... .......... .......... .......... .......... ..........  770
SEQIDNO:87       701   .......... .......... .......... .......... .......... .......... ..........  770
SEQIDNO:89       701   .......... .......... .......... .......... .......... .......... ..........  770
SEQIDNO:91       701   .......... .......... .......... .......... .......... .......... ..........  770
SEQIDNO:93       701   .......... .......... .......... .......... .......... .......... ..........  770
SEQIDNO:95       701   .......... .......... .......... .......... .......... .......... ..........  770
SEQIDNO:97       701   .......... .......... .......... .......... .......... .......... ..........  770
SEQIDNO:99       701   .......... .......... .......... .......... .......... .......... ..........  770
SEQIDNO:101      701   .......... .......... .......... .......... .......... .......... ..........  770
SEQIDNO:103      701   .......... .......... .......... .......... .......... .......... ..........  770
SEQIDNO:105      701   .......... .......... .......... .......... .......... .......... ..........  770
SEQIDNO:107      701   .......... .......... .......... .......... .......... .......... ..........  770
SEQIDNO:109      701   .......... .......... .......... .......... .......... .......... ..........  770
SEQIDNO:111      701   .......... .......... .......... .......... .......... .......... ..........  770
SEQIDNO:113      701   .......... .......... .......... .......... .......... .......... ..........  770
SEQIDNO:115      701   .......... .......... .......... .......... .......... .......... ..........  770
SEQIDNO:117      701   .......... .......... .......... .......... .......... .......... ..........  770
SEQIDNO:119      701   .......... .......... .......... .......... .......... .......... ..........  770
SEQIDNO:121      701   .......... .......... .......... .......... .......... .......... ..........  770
SEQIDNO:123      701   .......... .......... .......... .......... .......... .......... ..........  770
SEQIDNO:125      701   .......... .......... .......... .......... .......... .......... ..........  770
SEQIDNO:127      701   .......... .......... .......... .......... .......... .......... ..........  770
SEQIDNO:129      701   .......... .......... .......... .......... .......... .......... ..........  770
SEQIDNO:131      701   .......... .......... .......... .......... .......... .......... ..........  770
SEQIDNO:133      701   .......... .......... .......... .......... .......... .......... ..........  770
SEQIDNO:135      701   .......... .......... .......... .......... .......... .......... ..........  770
```

Figure 1, Continued

```
                               780        790        800        810        820        830        840
                        ....|....| ....|....| ....|....| ....|....| ....|....| ....|....| ....|....|
SEQIDNO:1         771   agttgcccaa gagattcaag gcgcgccaga tccagcagtt tggggtgcac gtattgcggg cggcagtgtg   840
SEQIDNO:3         771   .......... .......... .......... .......... .......... .......... ..........   840
SEQIDNO:5         771   .......... .......... .......... .......... .......... .......... ..........   840
SEQIDNO:7         771   .......... .......... .......... .......... .......... .......... ..........   840
SEQIDNO:9         771   .......... .......... .......... .......... .......... .......... ..........   840
SEQIDNO:11        771   .......... .......... .......... .......... .......... .......... ..........   840
SEQIDNO:13        771   .......... .......... .......... .......... .......... .......... ..........   840
SEQIDNO:15        771   .......... .......... .......... .......... .......... .......... ..........   840
SEQIDNO:17        771   .......... .......... .......... .......... .......... .......... ..........   840
SEQIDNO:19        771   .......... .......... .......... .......... .......... .......... ..........   840
SEQIDNO:21        771   .......... .......... .......... .......... .......... .......... ..........   840
SEQIDNO:23        771   .......... .......... .......... .......... .......... .......... ........g.   840
SEQIDNO:25        771   .......... .......... .......... .......... .......... .......... ..........   840
SEQIDNO:27        771   .......... .......... .......... .......... .......... .......... ..........   840
SEQIDNO:29        771   .......... .......... .......... .......... .......... .......... ..........   840
SEQIDNO:31        771   .......... .......... .......... .......... .......... .......... ..........   840
SEQIDNO:33        771   .......... .......... .......... .......... act....... .......... ..........   840
SEQIDNO:35        771   .......... .......... .......... .......... .......... .......... ..........   840
SEQIDNO:37        771   .......... .......... .......... .......... .......... .......... ..........   840
SEQIDNO:39        771   .......... .......... .......... .......... .......... .......... ..........   840
SEQIDNO:41        771   .......... .......... .......... .......... a......... .......... ..........   840
SEQIDNO:43        771   .......... .......... .......... .......... .......... .......... ..........   840
SEQIDNO:45        771   .......... .......... .......... .......... .......... .......... ..........   840
SEQIDNO:47        771   .......... .......... .......... .......... .......... .......... ..........   840
SEQIDNO:49        771   .......... .......... .......... .......... .......... .......... ..........   840
SEQIDNO:51        771   .......... .......... .......... .......... .......... .......... ..........   840
SEQIDNO:53        771   .......... .......... .......... .......... .......... .......... ..........   840
SEQIDNO:55        771   .......... .......... .......... .......... .......... .......... ..........   840
SEQIDNO:57        771   .......... .......... .......... .......... .......... .......... ..........   840
SEQIDNO:59        771   .......... .......... .......... .......... .......... .......... ..........   840
SEQIDNO:61        771   .......... .......... .......... .......... .......... .......... ..........   840
SEQIDNO:63        771   .......... .......... .......... .......... .......... .......... ..........   840
SEQIDNO:65        771   .......... .......... .......... .......... .......... .......... ..........   840
SEQIDNO:67        771   .......... .......... .......... .......... .......... .......... ..........   840
SEQIDNO:69        771   .......... .......... .......... .......... .......... .......... ..........   840
SEQIDNO:71        771   .......... .......... .......... .......... .at....... .......... ..........   840
SEQIDNO:73        771   .......... .......... .......... .......... .......... .......... ..........   840
SEQIDNO:75        771   .......... .......... .......... .......... .......... .......... ..........   840
SEQIDNO:77        771   .......... .......... .......... .......... .......... .......... .........t   840
SEQIDNO:79        771   .......... .......... .......... .......... .......... .......... ..........   840
SEQIDNO:81        771   .......... .......... .......... .......... .......... .......... ........gt   840
SEQIDNO:83        771   .......... .......... .......... .......... .at....... .......... ..........   840
SEQIDNO:85        771   .......... .......... .......... .......... .......... .......... ..........   840
SEQIDNO:87        771   .......... .......... .......... .......... .......... .......... .........t   840
SEQIDNO:89        771   .......... .......... .......... .......... .......... .......... ..........   840
SEQIDNO:91        771   .......... .......... .......... .......... .at....... .......... ..........   840
SEQIDNO:93        771   .......... .......... .......... .......... .......... .......... ..........   840
SEQIDNO:95        771   .......... .......... .......... .......... .......... .......... ..........   840
SEQIDNO:97        771   .......... .......... .......... .......... .......... .......... ..........   840
SEQIDNO:99        771   .......... .......... .......... .......... .......... .......... ..........   840
SEQIDNO:101       771   .......... .......... .......... .......... .......... .......... ..........   840
SEQIDNO:103       771   .......... .......... .......... .......... .......... .......... ..........   840
SEQIDNO:105       771   .......... .......... .......... .......... .......... .......... ..........   840
SEQIDNO:107       771   .......... .......... .......... ...g...... .......... .......... ..........   840
SEQIDNO:109       771   .......... .......... .......... ...g...... .......... .......... ..........   840
SEQIDNO:111       771   .......... .......... .......... .g.gaat... .......... .......... ..........   840
SEQIDNO:113       771   .......... .......... .......... .......... .......... .......... ..........   840
SEQIDNO:115       771   .......... .......... .......... .......... .......... .......... ..........   840
SEQIDNO:117       771   .......... .......... .......... .......... .......... .......... ..........   840
SEQIDNO:119       771   .......... .......... .......... .......... .......... .......... ..........   840
SEQIDNO:121       771   .......... .......... .......... .......... .......... .......... ..........   840
SEQIDNO:123       771   .......... .......... .......... .......... .......... .......... ..........   840
SEQIDNO:125       771   .......... .......... .......... .......... .......... .......... ..........   840
SEQIDNO:127       771   .......... .......... .......... .......... .......... .......... ..........   840
SEQIDNO:129       771   .......... .......... .......... ....tt.a.c .......... .......... ..........   840
SEQIDNO:131       771   .......... .......... .......... .......... .at....... .......... ..........   840
SEQIDNO:133       771   .......... .......... .......... .......... .......... .......... ..........   840
SEQIDNO:135       771   .......... .......... .......... .......... .......... .......... ..........   840
```

Figure 1, Continued

```
                              850        860        870        880        890        900        910
                       ....|....| ....|....| ....|....| ....|....| ....|....| ....|....| ....|....|
SEQIDNO:1       841    ctgctgccat ttgctcccgt cattgatggg gaactgctga gccaacgtcc agcggaagcc attgcgggcg  910
SEQIDNO:3       841    ....a..... .......... .......... .......... .......... .......... ..........  910
SEQIDNO:5       841    ...gct.... .......... .......... .......... .......... .......... ..........  910
SEQIDNO:7       841    ...ac..... .......... .......... .......... .......... .......... ..........  910
SEQIDNO:9       841    .......... ..ctg..... .......... .......... .......... .......... ..........  910
SEQIDNO:11      841    ...tgt.... .......... .......... .......... .......... .......... ..........  910
SEQIDNO:13      841    .......... .......... .......... .......... .......... .......... ..........  910
SEQIDNO:15      841    .......... .......... .......... .......... .......... .......... ..........  910
SEQIDNO:17      841    .ct....... .......... .......... .......... .......... .......... ..........  910
SEQIDNO:19      841    .......... .......... .......... .......... .......... .......... ..........  910
SEQIDNO:21      841    .......... .......... .......... .......... .......... .......... ..........  910
SEQIDNO:23      841    .......... .......... .......... .......... .......... .......... ..........  910
SEQIDNO:25      841    .......... .......... .......... .......... .......... .......... ..........  910
SEQIDNO:27      841    ......gat. .......... .......... .......... .......... .......... ..........  910
SEQIDNO:29      841    .......... .......... .......... .......... .......... .......... ..........  910
SEQIDNO:31      841    .......... .......... .......... .......... .......... .......... ..........  910
SEQIDNO:33      841    .......... .......... .......... .......... .......... .......... ..........  910
SEQIDNO:35      841    .......... .......... .......... .......... .......... .......... ..........  910
SEQIDNO:37      841    .......... .......... .......... .......... .......... .......... ..........  910
SEQIDNO:39      841    .......... .......... .......... .......... .......... .......... ..........  910
SEQIDNO:41      841    .......... .......... .......... .......... .......... .......... ..........  910
SEQIDNO:43      841    ......gtt. .......... .......... .......... .......... .......... ..........  910
SEQIDNO:45      841    .......... .......... .......... .......... .......... .......... ..........  910
SEQIDNO:47      841    ......tat. .......... .......... .......... .......... .......... ..........  910
SEQIDNO:49      841    .......... .......... .......... .......... .......... .......... ..........  910
SEQIDNO:51      841    .........a c......... .......... .......... .......... .......... ..........  910
SEQIDNO:53      841    .......... .......... .......... .......... .......... .......... ..........  910
SEQIDNO:55      841    .......... .......... .......... .......... .......... .......... ..........  910
SEQIDNO:57      841    .......... .......... .......... .......... .......... .......... ..........  910
SEQIDNO:59      841    .......... .......... .......... .......... .......... .......... ..........  910
SEQIDNO:61      841    .......... .......... .......... .......... .......... .......... ..........  910
SEQIDNO:63      841    .......... .......... .......... .......... .......... .......... ..........  910
SEQIDNO:65      841    .......... .......... .......... .......... .......... .......... ..........  910
SEQIDNO:67      841    ...ac..... .......... .......... .......... .......... .......... ..........  910
SEQIDNO:69      841    ...ac..... .......... .......... .......... .......... .......... ..........  910
SEQIDNO:71      841    ...ac..... .......... .......... .......... .......... .......... ..........  910
SEQIDNO:73      841    ...ac..... .......... .......... .......... .......... .......... ..........  910
SEQIDNO:75      841    ...ac..... .......... .......... .......... .......... .......... ..........  910
SEQIDNO:77      841    .c.ac..... .......... .......... .......... .......... .......... ..........  910
SEQIDNO:79      841    ...ac..... .......... .......... .......... .......... .......... ..........  910
SEQIDNO:81      841    ...ac..... ..ctg..... .......... .......... .......... .......... ..........  910
SEQIDNO:83      841    ...ac..... .......... .......... .......... .......... .......... ..........  910
SEQIDNO:85      841    ...ac..... .......... .......... .......... .......... .......... ..........  910
SEQIDNO:87      841    .c.ac..... .......... .......... .......... .......... .......... ..........  910
SEQIDNO:89      841    ...ac..... .......... .......... .......... .......... .......... ..........  910
SEQIDNO:91      841    ...ac..... .......... .......... .......... .......... .......... ..........  910
SEQIDNO:93      841    ...acc.... ..tta..... .......... .......... .......... .......... ..........  910
SEQIDNO:95      841    ...ac..... .......... .......... .......... .......... .......... ..........  910
SEQIDNO:97      841    ...ac..... .......... .......... .......... .......... .......... ..........  910
SEQIDNO:99      841    ...ac..... .......... .......... .......... .......... .......... ..........  910
SEQIDNO:101     841    .c.ac..... ..tta..... .......... .......... .......... .......... ..........  910
SEQIDNO:103     841    ...ac..... .......... .......... .......... .......... .......... ..........  910
SEQIDNO:105     841    ...ac..... .......... .......... .......... .......... .......... ..........  910
SEQIDNO:107     841    ...ac..... .......... .......... .......... .......... .......... ..........  910
SEQIDNO:109     841    ...ac..... .......... .......... .......... .......... .......... ..........  910
SEQIDNO:111     841    ...ac..... .......... .......... .......... .......... .......... ..........  910
SEQIDNO:113     841    ...ac..... .......... .......... .......... .......... .......... ..........  910
SEQIDNO:115     841    ...ac..... .......... .......... .......... .......... .......... ..........  910
SEQIDNO:117     841    ...ac..... .......... .......... .......... .......... .......... ..........  910
SEQIDNO:119     841    ...ac..... .......... .......... .......... .......... .......... ..........  910
SEQIDNO:121     841    ...ac..... .......... .......... .......... .......... .......... ..........  910
SEQIDNO:123     841    .c.ac..... ..ctg..... .......... .......... .......... .......... ..........  910
SEQIDNO:125     841    ...ac..... ..ctg..... .......... .......... .......... .......... ..........  910
SEQIDNO:127     841    ...ac..... .......... .......... .......... .......... .......... ..........  910
SEQIDNO:129     841    ...ac..... .......... .......... .......... .......... .......... ..........  910
SEQIDNO:131     841    .c.tgc.... .......... .......... .......... .......... .......... ..........  910
SEQIDNO:133     841    ...ac..... .......... .......... .......... .......... .......... ..........  910
SEQIDNO:135     841    .......... .......... .......... .......... .......... .......... ..........  910
```

Figure 1, Continued

```
                              920        930        940        950        960        970        980
                       ....|....| ....|....| ....|....| ....|....| ....|....| ....|....| ....|....|
SEQIDNO:1        911   gcgcaggtca tgatgtagac ctcttgtttg gcactaccac cgatgaatac cgtctgtttc tggcaccaac  980
SEQIDNO:3        911   .......... .......... .......... .......... .......... .......... ..........  980
SEQIDNO:5        911   .......... .......... .......... .......... .......... .......... ..........  980
SEQIDNO:7        911   .......... .......... .......... .......... .......... .......... ..........  980
SEQIDNO:9        911   .......... .......... .......... .......... .......... .......... ..........  980
SEQIDNO:11       911   .......... .......... .......... .......... .......... .......... ..........  980
SEQIDNO:13       911   .......... .......... .......... .......... .......... .......... ..........  980
SEQIDNO:15       911   .......... .......... .......... .......... .......... .......... ..........  980
SEQIDNO:17       911   .......... .......... .......... .......... .......... .......... ..........  980
SEQIDNO:19       911   .......... .......... .......... .......... .......... .......... ..........  980
SEQIDNO:21       911   .......... .......... .......... .......... .......... .......... ..........  980
SEQIDNO:23       911   .......... .......... .......... .......... .......... .......... ..........  980
SEQIDNO:25       911   .......... .......... .......... .......... .......... .......... ..........  980
SEQIDNO:27       911   .......... .......... .......... .......... .......... .......... ..........  980
SEQIDNO:29       911   .......... .......... .......... .......... .......ggt .......... ..........  980
SEQIDNO:31       911   .......... .......... .......... .......... .......... ttg....... ..........  980
SEQIDNO:33       911   .......... .......... .......... .......... .......... .......... ..........  980
SEQIDNO:35       911   .......... .......... .......... .......... .......... .......... ..........  980
SEQIDNO:37       911   .......... .......... .......... .......... ........gg .......... ..........  980
SEQIDNO:39       911   .......... .......... .......... .......... .......... .......... ..........  980
SEQIDNO:41       911   .......... .......... .......... .......... .......... .......... ..........  980
SEQIDNO:43       911   .......... .......... .......... .......... .......... .......... ..........  980
SEQIDNO:45       911   .......... .......... .......... .......... .......... .......... ..........  980
SEQIDNO:47       911   .......... .......... .......... .......... .......... .......... ..........  980
SEQIDNO:49       911   .......... .......... .......... .......... .......... .......... ..........  980
SEQIDNO:51       911   .......... .......... .......... .......... .......... .......... ..........  980
SEQIDNO:53       911   .......... .......... .......... .......... .......... .......... ..........  980
SEQIDNO:55       911   .......... .......... .......... .......... .......... .......... ..........  980
SEQIDNO:57       911   .......... .......... .......... .......... .......... .......... ..........  980
SEQIDNO:59       911   .......... .......... .......... .......... .......... .......... ..........  980
SEQIDNO:61       911   .......... .......... .......... .......... .......... .......... ..........  980
SEQIDNO:63       911   .......... .......... .......... .......... .......... .......... ..........  980
SEQIDNO:65       911   .......... .......... .......... .......... .......... .......... ..........  980
SEQIDNO:67       911   .......... .......... .......... .......... .......... .......... ..........  980
SEQIDNO:69       911   .......... .......... .......... .......... .......... .......... ..........  980
SEQIDNO:71       911   .......... .......... .......... .......... .......... .......... ..........  980
SEQIDNO:73       911   .......... .......... .......... .......... .......... .......... ..........  980
SEQIDNO:75       911   .......... .......... .......... .......... .......... .......... ..........  980
SEQIDNO:77       911   .......... .......... .......... .......... .......... .......... ..........  980
SEQIDNO:79       911   .......... .......... .......... .......... .......... .......... ..........  980
SEQIDNO:81       911   .......... .......... .......... .......... .........t .......... ..........  980
SEQIDNO:83       911   .......... .......... .......... .......... .......... .......... ..........  980
SEQIDNO:85       911   .......... .......... .......... .......... .......... .......... ..........  980
SEQIDNO:87       911   .......... .......... .......... .......... .......... .......... ..........  980
SEQIDNO:89       911   .......... .......... .......... .......... .......... .......... ..........  980
SEQIDNO:91       911   .......... .......... .......... .......... .......... .......... ..........  980
SEQIDNO:93       911   .......... .......... .......... .......... .......... .......... ..........  980
SEQIDNO:95       911   .......... .......... .......... .......... .......... .......... ..........  980
SEQIDNO:97       911   .......... .......... .......... .......... .......... .......... ..........  980
SEQIDNO:99       911   .......... .......... .......... .......... .......... .......... ..........  980
SEQIDNO:101      911   .......... .......... .......... .......... .......... .......... ..........  980
SEQIDNO:103      911   .......... .......... .......... .......... .......... .......... ..........  980
SEQIDNO:105      911   .......... .......... .......... .......... .......... .......... ..........  980
SEQIDNO:107      911   .......... .......... .......... .......... .......... .......... ..........  980
SEQIDNO:109      911   .......... .......... .......... .......... .......... .......... ..........  980
SEQIDNO:111      911   .......... .......... .......... .......... .......... .......... ..........  980
SEQIDNO:113      911   .......... .......... .......... .......... .......... .......... ..........  980
SEQIDNO:115      911   .......... .......... .......... .......... .......... .......... ..........  980
SEQIDNO:117      911   .......... .......... .......... .......... g......... .......... ..........  980
SEQIDNO:119      911   .......... .......... .......... .......... .......... .......... ..........  980
SEQIDNO:121      911   .......... .......... .......... .......... .......... .......... ..........  980
SEQIDNO:123      911   .......... .......... .......... .......... .......... .......... ..........  980
SEQIDNO:125      911   .......... .......... .......... .......... g......... .......... ..........  980
SEQIDNO:127      911   .......... .......... .......... .......... .......... .......... ..........  980
SEQIDNO:129      911   .......... .......... .......... .......... .......... .......... ..........  980
SEQIDNO:131      911   .......... .......... .......... .......... .......... .......... ..........  980
SEQIDNO:133      911   .......... .......... .......... .......... .......... .......... ..........  980
SEQIDNO:135      911   .......... .......... .......... .......... .......... .......... ..........  980
```

Figure 1, Continued

```
                          990       1000       1010       1020       1030       1040       1050
                    ....|....| ....|....| ....|....| ....|....| ....|....| ....|....| ....|....|
SEQIDNO:1      981  tggctgctg  ccgttcatca caggggacta tgttaccact cacttagcca agagcggttt agatgcagat  1050
SEQIDNO:3      981  .......... .......... .......... .......... .......... .......... ..........  1050
SEQIDNO:5      981  .......... .......... .......... .......... .......... .......... ..........  1050
SEQIDNO:7      981  .......... .......... .......... .......... .......... .......... ..........  1050
SEQIDNO:9      981  .......... .......... .......... .......... .......... .......... ..........  1050
SEQIDNO:11     981  .......... .......... .......... .......... .......... .......... ..........  1050
SEQIDNO:13     981  .......... .......... .......... .......... .......... .......... ..........  1050
SEQIDNO:15     981  .......... .......... .......... .......... .......... .......... ..........  1050
SEQIDNO:17     981  .......... .......... .......... .......... .......... .......... ..........  1050
SEQIDNO:19     981  .......... .......... .......... .......... .......... .......... ..........  1050
SEQIDNO:21     981  .......... .......... .......... .......... .......... .......... ..........  1050
SEQIDNO:23     981  .......... .......... .......... .......... .......... .......... ..........  1050
SEQIDNO:25     981  .......... .......... .......... .......... .......... .......... ..........  1050
SEQIDNO:27     981  .......... .......... .......... .......... .......... .......... ..........  1050
SEQIDNO:29     981  .......... .......... .......... .......... .......... .......... ..........  1050
SEQIDNO:31     981  .......... .......... .......... .......... .......... .......... ..........  1050
SEQIDNO:33     981  .......... .......... .......... .......... .......... .......... ..........  1050
SEQIDNO:35     981  .......... .......... .......... .......... .......... .......... ..........  1050
SEQIDNO:37     981  .......... .......... .......... .......... .......... .......... ..........  1050
SEQIDNO:39     981  .......... .......... .......... .......... .......... .......... ..........  1050
SEQIDNO:41     981  .......... .......... .......... .......... .......... .......... ..........  1050
SEQIDNO:43     981  .......... .......... .......... .......... .......... .......... ..........  1050
SEQIDNO:45     981  .......... .......... .......... .......... .......... .......... ..........  1050
SEQIDNO:47     981  .......... .......... .......... .......... .......... .......... ..........  1050
SEQIDNO:49     981  .......... .......... .......... .......... .......... .......... ..........  1050
SEQIDNO:51     981  .......... .......... .......... .......... .......... .......... ..........  1050
SEQIDNO:53     981  .......... .......... .......... .......... .......... .......... ..........  1050
SEQIDNO:55     981  .......... .......... .......... .......... .......... .......... ..........  1050
SEQIDNO:57     981  .......... .......... .......... .......... .......... .......... ..........  1050
SEQIDNO:59     981  .......... .......... .......... .......... .......... .......... ..........  1050
SEQIDNO:61     981  .......... .......... .......... .......... .......... .......... ..........  1050
SEQIDNO:63     981  .......... .......... .......... .......... .......... .......... ..........  1050
SEQIDNO:65     981  .......... .......... .......... .......... .......... .......... ..........  1050
SEQIDNO:67     981  .......... .......... .......... .......... .......... .......... ..........  1050
SEQIDNO:69     981  .......... .......... .......... .......... .......tg. .......... ..........  1050
SEQIDNO:71     981  .......... .......... .......... .......... .......... .......... ..........  1050
SEQIDNO:73     981  .......... .......... .......... .......... .......... .......... ..........  1050
SEQIDNO:75     981  .......... .......... .......... .......... .......... .......... ..........  1050
SEQIDNO:77     981  .......... .......... .......... .......... .......... .......... ..........  1050
SEQIDNO:79     981  .......... .......... .......... .......... .......... .......... ..........  1050
SEQIDNO:81     981  .......... .......... .......... .......... .......... .......... ..........  1050
SEQIDNO:83     981  .......... .......... .......... .......... .......tg. .......... ..........  1050
SEQIDNO:85     981  .......... .......... .......... .......... .......... .......... ..........  1050
SEQIDNO:87     981  .......... .......... .......... .......... .......... .......... ..........  1050
SEQIDNO:89     981  .......... .......... .......... .......... .......... .......... ..........  1050
SEQIDNO:91     981  .......... .......... .......... .......... .......... .......... ..........  1050
SEQIDNO:93     981  .......... .......... .......... .......... .......... .......... ..........  1050
SEQIDNO:95     981  .......... .......... .......... .......... .......... .......... ..........  1050
SEQIDNO:97     981  .......... .......... .......... .......... .......... .......... ..........  1050
SEQIDNO:99     981  .......... .......... .......... .......... .......... .......... ..........  1050
SEQIDNO:101    981  .......... .......... .......... .......... .......... .......... ..........  1050
SEQIDNO:103    981  .......... .......... .......... .......... .......... .......... ..........  1050
SEQIDNO:105    981  .......... .......... .......... .......... .......... .......... ..........  1050
SEQIDNO:107    981  .......... .......... .......... .......... .......tg. .......... ..........  1050
SEQIDNO:109    981  .......... .......... .......... .......... .......... .......... ..........  1050
SEQIDNO:111    981  .......... .......... .......... .......... .......tg. .......... ..........  1050
SEQIDNO:113    981  .......... .......... .......... .......... ........g. .......... ..........  1050
SEQIDNO:115    981  .......... .......... .......... .......... .......... .......... ..........  1050
SEQIDNO:117    981  .......... .......... .......... .......... .......... .......... ..........  1050
SEQIDNO:119    981  .......... .......... .......... .......... .......... .......... ..........  1050
SEQIDNO:121    981  .......... .......... .......... .......... .......tg. .......... ..........  1050
SEQIDNO:123    981  .......... .......... .......... .......... .......... .......... ..........  1050
SEQIDNO:125    981  .......... .......... .......... .......... .......... .....a.... ..........  1050
SEQIDNO:127    981  .......... .......... .......... .......... .......... .......... ..........  1050
SEQIDNO:129    981  .......... .......... .......... .......... .......... .......... ..........  1050
SEQIDNO:131    981  .......... .......... .......... .......... .......... .......... ..........  1050
SEQIDNO:133    981  .......... .......... .......... .......... .......... .......... ..........  1050
SEQIDNO:135    981  .......... .......... .......... .......... .......... .......... ..........  1050
```

Figure 1, Continued

```
                        1060       1070       1080       1090       1100       1110       1120
                   ....|....| ....|....| ....|....| ....|....| ....|....| ....|....| ....|....|
SEQIDNO:1     1051 gcggccaaag cgtataccgc ggaaggtcgt ggtgaagaac cgggcgacat cttggccagc atcatcaccg  1120
SEQIDNO:3     1051 .......... .......... .......... .......... .......... .......... ..........  1120
SEQIDNO:5     1051 .......... .......... .......... .......... .......... .......... ..........  1120
SEQIDNO:7     1051 .......... .......... .......... .......... .......... .......... ..........  1120
SEQIDNO:9     1051 .......... .......... .......... .......... .......... .......... ..........  1120
SEQIDNO:11    1051 .......... .......... .......... .......... .......... .......... ..........  1120
SEQIDNO:13    1051 .......... .......... .......... .......... .......... .......... ..........  1120
SEQIDNO:15    1051 .......... .......... .......... .......... .......... .......... ..........  1120
SEQIDNO:17    1051 .......... .......... .......... .......... .......... .......... ..........  1120
SEQIDNO:19    1051 .......... .......... .......... .......... .......... .......... ..........  1120
SEQIDNO:21    1051 .......... .......... .......... .......... .......... .......... ..........  1120
SEQIDNO:23    1051 .......... .......... .......... .......... .......... .......... ..........  1120
SEQIDNO:25    1051 .......... .......... .......... .......... .......... .......... ..........  1120
SEQIDNO:27    1051 .......... .......... .......... .......... .......... .......... ..........  1120
SEQIDNO:29    1051 .......... .......... .......... .......... .......... .......... ..........  1120
SEQIDNO:31    1051 .......... .......... .......... .......... .......... .......... ..........  1120
SEQIDNO:33    1051 .......... .......... .......... .......... .......... .......... ..........  1120
SEQIDNO:35    1051 .......... .......... .......... .......... .......... .......... ..........  1120
SEQIDNO:37    1051 .......... .......... .......... .......... .......... .......... ..........  1120
SEQIDNO:39    1051 .......... .......... .......... .......... .......... .......... ..........  1120
SEQIDNO:41    1051 .......... .......... .......... .......... .......... .......... ..........  1120
SEQIDNO:43    1051 .......... .......... .......... .......... .......... .......... ..........  1120
SEQIDNO:45    1051 .......... .......... .......... .......... .......... .......... ..........  1120
SEQIDNO:47    1051 .......... .......... .......... .......... .......... .......... ..........  1120
SEQIDNO:49    1051 .......... .......... .......... .......... .......... .......... ..........  1120
SEQIDNO:51    1051 .......... .......... .......... .......... .......... .......... ..........  1120
SEQIDNO:53    1051 .......... .......... .......... .......... .......... .......... ..........  1120
SEQIDNO:55    1051 .......... .......... .......... .......... .......... .......... ..........  1120
SEQIDNO:57    1051 .......... .......... .......... .......... .......... .......... ..........  1120
SEQIDNO:59    1051 .......... .......... .......... .......... .......... .......... ..........  1120
SEQIDNO:61    1051 .......... .......... .......... .......... .......... .......... ..........  1120
SEQIDNO:63    1051 .......... .......... .......... .......... .......... .......... ..........  1120
SEQIDNO:65    1051 .......... .......... .......... .......... .......... .......... ..........  1120
SEQIDNO:67    1051 .......... .......... .......... .......... .......... .......... ...c.g....  1120
SEQIDNO:69    1051 .......... .......... .......... .......... .......... .......... ...c.g....  1120
SEQIDNO:71    1051 .......... .......... .......... .......... .......... .......... ...c.g....  1120
SEQIDNO:73    1051 .......... .......... .......... .......... .......... .......... ...c.t....  1120
SEQIDNO:75    1051 .......... .......... .......... .......... .......... .......... ..........  1120
SEQIDNO:77    1051 .......... .......... .......... .......... .......... .......... ...c.t....  1120
SEQIDNO:79    1051 .......... .......... .......... .......... .......... .......... .....g....  1120
SEQIDNO:81    1051 .......... .......... .......... .......... .......... .......... ...c.t....  1120
SEQIDNO:83    1051 .......... .......... .......... .......... .......... .......... ...c.g....  1120
SEQIDNO:85    1051 .......... .......... .......... .......... .......... .......... ..........  1120
SEQIDNO:87    1051 .......... .......... .......... .......... .......... .......... ...c.g....  1120
SEQIDNO:89    1051 .......... .......... .......... .......... .......... .......... ..........  1120
SEQIDNO:91    1051 .......... .......... .......... .......... .......... .......... ...c.g....  1120
SEQIDNO:93    1051 .......... .......... .......... .......... .......... .......... ..........  1120
SEQIDNO:95    1051 .......... .......... .......... .......... .......... .......... ..........  1120
SEQIDNO:97    1051 .......... .......... .......... .......... .......... .......... ..........  1120
SEQIDNO:99    1051 .......... .......... .......... .......... .......... .......... ...c.t....  1120
SEQIDNO:101   1051 .......... .......... .......... .......... .......... .......... ...c.t....  1120
SEQIDNO:103   1051 .......... .......... .......... .......... .......... .......... ..........  1120
SEQIDNO:105   1051 .......... .......... .......... .......... .......... .......... ..........  1120
SEQIDNO:107   1051 .......... .......... .......... .......... .......... .......... ..........  1120
SEQIDNO:109   1051 .......... .......... .......... .......... .......... .......... ..........  1120
SEQIDNO:111   1051 .......... .......... .......... .......... .......... .......... ..........  1120
SEQIDNO:113   1051 .......... .......... .......... .......... .......... .......... ..........  1120
SEQIDNO:115   1051 .......... .......... .......... .......... .......... .......... ..........  1120
SEQIDNO:117   1051 .......... .......... .......... .......... .......... .......... ......ggg.  1120
SEQIDNO:119   1051 .......... .......... .......... .......... .......... .......... ...c.t....  1120
SEQIDNO:121   1051 .......... .......... .......... .......... .......... .......... ..........  1120
SEQIDNO:123   1051 .......... .......... .......... .......... .......... .......... ......ggg.  1120
SEQIDNO:125   1051 .......... .......... .......... .......... .......... .......... ........t.  1120
SEQIDNO:127   1051 .......... .......... .......... .......... .......... .......... ..........  1120
SEQIDNO:129   1051 .......... .......... .......... .......... .......... .......... .....t....  1120
SEQIDNO:131   1051 .......... .......... .......... .......... .......... .......... ..........  1120
SEQIDNO:133   1051 .......... .......... .......... .......... .......... .......... .....t....  1120
SEQIDNO:135   1051 .......... .......... .......... .......... .......... .......... ...c.t....  1120
```

Figure 1, Continued

```
                      1130       1140       1150       1160       1170       1180       1190
                 ....|....| ....|....| ....|....| ....|....| ....|....| ....|....| ....|....|
SEQIDNO:1    1121 accaggtgtt tcgtattccg gcgctgcgta ttgcagcatc ccgtgttgat gcgcctgcac gtacctttgg  1190
SEQIDNO:3    1121 .......... .......... .......... .......... .......... .......... ..........  1190
SEQIDNO:5    1121 .......... .......... .......... .......... .......... .......... ..........  1190
SEQIDNO:7    1121 .......... .......... .......... .......... .......... .......... ..........  1190
SEQIDNO:9    1121 .......... .......... .......... .......... .......... .......... ..........  1190
SEQIDNO:11   1121 .......... .......... .......... .......... .......... .......... ..........  1190
SEQIDNO:13   1121 .......... .......... .......... .......... .......... .......... ..........  1190
SEQIDNO:15   1121 .......... .......... .......... .......... .......... .......... ..........  1190
SEQIDNO:17   1121 .......... .......... .......... .......... .......... .......... ..........  1190
SEQIDNO:19   1121 .......... .......... .......... .......... .......... .......... ..........  1190
SEQIDNO:21   1121 .......... .......... .......... .......... .......... .......... ..........  1190
SEQIDNO:23   1121 .......... .......... .......... .......... .......... .......... ..........  1190
SEQIDNO:25   1121 .......... .......... .......... .......... .......... .......... ..........  1190
SEQIDNO:27   1121 .......... .......... .......... .......... .......... .......... ..........  1190
SEQIDNO:29   1121 .......... .......... .......... .......... .......... .......... ..........  1190
SEQIDNO:31   1121 .......... .......... .......... .......... .......... .......... ..........  1190
SEQIDNO:33   1121 .......... .......... .......... .......... .......... .......... ..........  1190
SEQIDNO:35   1121 .......... .......... .......... .......... .......... .......... ..........  1190
SEQIDNO:37   1121 .......... .......... .......... .......... .......... .......... ..........  1190
SEQIDNO:39   1121 .......... .......... .......... .......... .......... .......... ..........  1190
SEQIDNO:41   1121 .......... .......... .......... .......... .......... .......... ..........  1190
SEQIDNO:43   1121 .......... .......... .......... .......... .......... .......... ..........  1190
SEQIDNO:45   1121 .......... .......... .......... .......... .......... .......... ..........  1190
SEQIDNO:47   1121 .......... .......... .......... .......... .......... .......... ..........  1190
SEQIDNO:49   1121 .......... .......... .......... .......... .......... .......... ..........  1190
SEQIDNO:51   1121 .......... .......... .......... .......... .......... .......... ..........  1190
SEQIDNO:53   1121 .......... .......... .......... .......... .......... .......... ..........  1190
SEQIDNO:55   1121 ........c. .......... .......... .......... .......... .......... ..........  1190
SEQIDNO:57   1121 .......... .......... .......... .......... .......... .......... ..........  1190
SEQIDNO:59   1121 .......... .......... .......... .......... .......... .......... ..........  1190
SEQIDNO:61   1121 .......... .......... .......... .......... .......... .......... ..........  1190
SEQIDNO:63   1121 .......... .......... .......... .......... .......... .......... ..........  1190
SEQIDNO:65   1121 .......... .......... .......... .......... .......... .......... ..........  1190
SEQIDNO:67   1121 .......... .......... .......... .......... .......... .......... ..........  1190
SEQIDNO:69   1121 .......... .......... .......... .......... .......... .......... ..........  1190
SEQIDNO:71   1121 .......... .......... .......... .......... .......... .......... ..........  1190
SEQIDNO:73   1121 .......... .......... .......... .......... .......... .......... ..........  1190
SEQIDNO:75   1121 .......... .......... .......... .......... .......... .......... ..........  1190
SEQIDNO:77   1121 .......... .......... .......... .......... .......... .......... ..........  1190
SEQIDNO:79   1121 .......... .......... .......... .......... .......... .......... ..........  1190
SEQIDNO:81   1121 .......... .......... .......... .......... .......... .......... ..........  1190
SEQIDNO:83   1121 .......... .......... .......... .......... .......... .......... ..........  1190
SEQIDNO:85   1121 .......... .......... .......... .......... .......... .......... ..........  1190
SEQIDNO:87   1121 .......... .......... .......... .......... .......... .......... ..........  1190
SEQIDNO:89   1121 .......... .......... .......... .......... .......... .......... ..........  1190
SEQIDNO:91   1121 .......... .......... .......... .......... .......... .......... ..........  1190
SEQIDNO:93   1121 .......... .......... .......... .......... .......... .......... ..........  1190
SEQIDNO:95   1121 .......... .......... .......... .......... .......... .......... ..........  1190
SEQIDNO:97   1121 .......... .......... .......... .......... .......... .......... ..........  1190
SEQIDNO:99   1121 .......... .......... .......... .......... .......... .......... ..........  1190
SEQIDNO:101  1121 .......... .......... .......... .......... .......... .......... ..........  1190
SEQIDNO:103  1121 .......... .......... .......... .......... .......... .......... ..........  1190
SEQIDNO:105  1121 .......... .......... .......... .......... .......... .......... ..........  1190
SEQIDNO:107  1121 .......... .......... .......... .......... .......... .......... ..........  1190
SEQIDNO:109  1121 .......... .......... .......... .......... .......... .......... ..........  1190
SEQIDNO:111  1121 .......... .......... .......... .......... .......... .......... ..........  1190
SEQIDNO:113  1121 .......... .......... .......... .......... .......... .......... ..........  1190
SEQIDNO:115  1121 .......... .......... .......... .......... .......... .......... ..........  1190
SEQIDNO:117  1121 .......... .......... .......... .......... .......... .......... ..........  1190
SEQIDNO:119  1121 .......... g......... .......... .......... .......... .......... ..........  1190
SEQIDNO:121  1121 .......... .......... .......... .......... .......... .......... ..........  1190
SEQIDNO:123  1121 .......... .......... .......... .......... .......... .......... ..........  1190
SEQIDNO:125  1121 .......... .......... .......... .......... .......... .......... ..........  1190
SEQIDNO:127  1121 .......... .......... .......... .......... .......... .......... ..........  1190
SEQIDNO:129  1121 .......... g......... .......... .......... .......... .......... ..........  1190
SEQIDNO:131  1121 .........a .......... .......... .......... .......... .......... ..........  1190
SEQIDNO:133  1121 .......... g......... .......... .......... .......... .......... ..........  1190
SEQIDNO:135  1121 .......... .......... .......... .......... .......... .......... ..........  1190
```

Figure 1, Continued

```
                          1200       1210       1220       1230       1240       1250       1260
                    ....|....| ....|....| ....|....| ....|....| ....|....| ....|....| ....|....|
SEQIDNO:1      1191 ctacgaattc gcgtggcgta cgccacaatt ggacggcatt ctgggtgctt gtcatgcggt ggaacttccg  1260
SEQIDNO:3      1191 .......... .......... .......... .......... .......... .......... ..........  1260
SEQIDNO:5      1191 .......... .......... .......... .......... .......... .......... ..........  1260
SEQIDNO:7      1191 .......... .......... .......... .......... .......... .......... ..........  1260
SEQIDNO:9      1191 .......... .......... .......... .......... .......... .......... ..........  1260
SEQIDNO:11     1191 .......... .......... .......... .......... .......... .......... ..........  1260
SEQIDNO:13     1191 .......... .......... .......... .......... .......... .......... ..........  1260
SEQIDNO:15     1191 .......... .......... .......... .......... .......... .......... ..........  1260
SEQIDNO:17     1191 .......... .......... .......... .......... .......... .......... ..........  1260
SEQIDNO:19     1191 .......... .......... .......... .......... .......... .......... ..........  1260
SEQIDNO:21     1191 .......... .......... .......... .......... .......... .......... ..........  1260
SEQIDNO:23     1191 .......... .......... .......... .......... .......... .......... ..........  1260
SEQIDNO:25     1191 .......... .......... .......... .......... .......... .......... ..........  1260
SEQIDNO:27     1191 .......... .......... .......... .......... .......... .......... ..........  1260
SEQIDNO:29     1191 .......... .......... .......... .......... .......... .......... ..........  1260
SEQIDNO:31     1191 .......... .......... .......... .......... .......... .......... ..........  1260
SEQIDNO:33     1191 .......... .......... .......... .......... .......... .......... ..........  1260
SEQIDNO:35     1191 .......... .......... .......... .......... .......... .......... ..........  1260
SEQIDNO:37     1191 .......... .......... .......... .......... .......... .......... ..........  1260
SEQIDNO:39     1191 .......... .......... .......... .......... .......... .......... ..........  1260
SEQIDNO:41     1191 .......... .......... .......... .......... .......... .......... ..........  1260
SEQIDNO:43     1191 .......... .......... .......... .......... .......... .......... ..........  1260
SEQIDNO:45     1191 .......... .......... .......... .......... .......... .......... ..........  1260
SEQIDNO:47     1191 .......... .......... .......... .......... .......... .......... ..........  1260
SEQIDNO:49     1191 .......... .......... .......... .......... .......... .......... ..........  1260
SEQIDNO:51     1191 .......... .......... .......... .......... .......... .......... ..........  1260
SEQIDNO:53     1191 .......... .......... .......... .......... .......... .......... ..........  1260
SEQIDNO:55     1191 .......... .......... .......... .......... .......... .......... ..........  1260
SEQIDNO:57     1191 .......... .......... .......... .......... .......... .......... ..........  1260
SEQIDNO:59     1191 .......... .......... .......... .......... .......... .......... ..........  1260
SEQIDNO:61     1191 .......... .......... .......... .......... .......... .......... ..........  1260
SEQIDNO:63     1191 .......... .......... .......... .......... .......... .......... ..........  1260
SEQIDNO:65     1191 .......... .......... .......... .......... .......... .......... ..........  1260
SEQIDNO:67     1191 .......... .......... .......... .......... .......... .......... ..........  1260
SEQIDNO:69     1191 .......... .......... .......... .......... .......... .......... ..........  1260
SEQIDNO:71     1191 .......... .......... .......... .......... .......... .......... ..........  1260
SEQIDNO:73     1191 .......... .......... .......... .......... .......... .......... ..........  1260
SEQIDNO:75     1191 .......... .......... .......... .......... .......... .......... ..........  1260
SEQIDNO:77     1191 .......... .......... .......... .......... .......... .......... ..........  1260
SEQIDNO:79     1191 .......... .......... .......... .......... .......... .......... ..........  1260
SEQIDNO:81     1191 .......... .......... .......... .......... .......... .......... ..........  1260
SEQIDNO:83     1191 .......... .......... .......... .......... .......... .......... ..........  1260
SEQIDNO:85     1191 .......... .......... .......... .......... .......... .......... ..........  1260
SEQIDNO:87     1191 .......... .......... .......... .......... .......... .......... ..........  1260
SEQIDNO:89     1191 .......... .......... .......... .......... .......... .......... ..........  1260
SEQIDNO:91     1191 .......... .......... .......... .......... .......... .......... ..........  1260
SEQIDNO:93     1191 .......... .......... .......... .......... .......... .......... ..........  1260
SEQIDNO:95     1191 .......... .......... .......... .......... .......... .......... ..........  1260
SEQIDNO:97     1191 .......... .......... .......... .......... .......... .......... ..........  1260
SEQIDNO:99     1191 .......... .......... .......... .......... .......... .......... ..........  1260
SEQIDNO:101    1191 .......... .......... .......... .......... .......... .......... ..........  1260
SEQIDNO:103    1191 .......... .......... .......... .......... .......... .......... ..........  1260
SEQIDNO:105    1191 .......... .......... .......... .......... .......... .......... ..........  1260
SEQIDNO:107    1191 .......... .......... .......... .......... .......... .......... ..........  1260
SEQIDNO:109    1191 .......... .......... .......... .......... .......... .......... ..........  1260
SEQIDNO:111    1191 .......... .......... .......... .......... .......... .......... ..........  1260
SEQIDNO:113    1191 .......... .......... .......... .......... .......... .......... ..........  1260
SEQIDNO:115    1191 .......... .......... .......... .......... .......... .......... ..........  1260
SEQIDNO:117    1191 .......... .......... .......... .......... .......... .......... ..........  1260
SEQIDNO:119    1191 .......... .......... .......... .......... .......... .......... ..........  1260
SEQIDNO:121    1191 .......... .......... .......... .......... .......... .......... ..........  1260
SEQIDNO:123    1191 .......... .......... .......... .......... .......... .......... ..........  1260
SEQIDNO:125    1191 .......... .......... .......... .......... .......... .......... ..........  1260
SEQIDNO:127    1191 .......... .......... .......... .......... .......... .......... ..........  1260
SEQIDNO:129    1191 .......... .......... .......... .......... .......... .......... ..........  1260
SEQIDNO:131    1191 .......... .......... .......... .......... .......... .......... ..........  1260
SEQIDNO:133    1191 .......... .......... .......... .......... .......... .......... ..........  1260
SEQIDNO:135    1191 .......... .......... .......... .......... .......... .......... ..........  1260
```

Figure 1, Continued

```
                         1270       1280       1290       1300       1310       1320       1330
                    ....|....| ....|....| ....|....| ....|....| ....|....| ....|....| ....|....|
SEQIDNO:1      1261 ttcgtgtttc gcaccttaga ccgtgcggca tcgctggtgg gcacaaaccc gccagaagaa ctggcagaaa  1330
SEQIDNO:3      1261 .......... .......... .......... .......... .......... .......... ..........  1330
SEQIDNO:5      1261 .......... .......... .......... .......... .......... .......... ..........  1330
SEQIDNO:7      1261 .......... .......... .......... .......... .......... .......... ..........  1330
SEQIDNO:9      1261 .......... .......... .......... .......... .......... .......... ..........  1330
SEQIDNO:11     1261 .......... .......... .......... .......... .......... .......... ..........  1330
SEQIDNO:13     1261 .......... .......... .......... .......... .......... .......... ..........  1330
SEQIDNO:15     1261 .......... .......... .......... .......... .......... .......... ..........  1330
SEQIDNO:17     1261 .......... .......... .......... .......... .......... .......... ..........  1330
SEQIDNO:19     1261 .......... .......... .......... .......... .......... .......... ..........  1330
SEQIDNO:21     1261 .......... .......... .......... .......... .......... .......... ..........  1330
SEQIDNO:23     1261 .......... .......... .......... .......... .......... .......... ..........  1330
SEQIDNO:25     1261 .......... .......... .......... .......... .......... .......... ..........  1330
SEQIDNO:27     1261 .......... .......... .......... .......... .......... .......... ..........  1330
SEQIDNO:29     1261 .......... .......... .......... .......... .......... .......... ..........  1330
SEQIDNO:31     1261 .......... .......... .......... .......... .......... .......... ..........  1330
SEQIDNO:33     1261 .......... .......... .......... .......... .......... .......... ..........  1330
SEQIDNO:35     1261 .......... .......... .......... .......... .......... .......... ..........  1330
SEQIDNO:37     1261 .......... .......... .......... .......... .......... .......... ..........  1330
SEQIDNO:39     1261 .......... .......... .......... .......... .......... .......... ..........  1330
SEQIDNO:41     1261 .......... .......... .......... .......... .......... .......... ..........  1330
SEQIDNO:43     1261 .......... .......... .......... .......... .......... .......... ..........  1330
SEQIDNO:45     1261 .......... .......... .......... .......... .......... .......... ..........  1330
SEQIDNO:47     1261 .......... .......... .......... .......... .......... .......... ..........  1330
SEQIDNO:49     1261 .......... .......... .......... .......... .......... .......... ..........  1330
SEQIDNO:51     1261 .......... .......... .......... .......... .......... .a........ ..........  1330
SEQIDNO:53     1261 .......... .......... .......... .......... .......... .......... ..........  1330
SEQIDNO:55     1261 .......... .......... .......... .......... .......... .......... ..........  1330
SEQIDNO:57     1261 .......... .......... .......... .......... .......... .......... ..........  1330
SEQIDNO:59     1261 .......... .......... .......... .......... .......... .......... ..........  1330
SEQIDNO:61     1261 .......... .......... .......... .......... .......... .......... ..........  1330
SEQIDNO:63     1261 .......... .......... .......... .......... .......... .......... ..........  1330
SEQIDNO:65     1261 .......... .......... .......... .......... .......... .......... ..........  1330
SEQIDNO:67     1261 .......... .......... .......... .......... .......... .......... ..........  1330
SEQIDNO:69     1261 .......... .......... .......... .......... .......... .......... ..........  1330
SEQIDNO:71     1261 .......... .......... .......... .......... .......... .......... ..........  1330
SEQIDNO:73     1261 .......... .......... .......... .......... .......... .......... ..........  1330
SEQIDNO:75     1261 .......... .......... .......... .......... .......... .......... ..........  1330
SEQIDNO:77     1261 .......... .......... .......... .......... .......... .......... ..........  1330
SEQIDNO:79     1261 .......... .......... .......... .......... .......... .......... ..........  1330
SEQIDNO:81     1261 .......... .......... .......... .......... .......... .......... ..........  1330
SEQIDNO:83     1261 .......... .......... .......... .......... .......... .......... ..........  1330
SEQIDNO:85     1261 .......... .......... .......... .......... .......... .......... ..........  1330
SEQIDNO:87     1261 .......... .......... .......... .......... .......... .......... ..........  1330
SEQIDNO:89     1261 .......... .......... .......... .......... .......... .......... ..........  1330
SEQIDNO:91     1261 .......... .......... .......... .......... .......... .......... ..........  1330
SEQIDNO:93     1261 .......... .......... .......... .......... .......... .......... ..........  1330
SEQIDNO:95     1261 .......... .......... .......... .......... .......... .......... ..........  1330
SEQIDNO:97     1261 .......... .......... .......... .......... .......... .......... ..........  1330
SEQIDNO:99     1261 .......... .......... .......... .......... .......... .......... ..........  1330
SEQIDNO:101    1261 .......... .......... .......... .......... .......... .......... ..........  1330
SEQIDNO:103    1261 .......... .......... .......... .......... .......... .......... ..........  1330
SEQIDNO:105    1261 .......... .......... .......... .......... .......... .......... ..........  1330
SEQIDNO:107    1261 .......... .......... .......... .......... .......... .......... ..........  1330
SEQIDNO:109    1261 .......... .......... .......... .......... .......... .......... ..........  1330
SEQIDNO:111    1261 .......... .......... .......... .......... .......... .......... ..........  1330
SEQIDNO:113    1261 .......... .......... .......... .......... .......... .......... ..........  1330
SEQIDNO:115    1261 .......... .......... .......... .......... .......... .......... ..........  1330
SEQIDNO:117    1261 .......... .......... .......... .......... .......... .......... ..........  1330
SEQIDNO:119    1261 .......... .......... .......... .......... .......... .......... ..........  1330
SEQIDNO:121    1261 .......... .......... .......... .......... .......... .......... ..........  1330
SEQIDNO:123    1261 .......... .......... .......... .......... .......... .......... ..........  1330
SEQIDNO:125    1261 .......... .......... .......... .......... .......... .......... ..........  1330
SEQIDNO:127    1261 .......... .......... .......... .......... .......... .......... ..........  1330
SEQIDNO:129    1261 .......... .......... .......... .......... .......... .......... ..........  1330
SEQIDNO:131    1261 .......... .......... .......... .......... .......... .......... ..........  1330
SEQIDNO:133    1261 .......... .......... .......... .......... .......... .......... ..........  1330
SEQIDNO:135    1261 .......... .......... .......... .......... .......... .......... ..........  1330
```

Figure 1, Continued

```
                      1340       1350       1360       1370       1380       1390       1400
                  ....|....| ....|....| ....|....| ....|....| ....|....| ....|....| ....|....|
SEQIDNO:1    1331 ccgtacacaa tgcctgggtg cgcttcgcga catcaggtga tccagggtgg ccggcgtgga atccggaaac  1400
SEQIDNO:3    1331 .......... .......... .......... .......... .......... .......... ..........  1400
SEQIDNO:5    1331 .......... .......... .......... .......... .......... .......... ..........  1400
SEQIDNO:7    1331 .......... .......... .......... .......... .......... .......... ..........  1400
SEQIDNO:9    1331 .......... .......... .......... .......... .......... .......... ..........  1400
SEQIDNO:11   1331 .......... .......... .......... .......... .......... .......... ..........  1400
SEQIDNO:13   1331 .......... .......... .......... .......... .......... .......... ..........  1400
SEQIDNO:15   1331 .......... .......... .......... .......... .......... .......... ..........  1400
SEQIDNO:17   1331 .......... .......... .......... .......... .......... .......... ..........  1400
SEQIDNO:19   1331 .......... .......... .......... .......... .......... .......... ..........  1400
SEQIDNO:21   1331 .......... .......... .......... .......... .......... .......... ..........  1400
SEQIDNO:23   1331 .......... .......... .......... .......... .......... .......... ..........  1400
SEQIDNO:25   1331 .......... .......... .......... .......... .......... .......... ..........  1400
SEQIDNO:27   1331 .......... .......... .......... .......... .......... .......... ..........  1400
SEQIDNO:29   1331 .......... .......... .......... .......... .......... .......... ..........  1400
SEQIDNO:31   1331 .......... .......... .......... .......... .......... .......... ..........  1400
SEQIDNO:33   1331 .......... .......... .......... .......... .......... .......... ..........  1400
SEQIDNO:35   1331 .......... .......... .......... .......... .......... .......... ..........  1400
SEQIDNO:37   1331 .......... .......... .......... .......... .......... .......... ..........  1400
SEQIDNO:39   1331 .......... .......... .......... .......... .......... .......... ..........  1400
SEQIDNO:41   1331 .......... .......... .......... .......... .......... .......... ..........  1400
SEQIDNO:43   1331 .......... .......... .......... .......... .......... .......... ..........  1400
SEQIDNO:45   1331 .......... .......... .......... .......... .......... .......... ..........  1400
SEQIDNO:47   1331 .......... .......... .......... .......... .......... .......... ..........  1400
SEQIDNO:49   1331 .......... .......... .......... .......... .......... .......... ..........  1400
SEQIDNO:51   1331 .......... .......... .......... .......... .......... .......... ..........  1400
SEQIDNO:53   1331 .......... .......... .......... .......... .......... .......... ..........  1400
SEQIDNO:55   1331 .......... .......... .......... .......... .......... .......... ..........  1400
SEQIDNO:57   1331 .......... .......... .......... .......... .......... .......... ..........  1400
SEQIDNO:59   1331 .......... .......... .......... .......... .......... .......... ..........  1400
SEQIDNO:61   1331 .......... .......... .......... .......... .......... .......... ..........  1400
SEQIDNO:63   1331 .......... .......... .......... .......... .......... .......... ..........  1400
SEQIDNO:65   1331 .......... .......... .......... .......... .......... .......... ..........  1400
SEQIDNO:67   1331 .......... .......... .......... .......... .......... .......... ..........  1400
SEQIDNO:69   1331 .......... .......... .......... .......... .......... .......... ..........  1400
SEQIDNO:71   1331 .......... .......... .......... .......... .......... .......... ..........  1400
SEQIDNO:73   1331 .......... .......... .......... .......... .......... .......... ..........  1400
SEQIDNO:75   1331 .......... .......... .......... .......... .......... .......... ..........  1400
SEQIDNO:77   1331 .......... .......... .......... .......... .......... .......... ..........  1400
SEQIDNO:79   1331 .......... .......... .......... .......... .......... .......... ..........  1400
SEQIDNO:81   1331 .......... .......... .......... .......... .......... .......... ..........  1400
SEQIDNO:83   1331 .......... .......... .......... .......... .......... .......... ..........  1400
SEQIDNO:85   1331 .......... .......... .......... .......... .......... .......... ..........  1400
SEQIDNO:87   1331 .......... .......... .......... .......... .......... .......... ..........  1400
SEQIDNO:89   1331 .......... .......... .......... .......... .......... .......... ..........  1400
SEQIDNO:91   1331 .......... .......... .......... .......... .......... .......... ..........  1400
SEQIDNO:93   1331 .......... .......... .......... .......... .......... .......... ..........  1400
SEQIDNO:95   1331 .......... .......... .......... .......... .......... .......... ..........  1400
SEQIDNO:97   1331 .......... .......... .......... .......... .......... .......... ..........  1400
SEQIDNO:99   1331 .......... .......... .......... .......... .......... .......... ..........  1400
SEQIDNO:101  1331 .......... .......... .......... .......... .......... .......... ..........  1400
SEQIDNO:103  1331 .......... .......... .......... .......... .......... .......... ..........  1400
SEQIDNO:105  1331 .......... .......... .......... .......... .......... .......... ..........  1400
SEQIDNO:107  1331 .......... .......... .......... .......... .......... .......... ..........  1400
SEQIDNO:109  1331 .......... .......... .......... .......... .......... .......... ..........  1400
SEQIDNO:111  1331 .......... .......... .......... .......... .......... .......... ..........  1400
SEQIDNO:113  1331 .......... .......... .......... .......... .......... .......... ..........  1400
SEQIDNO:115  1331 .......... .......... .......... .......... .......... .......... ..........  1400
SEQIDNO:117  1331 .......... .......... .......... .......... .......... .......... ..........  1400
SEQIDNO:119  1331 .......... .......... .......... .......... .......... .......... ..........  1400
SEQIDNO:121  1331 .......... .......... .......... .......... .......... .......... ..........  1400
SEQIDNO:123  1331 .......... .......... .......... .......... .......... .......... ..........  1400
SEQIDNO:125  1331 .......... .......... .......... .......... .......... .......... ..........  1400
SEQIDNO:127  1331 .......... .......... .......... .......... .......... .......... ..........  1400
SEQIDNO:129  1331 .......... .......... .......... .......... .......... .......... ..........  1400
SEQIDNO:131  1331 .......... .......... .......... .......... .......... .......... ..........  1400
SEQIDNO:133  1331 .......... .......... .......... .......... .......... .......... ..........  1400
SEQIDNO:135  1331 .......... .......... .......... .......... .......... .......... ..........  1400
```

Figure 1, Continued

```
                        1410       1420       1430       1440       1450       1460       1470
                    ....|....| ....|....| ....|....| ....|....| ....|....| ....|....| ....|....|
SEQIDNO:1     1401 ccgcagcgtg atgcgctttg atcacccggt ttccgagatg gttaccgacc cgtacccggc gacccgtgca  1470
SEQIDNO:3     1401 .......... .......... .......... .......... .......... .......... ..........  1470
SEQIDNO:5     1401 .......... .......... .......... .......... .......... .......... ..........  1470
SEQIDNO:7     1401 .......... .......... .......... .......... .......... .......... ..........  1470
SEQIDNO:9     1401 .......... .......... .......... .......... .......... .......... ..........  1470
SEQIDNO:11    1401 .......... .......... .......... .......... .......... .......... ..........  1470
SEQIDNO:13    1401 .......... .......... .......... .......... .......... .......... ..........  1470
SEQIDNO:15    1401 .......... .......... .......... .......... .......... .......... ..........  1470
SEQIDNO:17    1401 .......... .......... .......... .......... .......... .......... ..........  1470
SEQIDNO:19    1401 .......... .......... .......... .......... .......... .......... ..........  1470
SEQIDNO:21    1401 .......... .......... .......... .......... .......... .......... ..........  1470
SEQIDNO:23    1401 .......... .......... .......... .......... .......... .......... ..........  1470
SEQIDNO:25    1401 .......... .......... .......... .......... .......... .......... ..........  1470
SEQIDNO:27    1401 .......... .......... .......... .......... .......... .......... ..........  1470
SEQIDNO:29    1401 .......... .......... .......... .......... .......... .......... ..........  1470
SEQIDNO:31    1401 .......... .......... .......... .......... .......... .......a.. ..........  1470
SEQIDNO:33    1401 .......... .......... .......... .......... .......... .......... ..........  1470
SEQIDNO:35    1401 .......... .......... .......... .......... .......... .......... ..........  1470
SEQIDNO:37    1401 .......... .......... .......... .......... .......... .......... ..........  1470
SEQIDNO:39    1401 .......... .......... .......... .......... .......... .......... ..........  1470
SEQIDNO:41    1401 .......... .......... .......... .......... .......... .......... ..........  1470
SEQIDNO:43    1401 .......... .......... .......... .......... .......... .......... ..........  1470
SEQIDNO:45    1401 .......... .......... .......... .......... .......... .......... ..........  1470
SEQIDNO:47    1401 .......... .......... .......... .......... .......... .......... ..........  1470
SEQIDNO:49    1401 .......... .......... .......... .......... .......... .......... ..........  1470
SEQIDNO:51    1401 .......... .......... .......... .......... .......... .......... ..........  1470
SEQIDNO:53    1401 .......... .......... .......... .......... .......... .......... ..........  1470
SEQIDNO:55    1401 .......... .......... .......... .......... .......... .......... ..........  1470
SEQIDNO:57    1401 .......... .......... .......... .......... .......... .......... ..........  1470
SEQIDNO:59    1401 .......... .......... .......... .......... .......... .......... ..........  1470
SEQIDNO:61    1401 .......... .......... .......... .......... .......... .......... ..........  1470
SEQIDNO:63    1401 .......... .......... .......... .......... .......... .......... ..........  1470
SEQIDNO:65    1401 .......... .......... .......... .......... .......... .......... ..........  1470
SEQIDNO:67    1401 .......... .......... .......... .......... .......... .......... ..........  1470
SEQIDNO:69    1401 .......... .......... .......... .......... .......... .......... ..........  1470
SEQIDNO:71    1401 .......... .......... .......... .......... .......... .......... ..........  1470
SEQIDNO:73    1401 .......... .......... .......... .......... .......... .......... ..........  1470
SEQIDNO:75    1401 .......... .......... .......... .......... .......... .......... ..........  1470
SEQIDNO:77    1401 .......... .......... .......... .......... .......... .......... ..........  1470
SEQIDNO:79    1401 .......... .......... .......... .......... .......... .......... ..........  1470
SEQIDNO:81    1401 .......... .......... .......... .......... .......... .......... ..........  1470
SEQIDNO:83    1401 .......... .......... .......... .......... .......... .......... ..........  1470
SEQIDNO:85    1401 .......... .......... .......... .......... .......... .......... ..........  1470
SEQIDNO:87    1401 .......... .......... .......... .......... .......... .......... ..........  1470
SEQIDNO:89    1401 .......... .......... .......... .......... .......... .......... ..........  1470
SEQIDNO:91    1401 .......... .......... .......... .......... .......... .......... ..........  1470
SEQIDNO:93    1401 .......... .......... .......... .......... .......... .......... ..........  1470
SEQIDNO:95    1401 .......... .......... .......... .......... .......... .......... ..........  1470
SEQIDNO:97    1401 .......... .......... .......... .......... .......... .......... ..........  1470
SEQIDNO:99    1401 .......... .......... .......... .......... .......... .......... ..........  1470
SEQIDNO:101   1401 .......... .......... .......... .......... .......... .......... ..........  1470
SEQIDNO:103   1401 .......... .......... .......... .......... .......... .......... ..........  1470
SEQIDNO:105   1401 .......... .......... .......... .......... .......... .......... ..........  1470
SEQIDNO:107   1401 .......... .......... .......... .......... .......... .......... ..........  1470
SEQIDNO:109   1401 .......... .......... .......... .......... .......... .......... ..........  1470
SEQIDNO:111   1401 .......... .......... .......... .......... .......... .......... ..........  1470
SEQIDNO:113   1401 .......... .......... .......... .......... .......... .......... ..........  1470
SEQIDNO:115   1401 .......... .......... .......... .......... .......... .......... ..........  1470
SEQIDNO:117   1401 .......... .......... .......... .......... .......... .......... ..........  1470
SEQIDNO:119   1401 .......... .......... .......... .......... .......... .......... ..........  1470
SEQIDNO:121   1401 .......... .......... .......... .......... .......... .......... ..........  1470
SEQIDNO:123   1401 .......... .......... .......... .......... .......... .......... ..........  1470
SEQIDNO:125   1401 .......... .......... .......... .......... .......... .......... ..........  1470
SEQIDNO:127   1401 .......... .......... .......... .......... .......... .......... ..........  1470
SEQIDNO:129   1401 .......... .......... .......... .......... .......... .......... ..........  1470
SEQIDNO:131   1401 .......... .......... .......... .......... .......... .......... ..........  1470
SEQIDNO:133   1401 .......... .......... .......... .......... .......... .......... ..........  1470
SEQIDNO:135   1401 .......... .......... .......... .......... .......... .......... ..........  1470
```

Figure 1, Continued

```
                          1480        1490
                    ....|....| ....|....| .
SEQIDNO:1      1471 ctgtgggatg gtgtgccatt g 1491
SEQIDNO:3      1471 .......... .......... . 1491
SEQIDNO:5      1471 .......... .......... . 1491
SEQIDNO:7      1471 .......... .......... . 1491
SEQIDNO:9      1471 .......... .......... . 1491
SEQIDNO:11     1471 .......... .......... . 1491
SEQIDNO:13     1471 .......... .......... . 1491
SEQIDNO:15     1471 .......... .......... . 1491
SEQIDNO:17     1471 .......... .......... . 1491
SEQIDNO:19     1471 .......... .......... . 1491
SEQIDNO:21     1471 .......... .......... . 1491
SEQIDNO:23     1471 .......... .......... . 1491
SEQIDNO:25     1471 .......... .......... . 1491
SEQIDNO:27     1471 .......... .......... . 1491
SEQIDNO:29     1471 .......... .......... . 1491
SEQIDNO:31     1471 .......... .......... . 1491
SEQIDNO:33     1471 .......... .......... . 1491
SEQIDNO:35     1471 .......... .......... . 1491
SEQIDNO:37     1471 .......... .......... . 1491
SEQIDNO:39     1471 .......... .......... . 1491
SEQIDNO:41     1471 .......... .......... . 1491
SEQIDNO:43     1471 .......... .......... . 1491
SEQIDNO:45     1471 .......... .......... . 1491
SEQIDNO:47     1471 .......... .......... . 1491
SEQIDNO:49     1471 .......... .......... . 1491
SEQIDNO:51     1471 .......... .......... . 1491
SEQIDNO:53     1471 .......... .......... . 1491
SEQIDNO:55     1471 .......... .......... . 1491
SEQIDNO:57     1471 .......... .......... . 1491
SEQIDNO:59     1471 .......... .......... . 1491
SEQIDNO:61     1471 .......... .......... . 1491
SEQIDNO:63     1471 .......... .......... . 1491
SEQIDNO:65     1471 .......... .......... . 1491
SEQIDNO:67     1471 .......... .......... . 1491
SEQIDNO:69     1471 .......... .......... . 1491
SEQIDNO:71     1471 .......... .......... . 1491
SEQIDNO:73     1471 .......... .......... . 1491
SEQIDNO:75     1471 .......... .......... . 1491
SEQIDNO:77     1471 .......... .......... . 1491
SEQIDNO:79     1471 .......... .......... . 1491
SEQIDNO:81     1471 .......... .......... . 1491
SEQIDNO:83     1471 .......... .......... . 1491
SEQIDNO:85     1471 .......... .......... . 1491
SEQIDNO:87     1471 .......... .......... . 1491
SEQIDNO:89     1471 .......... .......... . 1491
SEQIDNO:91     1471 .......... .......... . 1491
SEQIDNO:93     1471 .......... .......... . 1491
SEQIDNO:95     1471 .......... .......... . 1491
SEQIDNO:97     1471 .......... .......... . 1491
SEQIDNO:99     1471 .......... .......... . 1491
SEQIDNO:101    1471 .......... .......... . 1491
SEQIDNO:103    1471 .......... .......... . 1491
SEQIDNO:105    1471 .......... .......... . 1491
SEQIDNO:107    1471 .......... .......... . 1491
SEQIDNO:109    1471 .......... .......... . 1491
SEQIDNO:111    1471 .......... .......... . 1491
SEQIDNO:113    1471 .......... .......... . 1491
SEQIDNO:115    1471 .......... .......... . 1491
SEQIDNO:117    1471 .......... .......... . 1491
SEQIDNO:119    1471 .......... .......... . 1491
SEQIDNO:121    1471 .......... .......... . 1491
SEQIDNO:123    1471 .......... .......... . 1491
SEQIDNO:125    1471 .......... .......... . 1491
SEQIDNO:127    1471 .......... .......... . 1491
SEQIDNO:129    1471 .......... .......... . 1491
SEQIDNO:131    1471 .......... .......... . 1491
SEQIDNO:133    1471 .......... .......... . 1491
SEQIDNO:135    1471 .......... .......... . 1491
```

**Figure 2. Pairwise alignment of the Polypeptide Sequence Encoding the Wild-Type Carboxyesterase enzyme, *Thermobifida fusca* (*T. fusca*) (SEQ ID NO: 2) against the polypeptide sequences of *T. fusca* variants**

```
                          10         20         30         40         50         60         70
                  ....|....| ....|....| ....|....| ....|....| ....|....| ....|....| ....|....|
SEQIDNO:2      1  MEIVIRTGSG DVRGSKENGI AVFRGIPYAE PPVGAHRFTA PRPPRPWDGV RDATEFSATA PRPPYPEAIG  70
SEQIDNO:4      1  .......... .......... .......... .......... .......... .......... ..........  70
SEQIDNO:6      1  .......... .......... .......... .......... .......... .......... ..........  70
SEQIDNO:8      1  .......... .......... .......... .......... .......... .......... ..........  70
SEQIDNO:10     1  .......... .......... .......... .......... .......... .......... ..........  70
SEQIDNO:12     1  .......... .......... .......... .......... .......... .......... ..........  70
SEQIDNO:14     1  .......... .......... .......... .......... .......... .......... ..........  70
SEQIDNO:16     1  .......... .......... .......... .......... .......... .......... ..........  70
SEQIDNO:18     1  .......... .......... .......... .......... .......... .......... ..........  70
SEQIDNO:20     1  .......... .......... .......... .......... .......... .......... ..........  70
SEQIDNO:22     1  .......... .......... .......... .......... .......... .......... ..........  70
SEQIDNO:24     1  .......... .......... .......... .......... .......... .......... ..........  70
SEQIDNO:26     1  .......... .......... .......... .......... .......... .......... ..........  70
SEQIDNO:28     1  .......... .......... .......... .......... .......... .......... ..........  70
SEQIDNO:30     1  .......... .......... .......... .......... .......... .......... ..........  70
SEQIDNO:32     1  .......... .......... .......... .......... .......... .......... ..........  70
SEQIDNO:34     1  .......... .......... .......... .......... .......... .......... ..........  70
SEQIDNO:36     1  .......... .......... .......... .......... .......... .......... ..R.......  70
SEQIDNO:38     1  .......... .......... .......... .......... .......... .......... ..........  70
SEQIDNO:40     1  .......... .......... .......... .......... .......... .......... ..........  70
SEQIDNO:42     1  .......... .......... .......... .......... .......... .......... ..........  70
SEQIDNO:44     1  .......... .......... .......... .......... .......... .......... ..........  70
SEQIDNO:46     1  .......... .......... .......... .......... .......... .......... .......P..  70
SEQIDNO:48     1  .......... .......... .......... .......... .......... .......... ..........  70
SEQIDNO:50     1  .......... .......... .......... .......... .......... .......... ..........  70
SEQIDNO:52     1  .......... .......... .......... .......... .......... .......... ..........  70
SEQIDNO:54     1  .......... .......... .......... .......... .......... .......... ..........  70
SEQIDNO:56     1  .......... .......... .......... .......... .......... .......... ..........  70
SEQIDNO:58     1  .......... .......... .......... .......... .......... .......... ..........  70
SEQIDNO:60     1  .......... .......... .......... .......... .......... .......... ..........  70
SEQIDNO:62     1  .......... .......... .......... .......... .......... .......... ..........  70
SEQIDNO:64     1  .......... .......... .......... .......... .......... .......... ..........  70
SEQIDNO:66     1  .......... .......... .......... .......... .......... .......... ..........  70
SEQIDNO:68     1  .......... .......... .......... .......... .......... .......... ....W...L.  70
SEQIDNO:70     1  .......... .......... .......... .......... .......... .......... .......PL.  70
SEQIDNO:72     1  .......... .......... .......... .......... .......... .......... ........L.  70
SEQIDNO:74     1  .......... .......... .......... .......... .......... .......... ..........  70
SEQIDNO:76     1  .......... .......... .......... .......... .......... .......... ..R.......  70
SEQIDNO:78     1  .......... .......... .......... .......... .......... .......... ....W...MA  70
SEQIDNO:80     1  .......... .......... .......... .......... .......... .......... ........W.  70
SEQIDNO:82     1  .......... .......... .......... .......... .......... .......... ..........  70
SEQIDNO:84     1  .......... .......... .......... .......... .......... .......... ..........  70
SEQIDNO:86     1  .......... .......... .......... .......... .......... .......... ........L.  70
SEQIDNO:88     1  .......... .......... .......... .......... .......... .......... ..........  70
SEQIDNO:90     1  .......... .......... .......... .......... .......... .......... ..R.G.....  70
SEQIDNO:92     1  .......... .......... .......... .......... .......... .......... .......P..  70
SEQIDNO:94     1  .......... .......... .......... .......... .......... .......... ..........  70
SEQIDNO:96     1  .......... .......... .......... .......... .......... .......... ..........  70
SEQIDNO:98     1  .......... .......... .......... .......... .......... .......... .......P..  70
SEQIDNO:100    1  .......... .......... .......... .......... .......... .......... ..........  70
SEQIDNO:102    1  .......... .......... .......... .......... .......... .......... ..........  70
SEQIDNO:104    1  .......... .......... .......... .......... .......... .......... ..T.......  70
SEQIDNO:106    1  .......... .......... .......... .......... .......... .......... ........W.  70
SEQIDNO:108    1  .......... .......... .......... .......... .......... .......... ..A.......  70
SEQIDNO:110    1  .......... .......... .......... .......... .......... .......... ..Y.......  70
SEQIDNO:112    1  .......... .......... .......... .......... .......... .......... ..Y.......  70
SEQIDNO:114    1  .......... .......... .......... .......... .......... .......... ..Y.......  70
SEQIDNO:116    1  .......... .......... .......... .......... .......... .......... .......PW.  70
SEQIDNO:118    1  .......... .......... .......... .......... .......... .......... ..........  70
SEQIDNO:120    1  .......... .......... .......... .......... .......... .......... ..........  70
SEQIDNO:122    1  .......... .......... .......... .......... .......... .......... ..........  70
SEQIDNO:124    1  .......... .......... .......... .......... .......... .......... ..........  70
SEQIDNO:126    1  .......... .......... .......... .......... .......... .......... ..........  70
SEQIDNO:128    1  .......... .......... .......... .......... .......... .......... ..........  70
SEQIDNO:130    1  .......... .......... .......... .......... .......... .......... ........F.  70
SEQIDNO:132    1  .......... .......... .......... .......... .......... .......... ..........  70
SEQIDNO:134    1  .......... .......... .......... .......... .......... .......... ..........  70
SEQIDNO:136    1  .......... .......... .......... .......... .......... .......... ..........  70
```

Figure 2, Continued

```
                             80         90        100        110        120        130        140
                     ....|....| ....|....| ....|....| ....|....| ....|....| ....|....| ....|....|
SEQIDNO:2       71   ALLIERFIPG DDYLTLNVWT PDPNAVGLPV MVWIHGGAFT NGSGSEPVYD GAAFARDGVV FVSFNYRLGI  140
SEQIDNO:4       71   .......... .......... .......... .......... .......... .......... ..........  140
SEQIDNO:6       71   .......... .......... .......... .......... .......... .......... ..........  140
SEQIDNO:8       71   .......... .......... .......... .......... .......... .......... ..........  140
SEQIDNO:10      71   .......... .......... .......... .......... .......... .......... ..........  140
SEQIDNO:12      71   .......... .......... .......... .......... .......... .......... ..........  140
SEQIDNO:14      71   .......... .......... .......... .......G.. .......... .......... ..........  140
SEQIDNO:16      71   .......... .......... .......... .......... .......... .......... ..........  140
SEQIDNO:18      71   .......... .......... .......... .......... .......... .......... ..........  140
SEQIDNO:20      71   .......... .......... .......... .......... .......... .......... ..........  140
SEQIDNO:22      71   .......... .......... .......... .......... .......... .......... ..........  140
SEQIDNO:24      71   .......... .......... .......... .......... .......... .......... ..........  140
SEQIDNO:26      71   .......... .......... .......... .......... .......... .......... ..........  140
SEQIDNO:28      71   .......... .......... .......... .......... .......... .......... ..........  140
SEQIDNO:30      71   .......... .......... .......... .......... .......... .......... ..........  140
SEQIDNO:32      71   .......... .......... .......... .......... .......... .......... ..........  140
SEQIDNO:34      71   .......... .......... .......... .......... .......... .......... ..........  140
SEQIDNO:36      71   .......... .......... .......... .......... .......... .......... ..........  140
SEQIDNO:38      71   .......... .......... .......... .......... .......... .......... ..........  140
SEQIDNO:40      71   .......... .......... .......... .......... .......... .......... ..........  140
SEQIDNO:42      71   .......... .......... .......... .......... .......... .......... ..........  140
SEQIDNO:44      71   .......... .......... .......... .......... .......... .......... ..........  140
SEQIDNO:46      71   .......... .......... .......... .......... .......... .......... ..........  140
SEQIDNO:48      71   .......... .......... .......... .......... .......... .......... ..........  140
SEQIDNO:50      71   .......... .......... .......... .......... .......... .......... ..........  140
SEQIDNO:52      71   .......... .......... .......... .......... .......... .......... ..........  140
SEQIDNO:54      71   .......... .......... .......... .......... .......... .......... ..........  140
SEQIDNO:56      71   .......... .......... .......... .......... .......... .......... ..........  140
SEQIDNO:58      71   .......... .......... .......... .......... .......... .......... ..........  140
SEQIDNO:60      71   .......... .......... .......... .......... .......... .......... ..........  140
SEQIDNO:62      71   .......... .......... .......... .......... .......... .......... ..........  140
SEQIDNO:64      71   .......... .......... .......... .......... .......... .......... ..........  140
SEQIDNO:66      71   ......S... .......... .......... .......... .......... .......... ..........  140
SEQIDNO:68      71   .......... .......... .......... .......... .......... .......... ..........  140
SEQIDNO:70      71   .......... .......... .......... .......... .......... .......... ..........  140
SEQIDNO:72      71   .......... .......... .......... .......... .......... .......... ..........  140
SEQIDNO:74      71   .......... .......... .......... .......... .......... .......... ..........  140
SEQIDNO:76      71   .......... .......... .......... .......G.. .......... .......... ..........  140
SEQIDNO:78      71   .......... .......... .......... .......... .......... .......... ..........  140
SEQIDNO:80      71   .......... .......... .......... .......... .......... .......... ..........  140
SEQIDNO:82      71   .......... .......... .......... .......... .......... .......... ..........  140
SEQIDNO:84      71   .......... .......... .......... .......... .......... .......... ..........  140
SEQIDNO:86      71   .......... .......... .......... .......... .......... .......... ..........  140
SEQIDNO:88      71   .......... .......... .......... .......... .......... .......... ..........  140
SEQIDNO:90      71   .......... .......... .......... .......G.. .......... .......... ..........  140
SEQIDNO:92      71   .......... .......... .......... .......... .......... .......... ..........  140
SEQIDNO:94      71   .......... .......... .......... .......G.. .......... .......... ..........  140
SEQIDNO:96      71   .......... .......... .......... .......G.. .......... .......... ..........  140
SEQIDNO:98      71   .......... .......... .......... .......... .......... .......... ..........  140
SEQIDNO:100     71   .......... .......... .......... .......... .......... .......... ..........  140
SEQIDNO:102     71   .......... .......... .......... .......... .......... .......... ..........  140
SEQIDNO:104     71   .......... .......... .......... .......... .......... .......... ..........  140
SEQIDNO:106     71   .......... .......... .......... .......... .......... .......... ..........  140
SEQIDNO:108     71   .......... .......... .......... .......... .......... .......... ..........  140
SEQIDNO:110     71   .......... .......... .......... .......... .......... .......... ..........  140
SEQIDNO:112     71   .......... .......... .......... .......... .......... .......... ..........  140
SEQIDNO:114     71   .......... .......... .......... .......... .......... .......... ..........  140
SEQIDNO:116     71   .......... .......... .......... .......... .......... .......... ..........  140
SEQIDNO:118     71   .......... .......... .......... .......... .......... .......... ..........  140
SEQIDNO:120     71   .......... .......... .......... .......... .......... .......... ..........  140
SEQIDNO:122     71   .......... .......... .......... .......... .......... .......... ..........  140
SEQIDNO:124     71   .......... .......... .......... .......... .......... .......... ..........  140
SEQIDNO:126     71   .......... .......... .......... .......... .......... .......... ..........  140
SEQIDNO:128     71   .......... .......... .......... .......... .......... .......... ..........  140
SEQIDNO:130     71   .......... .......... .......... .......... .......... .......... ..........  140
SEQIDNO:132     71   .......... .......... .......... .......... .......... .......... ..........  140
SEQIDNO:134     71   .......... .......... .......... .......G.. .......... .......... ..........  140
SEQIDNO:136     71   .......... .......... .......... .......... .......... .......... ..........  140
```

Figure 2, Continued

```
                          150        160        170        180        190        200        210
                   ....|....| ....|....| ....|....| ....|....| ....|....| ....|....| ....|....|
SEQIDNO:2      141 IGFADLPDAP SNRGLLDQIA ALENVRDNIA RFGGDPGNVT VFGESAGAMS VCTLMATPRA RGLFRRAILQ  210
SEQIDNO:4      141 .......... .......... .......... .......... .......... .......... ..........  210
SEQIDNO:6      141 .......... .......... .......... .......... .......... .......... ..........  210
SEQIDNO:8      141 .......... .......... .......... .......... .......... .......... ..........  210
SEQIDNO:10     141 .......... .......... .......... .......... .......... .......... ..........  210
SEQIDNO:12     141 .......... .......... .......... .......... .......... .......... ..........  210
SEQIDNO:14     141 .......... .......... .......... .......... .......... .......... ..........  210
SEQIDNO:16     141 .......... .......... .......... .......... .......... .......... ..........  210
SEQIDNO:18     141 .......... .......... .......... .......... .......... .......... ..........  210
SEQIDNO:20     141 .......... .......... .......... .......... .......... .......... ..........  210
SEQIDNO:22     141 .......... .......... .......... .......... .......... .......... ..........  210
SEQIDNO:24     141 .......... .......... .......... .......... .......... .......... ..........  210
SEQIDNO:26     141 .......... .......... .......... .......... .......... .......... ..........  210
SEQIDNO:28     141 .......... .......... .......... .......... .......... .......... ..........  210
SEQIDNO:30     141 .......... .......... .......... .......... .......... .......... ..........  210
SEQIDNO:32     141 .......... .......... .......... .......... .......... .......... ..........  210
SEQIDNO:34     141 .......... .......... .......... .......... .......... .......... ..........  210
SEQIDNO:36     141 .......... .......... .......... .......... .......... .......... ..........  210
SEQIDNO:38     141 .......... .......... .......... .......... .......... .......... ..........  210
SEQIDNO:40     141 .......... .......... .......... .......... .........K .......... ..........  210
SEQIDNO:42     141 .......... .......... .......... .......... .......... .......... ..........  210
SEQIDNO:44     141 .......... .......... .......... .......... .......... .......... ..........  210
SEQIDNO:46     141 .......... .......... .......... .......... .......... .......... ..........  210
SEQIDNO:48     141 .......... .......... .......... .......... .......... .......... ..........  210
SEQIDNO:50     141 .......... .......... .......... .......... ...S...... .......... ..........  210
SEQIDNO:52     141 .......... .......... .......... .......... .......... .......... ..........  210
SEQIDNO:54     141 .......... .......... .......... .......... .......... .......... ..........  210
SEQIDNO:56     141 .......... .......... .......... .......... .......... .......... ..........  210
SEQIDNO:58     141 .......... .......... .......... .......... ...G...... .......... ..........  210
SEQIDNO:60     141 .......... ..H....... .......... .......... .......... .......... ..........  210
SEQIDNO:62     141 .......... .......... .......... .......... .......... .......... ..........  210
SEQIDNO:64     141 .......... .......... .......... .......... .........N .......... ..........  210
SEQIDNO:66     141 .......... .......... .......... .......... ...G...... .......... ..........  210
SEQIDNO:68     141 .......... .......... .......... .......... .......... .......... ..........  210
SEQIDNO:70     141 .......... .......... .......... .......... .......... .......... ..........  210
SEQIDNO:72     141 .......... .......... .......... .......... .......... .......... ..........  210
SEQIDNO:74     141 .......... .......... .......... .......... .......... .......... ..........  210
SEQIDNO:76     141 .......... .......... .......... .......... .......... .......... ..........  210
SEQIDNO:78     141 .......... .......... .......... .......... .......... .......... ..........  210
SEQIDNO:80     141 .......... .......... .......... .......... .......... .......... ..........  210
SEQIDNO:82     141 .......... .......... .......... .......... .......... .......... ..........  210
SEQIDNO:84     141 .......... .......... .......... .......... .......... .......... ..........  210
SEQIDNO:86     141 .......... .......... .......... .......... .......... .......... ..........  210
SEQIDNO:88     141 .......... .......... .......... .......... .......... .......... ..........  210
SEQIDNO:90     141 .......... .......... .......... .......... .......... .......... ..........  210
SEQIDNO:92     141 .......... .......... .......... .......... .......... .......... ..........  210
SEQIDNO:94     141 .......... .......... .......... .......... .......... .......... ..........  210
SEQIDNO:96     141 .......... .......... .......... .......... .......... .......... ..........  210
SEQIDNO:98     141 .......... .......... .......... .......... .......... .......... ..........  210
SEQIDNO:100    141 .......... .......... .......... .......... .......... .......... ..........  210
SEQIDNO:102    141 .......... .......... .......... .......... .......... .......... ..........  210
SEQIDNO:104    141 .......... .......... .......... .......... .......... .......... ..........  210
SEQIDNO:106    141 .......... .......... .......... .......... .......... .......... ..........  210
SEQIDNO:108    141 .......... .......... .......... .......... .......... .......... ..........  210
SEQIDNO:110    141 .......... .......... .......... .......... .......... .......... ..........  210
SEQIDNO:112    141 .......... .......... .......... .......... .......... .......... ..........  210
SEQIDNO:114    141 .......... .......... .......... .......... .......... .......... ..........  210
SEQIDNO:116    141 .......... .......... .......... .......... ........I. .......... ..........  210
SEQIDNO:118    141 .......... .......... .......... .......... .......... .......... ..........  210
SEQIDNO:120    141 .......... .......... .......... .......... .......... .......... ..........  210
SEQIDNO:122    141 .......... .......... .......... .......... ........I. .......... ..........  210
SEQIDNO:124    141 .......... .......... .......... .......... .......... .......... ..........  210
SEQIDNO:126    141 .......... .......... .......... .......... .......... .......... ..........  210
SEQIDNO:128    141 .......... .......... .......... .......... ........I. .......... ..........  210
SEQIDNO:130    141 .......... .......... .......... .......... .......... .......... ..........  210
SEQIDNO:132    141 .......... .......... .......... .......... ........Q. .......... ..........  210
SEQIDNO:134    141 .......... .......... .......... .......... .......... .......... ..........  210
SEQIDNO:136    141 .......... .......... .......... .......... .......... .......... ..........  210
```

Figure 2, Continued

```
                              220        230        240        250        260        270        280
                       ....|....| ....|....| ....|....| ....|....| ....|....| ....|....| ....|....|
SEQIDNO:2         211 SGAGNMAVAA EDATTIAAVI AHRLGVEPTA AALAHVPVAQ LLDVQQQVAQ EIQGAPDPAV NGERIAGGSV  280
SEQIDNO:4         211 .......... .......... .......... .......... .......... .......... ..........  280
SEQIDNO:6         211 .......... .......... .......... .......... .......... .......... ..........  280
SEQIDNO:8         211 .......... .......... .......... .......... .......... .......... ..........  280
SEQIDNO:10        211 .......... .......... .......... .......... .......... .......... ..........  280
SEQIDNO:12        211 .......... .......... .......... .......... .......... .......... ..........  280
SEQIDNO:14        211 .......... .......... .......... .......... .......... .......... ..........  280
SEQIDNO:16        211 ....R..... .......... .......... .......... .......... .......... ..........  280
SEQIDNO:18        211 .......... .......... .......... .......... .......... .......... ..........  280
SEQIDNO:20        211 ....W..... .......... .......... .......... .......... .......... ..........  280
SEQIDNO:22        211 .P........ .......... .......... .......... .......... .......... ..........  280
SEQIDNO:24        211 .......... .......... .......... .......... .......... .......... .........G  280
SEQIDNO:26        211 ....P..... .......... .......... .......... .......... .......... ..........  280
SEQIDNO:28        211 .......... .......... .......... .......... .......... .......... ..........  280
SEQIDNO:30        211 .......... .......... .......... .......... .......... .......... ..........  280
SEQIDNO:32        211 .......... .......... .......... .......... .......... .......... ..........  280
SEQIDNO:34        211 .......... .......... .......... .......... .......... .......... T.........  280
SEQIDNO:36        211 .......... .......... .......... .......... .......... .......... ..........  280
SEQIDNO:38        211 .......... .......... .......... .......... .......... .......... ..........  280
SEQIDNO:40        211 .......... .......... .......... .......... .......... .......... ..........  280
SEQIDNO:42        211 ....R..... .......... .......... .......... .......... .......... R.........  280
SEQIDNO:44        211 .......... .......... .......... .......... .......... .......... ..........  280
SEQIDNO:46        211 .......... .......... .......... .......... .......... .......... ..........  280
SEQIDNO:48        211 .......... .......... .......... .......... .......... .......... ..........  280
SEQIDNO:50        211 .......... .......... .......... ........T. .......... .......... ..........  280
SEQIDNO:52        211 .......... .......... .......... .......... .......... .......... ..........  280
SEQIDNO:54        211 ..L....... .......... .......... .......... .......... .......... ..........  280
SEQIDNO:56        211 .......... .......... .......... .......... .......... .......... ..........  280
SEQIDNO:58        211 .......... .......... .......... .......... .......... .......... ..........  280
SEQIDNO:60        211 ....P..... .......... .......... .......... .......... .......... ..........  280
SEQIDNO:62        211 ...L...... .......... .......... .......... .......... .......... ..........  280
SEQIDNO:64        211 .......... .......... .......... .......... .......... .......... ..........  280
SEQIDNO:66        211 .......... .......... .......... .......... .......... .......... ..........  280
SEQIDNO:68        211 .......... .......... .......... .......... .......... .......... ..........  280
SEQIDNO:70        211 .......... .......... .......... .......... .......... .......... ..........  280
SEQIDNO:72        211 .......... .......... .......... .......... .......... .......... Y.........  280
SEQIDNO:74        211 .......... .......... .......... .......... .......... .......... ..........  280
SEQIDNO:76        211 .......... .......... .......... .......... .......... .......... ..........  280
SEQIDNO:78        211 .......... .......... .......... .......... .......... .......... ..........  280
SEQIDNO:80        211 .......... .......... .......... .......... .......... .......... ..........  280
SEQIDNO:82        211 .......... .......... .......... .......... .......... .......... .........G  280
SEQIDNO:84        211 .......... .......... .......... .......... .......... .......... Y.........  280
SEQIDNO:86        211 .......... .......... .......... .......... .......... .......... ..........  280
SEQIDNO:88        211 .......... .......... .......... .......... .......... .......... ..........  280
SEQIDNO:90        211 .......... .......... .......... .......... .......... .......... ..........  280
SEQIDNO:92        211 .......... .......... .......... .......... .......... .......... Y.........  280
SEQIDNO:94        211 .......... .......... .......... .......... .......... .......... ..........  280
SEQIDNO:96        211 ....K..... .......... .......... .......... .......... .......... ..........  280
SEQIDNO:98        211 .......... .......... .......... .......... .......... .......... ..........  280
SEQIDNO:100       211 ....R..... .......... .......... .......... .......... .......... ..........  280
SEQIDNO:102       211 ....K..... .......... .......... .......... .......... .......... ..........  280
SEQIDNO:104       211 ....R..... .......... .......... .......... .......... .......... ..........  280
SEQIDNO:106       211 ....R..... .......... .......... .......... .......... .......... ..........  280
SEQIDNO:108       211 ....R..... .......... .......... .......... .......... .......... ..........  280
SEQIDNO:110       211 .P..R..... .......... .......... .......... .......... .......... ..........  280
SEQIDNO:112       211 .P..R..... .......... .......... .......... .......... .......AN. ..........  280
SEQIDNO:114       211 ....R..... .......... .......... .......... .......... .......... ..........  280
SEQIDNO:116       211 ...RP..... .......... .......... .......... .......... .......... ..........  280
SEQIDNO:118       211 ....K..... .......... .......... .......... .......... .......... ..........  280
SEQIDNO:120       211 ....K..... .......... .......... .......... .......... .......... ..........  280
SEQIDNO:122       211 .......... .......... .......... .......... .......... .......... ..........  280
SEQIDNO:124       211 ....R..... .......... .......... .......... .......... .......... ..........  280
SEQIDNO:126       211 ....W..... .......... .......... .......... .......... .......... ..........  280
SEQIDNO:128       211 .......... .......... .......... .......... .......... .......... ..........  280
SEQIDNO:130       211 ....K..... .......... .......... .......... .......... ........LI ..........  280
SEQIDNO:132       211 ....P..... .......... .......... .......... .......... .......... Y.........  280
SEQIDNO:134       211 ....P..... .......... .......... .......... .......... .......... ..........  280
SEQIDNO:136       211 .......... .......... .......... .......... .......... .......... ..........  280
```

Figure 2, Continued

```
                        290        300        310        320        330        340        350
                 ....|....| ....|....| ....|....| ....|....| ....|....| ....|....| ....|....|
SEQIDNO:2    281 LLPFAPVIDG ELLSQRFAEA IAGGAGHDVD LLFGTTTDEY RLFLAPTGLL PFITGDYVTY HLAKSGLDAD 350
SEQIDNO:4    281 .Q........ .......... .......... .......... .......... .......... .......... 350
SEQIDNO:6    281 .A........ .......... .......... .......... .......... .......... .......... 350
SEQIDNO:8    281 .T........ .......... .......... .......... .......... .......... .......... 350
SEQIDNO:10   281 ....L..... .......... .......... .......... .......... .......... .......... 350
SEQIDNO:12   281 .C........ .......... .......... .......... .......... .......... .......... 350
SEQIDNO:14   281 .......... .......... .......... .......... .......... .......... .......... 350
SEQIDNO:16   281 .......... .......... .......... .......... .......... .......... .......... 350
SEQIDNO:18   281 P......... .......... .......... .......... .......... .......... .......... 350
SEQIDNO:20   281 .......... .......... .......... .......... .......... .......... .......... 350
SEQIDNO:22   281 .......... .......... .......... .......... .......... .......... .......... 350
SEQIDNO:24   281 .......... .......... .......... .......... .......... .......... .......... 350
SEQIDNO:26   281 .......... .......... .......... .......... .......... .......... .......... 350
SEQIDNO:28   281 ..D....... .......... .......... .......... .......... .......... .......... 350
SEQIDNO:30   281 .......... .......... .......... .........G .......... .......... .......... 350
SEQIDNO:32   281 .......... .......... .......... .......... L......... .......... .......... 350
SEQIDNO:34   281 .......... .......... .......... .......... .......... .......... .......... 350
SEQIDNO:36   281 .......... .......... .......... .......... .......... .......... .......... 350
SEQIDNO:38   281 .......... .......... .......... .........N .......... .......... .......... 350
SEQIDNO:40   281 .......... .......... .......... .......... .......... .......... .......... 350
SEQIDNO:42   281 .......... .......... .......... .......... .......... .......... .......... 350
SEQIDNO:44   281 ..V....... .......... .......... .......... .......... .......... .......... 350
SEQIDNO:46   281 .......... .......... .......... .......... .......... .......... .......... 350
SEQIDNO:48   281 ..Y....... .......... .......... .......... .......... .......... .......... 350
SEQIDNO:50   281 .......... .......... .......... .......... .......... .......... .......... 350
SEQIDNO:52   281 ...T...... .......... .......... .......... .......... .......... .......... 350
SEQIDNO:54   281 .......... .......... .......... .......... .......... .......... .......... 350
SEQIDNO:56   281 .......... .......... .......... .......... .......... .......... .......... 350
SEQIDNO:58   281 .......... .......... .......... .......... .......... .......... .......... 350
SEQIDNO:60   281 .......... .......... .......... .......... .......... .......... .......... 350
SEQIDNO:62   281 .......... .......... .......... .......... .......... .......... .......... 350
SEQIDNO:64   281 .......... .......... .......... .......... .......... .......... .......... 350
SEQIDNO:66   281 .......... .......... .......... .......... .......... .......... .......... 350
SEQIDNO:68   281 .T........ .......... .......... .......... .......... .......... .......... 350
SEQIDNO:70   281 .T........ .......... .......... .......... .......... .......... ..V....... 350
SEQIDNO:72   281 .T........ .......... .......... .......... .......... .......... .......... 350
SEQIDNO:74   281 .T........ .......... .......... .......... .......... .......... .......... 350
SEQIDNO:76   281 .T........ .......... .......... .......... .......... .......... .......... 350
SEQIDNO:78   281 PT........ .......... .......... .......... .......... .......... .......... 350
SEQIDNO:80   281 .T........ .......... .......... .......... .......... .......... .......... 350
SEQIDNO:82   281 .T..L..... .......... .......... .......... .......... .......... .......... 350
SEQIDNO:84   281 .T........ .......... .......... .......... .......... .......... ..V....... 350
SEQIDNO:86   281 .T........ .......... .......... .......... .......... .......... .......... 350
SEQIDNO:88   281 PT........ .......... .......... .......... .......... .......... .......... 350
SEQIDNO:90   281 .T........ .......... .......... .......... .......... .......... .......... 350
SEQIDNO:92   281 .T........ .......... .......... .......... .......... .......... .......... 350
SEQIDNO:94   281 .T..L..... .......... .......... .......... .......... .......... .......... 350
SEQIDNO:96   281 .T........ .......... .......... .......... .......... .......... .......... 350
SEQIDNO:98   281 .T........ .......... .......... .......... .......... .......... .......... 350
SEQIDNO:100  281 .T........ .......... .......... .......... .......... .......... .......... 350
SEQIDNO:102  281 PT..L..... .......... .......... .......... .......... .......... .......... 350
SEQIDNO:104  281 .T........ .......... .......... .......... .......... .......... .......... 350
SEQIDNO:106  281 .T........ .......... .......... .......... .......... .......... .......... 350
SEQIDNO:108  281 .T........ .......... .......... .......... .......... .......... ..V....... 350
SEQIDNO:110  281 .T........ .......... .......... .......... .......... .......... .......... 350
SEQIDNO:112  281 .T........ .......... .......... .......... .......... .......... ..V....... 350
SEQIDNO:114  281 .T........ .......... .......... .......... .......... .......... .......... 350
SEQIDNO:116  281 .T........ .......... .......... .......... .......... .......... .......... 350
SEQIDNO:118  281 .T........ .......... .......... .......... .......... .......... .......... 350
SEQIDNO:120  281 .T........ .......... .......... .......... .......... .......... .......... 350
SEQIDNO:122  281 .T........ .......... .......... .......... .......... .......... ..V....... 350
SEQIDNO:124  281 PT..L..... .......... .......... .......... .......... .......... .......... 350
SEQIDNO:126  281 .T..L..... .......... .......... .......... .......... .......... .....S.... 350
SEQIDNO:128  281 .T........ .......... .......... .......... .......... .......... .......... 350
SEQIDNO:130  281 .T........ .......... .......... .......... .......... .......... .......... 350
SEQIDNO:132  281 PC........ .......... .......... .......... .......... .......... .......... 350
SEQIDNO:134  281 .T........ .......... .......... .......... .......... .......... .......... 350
SEQIDNO:136  281 .......... .......... .......... .......... .......... .......... .......... 350
```

Figure 2, Continued

```
                            360        370        380        390        400        410        420
                     ....|....| ....|....| ....|....| ....|....| ....|....| ....|....| ....|....|
SEQIDNO:2        351 AAKRYTAEGR GEEPGDILAS IITDQVFRIP ALRIAESRVD APARTFGYEF AWRTPQLDGI LGACHAVELP  420
SEQIDNO:4        351 .......... .......... .......... .......... .......... .......... ..........  420
SEQIDNO:6        351 .......... .......... .......... .......... .......... .......... ..........  420
SEQIDNO:8        351 .......... .......... .......... .......... .......... .......... ..........  420
SEQIDNO:10       351 .......... .......... .......... .......... .......... .......... ..........  420
SEQIDNO:12       351 .......... .......... .......... .......... .......... .......... ..........  420
SEQIDNO:14       351 .......... .......... .......... .......... .......... .......... ..........  420
SEQIDNO:16       351 .......... .......... .......... .......... .......... .......... ..........  420
SEQIDNO:18       351 .......... .......... .......... .......... .......... .......... ..........  420
SEQIDNO:20       351 .......... .......... .......... .......... .......... .......... ..........  420
SEQIDNO:22       351 .......... .......... .......... .......... .......... .......... ..........  420
SEQIDNO:24       351 .......... .......... .......... .......... .......... .......... ..........  420
SEQIDNO:26       351 .......... .......... .......... .......... .......... .......... ..........  420
SEQIDNO:28       351 .......... .......... .......... .......... .......... .......... ..........  420
SEQIDNO:30       351 .......... .......... .......... .......... .......... .......... ..........  420
SEQIDNO:32       351 .......... .......... .......... .......... .......... .......... ..........  420
SEQIDNO:34       351 .......... .......... .......... .......... .......... .......... ..........  420
SEQIDNO:36       351 .......... .......... .......... .......... .......... .......... ..........  420
SEQIDNO:38       351 .......... .......... .......... .......... .......... .......... ..........  420
SEQIDNO:40       351 .......... .......... .......... .......... .......... .......... ..........  420
SEQIDNO:42       351 .......... .......... .......... .......... .......... .......... ..........  420
SEQIDNO:44       351 .......... .......... .......... .......... .......... .......... ..........  420
SEQIDNO:46       351 .......... .......... .......... .......... .......... .......... ..........  420
SEQIDNO:48       351 .......... .......... .......... .......... .......... .......... ..........  420
SEQIDNO:50       351 .......... .......... .......... .......... .......... .......... ..........  420
SEQIDNO:52       351 .......... .......... .......... .......... .......... .......... ..........  420
SEQIDNO:54       351 .......... .......... .......... .......... .......... .......... ..........  420
SEQIDNO:56       351 .......... .......... ......L... .......... .......... .......... ..........  420
SEQIDNO:58       351 .......... .......... .......... .......... .......... .......... ..........  420
SEQIDNO:60       351 .......... .......... .......... .......... .......... .......... ..........  420
SEQIDNO:62       351 .......... .......... .......... .......... .......... .......... ..........  420
SEQIDNO:64       351 .......... .......... .......... .......... .......... .......... ..........  420
SEQIDNO:66       351 .......... .......... .......... .......... .......... .......... ..........  420
SEQIDNO:68       351 .......... .......... .L........ .......... .......... .......... ..........  420
SEQIDNO:70       351 .......... .......... .L........ .......... .......... .......... ..........  420
SEQIDNO:72       351 .......... .......... .L........ .......... .......... .......... ..........  420
SEQIDNO:74       351 .......... .......... .L........ .......... .......... .......... ..........  420
SEQIDNO:76       351 .......... .......... .......... .......... .......... .......... ..........  420
SEQIDNO:78       351 .......... .......... .L........ .......... .......... .......... ..........  420
SEQIDNO:80       351 .......... .......... .M........ .......... .......... .......... ..........  420
SEQIDNO:82       351 .......... .......... .L........ .......... .......... .......... ..........  420
SEQIDNO:84       351 .......... .......... .L........ .......... .......... .......... ..........  420
SEQIDNO:86       351 .......... .......... .......... .......... .......... .......... ..........  420
SEQIDNO:88       351 .......... .......... .L........ .......... .......... .......... ..........  420
SEQIDNO:90       351 .......... .......... .......... .......... .......... .......... ..........  420
SEQIDNO:92       351 .......... .......... .L........ .......... .......... .......... ..........  420
SEQIDNO:94       351 .......... .......... .......... .......... .......... .......... ..........  420
SEQIDNO:96       351 .......... .......... .......... .......... .......... .......... ..........  420
SEQIDNO:98       351 .......... .......... .......... .......... .......... .......... ..........  420
SEQIDNO:100      351 .......... .......... .L........ .......... .......... .......... ..........  420
SEQIDNO:102      351 .......... .......... .L........ .......... .......... .......... ..........  420
SEQIDNO:104      351 .......... .......... .......... .......... .......... .......... ..........  420
SEQIDNO:106      351 .......... .......... .......... .......... .......... .......... ..........  420
SEQIDNO:108      351 .......... .......... .......... .......... .......... .......... ..........  420
SEQIDNO:110      351 .......... .......... .......... .......... .......... .......... ..........  420
SEQIDNO:112      351 .......... .......... .......... .......... .......... .......... ..........  420
SEQIDNO:114      351 .......... .......... .......... .......... .......... .......... ..........  420
SEQIDNO:116      351 .......... .......... .......... .......... .......... .......... ..........  420
SEQIDNO:118      351 .......... .......... ..G....... .......... .......... .......... ..........  420
SEQIDNO:120      351 .......... .......... .L....L... .......... .......... .......... ..........  420
SEQIDNO:122      351 .......... .......... .......... .......... .......... .......... ..........  420
SEQIDNO:124      351 .......... .......... ..G....... .......... .......... .......... ..........  420
SEQIDNO:126      351 .......... .......... .......... .......... .......... .......... ..........  420
SEQIDNO:128      351 .......... .......... .......... .......... .......... .......... ..........  420
SEQIDNO:130      351 .......... .......... ......L... .......... .......... .......... ..........  420
SEQIDNO:132      351 .......... .......... ......Y... .......... .......... .......... ..........  420
SEQIDNO:134      351 .......... .......... ......L... .......... .......... .......... ..........  420
SEQIDNO:136      351 .......... .......... .L........ .......... .......... .......... ..........  420
```

Figure 2, Continued

| | | 430 | 440 | 450 | 460 | 470 | 480 | 490 | |
|---|---|---|---|---|---|---|---|---|---|
| | | ....\|....\| | ....\|....\| | ....\|....\| | ....\|....\| | ....\|....\| | ....\|....\| | ....\|....\| | |
| SEQIDNO:2 | 421 | FVFRTLDRAA | SLVGTNPPEE | LAETVHNANV | RFATSGDPGN | PAWNPETRSV | NRFDHPVSEM | VTDPYPATRA | 490 |
| SEQIDNO:4 | 421 | .......... | .......... | .......... | .......... | .......... | .......... | .......... | 490 |
| SEQIDNO:6 | 421 | .......... | .......... | .......... | .......... | .......... | .......... | .......... | 490 |
| SEQIDNO:8 | 421 | .......... | .......... | .......... | .......... | .......... | .......... | .......... | 490 |
| SEQIDNO:10 | 421 | .......... | .......... | .......... | .......... | .......... | .......... | .......... | 490 |
| SEQIDNO:12 | 421 | .......... | .......... | .......... | .......... | .......... | .......... | .......... | 490 |
| SEQIDNO:14 | 421 | .......... | .......... | .......... | .......... | .......... | .......... | .......... | 490 |
| SEQIDNO:16 | 421 | .......... | .......... | .......... | .......... | .......... | .......... | .......... | 490 |
| SEQIDNO:18 | 421 | .......... | .......... | .......... | .......... | .......... | .......... | .......... | 490 |
| SEQIDNO:20 | 421 | .......... | .......... | .......... | .......... | .......... | .......... | .......... | 490 |
| SEQIDNO:22 | 421 | .......... | .......... | .......... | .......... | .......... | .......... | .......... | 490 |
| SEQIDNO:24 | 421 | .......... | .......... | .......... | .......... | .......... | .......... | .......... | 490 |
| SEQIDNO:26 | 421 | .......... | .......... | .......... | .......... | .......... | .......... | .......... | 490 |
| SEQIDNO:28 | 421 | .......... | .......... | .......... | .......... | .......... | .......... | .......... | 490 |
| SEQIDNO:30 | 421 | .......... | .......... | .......... | .......... | .......... | .......... | .......... | 490 |
| SEQIDNO:32 | 421 | .......... | .......... | .......... | .......... | .......... | .......... | .......... | 490 |
| SEQIDNO:34 | 421 | .......... | .......... | .......... | .......... | .......... | .......... | .......... | 490 |
| SEQIDNO:36 | 421 | .......... | .......... | .......... | .......... | .......... | .......... | .......... | 490 |
| SEQIDNO:38 | 421 | .......... | .......... | .......... | .......... | .......... | .......... | .......... | 490 |
| SEQIDNO:40 | 421 | .......... | .......... | .......... | .......... | .......... | .......... | .......... | 490 |
| SEQIDNO:42 | 421 | .......... | .......... | .......... | .......... | .......... | .......... | .......... | 490 |
| SEQIDNO:44 | 421 | .......... | .......... | .......... | .......... | .......... | .......... | .......... | 490 |
| SEQIDNO:46 | 421 | .......... | .......... | .......... | .......... | .......... | .......... | .......... | 490 |
| SEQIDNO:48 | 421 | .......... | .......... | .......... | .......... | .......... | .......... | .......... | 490 |
| SEQIDNO:50 | 421 | .......... | .......... | .......... | .......... | .......... | .......... | .......... | 490 |
| SEQIDNO:52 | 421 | .......... | .......T.. | .......... | .......... | .......... | .......... | .......... | 490 |
| SEQIDNO:54 | 421 | .......... | .......... | .......... | .......... | .......... | .......... | .......... | 490 |
| SEQIDNO:56 | 421 | .......... | .......... | .......... | .......... | .......... | .......... | .......... | 490 |
| SEQIDNO:58 | 421 | .......... | .......... | .......... | .......... | .......... | .......... | .......... | 490 |
| SEQIDNO:60 | 421 | .......... | .......... | .......... | .......... | .......... | .......... | .......... | 490 |
| SEQIDNO:62 | 421 | .......... | .......... | .......... | .......... | .......... | .......... | .......... | 490 |
| SEQIDNO:64 | 421 | .......... | .......... | .......... | .......... | .......... | .......... | .......... | 490 |
| SEQIDNO:66 | 421 | .......... | .......... | .......... | .......... | .......... | .......... | .......... | 490 |
| SEQIDNO:68 | 421 | .......... | .......... | .......... | .......... | .......... | .......... | .......... | 490 |
| SEQIDNO:70 | 421 | .......... | .......... | .......... | .......... | .......... | .......... | .......... | 490 |
| SEQIDNO:72 | 421 | .......... | .......... | .......... | .......... | .......... | .......... | .......... | 490 |
| SEQIDNO:74 | 421 | .......... | .......... | .......... | .......... | .......... | .......... | .......... | 490 |
| SEQIDNO:76 | 421 | .......... | .......... | .......... | .......... | .......... | .......... | .......... | 490 |
| SEQIDNO:78 | 421 | .......... | .......... | .......... | .......... | .......... | .......... | .......... | 490 |
| SEQIDNO:80 | 421 | .......... | .......... | .......... | .......... | .......... | .......... | .......... | 490 |
| SEQIDNO:82 | 421 | .......... | .......... | .......... | .......... | .......... | .......... | .......... | 490 |
| SEQIDNO:84 | 421 | .......... | .......... | .......... | .......... | .......... | .......... | .......... | 490 |
| SEQIDNO:86 | 421 | .......... | .......... | .......... | .......... | .......... | .......... | .......... | 490 |
| SEQIDNO:88 | 421 | .......... | .......... | .......... | .......... | .......... | .......... | .......... | 490 |
| SEQIDNO:90 | 421 | .......... | .......... | .......... | .......... | .......... | .......... | .......... | 490 |
| SEQIDNO:92 | 421 | .......... | .......... | .......... | .......... | .......... | .......... | .......... | 490 |
| SEQIDNO:94 | 421 | .......... | .......... | .......... | .......... | .......... | .......... | .......... | 490 |
| SEQIDNO:96 | 421 | .......... | .......... | .......... | .......... | .......... | .......... | .......... | 490 |
| SEQIDNO:98 | 421 | .......... | .......... | .......... | .......... | .......... | .......... | .......... | 490 |
| SEQIDNO:100 | 421 | .......... | .......... | .......... | .......... | .......... | .......... | .......... | 490 |
| SEQIDNO:102 | 421 | .......... | .......... | .......... | .......... | .......... | .......... | .......... | 490 |
| SEQIDNO:104 | 421 | .......... | .......... | .......... | .......... | .......... | .......... | .......... | 490 |
| SEQIDNO:106 | 421 | .......... | .......... | .......... | .......... | .......... | .......... | .......... | 490 |
| SEQIDNO:108 | 421 | .......... | .......... | .......... | .......... | .......... | .......... | .......... | 490 |
| SEQIDNO:110 | 421 | .......... | .......... | .......... | .......... | .......... | .......... | .......... | 490 |
| SEQIDNO:112 | 421 | .......... | .......... | .......... | .......... | .......... | .......... | .......... | 490 |
| SEQIDNO:114 | 421 | .......... | .......... | .......... | .......... | .......... | .......... | .......... | 490 |
| SEQIDNO:116 | 421 | .......... | .......... | .......... | .......... | .......... | .......... | .......... | 490 |
| SEQIDNO:118 | 421 | .......... | .......... | .......... | .......... | .......... | .......... | .......... | 490 |
| SEQIDNO:120 | 421 | .......... | .......... | .......... | .......... | .......... | .......... | .......... | 490 |
| SEQIDNO:122 | 421 | .......... | .......... | .......... | .......... | .......... | .......... | .......... | 490 |
| SEQIDNO:124 | 421 | .......... | .......... | .......... | .......... | .......... | .......... | .......... | 490 |
| SEQIDNO:126 | 421 | .......... | .......... | .......... | .......... | .......... | .......... | .......... | 490 |
| SEQIDNO:128 | 421 | .......... | .......... | .......... | .......... | .......... | .......... | .......... | 490 |
| SEQIDNO:130 | 421 | .......... | .......... | .......... | .......... | .......... | .......... | .......... | 490 |
| SEQIDNO:132 | 421 | .......... | .......... | .......... | .......... | .......... | .......... | .......... | 490 |
| SEQIDNO:134 | 421 | .......... | .......... | .......... | .......... | .......... | .......... | .......... | 490 |
| SEQIDNO:136 | 421 | .......... | .......... | .......... | .......... | .......... | .......... | .......... | 490 |

Figure 2, Continued

```
                   ....|..
SEQIDNO:2      491 LNDGVPL 497
SEQIDNO:4      491 ....... 497
SEQIDNO:6      491 ....... 497
SEQIDNO:8      491 ....... 497
SEQIDNO:10     491 ....... 497
SEQIDNO:12     491 ....... 497
SEQIDNO:14     491 ....... 497
SEQIDNO:16     491 ....... 497
SEQIDNO:18     491 ....... 497
SEQIDNO:20     491 ....... 497
SEQIDNO:22     491 ....... 497
SEQIDNO:24     491 ....... 497
SEQIDNO:26     491 ....... 497
SEQIDNO:28     491 ....... 497
SEQIDNO:30     491 ....... 497
SEQIDNO:32     491 ....... 497
SEQIDNO:34     491 ....... 497
SEQIDNO:36     491 ....... 497
SEQIDNO:38     491 ....... 497
SEQIDNO:40     491 ....... 497
SEQIDNO:42     491 ....... 497
SEQIDNO:44     491 ....... 497
SEQIDNO:46     491 ....... 497
SEQIDNO:48     491 ....... 497
SEQIDNO:50     491 ....... 497
SEQIDNO:52     491 ....... 497
SEQIDNO:54     491 ....... 497
SEQIDNO:56     491 ....... 497
SEQIDNO:58     491 ....... 497
SEQIDNO:60     491 ....... 497
SEQIDNO:62     491 ....... 497
SEQIDNO:64     491 ....... 497
SEQIDNO:66     491 ....... 497
SEQIDNO:68     491 ....... 497
SEQIDNO:70     491 ....... 497
SEQIDNO:72     491 ....... 497
SEQIDNO:74     491 ....... 497
SEQIDNO:76     491 ....... 497
SEQIDNO:78     491 ....... 497
SEQIDNO:80     491 ....... 497
SEQIDNO:82     491 ....... 497
SEQIDNO:84     491 ....... 497
SEQIDNO:86     491 ....... 497
SEQIDNO:88     491 ....... 497
SEQIDNO:90     491 ....... 497
SEQIDNO:92     491 ....... 497
SEQIDNO:94     491 ....... 497
SEQIDNO:96     491 ....... 497
SEQIDNO:98     491 ....... 497
SEQIDNO:100    491 ....... 497
SEQIDNO:102    491 ....... 497
SEQIDNO:104    491 ....... 497
SEQIDNO:106    491 ....... 497
SEQIDNO:108    491 ....... 497
SEQIDNO:110    491 ....... 497
SEQIDNO:112    491 ....... 497
SEQIDNO:114    491 ....... 497
SEQIDNO:116    491 ....... 497
SEQIDNO:118    491 ....... 497
SEQIDNO:120    491 ....... 497
SEQIDNO:122    491 ....... 497
SEQIDNO:124    491 ....... 497
SEQIDNO:126    491 ....... 497
SEQIDNO:128    491 ....... 497
SEQIDNO:130    491 ....... 497
SEQIDNO:132    491 ....... 497
SEQIDNO:134    491 ....... 497
SEQIDNO:136    491 ....... 497
```

CARBOXYESTERASE POLYPEPTIDES FOR AMIDE COUPLING

The present application is a divisional of co-pending U.S. patent application Ser. No. 16/218,003, filed Dec. 12, 2018, which claims priority to U.S. Prov. Pat. Appln. Ser. No. 62/598,189, filed Dec. 13, 2017, which is hereby incorporated by reference in its entirety for all purposes.

REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name, CX2-165US1_ST25.txt, is herein incorporated by reference. The electronic copy of the Sequence Listing was created on Dec. 7, 2018, with a file size of 420 Kbytes.

FIELD OF THE INVENTION

The present invention provides engineered carboxyesterases (E.C. 3.1.1) having improved non-native properties as compared to naturally occurring wild-type (WT) carboxyesterase enzymes, as well as polynucleotides encoding the engineered carboxyesterase enzymes, host cells capable of expressing the engineered carboxyesterase enzymes, and methods of applying the engineered carboxyesterase enzymes to amidation reactions.

BACKGROUND OF THE INVENTION

Amide bonds are key functional moieties in various synthetic molecules, including polymers (e.g., proteins, nylon), pesticides (e.g., propanil, chlorpropham), and pharmaceuticals (e.g., valsartan, lisdexamfetamine). A recent survey of the prevalence of reaction types employed in the pursuit of novel drug candidates listed N-acyl amidation at approximately 16% among all of those reactions. (Roughley and Jordan, J. Med. Chem., 54: 3451-3479 [2011]). When produced using traditional chemical methods, amide bond formation is a resource intensive transformation. Amide bonds are typically synthesized from carboxylic acids and amines. However, the reaction between these two functional groups does not occur spontaneously at ambient temperatures, with the necessary elimination of water only occurring at high temperatures (e.g., 200° C.). These conditions tend to be detrimental to the substrates and products.

For amidation to occur under more suitable conditions, activation of a carboxylic acid is generally required in order to couple to an amine. Carboxylic activation usually occurs with the aid of a coupling reagent to form an activated ester or anhydride or by transforming the carboxylic acid into the corresponding acid chloride (i.e., through the Schotten-Baumann reaction; See El-Faham and Albericio, Chem. Rev., 111: 6557-6602 [2011]). These reactions are performed with super- or stoichiometric concentrations of expensive coupling reagents that utilize atom-inefficient synthetic routes (See, Pattabiraman and Bode, Nature, 480: 471-479 [2011]). In addition, the reagents, as well as the resulting waste, can be highly toxic and environmentally unfriendly. At least one equivalent of waste is produced per product molecule formed in these reactions, resulting in very low atom economy. Removal of the waste from the reaction mixture is a tedious and expensive process. Thus, more efficient and environmentally friendly means are needed in the art for the production of amide bonds in various settings.

Lipases have found application on commercial scale for hydrolysis of fatty acid esters, and have been employed for amidation of esters (Seem Faber, Biotransformations in Organic Chemistry, In *Special Techniques*, Springer-Verlag, New York, N.Y., [2011]; and Kalkote, et al., Asian J. Biochem., 2: 279-283 [2007]). The formation of amide bonds using enzymes is a highly atom economical process, as there is no need to activate the carboxylic acid as under typical coupling approaches. The use of enzymes in these reactions provides great industrial value, as they are environmentally friendly, occur under mild conditions, and are less expensive than the currently available chemical routes. While eukaryotic proteases and lipases are capable of forming amide bonds (See, Adolfsson et al., Chem. Soc. Rev., 43: 2714-2742 [2014]; Guzman, et al., Elec. J. Biotech., 10(2) [2007]; and Asano et al., J. Biosci. Bioeng., 100(6):662-666 [2005]), these enzymes are typically poorly expressed in prokaryotic expression systems and may perform inferiorly in organic solvents. In contrast, with the aid of directed evolution, the carboxyesterases of the present invention have been easily produced in prokaryotic (*E. coli*) expression systems and have increased tolerance and practicality in organic solvent regimes more suited to this reaction type.

BRIEF DESCRIPTION OF THE FIGURES

FIG. 1 shows a sequence alignment of the polynucleotide sequence encoding the *E. coli* codon optimized for wild-type carboxyesterase enzyme, *Thermobifida fusca* (*T. fusca*) (SEQ ID NO: 1) against each of the polynucleotide sequences that encode the engineered carboxyesterase sequences shown in the Sequence Listing filed herewith (SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, and 135). All of these disclosed polynucleotide sequences are between 98.9-99.9% identical to each other.

FIG. 2 shows a sequence alignment of the polypeptide sequence derived from the wild-type carboxyesterase enzyme, *Thermobifida fusca* (*T. fusca*) (SEQ ID NO: 2) against each of the engineered polypeptide carboxyesterase sequences shown in the Sequence Listing filed herewith (SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 136). All of these disclosed polypeptide sequences are between 98.6-99.8% identical to each other.

SUMMARY OF THE INVENTION

The present invention provides engineered carboxyesterases (E.C. 3.1.1) having improved non-native properties as compared to naturally occurring wild-type (WT) carboxyesterase enzymes, as well as polynucleotides encoding the engineered carboxyesterase enzymes, host cells capable of expressing the engineered carboxyesterase enzymes, and methods of applying the engineered carboxyesterase enzymes to amidation reactions.

The present invention provides engineered carboxyesterases comprising polypeptide sequences having at least 80%, 85%, 86%, 87%, 88%, 89%, 90%, 91%, 92%, 93%, 94%, 95%, 96%, 97%, 98%, or 99% or more sequence identity to SEQ ID NO: 2 or a functional fragment thereof, wherein the engineered carboxyesterases comprise at least one substitution or substitution set in their polypeptide sequences, and wherein the amino acid positions of the polypeptide sequences are numbered with reference to SEQ ID NO: 2. In some embodiments, at least one substitution or substitution set in the polypeptide sequence comprises substitutions at positions selected from 39, 39/323, 62, 62/117, 63, 64, 65, 66, 68, 69, 70, 71, 71/263, 77, 77/184, 103, 103/147, 104, 104/429, 105, 107, 107/185, 108, 109, 109/117, 110, 111, 113, 114, 115, 117, 118, 118/269, 118/349, 119, 126, 147, 153, 153/215, 164, 164/271, 174, 174/282, 183, 184, 184/249, 185, 186, 187, 188, 190, 209, 210, 211, 212, 213, 213/271, 213/345, 214, 215, 215/271, 216, 217, 217/231, 224, 224/268/372, 231, 249, 249/284, 263, 268, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 345, 349, 372, 372/376, 373, 374, 376, 377, 405, 416, 420, 427, 428, 429, 438, and 470, wherein the amino acid positions of the polypeptide sequence are numbered with reference to SEQ ID NO: 2. In some additional embodiments, at least one substitution or substitution set in the polypeptide sequence comprises substitutions selected from: 39/323, 62/117, 63, 64, 65, 66, 68, 69, 70, 71, 71/263, 77/184, 103, 103/147, 104, 104/429, 105, 107, 107/185, 108, 109/117, 110, 111, 113, 114, 115, 117, 118, 118/269, 118/349, 119, 126, 153, 153/215, 164/271, 174/282, 183, 184, 184/249, 185, 186, 187, 188, 190, 209, 210, 211, 212, 213, 213/271, 213/345, 214, 215, 215/271, 216, 217, 217/231, 224/268/372, 249/284, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 372, 372/376, 373, 376, 377, 405, 420, 427, 428, and 429, wherein the amino acid positions of the polypeptide sequence are numbered with reference to SEQ ID NO: 2. In some additional embodiments, at least one substitution or substitution set in the polypeptide sequence comprises substitutions selected from: 39M/323I, 62H/117G, 63A, 63R, 63T, 63Y, 64A, 64E, 64G, 64I, 64T, 64V, 64W, 65G, 65S, 65T, 65W, 66N, 68L, 68P, 69F, 69G, 69H, 69L, 69V, 69W, 69Y, 70L, 70R, 70T, 70W, 71F, 71G, 71H/263R, 71P, 71R, 71V, 71Y, 77S/184G, 103P, 103R, 103T/147S, 104P, 104Q/429V, 105L, 107D/185W, 107L, 107P, 107S, 108G, 108K, 108Q, 108R, 108S, 108W, 109G/117M, 110A, 110H, 110P, 110S, 111L, 111M, 111R, 111S, 111V, 111W, 113P, 114A, 114H, 114Q, 115H, 115T, 115V, 117A, 117F, 118G/349V, 118I, 118N, 118N/269T, 119G, 119P, 119S, 126C, 153H/215P, 153L, 164R/271T, 174D/282V, 183P, 184F, 184G, 184P, 184S/249T, 184Y, 185A, 185T, 186C, 186G, 186P, 186R, 186T, 187P, 188E, 188G, 190H, 190K, 190L, 190M, 190Q, 190R, 190W, 209E, 209G, 209P, 209S, 209V, 210P, 210T, 210W, 211I, 211L, 211R, 211V, 212A, 212P, 212R, 212S, 213C, 213E, 213L, 213N, 213P, 213Q, 213R/345G, 213S, 213T/271K, 213V, 214K, 214L, 214T, 214V, 215K, 215M, 215P, 215R, 215R/271R, 215W, 216P, 217G, 217L, 217P, 217R, 217R/231V, 217S, 217V, 217W, 224I/268S/372F, 249V/284P, 269N, 269V, 270I, 270I/470M, 270R, 271A, 271K, 271L, 271P, 271Q/416V, 271S, 271T, 276F, 277M, 278H, 278S, 279C, 279E, 279G, 279L/280G/282M, 279V, 280E, 280G, 280S, 281P, 281V, 281Y/374N, 282A, 282C, 282Q, 282R, 282S, 282T, 282W, 283C, 283D, 283K, 283R/429V, 283T, 283V, 283Y, 284C, 284T, 284T/438T, 284V, 285L, 285M, 285P, 286V, 311I, 317C, 317P, 320A, 320F, 320G, 320G/323S, 320S, 320S/323S/372A, 320S/372A/376G, 320S/376G/377V, 320W, 321L, 321S, 323C, 323I, 323R, 323Y, 324A, 372A/376A, 372L, 373G, 376A, 376G, 376L, 376M, 377L, 377W, 377Y, 405D, 420G, 427A, 428V, and 429L, wherein the amino acid positions of the polypeptide sequence are numbered with reference to SEQ ID NO: 2. In some further embodiments, at least one substitution or substitution set in the polypeptide sequence comprises substitutions selected from: T39M/F323I, R62H/P117G, P63A, P63R, P63T, P63Y, P64A, P64E, P64G, P64I, P64T, P64V, P64W, Y65G, Y65S, Y65T, Y65W, P66N, A68L, A68P, I69F, I69G, I69H, I69L, I69V, I69W, I69Y, G70L, G70R, G70T, G70W, A71F, A71G, A71H/Q263R, A71P, A71R, A71V, A71Y, F77S/E184G, W103P, W103R, W103T/P147S, I104P, I104Q/A429V, H105L, G107D/S185W, G107L, G107P, G107S, A108G, A108K, A108Q, A108R, A108S, A108W, F109G/P117M, T110A, T110H, T110P, T110S, N111L, N111M, N111R, N111S, N111V, N111W, S113P, G114A, G114H, G114Q, S115H, S115T, S115V, P117A, P117F, V118G/A349V, V118I, V118N, V118N/A269T, Y119G, Y119P, Y119S, R126C, R153H/N215P, R153L, W164R/W271T, G174D/L282V, G183P, E184F, E184G, E184P, E184S/A249T, E184Y, S185A, S185T, A186C, A186G, A186P, A186R, A186T, G187P, A188E, A188G, S190H, S190K, S190L, S190M, S190Q, S190R, S190W, L209E, L209G, L209P, L209S, L209V, Q210P, Q210T, Q210W, S211I, S211L, S211R, S211V, G212A, G212P, G212R, G212S, A213C, A213E, A213L, A213N, A213P, A213Q, A213R/S345G, A213S, A213T/W271K, A213V, G214K, G214L, G214T, G214V, N215K, N215M, N215P, N215R, N215R/W271R, N215W, M216P, A217G, A217L, A217P, A217R, A217R/A231V, A217S, A217V, A217W, T224I/P268S/I372F, A249V/F284P, A269N, A269V, V270I, V270I/V470M, V270R, W271A, W271K, W271L, W271P, W271Q/A416V, W271S, W271T, A276F, G277M, G278H, G278S, S279C, S279E, S279G, S279L/V280G/L282M, S279V, V280E, V280G, V280S, L281P, L281V, L281Y/D374N, L282A, L282C, L282Q, L282R, L282S, L282T, L282W, P283C, P283D, P283K, P283R/A429V, P283T, P283V, P283Y, F284C, F284T, F284T/P438T, F284V, A285L, A285M, A285P, P286V, L311I, T317C, T317P, Y320A, Y320F, Y320G, Y320G/F323S, Y320S, Y320S/F323S/I372A, Y320S/I372A/V376G, Y320S/V376G/F377V, Y320W, R321L, R321S, F323C, F323I, F323R, F323Y, L324A, I372A/V376A, I372L, T373G, V376A, V376G, V376L, V376M, F377L, F377W, F377Y, P405D, P420G, D427A, R428V, and A429L, wherein the amino acid positions of the polypeptide sequence are numbered with reference to SEQ ID NO: 2. In some embodiments, the engineered carboxyesterases comprise a substitution at position 282, wherein the position is numbered with reference to SEQ ID NO: 2. In some further embodiments, the substitution at position 282 is aliphatic, non-polar, basic, polar, or aromatic. In yet some additional embodiments, the substitution is selected from: X282T, X282G, X282A, X282V, X282M, X282C, X282W, X282Q, X282S, X282T, and X282R.

The present invention also provides engineered carboxyesterases comprising a polypeptide sequences having at least 80%, 85%, 86%, 87%, 88%, 89%, 90%, 91%, 92%, 93%, 94%, 95%, 96%, 97%, 98%, 99%, or more sequence identity to SEQ ID NO: 8 or a functional fragment thereof, wherein the engineered carboxyesterases comprises at least one substitution or substitution set in the polypeptide sequences, wherein the amino acid positions of the polypeptide sequences are numbered with reference to SEQ ID NO: 8. In some embodiments, at least one substitution or substitution set in the polypeptide sequence comprises substitutions at positions selected from: 63, 63/65/108, 63/65/

108/189, 63/65/108/377, 63/65/282/285/320/323, 63/65/320/323, 63/108, 63/108/282/285/377, 63/108/285/377, 63/108/320/323, 63/189, 63/212/215, 63/212/215/268/269/343, 63/215, 63/215/269, 63/215/270/271, 63/215/343, 63/268/269/270/429, 63/377, 65/69/70/281/372, 65/69/70/372, 65/69/372, 65/70/372, 65/320, 65/320/323, 68, 68/69/189/214, 68/69/189/214/215, 68/69/189/214/215/271, 68/69/189/214/215/271/281/282/343/381, 68/69/189/214/271/280, 68/69/189/214/372, 68/69/189/214/377/381, 68/69/189/271, 68/69/189/271/280/372/381, 68/69/189/280/281/282/372/377, 68/69/189/281/282/372/377/381, 68/69/189/343/381, 68/69/189/372, 68/69/189/381, 68/69/214/215/271, 68/69/214/343, 68/69/215, 68/69/271, 68/69/282/287, 68/69/343/372, 68/108/377, 68/184, 68/184/189, 68/189/271/372, 68/189/343, 68/214/215/271/281/282/372, 68/215/271/343/372/381, 68/215/377, 68/271/372, 68/377, 69, 69/70, 69/70/331/372, 69/70/372, 69/70/459, 69/108, 69/108/270/372/377, 69/108/281/285, 69/110/215/281, 69/189, 69/189/214/271/281/282/343, 69/189/214/343/372, 69/189/215/343, 69/189/271, 69/189/271/281/282, 69/189/271/343, 69/189/271/343/381, 69/189/280/282/343/372/381, 69/189/281/373, 69/189/282, 69/189/343/381, 69/189/372, 69/189/372/377, 69/189/377, 69/212/213/215/280/281, 69/214/215/271/372/377/381, 69/214/271/282, 69/214/271/343, 69/215, 69/215/269/270/377, 69/215/271/280/281/282, 69/215/271/282, 69/215/271/372, 69/215/285/317, 69/215/323, 69/215/343, 69/215/343/372/381, 69/271, 69/271/372, 69/282, 69/282/343/372, 69/285/373, 69/372, 70, 70/212, 108, 108/189, 108/189/282/285/320, 108/189/320, 108/189/377, 108/215, 108/215/377, 108/269/270, 108/270, 108/282/285/377, 108/285, 108/320/323, 108/377, 126, 126/184/213/280/281/285/320, 126/184/213/372, 126/189/285/372, 126/215, 126/372, 181/215, 189, 189/214, 189/214/215/271/282, 189/215, 189/215/249/277, 189/215/271/281/282/377, 189/215/343/372, 189/270/285, 189/270/372, 189/280/282, 189/320/377, 189/343, 189/343/377, 189/372/377, 189/377, 189/381, 213/215/320, 214/215/271, 214/215/271/377, 214/271, 214/280/282/343/377/381, 215, 215/249/280/281/285/372, 215/271/372, 215/280/281/285/372, 215/281/285/372, 215/281/285/373, 215/281/373, 215/285, 215/285/317, 215/285/346, 215/285/445, 215/320, 215/320/372, 215/323, 215/372, 215/372/377, 215/373, 215/377, 215/381, 249/377, 269/270/281/372/377, 270/377, 271, 271/343, 271/343/372, 271/343/372/381, 280/285/372, 281/372, 282/285/320/323, 285/323, 320, 343/372, 372, 372/377, 372/381, 373, and 377, wherein the amino acid positions of the polypeptide sequence are numbered with reference to SEQ ID NO: 8. In some further embodiments, at least one substitution or substitution set in the polypeptide sequence comprises at least one substitution selected from: 63A, 63A/189A, 63A/215R/343V, 63R, 63R/65G/108G, 63R/65G/108G/189L, 63R/65G/108G/377I, 63R/65G/282A/285L/320W/323I, 63R/65G/320W/323I, 63R/108G, 63R/108G/282A/285L/377L, 63R/108G/285L/377I, 63R/108G/320W/323C, 63R/377I, 63T/215R, 63Y, 63Y/189L, 63Y/212P/215R, 63Y/212P/215R/268A/269N/343V, 63Y/215P/269N, 63Y/215R, 63Y/215R/270I/271S, 63Y/268A/269N/270I/429V, 65G/320W, 65G/320W/323I, 65W/69L/372L, 65W/69M/70A/281P/372L, 65W/69W/70L/372L, 65W/70L/372M, 68P, 68P/69L/189E/214R/271Y/280G, 68P/69L/189E/214R/372L, 68P/69L/189I/214R/215P/271Y, 68P/69L/189I/281P/282C/372L/377Y/381L, 68P/69L/189Q/214R, 68P/69L/189Q/271Y/280G/372L/381L, 68P/69L/215P, 68P/69L/271Y, 68P/69L/282C/287I, 68P/69L/343V/372L, 68P/69W/189E/214R/215P/271Y/281P/282G/343V/381L, 68P/69W/189E/280G/281P/282A/372L/377Y, 68P/69W/189E/343V/381L, 68P/69W/189I/214R/215P, 68P/69W/189I/214R/377Y/381L, 68P/69W/189I/271Y, 68P/69W/189I/372L, 68P/69W/189I/381L, 68P/69W/214R/215P/271Y, 68P/69W/214R/343V, 68P/69W/215P, 68P/108G/377L, 68P/184S, 68P/184S/189E, 68P/189I/271Y/372L, 68P/189I/343V, 68P/214R/215P/271Y/281P/282A/372L, 68P/215P/271Y/343V/372L/381L, 68P/215P/377L, 68P/271Y/372L, 68P/377L, 69F/108G/270E/372L/377L, 69F/189L, 69F/215K, 69F/215K/269L/270I/377L, 69F/215R, 69F/285L/373G, 69L, 69L/70L/331Q/372M, 69L/189E/271Y/281P/282A, 69L/189I, 69L/189I/214R/271Y/281P/282A/343V, 69L/189I/271Y/343V/381L, 69L/189I/280G/282G/343V/372L/381L, 69L/189I/282A, 69L/189Q/377Y, 69L/215P/271Y/280G/281P/282C, 69L/215P/271Y/282A, 69L/215P/271Y/372L, 69L/215P/343V/372L/381L, 69L/215R/285P/317P, 69L/271Y, 69L/271Y/372L, 69L/282C/343V/372L, 69L/372L, 69M/70A/372M, 69W, 69W/70L, 69W/70L/372M, 69W/70L/459R, 69W/108S, 69W/189E/214R/343V/372L, 69W/189E/271Y/343V, 69W/189E/372L, 69W/189I, 69W/189I/215P/343V, 69W/189I/271Y, 69W/189I/343V/381L, 69W/189Q/372L/377Y, 69W/212A/213L/215R/280G/281P, 69W/214R/215P/271Y/372L/377Y/381L, 69W/214R/271Y/282A, 69W/214R/271Y/343V, 69W/215K/343V, 69W/215P, 69W/215R, 69W/215R/323Y, 69W/282A, 69W/372M, 69Y/108G/281P/285P, 69Y/110A/215R/281P, 69Y/189L/281P/373G, 70L, 70L/212P, 108G, 108G/189I/282A/285L/320W, 108G/189L, 108G/189L/320W, 108G/189L/377I, 108G/215K, 108G/215P/377L, 108G/269L/270E, 108G/270E, 108G/282A/285L/377L, 108G/285L, 108G/320W/323I, 108G/377I, 108G/377L, 126C, 126C/184S/213S/280G/281P/285L/320G, 126C/184S/213S/372L, 126C/189I/285L/372L, 126C/215P, 126C/372L, 181L/215P, 189E/372L/377Y, 189I, 189I/214R/215P/271Y/282G, 189I/215K, 189I/215P/343V/372L, 189I/215R/249T/277M, 189I/270E/285L, 189I/270E/372L, 189I/280G/282A, 189I/320W/377I, 189I/343V, 189I/377I, 189L, 189Q, 189Q/214R, 189Q/215P/271Y/281P/282C/377Y, 189Q/343V, 189Q/343V/377Y, 189Q/381L, 213S/215P/320G, 214R/215P/271Y, 214R/215P/271Y/377Y, 214R/271Y, 214R/280G/282A/343V/377Y/381L, 215K, 215K/281P/285L/372L, 215K/281P/373G, 215K/285L/317P, 215K/285L/445L, 215K/323Y, 215K/372L, 215K/372L/377L, 215K/373G, 215P, 215P/271Y/372L, 215P/320G, 215P/320G/372L, 215P/372L, 215P/372L/377L, 215P/377L, 215P/381L, 215R, 215R/249T/280G/281P/285L/372L, 215R/280G/281P/285L/372L, 215R/281P/285L/373G, 215R/285P, 215R/320G, 215R/372L, 215W, 215W/285L/346S, 215W/285P, 215W/373G, 249T/377L, 269L/270E/281P/372L/377L, 270E/377L, 271Y, 271Y/343V, 271Y/343V/372L, 271Y/343V/372L/381L, 280G/285L/372L, 281P/372L, 282A/285L/320W/323I, 285L/323I, 320W, 343V/372L, 372L, 372L/377L, 372L/381L, 372M, 373G, and 377L, wherein the amino acid positions of the polypeptide sequence are numbered with reference to SEQ ID NO: 8. In some further embodiments, at least one substitution or substitution set in the polypeptide sequence comprises at least one substitution selected from: P63A, P63A/M189A, P63A/N215R/A343V, P63R, P63R/Y65G/A108G, P63R/Y65G/A108G/M189L, P63R/Y65G/A108G/F377I, P63R/Y65G/T282A/A285L/Y320W/F323I, P63R/Y65G/Y320W/F323I, P63R/A108G, P63R/A108G/T282A/A285L/F377L, P63R/A108G/A285L/F377I, P63R/A108G/Y320W/F323C, P63R/F377I, P63T/N215R, P63Y, P63Y/M189L, P63Y/G212P/N215R, P63Y/G212P/N215R/P268A/A269N/A343V, P63Y/N215P/A269N, P63Y/N215R, P63Y/N215R/V270I/W271S, P63Y/P268A/A269N/V270I/A429V, Y65G/Y320W, Y65G/Y320W/F323I, Y65W/I69L/I372L, Y65W/I69M/G70A/L281P/I372L, Y65W/I69W/G70L/I372L, Y65W/G70L/I372M, A68P, A68P/I69L/M189E/G214R/W271Y/V280G, A68P/I69L/M189E/G214R/I372L, A68P/I69L/M189I/G214R/N215P/W271Y, A68P/I69L/M189I/L281P/T282C/I372L/F377Y/A381L, A68P/I69L/M189Q/G214R, A68P/I69L/M189Q/W271Y/V280G/I372L/A381L, A68P/I69L/N215P, A68P/I69L/W271Y, A68P/I69L/T282C/V287I, A68P/I69L/A343V/I372L, A68P/I69W/M189E/G214R/N215P/W271Y/L281P/T282G/A343V/A381L, A68P/I69W/M189E/V280G/L281P/T282A/I372L/F377Y, A68P/I69W/M189E/A343V/A381L, A68P/I69W/M189I/G214R/N215P, A68P/I69W/M189I/G214R/F377Y/A381L, A68P/I69W/M189I/W271Y, A68P/I69W/M189I/I372L, A68P/I69W/M189I/A381L, A68P/I69W/G214R/N215P/W271Y, A68P/I69W/G214R/A343V, A68P/I69W/N215P, A68P/A108G/F377L, A68P/E184S, A68P/E184S/M189E, A68P/M189I/W271Y/I372L, A68P/M189I/A343V, A68P/G214R/N215P/W271Y/L281P/T282A/I372L, A68P/N215P/W271Y/A343V/I372L/A381L, A68P/N215P/F377L, A68P/W271Y/I372L, A68P/F377L, I69F/A108G/V270E/I372L/F377L, I69F/M189L, I69F/N215K, I69F/N215K/A269L/V270I/F377L, I69F/N215R, I69F/A285L/T373G, I69L, I69L/G70L/P331Q/I372M, I69L/M189E/W271Y/L281P/T282A, I69L/M189I, I69L/M189I/G214R/W271Y/L281P/T282A/A343V, I69L/M189I/W271Y/A343V/A381L, I69L/M189I/V280G/T282G/A343V/I372L/A381L, I69L/M189I/T282A, I69L/M189Q/F377Y, I69L/N215P/W271Y/V280G/L281P/T282C, I69L/N215P/W271Y/T282A, I69L/N215P/W271Y/I372L, I69L/N215P/A343V/I372L/A381L, I69L/N215R/A285P/T317P, I69L/W271Y, I69L/W271Y/I372L, I69L/T282C/A343V/I372L, I69L/I372L, I69M/G70A/I372M, I69W, I69W/G70L, I69W/G70L/I372M, I69W/G70L/G459R, I69W/A108S, I69W/M189E/G214R/A343V/I372L, I69W/M189E/W271Y/A343V, I69W/M189E/I372L, I69W/M189I, I69W/M189I/N215P/A343V, I69W/M189I/W271Y, I69W/M189I/A343V/A381L, I69W/M189Q/I372L/F377Y, I69W/G212A/A213L/N215R/V280G/L281P, I69W/G214R/N215P/W271Y/I372L/F377Y/A381L, I69W/G214R/W271Y/T282A, I69W/G214R/W271Y/A343V, I69W/N215K/A343V, I69W/N215P, I69W/N215R, I69W/N215R/F323Y, I69W/T282A, I69W/I372M, I69Y/A108G/L281P/A285P, I69Y/T110A/N215R/L281P, I69Y/M189L/L281P/T373G, G70L, G70L/G212P, A108G, A108G/M189I/T282A/A285L/Y320W, A108G/M189L, A108G/M189L/Y320W, A108G/M189L/F377I, A108G/N215K, A108G/N215P/F377L, A108G/A269L/V270E, A108G/V270E, A108G/T282A/A285L/F377L, A108G/A285L, A108G/Y320W/F323I, A108G/F377I, A108G/F377L, R126C, R126C/E184S/A213S/V280G/L281P/A285L/Y320G, R126C/E184S/A213S/I372L, R126C/M189I/A285L/I372L, R126C/N215P, R126C/I372L, V181L/N215P, M189E/I372L/F377Y, M189I, M189I/G214R/N215P/W271Y/T282G, M189I/N215K, M189I/N215P/A343V/I372L, M189I/N215R/A249T/G277M, M189I/V270E/A285L, M189I/V270E/I372L, M189I/V280G/T282A, M189I/Y320W/F377I, M189I/A343V, M189I/F377I, M189L, M189Q, M189Q/G214R, M189Q/N215P/W271Y/L281P/T282C/F377Y, M189Q/A343V, M189Q/A343V/F377Y, M189Q/A381L, A213S/N215P/Y320G, G214R/N215P/W271Y, G214R/N215P/W271Y/F377Y, G214R/W271Y, G214R/V280G/T282A/A343V/F377Y/A381L, N215K, N215K/L281P/A285L/I372L, N215K/L281P/T373G, N215K/A285L/T317P, N215K/A285L/V445L, N215K/F323Y, N215K/I372L, N215K/I372L/F377L, N215K/T373G, N215P, N215P/W271Y/I372L, N215P/Y320G, N215P/Y320G/I372L, N215P/I372L, N215P/I372L/F377L, N215P/F377L, N215P/A381L, N215R, N215R/A249T/V280G/L281P/A285L/I372L, N215R/V280G/L281P/A285L/I372L, N215R/L281P/A285L/T373G, N215R/A285P, N215R/Y320G, N215R/I372L, N215W, N215W/A285L/G346S, N215W/A285P, N215W/T373G, A249T/F377L, A269L/V270E/L281P/I372L/F377L, V270E/F377L, W271Y, W271Y/A343V, W271Y/A343V/I372L, W271Y/A343V/I372L/A381L, V280G/A285L/I372L, L281P/I372L, T282A/A285L/Y320W/F323I, A285L/F323I, Y320W, A343V/I372L, I372L, I372L/F377L, I372L/A381L, I372M, T373G, and F377L, wherein the amino acid positions of the polypeptide sequence are numbered with reference to SEQ ID NO: 8.

The present invention also provides engineered carboxyesterases comprising polypeptide sequences having at least 80%, 85%, 86%, 87%, 88%, 89%, 90%, 91%, 92%, 93%, 94%, 95%, 96%, 97%, 98%, 99%, or more sequence identity to SEQ ID NO: 138 or a functional fragment thereof, wherein the engineered carboxyesterases comprise at least one substitution or substitution set in their polypeptide sequences, and wherein the amino acid positions of the polypeptide sequences are numbered with reference to SEQ ID NO: 138.

The present invention also provides engineered carboxyesterases comprising polypeptide sequences having at least 80%, 85%, 86%, 87%, 88%, 89%, 90%, 91%, 92%, 93%, 94%, 95%, 96%, 97%, 98%, or 99%, sequence identity to SEQ ID NO: 140 or a functional fragment thereof, wherein the engineered carboxyesterases comprise at least one substitution or substitution set in the polypeptide sequences, and wherein the amino acid positions of the polypeptide sequences are numbered with reference to SEQ ID NO: 140.

The present invention also provides engineered carboxyesterases comprising polypeptide sequences selected from: SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 136.

The present invention further provides engineered carboxyesterases exhibiting at least one improved property as compared to the wild-type *T. fusca* carboxyesterase of SEQ ID NO:2. In some embodiments, the improved property is selected from: improved amidation activity, solvent tolerance, thermostability, pH stability, regiosteroselectivity, stereoselectivity, substrate scope, and/or reduced substrate or product inhibition, and reduced toxicity to bacterial host cells producing the engineered carboxyesterase. In some additional embodiments, the bacterial host cells comprise *E. coli*. In still some additional embodiments, the engineered carboxyesterases exhibit improved solvent tolerance to at least one solvent selected from: acetone, acetonitrile, toluene, tetrahydrofuran, isopropanol, isopropyl acetate, dimethyl sulfoxide and/or methyl ethyl ketone. In some further embodiments, the engineered carboxyesterases exhibit greater activity than wild-type *T. fusca* carboxyesterase on at least one substrate selected from: aniline, isobutylamine, n-butylamine, t-butylamine, N'-t-butoxycarbonyl-benzhydrazide, 4-methylpiperidine, O-t-butylhdroxylamine, benzylamine, 2,6-dimethylaniline, (S)-(−)-α-methylbenzylamine, (R)-(+)-α-methylbenzylamine, methyl phenylacetate, ethyl acetate, ethyl benzoate, 2-pyrazinyl ethyl ester, 4-ethyl-1H-indole ester, N,N-diethylglycyl methyl ester. In some additional embodiments, the engineered carboxyesterases exhibit greater activity than wild-type *T. fusca* carboxyesterase on at least one substrate or substrate set selected from aniline, isobutylamine, n-butylamine, t-butylamine, N'-t-butoxycarbonyl-benzhydrazide, 4-methylpiperidine, O-t-butylhdroxylamine, benzylamine, 2,6-dimethylaniline, (S)-(−)-α-methylbenzylamine, (R)-(+)-α-methylbenzylamine, methyl phenylacetate, ethyl acetate, ethyl benzoate, 2-pyrazinyl ethyl ester, 4-ethyl-1H-indole ester, N,N-diethylglycyl methyl ester. In yet some further embodiments, the engineered carboxyesterases exhibit greater activity than wild-type *T. fusca* carboxyesterase in producing at least one product selected from: acetanilide, N-n-butyl-benzylacetamide, N—[(S)-1-phenylethyl]-pyrazinylamide, N—[(S)-1-phenylethyl]-benzamide, N—[(R)-1-phenylethyl]-benzamide, N'-t-butoxycarbonyl-benzhydrazide, 1-benzoyl-4-methylpiperidine, 2-pyrazinyl-4-methylpiperidine, N-isobutyl-benzamide, N-t-butyl-benzamide, N-t-butylhydroxyl-benzamide, N-isobutyl-1H-indol-4-amide, N',N'-(diethylamino)-N-phenylacetamide, N',N'-(diethylamino)-N-benzylacetamide, N',N'-(diethylamino)-N-2,6-dimethylphenylacetamide (i.e., lidocaine). In some embodiments, the engineered carboxyesterases of the invention comprises at least one substitution selected from: X343V, X372L, X320W/G, X214R, X282C, X271Y, X65G, wherein the substitutions are numbered with reference to SEQ ID NO:2, and wherein the engineered carboxyesterase exhibits greater activity than wild-type *T. fusca* carboxyesterase on a hindered amine for formation of N',N'-(diethylamino)-N-2,6-dimethylphenylacetamide from ethyl benzoate and 2,6-dimethylaniline, as shown in the following schematic.

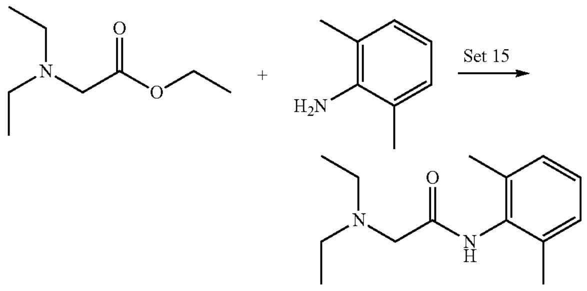

Lidocaine

In yet some additional embodiments, the engineered carboxyesterases comprise at least one substitution selected from: X268A, X63A/R, X189Q/I/E, X214R, X282G/C, X381L, and X69W, wherein the substitutions are numbered with reference to SEQ ID NO:2, and wherein the engineered carboxyesterase exhibits greater activity than wild-type *T. fusca* carboxyesterase on a secondary amine for formation of 1-benzoyl-4-methyl-piperidine from ethyl benzoate and 4-methyl-piperidine, as shown in the following schematic.

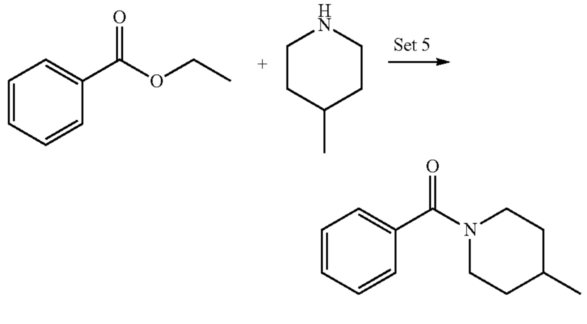

In yet some additional embodiments, the engineered carboxyesterases provided herein are purified. In still some further embodiments, the engineered carboxyesterases are immobilized. The present invention also provides compositions comprising at least one engineered carboxyesterase provided herein.

The present invention also provides polynucleotide sequences encoding at least one engineered carboxyesterase provided herein. In some embodiments, the polynucleotide sequences encode at least one engineered carboxyesterase comprising a polypeptide sequence having at least 80%, 85%, 86%, 87%, 88%, 89%, 90%, 91%, 92%, 93%, 94%, 95%, 96%, 97%, 98%, 99%, or more sequence identity to SEQ ID NO: 2 or a functional fragment thereof, wherein the engineered carboxyesterase comprises at least one substitution or substitution set in its polypeptide sequence, wherein the amino acid positions of the polypeptide sequence are numbered with reference to SEQ ID NO: 2. In some embodiments, the polynucleotide sequences encode at least one engineered carboxyesterase comprising substitutions at positions selected from: 39, 39/323, 62, 62/117, 63, 64, 65, 66, 68, 69, 70, 71, 71/263, 77, 77/184, 103, 103/147, 104, 104/429, 105, 107, 107/185, 108, 109, 109/117, 110, 111, 113, 114, 115, 117, 118, 118/269, 118/349, 119, 126, 147, 153, 153/215, 164, 164/271, 174, 174/282, 183, 184, 184/249, 185, 186, 187, 188, 190, 209, 210, 211, 212, 213, 213/271, 213/345, 214, 215, 215/271, 216, 217, 217/231, 224, 224/268/372, 231, 249, 249/284, 263, 268, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 345, 349, 372, 372/376, 373, 374, 376, 377, 405, 416, 420, 427, 428, 429, 438, and 470, wherein the amino acid positions of the polypeptide sequence are numbered with reference to SEQ ID NO: 2. In some additional embodiments, the polynucleotide sequences encode at least one engineered carboxyesterase comprising at least one substitution or substitution set selected from: 39/323, 62/117, 63, 64, 65, 66, 68, 69, 70, 71, 71/263, 77/184, 103, 103/147, 104, 104/429, 105, 107, 107/185, 108, 109/117, 110, 111, 113, 114, 115, 117, 118, 118/269, 118/349, 119, 126, 153, 153/215, 164/271, 174/282, 183, 184, 184/249, 185, 186, 187, 188, 190, 209, 210, 211, 212, 213, 213/271, 213/345, 214, 215, 215/271, 216, 217, 217/231, 224/268/372, 249/284, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 372, 372/376, 373, 376, 377, 405, 420, 427, 428, and 429, wherein the amino acid positions of the polypeptide sequence are numbered with reference to SEQ ID NO: 2. In some additional embodiments, the polynucleotide sequences encode at least one engineered carboxyesterase comprising at least one substitution or substitution set selected from: 39M/323I, 62H/117G, 63A, 63R, 63T, 63Y, 64A, 64E, 64G, 64I, 64T, 64V, 64W, 65G, 65S, 65T, 65W, 66N, 68L, 68P, 69F, 69G, 69H, 69L, 69V, 69W, 69Y, 70L, 70R, 70T, 70W, 71F, 71G, 71H/263R, 71P, 71R, 71V, 71Y, 77S/184G, 103P, 103R, 103T/147S, 104P, 104Q/429V, 105L, 107D/185W, 107L, 107P, 107S, 108G, 108K, 108Q, 108R, 108S, 108W, 109G/117M, 110A, 110H, 110P, 110S, 111L, 111M, 111R, 111S, 111V, 111W, 113P, 114A, 114H, 114Q, 115H, 115T, 115V, 117A, 117F, 118G/349V, 118I, 118N, 118N/269T, 119G, 119P, 119S, 126C, 153H/215P, 153L, 164R/271T, 174D/282V, 183P, 184F, 184G, 184P, 184S/249T, 184Y, 185A, 185T, 186C, 186G, 186P, 186R, 186T, 187P, 188E, 188G, 190H, 190K, 190L, 190M, 190Q, 190R, 190W, 209E, 209G, 209P, 209S, 209V, 210P, 210T, 210W, 211I, 211L, 211R, 211V, 212A, 212P, 212R, 212S, 213C, 213E, 213L, 213N, 213P, 213Q, 213R/345G, 213S, 213T/271K, 213V, 214K, 214L, 214T, 214V, 215K, 215M, 215P, 215R, 215R/271R, 215W, 216P, 217G, 217L, 217P, 217R, 217R/231V, 217S, 217V, 217W, 224I/268S/372F, 249V/284P, 269N, 269V, 270I, 270I/470M, 270R, 271A, 271K, 271L, 271P, 271Q/416V, 271S, 271T, 276F, 277M, 278H, 278S, 279C, 279E, 279G, 279L/280G/282M, 279V, 280E, 280G, 280S, 281P, 281V, 281Y/374N, 282A, 282C, 282Q, 282R, 282S, 282T, 282W, 283C, 283D, 283K, 283R/429V, 283T, 283V, 283Y, 284C, 284T, 284T/438T, 284V, 285L, 285M, 285P, 286V, 311I, 317C, 317P, 320A, 320F, 320G, 320G/323S, 320S, 320S/323S/372A, 320S/372A/376G, 320S/376G/377V, 320W, 321L, 321S, 323C, 323I, 323R, 323Y, 324A, 372A/376A, 372L, 373G, 376A, 376G, 376L, 376M, 377L, 377W, 377Y, 405D, 420G, 427A, 428V, and 429L, wherein the amino acid positions are numbered with reference to SEQ ID NO: 2. In some further embodiments, the polynucleotide sequences encode at least one engineered carboxyesterase comprising at least one substitution or substitution set selected from: T39M/F323I, R62H/P117G, P63A, P63R, P63T, P63Y, P64A, P64E, P64G, P64I, P64T, P64V, P64W, Y65G, Y65S, Y65T, Y65W, P66N, A68L, A68P, I69F, I69G, I69H, I69L, I69V, I69W, I69Y, G70L, G70R, G70T, G70W, A71F, A71G, A71H/Q263R, A71P, A71R, A71V, A71Y, F77S/E184G, W103P, W103R, W103T/P147S, I104P, I104Q/A429V, H105L, G107D/S185W, G107L, G107P, G107S, A108G, A108K, A108Q, A108R, A108S, A108W, F109G/P117M, T110A, T110H, T110P, T110S, N111L, N111M, N111R, N111S, N111V, N111W, S113P, G114A, G114H, G114Q, S115H, S115T, S115V, P117A, P117F, V118G/A349V, V118I, V118N, V118N/A269T, Y119G, Y119P, Y119S, R126C, R153H/N215P, R153L, W164R/W271T, G174D/L282V, G183P, E184F, E184G, E184P, E184S/A249T, E184Y, S185A, S185T, A186C, A186G, A186P, A186R, A186T, G187P, A188E, A188G, S190H, S190K, S190L, S190M, S190Q, S190R, S190W, L209E, L209G, L209P, L209S, L209V, Q210P, Q210T, Q210W, S211I, S211L, S211R, S211V, G212A, G212P, G212R, G212S, A213C, A213E, A213L, A213N, A213P, A213Q, A213R/S345G, A213S, A213T/W271K, A213V, G214K, G214L, G214T, G214V, N215K, N215M, N215P, N215R, N215R/W271R, N215W, M216P, A217G, A217L, A217P, A217R, A217R/A231V, A217S, A217V, A217W, T224I/P268S/I372F, A249V/F284P, A269N, A269V, V270I, V270I/V470M, V270R, W271A, W271K, W271L, W271P, W271Q/A416V, W271S, W271T, A276F, G277M, G278H, G278S, S279C, S279E, S279G, S279L/V280G/L282M, S279V, V280E, V280G, V280S, L281P, L281V, L281Y/D374N, L282A, L282C, L282Q, L282R, L282S, L282T, L282W, P283C, P283D, P283K, P283R/A429V, P283T, P283V, P283Y, F284C, F284T, F284T/P438T, F284V, A285L, A285M, A285P, P286V, L311I, T317C, T317P, Y320A, Y320F, Y320G, Y320G/F323S, Y320S, Y320S/F323S/I372A, Y320S/I372A/V376G, Y320S/V376G/F377V, Y320W, R321L, R321S, F323C, F323I, F323R, F323Y, L324A, I372A/V376A, I372L, T373G, V376A, V376G, V376L, V376M, F377L, F377W, F377Y, P405D, P420G, D427A, R428V, and A429L, wherein the amino acids are numbered with reference to SEQ ID NO: 2. In some embodiments, the polynucleotide sequences encode at least one engineered carboxyesterase comprising a substitution at position 282, wherein the position is numbered with reference to SEQ ID NO: 2. In some further embodiments, the substitution at position 282 is aliphatic, non-polar, basic, polar, or aromatic. In yet some additional embodiments, the substitution selected from X282T, X282G, X282A, X282V, X282M, X282C, X282W, X282Q, X282S, X282T, and X282R.

The present invention also provides polynucleotide sequences encoding at least one engineered carboxyesterase comprising a polypeptide sequence having at least 80%, 85%, 86%, 87%, 88%, 89%, 90%, 91%, 92%, 93%, 94%, 95%, 96%, 97%, 98%, 99%, or more sequence identity to SEQ ID NO: 8 or a functional fragment thereof, wherein the engineered carboxyesterase comprises at least one substitution or substitution set in its polypeptide sequence, wherein the amino acid positions of the polypeptide sequence are numbered with reference to SEQ ID NO: 8. In some embodiments, the polynucleotide sequences encode engineered carboxyesterases comprising at least one substitution or substitution set at positions selected from: 63, 63/65/108, 63/65/108/189, 63/65/108/377, 63/65/282/285/320/323, 63/65/320/323, 63/108, 63/108/282/285/377, 63/108/285/377, 63/108/320/323, 63/189, 63/212/215, 63/212/215/268/269/343, 63/215, 63/215/269, 63/215/270/271, 63/215/343, 63/268/269/270/429, 63/377, 65/69/70/281/372, 65/69/70/372, 65/69/372, 65/70/372, 65/320, 65/320/323, 68, 68/69/189/214, 68/69/189/214/215, 68/69/189/214/215/271, 68/69/189/214/215/271/281/282/343/381, 68/69/189/214/271/280, 68/69/189/214/372, 68/69/189/214/377/381, 68/69/189/271, 68/69/189/271/280/372/381, 68/69/189/280/281/282/372/377, 68/69/189/281/282/372/377/381, 68/69/189/343/381, 68/69/189/372, 68/69/189/381, 68/69/214/215/271, 68/69/214/343, 68/69/215, 68/69/271, 68/69/282/287, 68/69/343/372, 68/108/377, 68/184, 68/184/189, 68/189/271/372, 68/189/343, 68/214/215/271/281/282/372, 68/215/271/343/372/381, 68/215/377, 68/271/372, 68/377, 69, 69/70, 69/70/331/372, 69/70/372, 69/70/459, 69/108, 69/108/270/372/377, 69/108/281/285, 69/110/215/281, 69/189, 69/189/214/271/281/282/343, 69/189/214/343/372, 69/189/215/343, 69/189/271, 69/189/271/281/282, 69/189/271/343, 69/189/271/343/381, 69/189/280/282/343/372/381, 69/189/281/373, 69/189/282, 69/189/343/381, 69/189/372, 69/189/372/377, 69/189/377, 69/212/213/215/280/281, 69/214/215/271/372/377/381, 69/214/271/282, 69/214/271/343, 69/215, 69/215/269/270/377, 69/215/271/280/281/282, 69/215/271/282, 69/215/271/372, 69/215/285/317, 69/215/323, 69/215/343, 69/215/343/372/381, 69/271, 69/271/372, 69/282, 69/282/343/372, 69/285/373, 69/372, 70, 70/212, 108, 108/189, 108/189/282/285/320, 108/189/320, 108/189/377, 108/215, 108/215/377, 108/269/270, 108/270, 108/282/285/377, 108/285, 108/320/323, 108/377, 126, 126/184/213/280/281/285/320, 126/184/213/372, 126/189/285/372, 126/215, 126/372, 181/215, 189, 189/214, 189/214/215/271/282, 189/215, 189/215/249/277, 189/215/271/281/282/377, 189/215/343/372, 189/270/285, 189/270/372, 189/280/282, 189/320/377, 189/343, 189/343/377, 189/372/377, 189/377, 189/381, 213/215/320, 214/215/271, 214/215/271/377, 214/271, 214/280/282/343/377/381, 215, 215/249/280/281/285/372, 215/271/372, 215/280/281/285/372, 215/281/285/372, 215/281/285/373, 215/281/373, 215/285, 215/285/317, 215/285/346, 215/285/445, 215/320, 215/320/372, 215/323, 215/372, 215/372/377, 215/373, 215/377, 215/381, 249/377, 269/270/281/372/377, 270/377, 271, 271/343, 271/343/372, 271/343/372/381, 280/285/372, 281/372, 282/285/320/323, 285/323, 320, 343/372, 372, 372/377, 372/381, 373, and 377, wherein the amino acid positions are numbered with reference to SEQ ID NO: 8. In some further embodiments, the polynucleotide sequence encodes an engineered carboxyesterase comprising at least one substitution or substitution set selected from: 63A, 63A/189A, 63A/215R/343V, 63R, 63R/65G/108G, 63R/65G/108G/189L, 63R/65G/108G/377I, 63R/65G/282A/285L/320W/323I, 63R/65G/320W/323I, 63R/108G, 63R/108G/282A/285L/377L, 63R/108G/285L/377I, 63R/108G/320W/323C, 63R/377I, 63T/215R, 63Y, 63Y/189L, 63Y/212P/215R, 63Y/212P/215R/268A/269N/343V, 63Y/215P/269N, 63Y/215R, 63Y/215R/270I/271S, 63Y/268A/269N/270I/429V, 65G/320W, 65G/320W/323I, 65W/69L/372L, 65W/69M/70A/281P/372L, 65W/69W/70L/372L, 65W/70L/372M, 68P, 68P/69L/189E/214R/271Y/280G, 68P/69L/189E/214R/372L, 68P/69L/189I/214R/215P/271Y, 68P/69L/189I/281P/282C/372L/377Y/381L, 68P/69L/189Q/214R, 68P/69L/189Q/271Y/280G/372L/381L, 68P/69L/215P, 68P/69L/271Y, 68P/69L/282C/287I, 68P/69L/343V/372L, 68P/69W/189E/214R/215P/271Y/281P/282G/343V/381L, 68P/69W/189E/280G/281P/282A/372L/377Y, 68P/69W/189E/343V/381L, 68P/69W/189I/214R/215P, 68P/69W/189I/214R/377Y/381L, 68P/69W/189I/271Y, 68P/69W/189I/372L, 68P/69W/189I/381L, 68P/69W/214R/215P/271Y, 68P/69W/214R/343V, 68P/69W/215P, 68P/108G/377L, 68P/184S, 68P/184S/189E, 68P/189I/271Y/372L, 68P/189I/343V, 68P/214R/215P/271Y/281P/282A/372L, 68P/215P/271Y/343V/372L/381L, 68P/215P/377L, 68P/271Y/372L, 68P/377L, 69F/108G/270E/372L/377L, 69F/189L, 69F/215K, 69F/215K/269L/270I/377L, 69F/215R, 69F/285L/373G, 69L, 69L/70L/331Q/372M, 69L/189E/271Y/281P/282A, 69L/189I, 69L/189I/214R/271Y/281P/282A/343V, 69L/189I/271Y/343V/381L, 69L/189I/280G/282G/343V/372L/381L, 69L/189I/282A, 69L/189Q/377Y, 69L/215P/271Y/280G/281P/282C, 69L/215P/271Y/282A, 69L/215P/271Y/372L, 69L/215P/343V/372L/381L, 69L/215R/285P/317P, 69L/271Y, 69L/271Y/372L, 69L/282C/343V/372L, 69L/372L, 69M/70A/372M, 69W, 69W/70L, 69W/70L/372M, 69W/70L/459R, 69W/108S, 69W/189E/214R/343V/372L, 69W/189E/271Y/343V, 69W/189E/372L, 69W/189I, 69W/189I/215P/343V, 69W/189I/271Y, 69W/189I/343V/381L, 69W/189Q/372L/377Y, 69W/212A/213L/215R/280G/281P, 69W/214R/215P/271Y/372L/377Y/381L, 69W/214R/271Y/282A, 69W/214R/271Y/343V, 69W/215K/343V, 69W/215P, 69W/215R, 69W/215R/323Y, 69W/282A, 69W/372M, 69Y/108G/281P/285P, 69Y/110A/215R/281P, 69Y/189L/281P/373G, 70L, 70L/212P, 108G, 108G/189I/282A/285L/320W, 108G/189L, 108G/189L/320W, 108G/189L/377I, 108G/215K, 108G/215P/377L, 108G/269L/270E, 108G/270E, 108G/282A/285L/377L, 108G/285L, 108G/320W/323I, 108G/377I, 108G/377L, 126C, 126C/184S/213S/280G/281P/285L/320G, 126C/184S/213S/372L, 126C/189I/285L/372L, 126C/215P, 126C/372L, 181L/215P, 189E/372L/377Y, 189I, 189I/214R/215P/271Y/282G, 189I/215K, 189I/215P/343V/372L, 189I/215R/249T/277M, 189I/270E/285L, 189I/270E/372L, 189I/280G/282A, 189I/320W/377I, 189I/343V, 189I/377I, 189L, 189Q, 189Q/214R, 189Q/215P/271Y/281P/282C/377Y, 189Q/343V, 189Q/343V/377Y, 189Q/381L, 213S/215P/320G, 214R/215P/271Y, 214R/215P/271Y/377Y, 214R/271Y, 214R/280G/282A/343V/377Y/381L, 215K, 215K/281P/285L/372L, 215K/281P/373G, 215K/285L/317P, 215K/285L/445L, 215K/323Y, 215K/372L, 215K/372L/377L, 215K/373G, 215P, 215P/271Y/372L, 215P/320G, 215P/320G/372L, 215P/372L, 215P/372L/377L, 215P/377L, 215P/381L, 215R, 215R/249T/280G/281P/285L/372L, 215R/280G/281P/285L/372L, 215R/281P/285L/373G, 215R/285P, 215R/320G, 215R/372L, 215W, 215W/285L/346S, 215W/285P, 215W/373G, 249T/377L, 269L/270E/281P/372L/377L, 270E/377L, 271Y, 271Y/343V, 271Y/343V/372L, 271Y/343V/372L/381L, 280G/285L/372L, 281P/372L, 282A/285L/320W/323I, 285L/323I, 320W, 343V/372L, 372L, 372L/377L, 372L/381L, 372M, 373G, and 377L, wherein the amino acid positions are numbered with reference to SEQ ID NO: 8. In some further embodiments, the polynucleotide sequence encodes an engineered carboxyesterase comprisng at least one substitution or substitution set selected from: P63A, P63A/M189A, P63A/N215R/A343V, P63R, P63R/Y65G/A108G, P63R/Y65G/A108G/M189L, P63R/Y65G/A108G/F377I, P63R/Y65G/T282A/A285L/Y320W/F323I, P63R/Y65G/Y320W/F323I, P63R/A108G, P63R/A108G/T282A/A285L/F377L, P63R/A108G/A285L/F377I, P63R/A108G/Y320W/F323C, P63R/F377I, P63T/N215R, P63Y, P63Y/M189L, P63Y/G212P/N215R, P63Y/G212P/N215R/P268A/A269N/A343V, P63Y/N215P/A269N, P63Y/N215R, P63Y/N215R/V270I/W271S, P63Y/P268A/A269N/V270I/A429V, Y65G/Y320W, Y65G/Y320W/F323I, Y65W/I69L/I372L, Y65W/I69M/G70A/L281P/I372L, Y65W/I69W/G70L/I372L, Y65W/G70L/I372M, A68P, A68P/I69L/M189E/G214R/W271Y/V280G, A68P/I69L/M189E/G214R/I372L, A68P/I69L/M189I/G214R/N215P/W271Y, A68P/I69L/M189I/L281P/T282C/I372L/F377Y/A381L, A68P/I69L/M189Q/G214R, A68P/I69L/M189Q/W271Y/V280G/I372L/A381L, A68P/I69L/N215P, A68P/I69L/W271Y, A68P/I69L/T282C/V287I, A68P/I69L/A343V/I372L, A68P/I69W/M189E/G214R/N215P/W271Y/L281P/T282G/A343V/A381L, A68P/I69W/M189E/V280G/L281P/T282A/I372L/F377Y, A68P/I69W/M189E/A343V/A381L, A68P/I69W/M189I/G214R/N215P, A68P/I69W/M189I/G214R/F377Y/A381L, A68P/I69W/M189I/W271Y, A68P/I69W/M189I/I372L, A68P/I69W/M189I/A381L, A68P/I69W/G214R/N215P/W271Y, A68P/I69W/G214R/A343V, A68P/I69W/N215P, A68P/A108G/F377L, A68P/E184S, A68P/E184S/M189E, A68P/M189I/W271Y/I372L, A68P/M189I/A343V, A68P/G214R/N215P/W271Y/L281P/T282A/I372L, A68P/N215P/W271Y/A343V/I372L/A381L, A68P/N215P/F377L, A68P/W271Y/I372L, A68P/F377L, I69F/A108G/V270E/I372L/F377L, I69F/M189L, I69F/N215K, I69F/N215K/A269L/V270I/F377L, I69F/N215R, I69F/A285L/T373G, I69L, I69L/G70L/P331Q/I372M, I69L/M189E/W271Y/L281P/T282A, I69L/M189I, I69L/M189I/G214R/W271Y/L281P/T282A/A343V, I69L/M189I/W271Y/A343V/A381L, I69L/M189I/V280G/T282G/A343V/I372L/A381L, I69L/M189I/T282A, I69L/M189Q/F377Y, I69L/N215P/W271Y/V280G/L281P/T282C, I69L/N215P/W271Y/T282A, I69L/N215P/W271Y/I372L, I69L/N215P/A343V/I372L/A381L, I69L/N215R/A285P/T317P, I69L/W271Y, I69L/W271Y/I372L, I69L/T282C/A343V/I372L, I69L/I372L, I69M/G70A/I372M, I69W, I69W/G70L, I69W/G70L/I372M, I69W/G70L/G459R, I69W/A108S, I69W/M189E/G214R/A343V/I372L, I69W/M189E/W271Y/A343V, I69W/M189E/I372L, I69W/M189I, I69W/M189I/N215P/A343V, I69W/M189I/W271Y, I69W/M189I/A343V/A381L, I69W/M189Q/I372L/F377Y, I69W/G212A/A213L/N215R/V280G/L281P, I69W/G214R/N215P/W271Y/I372L/F377Y/A381L, I69W/G214R/W271Y/T282A, I69W/G214R/W271Y/A343V, I69W/N215K/A343V, I69W/N215P, I69W/N215R, I69W/N215R/F323Y, I69W/T282A, I69W/I372M, I69Y/A108G/L281P/A285P, I69Y/T110A/N215R/L281P, I69Y/M189L/L281P/T373G, G70L, G70L/G212P, A108G, A108G/M189I/T282A/A285L/Y320W, A108G/M189L, A108G/M189L/Y320W, A108G/M189L/F377I, A108G/N215K, A108G/N215P/F377L, A108G/A269L/V270E, A108G/V270E, A108G/T282A/A285L/F377L, A108G/A285L, A108G/Y320W/F323I, A108G/F377I, A108G/F377L, R126C, R126C/E184S/A213S/V280G/L281P/A285L/Y320G, R126C/E184S/A213S/I372L, R126C/M189I/A285L/I372L, R126C/N215P, R126C/I372L, V181L/N215P, M189E/

I372L/F377Y, M189I, M189I/G214R/N215P/W271Y/T282G, M189I/N215K, M189I/N215P/A343V/I372L, M189I/N215R/A249T/G277M, M189I/V270E/A285L, M189I/V270E/I372L, M189I/V280G/T282A, M189I/Y320W/F377I, M189I/A343V, M189I/F377I, M189L, M189Q, M189Q/G214R, M189Q/N215P/W271Y/L281P/T282C/F377Y, M189Q/A343V, M189Q/A343V/F377Y, M189Q/A381L, A213S/N215P/Y320G, G214R/N215P/W271Y, G214R/N215P/W271Y/F377Y, G214R/W271Y, G214R/V280G/T282A/A343V/F377Y/A381L, N215K, N215K/L281P/A285L/I372L, N215K/L281P/T373G, N215K/A285L/T317P, N215K/A285L/V445L, N215K/F323Y, N215K/I372L, N215K/I372L/F377L, N215K/T373G, N215P, N215P/W271Y/I372L, N215P/Y320G, N215P/Y320G/I372L, N215P/I372L, N215P/I372L/F377L, N215P/F377L, N215P/A381L, N215R, N215R/A249T/V280G/L281P/A285L/I372L, N215R/V280G/L281P/A285L/I372L, N215R/L281P/A285L/T373G, N215R/A285P, N215R/Y320G, N215R/I372L, N215W, N215W/A285L/G346S, N215W/A285P, N215W/T373G, A249T/F377L, A269L/V270E/L281P/I372L/F377L, V270E/F377L, W271Y, W271Y/A343V, W271Y/A343V/I372L, W271Y/A343V/I372L/A381L, V280G/A285L/I372L, L281P/I372L, T282A/A285L/Y320W/F323I, A285L/F323I, Y320W, A343V/I372L, I372L, I372L/F377L, I372L/A381L, I372M, T373G, and F377L, wherein the amino acid positions are numbered with reference to SEQ ID NO: 8.

The present invention also provides polynucleotide sequences encoding at least one engineered carboxyesterase or a functional fragment thereof, the polynucleotide sequence comprising at least 85%, 86%, 87%, 88%, 89%, 90%, 91%, 92%, 93%, 94%, 95%, 96%, 97%, 98%, 99%, or more sequence identity to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and/or 139.

The present invention further provides polynucleotide sequences encoding engineered carboxyesterases provided herein, wherein the polynucleotide sequence is operably linked to a control sequence. In some additional embodiments, the polynucleotide sequences are codon optimized.

The present invention also provides expression vectors comprising at least one polynucleotide sequence encoding an engineered carboxyesterase provided herein. In addition, the present invention provides host cells comprising at least one expression vector provided herein. In some embodiments, the present invention also provides host cells comprising at least one polynucleotide sequence encoding at least one engineered carboxyesterase provided herein.

The present invention also provides methods of producing an engineered carboxyesterase in a host cell, comprising culturing a host cell comprising an expression vector comprising at least one polynucleotide encoding at least one engineered carboxyesterase, under suitable conditions, such that at least one engineered carboxyesterase is produced. In some embodiments, the methods further comprise recovering at least one engineered carboxyesterase from the culture and/or host cell. In some additional embodiments, the methods further comprise the step of purifying the at least one engineered carboxyesterase.

DESCRIPTION OF THE INVENTION

The present invention provides engineered carboxyesterases (E.C. 3.1.1) having improved non-native properties as compared to naturally occurring wild-type (WT) carboxyesterase enzymes, as well as polynucleotides encoding the engineered carboxyesterase enzymes, host cells capable of expressing the engineered carboxyesterase enzymes, and methods of applying the engineered carboxyesterase enzymes to amidation reactions.

Switching enzyme function and enzyme substrate scope is feasible, as it has been observed that enzyme active sites are capable of catalyzing several different chemical reactions via one amino acid mutation (See Rauwerdink and Kazluaskas, ACS Cat., 5: 6153-6176 [2015]). To improve carboxyesterase functionality, and substrate scope, wild-type carboxyesterases were subjected to directed evolution. The resultant variants possessed improved capabilities in the generation of amide bonds using a diverse set of amine and carboxyester substrate pairs (See, Scheme 1, below). The engineered carboxyesterases had activity not only in aqueous systems, but also are active in the presence of organic co-solvents and even near-total organic solvent concentrations (e.g., ~98% v/v), as described herein. Further, immobilization of these engineered carboxyesterases facilitates continuous flow operations for amide production, aids in the purification of the final amide product, as well as improves the efficiency and overall cost of amidation operations.

The present invention provides novel engineered carboxyesterase polypeptides, along with their corresponding polynucleotide sequences and methods of application, which demonstrate general amide bond formation (See, Scheme 1, below). In some embodiments, the engineered polypeptides possess modified properties that broaden the functionality and scope of activity of these enzymes as compared to the naturally occurring wild-type *Thermobifida fusca* (*T. fusca*) carboxyesterase (SEQ ID NO: 2). The improved carboxyesterase properties include, but are not limited to: solvent stability, enzymatic activity, regiospecificity, stereoselectivity, reduced host cell toxicity, thermal stability, pH stability, substrate scope, and/or reduced substrate or product inhibition. The present invention also provides polynucleotides that have been improved to facilitate expression of the desired polypeptides in non-natural host organisms (e.g., *E. coli*).

In some embodiments, the carboxyesterase polypeptides provided herein possess modified properties that expand the functionality and scope of activity of these enzymes as compared to the naturally occurring wild-type *Geobacillus stearothermophilus* carboxyesterase (SEQ ID NO: 138). In some instances, these polypeptides are carboxyesterase enzymes which are enhanced relative to the wild-type *Mycobacterium tuberculosis* carboxyesterase (SEQ ID NO: 140). Further, in some embodiments, the present invention provides polynucleotides that have been improved to facilitate expression of the desired polypeptides in a non-native host organisms (e.g., *E. coli*).

The improved properties of the carboxyesterase variants presented are related to the engineered amidation polypeptides containing residue differences at specific residue positions as compared to the reference carboxyesterase sequence of *T. fusca* or another referred engineered amidation polypeptide, such as the sequence of SEQ ID NO: 8. In some embodiments, the residue differences are present at least one of the following amino acid positions: X39, X62, X63, X64, X65, X66, X68, X69, X70, X71, X77, X103, X104, X105, X107, X108, X109, X110, X111, X113, X114, X115, X117, X118, X119, X126, X147, X153, X164, X174, X181, X183, X184, X185, X186, X187, X188, X189, X190, X209, X210, X211, X212, X213, X214, X215, X216, X217, X224, X231, X249, X263, X268, X269, X270, X271, X276, X277, X278, X279, X280, X281, X282, X283, X284, X285, X286, X287, X311, X317, X320, X321, X323, X324, X331, X343, X345, X346, X349, X372, X373, X374, X376, X377, X381, X405, X416, X420, X427, X428, X429, X438, X445, X459, and X470.

In some embodiments, the engineered carboxyesterases provided herein are characterized as exhibiting increased thermostability as compared to the wild-type polypeptide under the same reaction conditions. The engineered carboxyesterases are capable of mediating amidation conversion (See, Scheme 1, below), as indicated by continued formation of products, at higher temperatures and for longer times than the WT carboxyesterase. In some embodiments, the engineered carboxyesterase polypeptides maintain or have increased activity in the presence of higher concentrations of substrate ester (I) and/or amine (II), such as 300 mM isobutylamine. In some embodiments, the engineered carboxyesterase polypeptides maintain or have increased activity under conditions with various pH levels (e.g., pH 9.0), as compared to the WT carboxyesterase. In some embodiments, the engineered polypeptides with increased thermostability, pH stability, and/or substrate stability comprise and amino acid sequence that is at least 80%, 82%, 85%, 86%, 87%, 88%, 89%, 90%, 91%, 92%, 93%, 94%, 95%, 96%, 97%, 98%, 99%, or more identical to the reference sequence of SEQ ID NOs: 2 and/or 8.

In some embodiments, the engineered carboxyesterases are capable of biocatalytic activity improvements for converting the substrate compound(s) to product(s) (See, Scheme 1, below) at least about 1.2-fold, 1.5-fold, 2-fold, 3-fold, 4-fold, 5-fold, 10-fold, 20-fold, 30-fold, 40-fold, 50-fold, 150-fold, 500-fold or more relative to the activity of wild-type carboxyesterase (SEQ ID NO: 2) or a reference engineered carboxyesterase (SEQ ID NO: 8), under suitable reaction conditions. In some embodiments, these improvements in enzyme activity extend to associated increases in thermostability, stereoselectivity, stereospecificity, regiospecificity, solvent stability, pH stability, and/or substrate binding, or reduced substrate and/or product inhibition.

In some embodiments, the engineered carboxyesterases are characterized by activity on a variety of structurally different carboxyester (I) or amine (II) substrates. In some embodiments, engineered polypeptides are capable of biocatalytically converting esters (N,N-diethylamino glycine methyl ester, ethyl benzoate, ethyl acetate, pyrazine-2-carboxylic ethyl ester, 1H-indole-4-carboxylic ethyl ester, methyl phenylacetate), and amines (n-butylamine, isobutylamine, aniline, benzylamine, 2,6-dimethylaniline, t-butylamine, N'-t-butoxycarbonyl-benzhydrazide, 4-methylpiperidine, 0-t-butylhydroxylamine, 2,6-dimethylaniline, or stereoselective conversion of (S)-(−)-α-methylbenzylamine, (R)-(+)-α-methylbenzylamine), to their corresponding amide product at a greater rate than the WT polypeptides of SEQ ID NO: 2 and/or the engineered polypeptide SEQ ID NO: 8.

In some embodiments, the improved engineered variant polypeptide comprises an amino acid sequence corresponding to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88. 90, 92, 94, 96, 98, 100, 102, 104, 106, 108, 110, 112, 114, 116, 118, 120, 122, 124, 126, 128, 130, 132, 134, 136, 138, or 140. In some embodiments, the carboxyesterase enzymes provided herein are obtained by mutagenizing a gene encoding an engineered carboxyesterase polypeptide that is at least 80%, 85%, 86%, 87%, 88%, 89%, 90%, 91%, 92%, 93%, 94%, 95%, 96%, 97%, 98%, 99%, or more identical to the amino acid sequence of the naturally-occurring *T. fusca* carboxyesterase (SEQ ID NO: 2).

In some additional embodiments of the present invention, the carboxyesterase polypeptide variants are encoded by polynucleotides or polynucleotides that hybridize to yield such polynucleotides under highly stringent conditions, as provided herein. In some embodiments, the polynucleotides comprise promoters and/or other regulatory elements useful for expression of the encoded engineered carboxyesterase, and can utilize codons optimized for specific expression systems.

In some embodiments, the polynucleotides encoding the improved carboxyesterase enzymes comprise a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and 139.

In some additional embodiments, the present invention provides host cells comprising the polynucleotides and/or expression vectors provided herein. In some embodiments, the host cells are *T. fusca*, while in some alternative embodiments, they are other organisms (e.g., *E. coli*). The host cells find use in the expression of the encoded polynucleotides to produce the engineered carboxyesterases, and isolation of the engineered carboxyesterases described herein. In some embodiments, the host cells fine use in directly converting substrate(s) to the desired product(s).

In some additional embodiments, the present invention provides methods for carrying out reaction Scheme 1 (shown below) using any of the engineered carboxyesterase enzymes provided herein. In some embodiments, the methods comprise contacting or incubating carboxyester (I) and amine (II) substrates with an engineered carboxyesterase polypeptide of the present invention under suitable reaction conditions for the conversion of the substrates to the corresponding amide product, thereby transforming the substrates to the product compounds. Whether carrying out the method with whole cells, cell extracts or purified carboxyesterase enzymes, a single carboxyesterase enzyme can be used or, alternatively, mixtures of at least two carboxyesterase enzymes find use.

Scheme 1

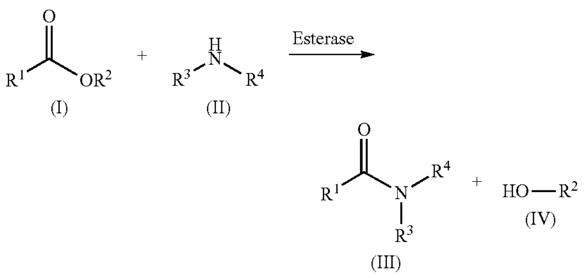

The engineered carboxyesterases of the present invention are capable of converting a diverse set of carboxyester (Scheme 1, I) and amine (II) substrates to their corresponding amide products (III). The scope of carboxyester substrates available can be detailed while considering $R^1$ and $R^2$ of formula (I). In some embodiments, the functionality of groups at $R^1$ and $R^2$ encompasses various components, from a hydrogen atom to alkyl, alkenyl, alkynyl, alkoxy, carboxy, heteroalkyl, heteroalkenyl, heteroalkynyl, carboxyalkyl, aminoalkyl, haloalkyl, alkythioalkyl, cycloalkyl, aryl, arylalkyl, heterocycloalkyl, heteroaryl, and heteroarylalkyl components, excepting that $R^2$ cannot be a hydrogen. In some additional embodiments, selected functionality at the $R^3$ and $R^4$ positions of the amine (II) consist of a hydrogen atom, alkyl, alkenyl, alkynyl, alkoxy, carboxy, heteroalkyl, heteroalkenyl, heteroalkynyl, carboxyalkyl, aminoalkyl, haloalkyl, alkythioalkyl, cycloalkyl, aryl, arylalkyl, heterocycloalkyl, heteroaryl, and heteroarylalkyl. In some further embodiments, the selected $R^1$ and $R^2$ may be linked to form a 3-membered to 10-membered ring, with the caveat that groups at $R^3$ and $R^4$ are separately chosen from alkyl, alkenyl, alkynyl, alkoxy, carboxy, heteroalkyl, heteroalkenyl, heteroalkynyl, carboxyalkyl, aminoalkyl, haloalkyl, alkythioalkyl, cycloalkyl, aryl, arylalkyl, heterocycloalkyl, heteroaryl, heteroarylalkyl, and may also be linked to form a 3-membered to 10-membered ring; and optionally R' or $R^2$ may be linked via a alkyl, alkenyl, alkynyl, alkoxy, carboxy, heteroalkyl, heteroalkenyl, heteroalkynyl, carboxyalkyl, aminoalkyl, haloalkyl, alkythioalkyl, cycloalkyl, aryl, arylalkyl, heterocycloalkyl, heteroaryl, or heteroarylalkyl tether to $R^3$ or $R^4$. The amidation process proceeds as the compound (I), (I)

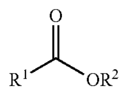

wherein $R^1$, and $R^2$ are as defined above, and a compound of formula (II), (II)

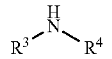

wherein $R^3$, and $R^4$ are as defined above, and an engineered polypeptide having amidative activity under suitable reaction conditions. In some embodiments of the reaction methods provided herein, the WT *T. fusca* carboxyesterase (SEQ ID NO: 2), or a reference engineered polypeptide (e.g., SEQ ID NO: 8), carboxyesterase derivatives presented herein are capable of generating primary and secondary amides matching the generic formula (III). The engineered amidation enzymes provided herein (e.g., the engineered carboxyesterase polypeptides of even numbered sequence identifiers SEQ ID NO: 4-136) find use as biocatalysts of the reaction above (Scheme 1).

Definitions

In reference to the present invention, the technical and scientific terms used in the descriptions herein will have the meanings commonly understood by one of ordinary skill in the art, unless specifically defined otherwise. Accordingly, the following terms are intended to have the following meanings. All U.S patents and published U.S. patent applications, including all sequences disclosed within such patents and patent applications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation and amino acid sequences are written left to right in amino to carboxy orientation, respectively.

The headings provided herein are not limitations of the various aspects or embodiments of the invention that can be had by reference to the specification as a whole. Accordingly, the terms defined below are more fully defined by reference to the specification as a whole.

As used herein, "carboxyesterases" are defined as enzymes that naturally have catalytic activity toward the hydrolysis of carboxyesters which results in the formation of an organic acid and an alcohol.

As used herein, "amidation," or amide synthesis, refers to the process of generating an amide bond, resulting in a carboxamide (organic amide).

As used herein, the terms "protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

As used herein, "polynucleotide" and "nucleic acid" refer to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases (e.g., inosine, xanthine, hypoxanthine, etc.). In one embodiment of the invention, such modified or synthetic nucleobases will be encoding nucleobases.

As used herein, "coding sequence" refers to that portion of a nucleic acid (e.g., a gene) that encodes an amino acid sequence of a protein.

As used herein, "naturally occurring," "wild-type," and "WT" refer to the form found in nature. For example, a naturally occurring or wild-type polypeptide or polynucleotide sequence is a sequence present in an organism that can be isolated from a source in nature and which has not been intentionally modified by human manipulation.

As used herein, "non-naturally occurring" or "engineered" or "recombinant" when used in the present invention with reference to (e.g., a cell, nucleic acid, or polypeptide), refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein, "percentage of sequence identity," "percent identity," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (See, e.g., Altschul et al., J. Mol. Biol. 215: 403-410 [1990]; and Altschul, et al., Nucleic Acids Res. 3389-3402 [1977]). Software for performing BLAST analyses is publicly available through the National Center for Biotechnology Information website.

Briefly, the BLAST analyses involve first identifying high scoring sequence pairs (HSPs) by identifying short words of length within the query sequence, which either match or satisfy some positive-valued threshold score T when aligned with a word of the same length in a database sequence. T is referred to as, the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, e.g., Henikoff and Henikoff, Proc Natl Acad Sci USA 89:10915 [1989]).

Numerous other algorithms are available and known in the art that function similarly to BLAST in providing percent identity for two sequences. Optimal alignment of sequences for comparison can be conducted using any suitable method known in the art (e.g., by the local homology algorithm of Smith and Waterman, Adv. Appl. Math. 2:482 [1981]; by the homology alignment algorithm of Needleman and Wunsch, J. Mol. Biol. 48:443 [1970]; by the search for similarity method of Pearson and Lipman, Proc. Natl. Acad. Sci. USA 85:2444 [1988]; and/or by computerized implementations of these algorithms [GAP, BESTFIT, FASTA, and TFASTA in the GCG Wisconsin Software Package]), or by visual inspection, using methods commonly known in the art. Additionally, determination of sequence alignment and percent sequence identity can employ the BESTFIT or GAP programs in the GCG Wisconsin Software package (Accelrys, Madison Wis.), using the default parameters provided.

As used herein, "reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

As used herein, "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered carboxyesterase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn" as further described below, is to be construed as referring to "a residue corresponding to", unless specifically denoted otherwise. Thus, for example, "X94" refers to any amino acid at position 94 in a polypeptide sequence (e.g., SEQ ID NOs:2, 4, 10, 26, or 42).

As used herein, "stereoselectivity" refers to the preferential formation in a chemical or enzymatic reaction of one stereoisomer over another stereoisomer or another set of stereoisomers. Stereoselectivity can be partial, where the formation of a stereoisomer is favored over another, or it may be complete where only one stereoisomer is formed. When the stereoisomers are enantiomers, the stereoselectivity is referred to as enantioselectivity, the fraction (typically reported as a percentage) of one enantiomer in the sum of both enantiomers. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. It is also to be understood that stereoselectivity is not limited to single stereoisomers and can be described for sets of stereoisomers.

As used herein, "highly stereoselective" refers to a chemical or enzymatic reaction that is capable of converting a substrate to its corresponding chiral amide product, with at least about 75% stereomeric excess.

As used herein, "increased enzymatic activity" and "increased activity" refer to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of carboxyesterase) as compared to a reference enzyme. Exemplary methods to determine enzyme activity are provided in the Examples. Any property relating to enzyme activity may be affected, including the classical enzyme properties of Km, Vmax or kcat, changes of which can lead to increased enzymatic activity. The carboxyesterase activity can be measured by any one of standard assays used for measuring carboxyesterases, such as change in substrate or product concentration. Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

As used herein, "conversion" refers to the enzymatic transformation of a substrate to the corresponding product.

As used herein "percent conversion" refers to the percent of the substrate that is converted to the product within a period of time under specified conditions. Thus, for example, the "enzymatic activity" or "activity" of a carboxyesterase polypeptide can be expressed as "percent conversion" of the substrate to the product.

As used herein, "regiospecificity" refers to chemical reactions in which one structural isomer is produced exclusively when other isomers are also theoretically possible.

As used herein, "thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

As used herein, "solvent stable" refers to the ability of a polypeptide to maintain similar activity (e.g., more than e.g., 60% to 80%) after exposure to varying concentrations (e.g., 5-99%) of solvent (e.g., isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

As used herein, "amino acid difference" or "residue difference" refers to a difference in the amino acid residue at a position of a polypeptide sequence relative to the amino acid residue at a corresponding position in a reference sequence. The positions of amino acid differences generally are referred to herein as "Xn", where n refers to the corresponding position in the reference sequence upon which the residue difference is based. For example, a "residue difference at position X40 as compared to SEQ ID NO:2" refers to a difference of the amino acid residue at the polypeptide position corresponding to position 40 of SEQ ID NO:2. Thus, if the reference polypeptide of SEQ ID NO:2 has a histidine at position 40, then a "residue difference at position X40 as compared to SEQ ID NO:2" refers to an amino acid substitution of any residue other than histidine at the position of the polypeptide corresponding to position 40 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances, the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present invention can include at least one amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X192A/G). The present invention includes engineered polypeptide sequences comprising at least one amino acid differences that include either/or both conservative and non-conservative amino acid substitutions. The amino acid sequences of the specific recombinant carbonic anhydrase polypeptides included in the Sequence Listing of the present invention include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO:2 at position Xn" as used herein may refer to position "Xn" or to the corresponding position (e.g., position (X-1)n) in a reference sequence that has been processed so as to lack the starting methionine.

As used herein, the phrase "conservative amino acid substitutions" refers to the interchangeability of residues having similar side chains, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with a hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basic side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. The appropriate classification of any amino acid or residue will be apparent to those of skill in the art, especially in light of the detailed invention provided herein. Exemplary conservative substitutions are provided in Table 1.

TABLE 1

Exemplary Conservative Amino Acid Substitutions

| Residue | Possible Conservative Substitutions |
|---|---|
| A, L, V, I | Other aliphatic (A, L, V, I)<br>Other non-polar (A, L, V, I, G, M) |
| G, M | Other non-polar (A, L, V, I, G, M) |
| D, E | Other acidic (D, E) |
| K, R | Other basic (K, R) |
| P | none |
| N, Q, S, T | Other polar |
| H, Y, W, F | Other aromatic (H, Y, W, F) |
| C | none |

As used herein, the phrase "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

As used herein, "insertion" refers to modification of the polypeptide by addition of one or more amino acids to the reference polypeptide. In some embodiments, the improved engineered carboxyesterase enzymes comprise insertions of one or more amino acids to the naturally occurring carboxyesterase polypeptide as well as insertions of one or more amino acids to engineered carboxyesterase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 2, 3, 4, 5, 6, 7, 8, 9, 10, 11, 12, 13, 14, 15, or more amino acid substitutions. In some embodiments, a substitution set refers to the set of amino acid substitutions that is present in any of the variant carboxyesterases included in the Tables provided in the Examples.

As used herein, "fragment" refers to a polypeptide that has an amino-terminal and/or carboxy-terminal deletion, but where the remaining amino acid sequence is identical to the corresponding positions in the sequence. Fragments can typically have about 80%, about 90%, about 95%, about 98%, or about 99% of the full-length carboxyesterase polypeptide, for example, the polypeptide of SEQ ID NO:4. In some embodiments, the fragment is "biologically active" (i.e., it exhibits the same enzymatic activity as the full-length sequence).

A "functional fragment", or a "biologically active fragment", used interchangeably, herein refers to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered *T. fusca* enzyme of the present invention) and that retains substantially all of the activity of the full-length polypeptide.

As used herein, "isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The improved carboxyesterase enzymes may be present within a cell, present in the cellular medium, or prepared in various forms, such as lysates or isolated preparations. As such, in some embodiments, the engineered carboxyesterase polypeptides of the present invention can be an isolated polypeptide.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered carboxyesterase polypeptide composition will comprise about 60% or more, about 70% or more, about 80% or more, about 90% or more, about 91% or more, about 92% or more, about 93% or more, about 94% or more, about 95% or more, about 96% or more, about 97% or more, about 98% or more, or about 99% of all macromolecular species by mole or % weight present in the composition. Solvent species, small molecules (<500 Daltons), and elemental ion species are not considered macromolecular species. In some embodiments, the isolated improved carboxyesterase polypeptide is a substantially pure polypeptide composition.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector). In some embodiments, "heterologous polynucleotide" refers to any polynucleotide that is introduced into a host cell by laboratory techniques, and includes polynucleotides that are removed from a host cell, subjected to laboratory manipulation, and then reintroduced into a host cell.

As used herein, "codon optimized" refers to changes in the codons of the polynucleotide encoding a protein to those preferentially used in a particular organism such that the encoded protein is efficiently expressed in the organism of interest. In some embodiments, the polynucleotides encoding the carboxyesterase enzymes may be codon optimized for optimal production from the host organism selected for expression.

As used herein, "control sequence" is defined herein to include all components, which are necessary or advantageous for the expression of a polynucleotide and/or polypeptide of the present invention. Each control sequence may be native or foreign to the polynucleotide of interest. Such control sequences include, but are not limited to, a leader, polyadenylation sequence, propeptide sequence, promoter, signal peptide sequence, and transcription terminator.

As used herein, "operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

As used herein, "suitable reaction conditions" refer to those conditions in the biocatalytic reaction solution (e.g., ranges of enzyme loading, substrate loading, temperature, pH, buffers, co-solvents, etc.) under which an carboxyesterase polypeptide of the present invention is capable of converting a substrate compound to a product compound (e.g., conversion of one compound to another compound). Exemplary "suitable reaction conditions" are provided in the present invention and illustrated by the Examples.

As used herein, "loading," such as in "compound loading," "enzyme loading," or "substrate loading" refers to the concentration or amount of a component in a reaction mixture at the start of the reaction.

As used herein, "substrate" in the context of a biocatalyst mediated process refers to the compound or molecule acted on by the biocatalyst.

As used herein "product" in the context of a biocatalyst mediated process refers to the compound or molecule resulting from the action of the biocatalyst.

As used herein, "equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

As used herein, "alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis (e.g., (C1-C4) alkyl refers to an alkyl of 1 to 4 carbon atoms).

As used herein, "alkenyl" refers to groups of from 2 to 12 carbon atoms inclusively, either straight or branched containing at least one double bond but optionally containing more than one double bond.

As used herein, "alkynyl" refers to groups of from 2 to 12 carbon atoms inclusively, either straight or branched containing at least one triple bond but optionally containing more than one triple bond, and additionally optionally containing one or more double bonded moieties.

As used herein, "heteroalkyl, "heteroalkenyl," and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —NRα—, —PH—, —S(O)—, —S(O)2-, —S(O) NRα-, —S(O) 2NRα-, and the like, including combinations thereof, where each Rα is independently selected from hydrogen, alkyl, heteroalkyl, cycloalkyl, heterocycloalkyl, aryl, and heteroaryl.

As used herein, "alkoxy" refers to the group —ORO wherein Rβ is an alkyl group is as defined above including optionally substituted alkyl groups as also defined herein.

As used herein, "aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

As used herein, "amino" refers to the group —NH2. Substituted amino refers to the group —NHRδ, NRδRδ, and NRδRδRδ, where each Rδ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

As used herein, "oxo" refers to =O.

As used herein, "oxy" refers to a divalent group —O—, which may have various substituents to form different oxy groups, including ethers and esters.

As used herein, "carboxy" refers to —COOH.

As used herein, "carbonyl" refers to —C(O)—, which may have a variety of substituents to form different carbonyl groups including acids, acid halides, aldehydes, amides, esters, and ketones.

As used herein, "alkyloxycarbonyl" refers to —C(O) ORE, where RE is an alkyl group as defined herein, which can be optionally substituted.

As used herein, "aminocarbonyl" refers to —C(O)NH2. Substituted aminocarbonyl refers to —C(O)NRδRδ, where the amino group NRδRδ is as defined herein.

As used herein, "halogen" and "halo" refer to fluoro, chloro, bromo and iodo.

As used herein, "hydroxy" refers to —OH.

As used herein, "cyano" refers to —CN.

As used herein, "heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

As used herein, "heteroarylalkyl" refers to an alkyl substituted with a heteroaryl (i.e., heteroaryl-alkyl-groups), preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

As used herein, "heteroarylalkenyl" refers to an alkenyl substituted with a heteroaryl (i.e., heteroaryl-alkenyl-groups), preferably having from 2 to 6 carbon atoms inclusively in the alkenyl moiety and from 5 to 12 ring atoms inclusively in the heteroaryl moiety.

As used herein, "heteroarylalkynyl" refers to an alkynyl substituted with a heteroaryl (i.e., heteroaryl-alkynyl-groups), preferably having from 2 to 6 carbon atoms inclusively in the alkynyl moiety and from 5 to 12 ring atoms inclusively in the heteroaryl moiety.

As used herein, "heterocycle," "heterocyclic," and interchangeably "heterocycloalkyl," refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

As used herein, "membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

As used herein, "optional" and "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included.

As used herein, "optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

As used herein, "protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups are well-known in the art. Functional groups that can have a protecting group include, but are not limited to, hydroxy, amino, and carboxy groups. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers. Other protecting groups can be found in the references noted herein.

Engineered Carboxyesterase Polypeptides

The present invention provides engineered polypeptides having carboxyesterase activity (also referred to herein as "engineered carboxyesterase polypeptides") useful for amidation reactions. Accordingly, in one aspect, the present invention provides engineered polypeptides having carboxyesterase activity which are capable of converting substrate compound(s) to product compound(s) as shown in Table 3.1 in Example 3. Further, the present invention provides polynucleotides encoding the engineered polypeptides, associated vectors and host cells comprising the polynucleotides, methods for making the engineered polypeptides, and methods for using the engineered polypeptides, including suitable reaction conditions.

The engineered polypeptides of the present invention are non-naturally occurring carboxyesterases engineered to have improved enzyme properties (e.g., increased stereoselectivity) as compared to the wild-type carboxyesterase polypeptide of *T. fusca* (GenBank Acc. No. WP_011292850.1; SEQ ID NO: 2). In some embodiments, various engineered carboxyesterase polypeptides provided herein exhibit improved enzyme properties as compared to other engineered reference carboxyesterase polypeptides provided herein. In some embodiments, the engineered polypeptides of the present invention are non-naturally occurring carboxyesterases engineered to have improved enzyme properties (e.g., increased thermostability) as compared to the wild-type carboxyesterase polypeptide of *G. stearothermophilus* (GenBank Acc. No. WP_033015113; SEQ ID NO: 138). In some further embodiments, the engineered polypeptides are non-naturally occurring carboxyesterases engineered to have improved enzyme properties (e.g., increased thermostability) as compared to the wild-type carboxyesterase polypeptide of *M. tuberculosis* (GenBank Acc. No. WP_003407276; SEQ ID NO: 140).

In some embodiments, the engineered carboxyesterase variants provided herein comprise polypeptide sequences having at least 80%, 85%, 86%, 87%, 88%, 89%, 90%, 91%, 92%, 93%, 94%, 95%, 96%, 97%, 98%, 99%, or more sequence identity to SEQ ID NO: 2, a reference engineered carboxyesterase (SEQ ID NO: 8), or a functional fragment thereof, wherein the engineered carboxyesterase comprises at least one substitution or substitution set in the polypeptide sequence, and wherein the amino acid positions of the polypeptide sequence are numbered with reference to SEQ ID NO: 2. In some embodiments, the engineered polypeptides having carboxyesterase activity comprise polypeptides having the amino acid substitutions provided herein (See, e.g., Tables 8.1 and 11.).

The present invention provides engineered carboxyesterases comprising polypeptide sequences having at least 80%, 85%, 86%, 87%, 88%, 89%, 90%, 91%, 92%, 93%, 94%, 95%, 96%, 97%, 98%, 99%, or more sequence identity to SEQ ID NO: 2 or a functional fragment thereof, wherein the engineered carboxyesterases comprise at least one substitution or substitution set in their polypeptide sequences, and wherein the amino acid positions of the polypeptide sequences are numbered with reference to SEQ ID NO: 2. In some embodiments, at least one substitution or substitution set in the polypeptide sequence comprises substitutions at positions selected from: 39, 39/323, 62, 62/117, 63, 64, 65, 66, 68, 69, 70, 71, 71/263, 77, 77/184, 103, 103/147, 104, 104/429, 105, 107, 107/185, 108, 109, 109/117, 110, 111, 113, 114, 115, 117, 118, 118/269, 118/349, 119, 126, 147, 153, 153/215, 164, 164/271, 174, 174/282, 183, 184, 184/249, 185, 186, 187, 188, 190, 209, 210, 211, 212, 213, 213/271, 213/345, 214, 215, 215/271, 216, 217, 217/231, 224, 224/268/372, 231, 249, 249/284, 263, 268, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 345, 349, 372, 372/376, 373, 374, 376, 377, 405, 416, 420, 427, 428, 429, 438, and 470, wherein the amino acid positions of the polypeptide sequence are numbered with reference to SEQ ID NO: 2. In some additional embodiments, at least one substitution or substitution set in the polypeptide sequence comprises substitutions selected from: 39/323, 62/117, 63, 64, 65, 66, 68, 69, 70, 71, 71/263, 77/184, 103, 103/147, 104, 104/429, 105, 107, 107/185, 108, 109/117, 110, 111, 113, 114, 115, 117, 118, 118/269, 118/349, 119, 126, 153, 153/215, 164/271, 174/282, 183, 184, 184/249, 185, 186, 187, 188, 190, 209, 210, 211, 212, 213, 213/271, 213/345, 214, 215, 215/271, 216, 217, 217/231, 224/268/372, 249/284, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 372, 372/376, 373, 376, 377, 405, 420, 427, 428, and 429, wherein the amino acid positions of the polypeptide sequence are numbered with reference to SEQ ID NO: 2. In some additional embodiments, at least one substitution or substitution set in the polypeptide sequence comprises substitutions selected from: 39M/323I, 62H/117G, 63A, 63R, 63T, 63Y, 64A, 64E, 64G, 64I, 64T, 64V, 64W, 65G, 65S, 65T, 65W, 66N, 68L, 68P, 69F, 69G, 69H, 69L, 69V, 69W, 69Y, 70L, 70R, 70T, 70W, 71F, 71G, 71H/263R, 71P, 71R, 71V, 71Y, 77S/184G, 103P, 103R, 103T/147S, 104P, 104Q/429V, 105L, 107D/185W, 107L, 107P, 107S, 108G, 108K, 108Q, 108R, 108S, 108W, 109G/117M, 110A, 110H, 110P, 110S, 111L, 111M, 111R, 111S, 111V, 111W, 113P, 114A, 114H, 114Q, 115H, 115T, 115V, 117A, 117F, 118G/349V, 118I, 118N, 118N/269T, 119G, 119P, 119S, 126C, 153H/215P, 153L, 164R/271T, 174D/282V, 183P, 184F, 184G, 184P, 184S/249T, 184Y, 185A, 185T, 186C, 186G, 186P, 186R, 186T, 187P, 188E, 188G, 190H, 190K, 190L, 190M, 190Q, 190R, 190W, 209E, 209G, 209P, 209S, 209V, 210P, 210T, 210W, 211I, 211L, 211R, 211V, 212A, 212P, 212R, 212S, 213C, 213E, 213L, 213N, 213P, 213Q, 213R/345G, 213S, 213T/271K, 213V, 214K, 214L, 214T, 214V, 215K, 215M, 215P, 215R, 215R/271R, 215W, 216P, 217G, 217L, 217P, 217R, 217R/231V, 217S, 217V, 217W, 224I/268S/372F, 249V/284P, 269N, 269V, 270I, 270I/470M, 270R, 271A, 271K, 271L, 271P, 271Q/416V, 271S, 271T, 276F, 277M, 278H, 278S, 279C, 279E, 279G, 279L/280G/282M, 279V, 280E, 280G, 280S, 281P, 281V, 281Y/374N, 282A, 282C, 282Q, 282R, 282S, 282T, 282W, 283C, 283D, 283K, 283R/429V, 283T, 283V, 283Y, 284C, 284T, 284T/438T, 284V, 285L, 285M, 285P, 286V, 311I, 317C, 317P, 320A, 320F, 320G, 320G/323S, 320S, 320S/323S/372A, 320S/372A/376G, 320S/376G/377V, 320W, 321L, 321S, 323C, 323I, 323R, 323Y, 324A, 372A/376A, 372L, 373G, 376A, 376G, 376L, 376M, 377L, 377W, 377Y, 405D, 420G, 427A, 428V, and 429L, wherein the amino acid positions of the polypeptide sequence are numbered with reference to SEQ ID NO: 2. In some further embodiments, at least one substitution or substitution set in the polypeptide sequence comprises substitutions selected from: T39M/F323I, R62H/P117G, P63A, P63R, P63T, P63Y, P64A, P64E, P64G, P64I, P64T, P64V, P64W, Y65G, Y65S, Y65T, Y65W, P66N, A68L, A68P, I69F, I69G, I69H, I69L, I69V, I69W, I69Y, G70L, G70R, G70T, G70W, A71F, A71G, A71H/Q263R, A71P, A71R, A71V, A71Y, F77S/E184G, W103P, W103R, W103T/P147S, I104P, I104Q/A429V, H105L, G107D/S185W, G107L, G107P, G107S, A108G, A108K, A108Q, A108R, A108S, A108W, F109G/P117M, T110A, T110H, T110P, T110S, N111L, N111M, N111R, N111S, N111V, N111W, S113P, G114A, G114H, G114Q, S115H, S115T, S115V, P117A, P117F, V118G/A349V, V118I, V118N, V118N/A269T, Y119G, Y119P, Y119S, R126C, R153H/N215P, R153L, W164R/W271T, G174D/L282V, G183P, E184F, E184G, E184P, E184S/A249T, E184Y, S185A, S185T, A186C, A186G, A186P, A186R, A186T, G187P, A188E, A188G, S190H, S190K, S190L, S190M, S190Q, S190R, S190W, L209E, L209G, L209P, L209S, L209V, Q210P, Q210T, Q210W, S211I, S211L, S211R, S211V, G212A, G212P, G212R, G212S, A213C, A213E, A213L, A213N, A213P, A213Q, A213R/S345G, A213S, A213T/W271K, A213V, G214K, G214L, G214T, G214V, N215K, N215M, N215P, N215R, N215R/W271R, N215W, M216P, A217G, A217L, A217P, A217R, A217R/A231V, A217S, A217V, A217W, T224I/P268S/I372F, A249V/F284P, A269N, A269V, V270I, V270I/V470M, V270R, W271A, W271K, W271L, W271P, W271Q/A416V, W271S, W271T, A276F, G277M, G278H, G278S, S279C, S279E, S279G, S279L/V280G/L282M, S279V, V280E, V280G, V280S, L281P, L281V, L281Y/D374N, L282A, L282C, L282Q, L282R, L282S, L282T, L282W, P283C, P283D, P283K, P283R/A429V, P283T, P283V, P283Y, F284C, F284T, F284T/P438T, F284V, A285L, A285M, A285P, P286V, L311I, T317C, T317P, Y320A, Y320F, Y320G, Y320G/F323S, Y320S, Y320S/F323S/I372A, Y320S/I372A/V376G, Y320S/V376G/F377V, Y320W, R321L, R321S, F323C, F323I, F323R, F323Y, L324A, I372A/V376A, I372L, T373G, V376A, V376G, V376L, V376M, F377L, F377W, F377Y, P405D, P420G, D427A, R428V, and A429L, wherein the amino acid positions of the polypeptide sequence are numbered with reference to SEQ ID NO: 2. In some embodiments, the engineered carboxyesterases comprise a substitution at position 282, wherein the position is numbered with reference to SEQ ID NO: 2. In some further embodiments, the substitution at position 282 is aliphatic, non-polar, basic, polar, or aromatic. In yet some additional embodiments, the substitution selected from: X282T, X282G, X282A, X282V, X282M, X282C, X282W, X282Q, X282S, X282T, and X282R.

The present invention also provides engineered carboxyesterases comprising a polypeptide sequences having at least 80%, 85%, 86%, 87%, 88%, 89%, 90%, 91%, 92%, 93%, 94%, 95%, 96%, 97%, 98%, 99%, or more sequence identity to SEQ ID NO: 8 or a functional fragment thereof, wherein the engineered carboxyesterases comprises at least one substitution or substitution set in the polypeptide sequences, wherein the amino acid positions of the polypeptide sequences are numbered with reference to SEQ ID NO: 8. In some embodiments, at least one substitution or substitution set in the polypeptide sequence comprises substitutions at positions selected from: 63, 63/65/108, 63/65/108/189, 63/65/108/377, 63/65/282/285/320/323, 63/65/320/323, 63/108, 63/108/282/285/377, 63/108/285/377, 63/108/320/323, 63/189, 63/212/215, 63/212/215/268/269/343, 63/215, 63/215/269, 63/215/270/271, 63/215/343, 63/268/269/270/429, 63/377, 65/69/70/281/372, 65/69/70/372, 65/69/372, 65/70/372, 65/320, 65/320/323, 68, 68/69/189/214, 68/69/189/214/215, 68/69/189/214/215/271, 68/69/189/214/215/271/281/282/343/381, 68/69/189/214/271/280, 68/69/189/214/372, 68/69/189/214/377/381, 68/69/189/271, 68/69/189/271/280/372/381, 68/69/189/280/281/282/372/377, 68/69/189/281/282/372/377/381, 68/69/189/343/381, 68/69/189/372, 68/69/189/381, 68/69/214/215/271, 68/69/214/343, 68/69/215, 68/69/271, 68/69/282/287, 68/69/343/372, 68/108/377, 68/184, 68/184/189, 68/189/271/372, 68/189/343, 68/214/215/271/281/282/372, 68/215/271/343/372/381, 68/215/377, 68/271/372, 68/377, 69, 69/70, 69/70/331/372, 69/70/372, 69/70/459, 69/108, 69/108/270/372/377, 69/108/281/285, 69/110/215/281, 69/189, 69/189/214/271/281/282/343, 69/189/214/343/372, 69/189/215/343, 69/189/271, 69/189/271/281/282, 69/189/271/343, 69/189/271/343/381, 69/189/280/282/343/372/381, 69/189/281/373, 69/189/282, 69/189/343/381, 69/189/372, 69/189/372/377, 69/189/377, 69/212/213/215/280/281, 69/214/215/271/372/377/381, 69/214/271/282, 69/214/271/343, 69/215, 69/215/269/270/377, 69/215/271/280/281/282, 69/215/271/282, 69/215/271/372, 69/215/285/317, 69/215/323, 69/215/343, 69/215/343/372/381, 69/271, 69/271/372, 69/282, 69/282/343/372, 69/285/373, 69/372, 70, 70/212, 108, 108/189, 108/189/282/285/320, 108/189/320, 108/189/377, 108/215, 108/215/377, 108/269/270, 108/270, 108/282/285/377, 108/285, 108/320/323, 108/377, 126, 126/184/213/280/281/285/320, 126/184/213/372, 126/189/285/372, 126/215, 126/372, 181/215, 189, 189/214, 189/214/215/271/282, 189/215, 189/215/249/277, 189/215/271/281/282/377, 189/215/343/372, 189/270/285, 189/270/372, 189/280/282, 189/320/377, 189/343, 189/343/377, 189/372/377, 189/377, 189/381, 213/215/320, 214/215/271, 214/215/271/377, 214/271, 214/280/282/343/377/381, 215, 215/249/280/281/285/372, 215/271/372, 215/280/281/285/372, 215/281/285/372, 215/281/285/373, 215/281/373, 215/285, 215/285/317, 215/285/346, 215/285/445, 215/320, 215/320/372, 215/323, 215/372, 215/372/377, 215/373, 215/377, 215/381, 249/377, 269/270/281/372/377, 270/377, 271, 271/343, 271/343/372, 271/343/372/381, 280/285/372, 281/372, 282/285/320/323, 285/323, 320, 343/372, 372, 372/377, 372/381, 373, and 377, wherein the amino acid positions of the polypeptide sequence are numbered with reference to SEQ ID NO: 8. In some further embodiments, at least one substitution or substitution set in the polypeptide sequence comprises substitutions selected from 63A, 63A/189A, 63A/215R/343V, 63R, 63R/65G/108G, 63R/65G/108G/189L, 63R/65G/108G/377I, 63R/65G/282A/285L/320W/323I, 63R/65G/320W/323I, 63R/108G, 63R/108G/282A/285L/377L, 63R/108G/285L/377I, 63R/108G/320W/323C, 63R/377I, 63T/215R, 63Y, 63Y/189L, 63Y/212P/215R, 63Y/212P/215R/268A/269N/343V, 63Y/215P/269N, 63Y/215R, 63Y/215R/270I/271S, 63Y/268A/269N/270I/429V, 65G/320W, 65G/320W/323I, 65W/69L/372L, 65W/69M/70A/281P/372L, 65W/69W/70L/372L, 65W/70L/372M, 68P, 68P/69L/189E/214R/271Y/280G, 68P/69L/189E/214R/372L, 68P/69L/189I/214R/215P/271Y, 68P/69L/189I/281P/282C/372L/377Y/381L, 68P/69L/189Q/214R, 68P/69L/189Q/271Y/280G/372L/381L, 68P/69L/215P, 68P/69L/271Y, 68P/69L/282C/287I, 68P/69L/343V/372L, 68P/69W/189E/214R/215P/271Y/281P/282G/343V/381L, 68P/69W/189E/280G/281P/282A/372L/377Y, 68P/69W/189E/343V/381L, 68P/69W/189I/214R/215P, 68P/69W/189I/214R/377Y/381L, 68P/69W/189I/271Y, 68P/69W/189I/372L, 68P/69W/189I/381L, 68P/69W/214R/215P/271Y, 68P/69W/214R/343V, 68P/69W/215P, 68P/108G/377L, 68P/184S, 68P/184S/189E, 68P/189I/271Y/372L, 68P/189I/343V, 68P/214R/215P/271Y/

281P/282A/372L, 68P/215P/271Y/343V/372L/381L, 68P/215P/377L, 68P/271Y/372L, 68P/377L, 69F/108G/270E/372L/377L, 69F/189L, 69F/215K, 69F/215K/269L/270I/377L, 69F/215R, 69F/285L/373G, 69L, 69L/70L/331Q/372M, 69L/189E/271Y/281P/282A, 69L/189I, 69L/189I/214R/271Y/281P/282A/343V, 69L/189I/271Y/343V/381L, 69L/189I/280G/282G/343V/372L/381L, 69L/189I/282A, 69L/189Q/377Y, 69L/215P/271Y/280G/281P/282C, 69L/215P/271Y/282A, 69L/215P/271Y/372L, 69L/215P/343V/372L/381L, 69L/215R/285P/317P, 69L/271Y, 69L/271Y/372L, 69L/282C/343V/372L, 69L/372L, 69M/70A/372M, 69W, 69W/70L, 69W/70L/372M, 69W/70L/459R, 69W/108S, 69W/189E/214R/343V/372L, 69W/189E/271Y/343V, 69W/189E/372L, 69W/189I, 69W/189I/215P/343V, 69W/189I/271Y, 69W/189I/343V/381L, 69W/189Q/372L/377Y, 69W/212A/213L/215R/280G/281P, 69W/214R/215P/271Y/372L/377Y/381L, 69W/214R/271Y/282A, 69W/214R/271Y/343V, 69W/215K/343V, 69W/215P, 69W/215R, 69W/215R/323Y, 69W/282A, 69W/372M, 69Y/108G/281P/285P, 69Y/110A/215R/281P, 69Y/189L/281P/373G, 70L, 70L/212P, 108G, 108G/189I/282A/285L/320W, 108G/189L, 108G/189L/320W, 108G/189L/377I, 108G/215K, 108G/215P/377L, 108G/269L/270E, 108G/270E, 108G/282A/285L/377L, 108G/285L, 108G/320W/323I, 108G/377I, 108G/377L, 126C, 126C/184S/213S/280G/281P/285L/320G, 126C/184S/213S/372L, 126C/189I/285L/372L, 126C/215P, 126C/372L, 181L/215P, 189E/372L/377Y, 189I, 189I/214R/215P/271Y/282G, 189I/215K, 189I/215P/343V/372L, 189I/215R/249T/277M, 189I/270E/285L, 189I/270E/372L, 189I/280G/282A, 189I/320W/377I, 189I/343V, 189I/377I, 189L, 189Q, 189Q/214R, 189Q/215P/271Y/281P/282C/377Y, 189Q/343V, 189Q/343V/377Y, 189Q/381L, 213S/215P/320G, 214R/215P/271Y, 214R/215P/271Y/377Y, 214R/271Y, 214R/280G/282A/343V/377Y/381L, 215K, 215K/281P/285L/372L, 215K/281P/373G, 215K/285L/317P, 215K/285L/445L, 215K/323Y, 215K/372L, 215K/372L/377L, 215K/373G, 215P, 215P/271Y/372L, 215P/320G, 215P/320G/372L, 215P/372L, 215P/372L/377L, 215P/377L, 215P/381L, 215R, 215R/249T/280G/281P/285L/372L, 215R/280G/281P/285L/372L, 215R/281P/285L/373G, 215R/285P, 215R/320G, 215R/372L, 215W, 215W/285L/346S, 215W/285P, 215W/373G, 249T/377L, 269L/270E/281P/372L/377L, 270E/377L, 271Y, 271Y/343V, 271Y/343V/372L, 271Y/343V/372L/381L, 280G/285L/372L, 281P/372L, 282A/285L/320W/323I, 285L/323I, 320W, 343V/372L, 372L, 372L/377L, 372L/381L, 372M, 373G, and 377L, wherein the amino acid positions of the polypeptide sequence are numbered with reference to SEQ ID NO: 8. In some further embodiments, at least one substitution or substitution set in the polypeptide sequence comprises substitutions selected from P63A, P63A/M189A, P63A/N215R/A343V, P63R, P63R/Y65G/A108G, P63R/Y65G/A108G/M189L, P63R/Y65G/A108G/F377I, P63R/Y65G/T282A/A285L/Y320W/F323I, P63R/Y65G/Y320W/F323I, P63R/A108G, P63R/A108G/T282A/A285L/F377L, P63R/A108G/A285L/F377I, P63R/A108G/Y320W/F323C, P63R/F377I, P63T/N215R, P63Y, P63Y/M189L, P63Y/G212P/N215R, P63Y/G212P/N215R/P268A/A269N/A343V, P63Y/N215P/A269N, P63Y/N215R, P63Y/N215R/V270I/W271S, P63Y/P268A/A269N/V270I/A429V, Y65G/Y320W, Y65G/Y320W/F323I, Y65W/I69L/I372L, Y65W/I69M/G70A/L281P/I372L, Y65W/I69W/G70L/I372L, Y65W/G70L/I372M, A68P, A68P/I69L/M189E/G214R/W271Y/V280G, A68P/I69L/M189E/G214R/I372L, A68P/I69L/M189I/G214R/N215P/W271Y, A68P/I69L/M189I/L281P/T282C/I372L/F377Y/A381L, A68P/I69L/M189Q/G214R, A68P/I69L/M189Q/W271Y/V280G/I372L/A381L, A68P/I69L/N215P, A68P/I69L/W271Y, A68P/I69L/T282C/V287I, A68P/I69L/A343V/I372L, A68P/I69W/M189E/G214R/N215P/W271Y/L281P/T282G/A343V/A381L, A68P/I69W/M189E/V280G/L281P/T282A/I372L/F377Y, A68P/I69W/M189E/A343V/A381L, A68P/I69W/M189I/G214R/N215P, A68P/I69W/M189I/G214R/F377Y/A381L, A68P/I69W/M189I/W271Y, A68P/I69W/M189I/I372L, A68P/I69W/M189I/A381L, A68P/I69W/G214R/N215P/W271Y, A68P/I69W/G214R/A343V, A68P/I69W/N215P, A68P/A108G/F377L, A68P/E184S, A68P/E184S/M189E, A68P/M189I/W271Y/I372L, A68P/M189I/A343V, A68P/G214R/N215P/W271Y/L281P/T282A/I372L, A68P/N215P/W271Y/A343V/I372L/A381L, A68P/N215P/F377L, A68P/W271Y/I372L, A68P/F377L, I69F/A108G/V270E/I372L/F377L, I69F/M189L, I69F/N215K, I69F/N215K/A269L/V270I/F377L, I69F/N215R, I69F/A285L/T373G, I69L, I69L/G70L/P331Q/I372M, I69L/M189E/W271Y/L281P/T282A, I69L/M189I, I69L/M189I/G214R/W271Y/L281P/T282A/A343V, I69L/M189I/W271Y/A343V/A381L, I69L/M189I/V280G/T282G/A343V/I372L/A381L, I69L/M189I/T282A, I69L/M189Q/F377Y, I69L/N215P/W271Y/V280G/L281P/T282C, I69L/N215P/W271Y/T282A, I69L/N215P/W271Y/I372L, I69L/N215P/A343V/I372L/A381L, I69L/N215R/A285P/T317P, I69L/W271Y, I69L/W271Y/I372L, I69L/T282C/A343V/I372L, I69L/I372L, I69M/G70A/I372M, I69W, I69W/G70L, I69W/G70L/I372M, I69W/G70L/G459R, I69W/A108S, I69W/M189E/G214R/A343V/I372L, I69W/M189E/W271Y/A343V, I69W/M189E/I372L, I69W/M189I, I69W/M189I/N215P/A343V, I69W/M189I/W271Y, I69W/M189I/A343V/A381L, I69W/M189Q/I372L/F377Y, I69W/G212A/A213L/N215R/V280G/L281P, I69W/G214R/N215P/W271Y/I372L/F377Y/A381L, I69W/G214R/W271Y/T282A, I69W/G214R/W271Y/A343V, I69W/N215K/A343V, I69W/N215P, I69W/N215R, I69W/N215R/F323Y, I69W/T282A, I69W/I372M, I69Y/A108G/L281P/A285P, I69Y/T110A/N215R/L281P, I69Y/M189L/L281P/T373G, G70L, G70L/G212P, A108G, A108G/M189I/T282A/A285L/Y320W, A108G/M189L, A108G/M189L/Y320W, A108G/M189L/F377I, A108G/N215K, A108G/N215P/F377L, A108G/A269L/V270E, A108G/V270E, A108G/T282A/A285L/F377L, A108G/A285L, A108G/Y320W/F323I, A108G/F377I, A108G/F377L, R126C, R126C/E184S/A213S/V280G/L281P/A285L/Y320G, R126C/E184S/A213S/I372L, R126C/M189I/A285L/I372L, R126C/N215P, R126C/I372L, V181L/N215P, M189E/I372L/F377Y, M189I, M189I/G214R/N215P/W271Y/T282G, M189I/N215K, M189I/N215P/A343V/I372L, M189I/N215R/A249T/G277M, M189I/V270E/A285L, M189I/V270E/I372L, M189I/V280G/T282A, M189I/Y320W/F377I, M189I/A343V, M189I/F377I, M189L, M189Q, M189Q/G214R, M189Q/N215P/W271Y/L281P/T282C/F377Y, M189Q/A343V, M189Q/A343V/F377Y, M189Q/A381L, A213S/N215P/Y320G, G214R/N215P/W271Y, G214R/N215P/W271Y/F377Y, G214R/W271Y, G214R/V280G/T282A/A343V/F377Y/A381L, N215K, N215K/L281P/A285L/I372L, N215K/L281P/T373G, N215K/A285L/T317P, N215K/A285L/V445L, N215K/F323Y, N215K/I372L, N215K/I372L/F377L, N215K/T373G, N215P, N215P/W271Y/I372L, N215P/Y320G, N215P/Y320G/I372L, N215P/I372L, N215P/I372L/F377L, N215P/F377L, N215P/A381L, N215R, N215R/A249T/V280G/L281P/A285L/I372L, N215R/V280G/L281P/A285L/I372L, N215R/L281P/A285L/T373G, N215R/A285P, N215R/Y320G, N215R/I372L, N215W, N215W/A285L/G346S, N215W/A285P, N215W/T373G, A249T/F377L, A269L/V270E/L281P/

I372L/F377L, V270E/F377L, W271Y, W271Y/A343V, W271Y/A343V/I372L, W271Y/A343V/I372L/A381L, V280G/A285L/I372L, L281P/I372L, T282A/A285L/Y320W/F323I, A285L/F323I, Y320W, A343V/I372L, I372L, I372L/F377L, I372L/A381L, I372M, T373G, and F377L, wherein the amino acid positions of the polypeptide sequence are numbered with reference to SEQ ID NO: 8.

In some embodiments, the present invention also provides engineered carboxyesterase polypeptides that comprise a fragment of any of the engineered carboxyesterase polypeptides described herein that retains the functional carboxyesterase activity and/or improved property of that engineered carboxyesterase polypeptide. Accordingly, in some embodiments, the present invention provides a polypeptide fragment having carboxyesterase activity (e.g., capable of converting substrate to product under suitable reaction conditions), wherein the fragment comprises at least about 80%, 90%, 95%, 98%, or 99% of a full-length amino acid sequence of an engineered polypeptide of the present invention, such as an exemplary engineered polypeptide of having the even-numbered sequence identifiers of SEQ ID NOs: 2-136.

In some embodiments, the engineered carboxyesterase polypeptide of the invention comprises an amino acid sequence comprising at least one deletion, addition, and/or substitution, as compared to any one of the engineered carboxyesterase polypeptide sequences described herein, such as the exemplary engineered polypeptide sequences having the even-numbered sequence identifiers of SEQ ID NOs: 2-136. Thus, for each and every embodiment of the engineered carboxyesterase polypeptides of the invention, the amino acid sequence can comprise deletions, additions, and/or substitutions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the carboxyesterase polypeptides, where the associated functional activity and/or improved properties of the engineered carboxyesterase described herein is maintained. In some embodiments, the deletions, additions, and/or substitutions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, 1-50, 1-55, or 1-60 additions, and/or substitutions of the amino acid residues. In some embodiments, the number of deletions, additions, and/or substitutions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, 50, 55, or 60 of the amino acid residues. In some embodiments, the deletions, additions, and/or substitutions can comprise deletions, additions, and/or substitutions of 1, 2, 3, 4, 5, 6, 7, 8, 9, 10, 11, 12, 13, 14, 15, 16, 18, 20, 21, 22, 23, 24, 25 or 30 amino acid residues.

In some embodiments, the present invention provides an engineered carboxyesterase polypeptide having an amino acid sequence comprising an insertion as compared to any one of the engineered carboxyesterase polypeptide sequences described herein, such as the exemplary engineered polypeptide sequences having the even-numbered sequence identifiers of SEQ ID NO: 2-136. Thus, for each and every embodiment of the carboxyesterase polypeptides of the invention, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, where the associated functional activity and/or improved properties of the engineered carboxyesterase described herein is maintained. The insertions can be to amino or carboxy terminus, or internal portions of the carboxyesterase polypeptide.

In some embodiments, the polypeptides of the present invention are in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

The engineered carboxyesterase polypeptides described herein are not restricted to the genetically encoded amino acids. Thus, in addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5f0; styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab);

N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art. These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As will be apparent to the skilled artisan, the foregoing residue positions and the specific amino acid residues for each residue position can be used individually or in various combinations to synthesize carboxyesterase polypeptides having desired improved properties, including, among others, enzyme activity, substrate/product preference, stereoselectivity, substrate/product tolerance, and stability under various conditions, such as increased temperature, solvent, and/or pH.

The engineered carboxyesterase polypeptides of the present invention were generated by directed evolution of SEQ ID NO: 2 for efficient amidation of substrates of interest to products of interest, under certain industrially relevant conditions and have one or more residue differences as compared to a reference carboxyesterase polypeptide. These residue differences are associated with improvements in various enzyme properties, particularly increased activity, increased solvent tolerance, and reduced toxicity to host cells (e.g., *E. coli*). In some additional embodiments, the variant carboxyesterases also exhibited increased stereoselectivity, increased stability, and tolerance of increased substrate and/or product concentration (e.g., decreased product inhibition). Accordingly, in some embodiments, the engineered polypeptides having carboxyesterase activity are capable of converting the substrate compound(s) to product(s) with an activity that is increased at least about 1.2 fold, 1.5 fold, 2 fold, 3 fold, 4 fold, 5 fold, 10 fold, 20 fold, 30 fold, 40 fold, 50 fold, 100 fold, 200 fold, 500 fold, 1000 fold, or more relative to the activity of wild-type *T. fusca* carboxyesterase polypeptide (e.g., SEQ ID NO: 2), under suitable reaction conditions. In some embodiments, the engineered polypeptides having carboxyesterase activity are capable of converting substrate to product with a percent conversion of at least about 40%, at least about 50%, at least about 60%, at least about 70%, at least about 80%, or at least about 90%, at least about 91%, at least about 92%, at least about 93%, at least about 94%, at least about 95%, at least about 96%, at least about 97%, at least about 98%, or at least about 99%, in a reaction time of about 48 h, about 36 h, about 24 h, or even a shorter length of time, under suitable reaction conditions. In some embodiments, the engineered polypeptides having carboxyesterase activity are capable of converting substrate to product diastereomeric excess of at least 90%, 95%, 97%, 98%, 99%, or greater, under suitable reaction conditions.

In some embodiments, the engineered polypeptides having carboxyesterase activity are capable of converting substrate to product with increased tolerance for the presence of the substrate relative to the substrate tolerance of a reference polypeptide (e.g., SEQ ID NO: 2), under suitable reaction conditions. Accordingly, in some embodiments the engineered polypeptides are capable of converting the substrate of substrate to product in the presence of a substrate loading concentration of at least about 1 g/L, 5 g/L, 10 g/L, 20 g/L, about 30 g/L, about 40 g/L, about 50 g/L, about 70 g/L, about 75 g/L, about 100 g/L, with a percent conversion of at least about 40%, at least about 50%, at least about 60%, at least about 70%, at least about 80%, at least about 90%, at least about 91%, at least about 92%, at least about 94%, at least about 94%, at least about 95%, at least about 96%, at least about 97%, at least about 98%, or at least about 99%, in a reaction time of about 72h, about 48h, about 36h, about 24 h, or even shorter length of time, under suitable reaction conditions.

Some suitable reaction conditions under which the above-described improved properties of the engineered polypeptides can be determined with respect to concentrations or amounts of polypeptide, substrate, buffer, co-solvent, pH, and/or conditions including temperature and reaction time are provided herein. In some embodiments, the suitable reaction conditions comprise the assay conditions described below and in the Examples.

In some embodiments, the engineered polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having carboxyesterase activity are bound or immobilized on the solid support such that they retain at least a portion of their improved properties relative to a reference polypeptide (e.g., SEQ ID NO: 2). In such embodiments, the immobilized polypeptides can facilitate the biocatalytic conversion of the substrate compound to the desired product, and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered carboxyesterase polypeptides of the present invention can be carried out using the same carboxyesterase polypeptides bound or immobilized on a solid support.

The engineered carboxyesterase polypeptide can be bound non-covalently or covalently. Various methods for conjugation and immobilization of enzymes to solid supports (e.g., resins, membranes, beads, glass, etc.) are well known in the art. Other methods for conjugation and immobilization of enzymes to solid supports (e.g., resins, membranes, beads, glass, etc.) are well known in the art (See, e.g., Yi et al., Proc. Biochem., 42: 895-898 [2007]; Martin et al., Appl. Microbiol. Biotechnol., 76: 843-851 [2007]; Koszelewski et al., *J. Mol. Cat. B: Enz.,* 63: 39-44 [2010]; Truppo et al., Org. Proc. Res. Develop., published online: dx.doi.org/10.1021/op200157c; and Mateo et al., Biotechnol. Prog., 18:629-34 [2002], etc.). Solid supports useful for immobilizing the engineered carboxyesterase polypeptides of the present invention include, but are not limited to, beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered carboxyesterases of the present invention include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the engineered carboxyesterase polypeptides can be provided in the form of an array in which the polypeptides are arranged in positionally distinct locations. In some embodiments, the positionally distinct locations are wells in a solid support such as a 96-well plate. A plurality of supports can be configured on an array at various locations, addressable for robotic delivery of reagents, or by detection methods and/or instruments. Such arrays can be used to test a variety of substrate compounds for conversion by the polypeptides.

In some embodiments, the engineered polypeptides described herein can be provided in the form of kits. The polypeptides in the kits may be present individually or as a plurality of polypeptides. The kits can further include reagents for carrying out enzymatic reactions, substrates for assessing the activity of polypeptides, as well as reagents for detecting the products. The kits can also include reagent dispensers and instructions for use of the kits. In some embodiments, the kits of the present invention include arrays comprising a plurality of different engineered carboxyesterase polypeptides at different addressable position, wherein the different polypeptides are different variants of a reference sequence each having at least one different improved enzyme property. Such arrays comprising a plurality of engineered polypeptides and methods of their use are known (See, e.g., WO2009/008908A2).

Polynucleotides Encoding Engineered Carboxyesterases

In another aspect, the present invention provides polynucleotides encoding the engineered carboxyesterase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered carboxyesterase can be introduced into appropriate host cells to express the corresponding carboxyesterase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved carboxyesterase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made by selecting combinations based on the possible codon choices, and all such variations are to be considered specifically disclosed for any polypeptide disclosed herein, including the amino acid sequences presented in the Tables in the Examples. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 1 has been codon optimized for expression in *E. coli*, but otherwise encodes the naturally occurring carboxyesterase of *T. fusca.*

In some embodiments, the polynucleotide encodes an engineered carboxyesterase polypeptide comprising an amino acid sequence selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, or 136.

In some embodiments, the polynucleotides encoding the engineered carboxyesterases or a functional fragment thereof, are selected from polynucleotide sequences comprising at least 85%, 86%, 87%, 88%, 89%, 90%, 91%, 92%, 93%, 94%, 95%, 96%, 97%, 98%, 99%, or more sequence identity to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and/or 139.

In some embodiments, the polynucleotides are capable of hybridizing under highly stringent conditions to a polynucleotide comprising SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and/or 139.

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered carboxyesterase. In some embodiments, the reference polynucleotide comprises SEQ ID NO: 1, while in some other embodiments, the reference polynucloeotide comprises SEQ ID NO:137. In some further embodiments, the reference polynucleotide sequence comprises SEQ ID NO:139. In some additional embodiments, the engineered carboxyesterase sequences comprise sequences that comprise positions identified to be beneficial, as described in the Examples.

The present invention also provides polynucleotide sequences encoding at least one engineered carboxyesterase provided herein. In some embodiments, the polynucleotide sequences encode at least one engineered carboxyesterase comprising a polypeptide sequence having at least 80%, 85%, 86%, 87%, 88%, 89%, 90%, 91%, 92%, 93%, 94%, 95%, 96%, 97%, 98%, 99%, or more sequence identity to SEQ ID NO: 2 or a functional fragment thereof, wherein the engineered carboxyesterase comprises at least one substitution or substitution set in its polypeptide sequence, wherein the amino acid positions of the polypeptide sequence are numbered with reference to SEQ ID NO: 2. In some embodiments, the polynucleotide sequences encode at least one engineered carboxyesterase comprising substitutions at positions selected from: 39, 39/323, 62, 62/117, 63, 64, 65, 66, 68, 69, 70, 71, 71/263, 77, 77/184, 103, 103/147, 104, 104/429, 105, 107, 107/185, 108, 109, 109/117, 110, 111, 113, 114, 115, 117, 118, 118/269, 118/349, 119, 126, 147, 153, 153/215, 164, 164/271, 174, 174/282, 183, 184, 184/249, 185, 186, 187, 188, 190, 209, 210, 211, 212, 213, 213/271, 213/345, 214, 215, 215/271, 216, 217, 217/231, 224, 224/268/372, 231, 249, 249/284, 263, 268, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 345, 349, 372, 372/376, 373, 374, 376, 377, 405, 416, 420, 427, 428, 429, 438, and 470, wherein the amino acid positions of the polypeptide sequence are numbered with reference to SEQ ID NO: 2. In some additional embodiments, the polynucleotide sequences encode at least one engineered carboxyesterase comprising at least one substitution or substitution set selected from: 39/323, 62/117, 63, 64, 65, 66, 68, 69, 70, 71, 71/263, 77/184, 103, 103/147, 104, 104/429, 105, 107, 107/185, 108, 109/117, 110, 111, 113, 114, 115, 117, 118, 118/269, 118/349, 119, 126, 153, 153/215, 164/271, 174/282, 183, 184, 184/249, 185, 186, 187, 188, 190, 209, 210, 211, 212, 213, 213/271, 213/345, 214, 215, 215/271, 216, 217, 217/231, 224/268/372, 249/284, 269, 270, 270/470, 271, 271/416, 276, 277, 278, 279, 279/280/282, 280, 281, 281/374, 282, 283, 283/429, 284, 284/438, 285, 286, 311, 317, 320, 320/323, 320/323/372, 320/372/376, 320/376/377, 321, 323, 324, 372, 372/376, 373, 376, 377, 405, 420, 427, 428, and 429, wherein the amino acid positions of the polypeptide sequence are numbered with reference to SEQ ID NO: 2. In some additional embodiments, the polynucleotide sequences encode at least one engineered carboxyesterase comprising at least one substitution or substitution set selected from: 39M/323I, 62H/117G, 63A, 63R, 63T, 63Y, 64A, 64E, 64G, 64I, 64T, 64V, 64W, 65G, 65S, 65T, 65W, 66N, 68L, 68P, 69F, 69G, 69H, 69L, 69V, 69W, 69Y, 70L, 70R, 70T, 70W, 71F, 71G, 71H/263R, 71P, 71R, 71V, 71Y, 77S/184G, 103P, 103R, 103T/147S, 104P, 104Q/429V, 105L, 107D/185W, 107L, 107P, 107S, 108G, 108K, 108Q, 108R, 108S, 108W, 109G/117M, 110A, 110H, 110P, 110S, 111L, 111M, 111R, 111S, 111V, 111W, 113P, 114A, 114H, 114Q, 115H, 115T, 115V, 117A, 117F, 118G/349V, 118I, 118N, 118N/269T, 119G, 119P, 119S, 126C, 153H/215P, 153L, 164R/271T, 174D/282V, 183P, 184F, 184G, 184P, 184S/249T, 184Y, 185A, 185T, 186C, 186G, 186P, 186R, 186T, 187P, 188E, 188G, 190H, 190K, 190L, 190M, 190Q, 190R, 190W, 209E, 209G, 209P, 209S, 209V, 210P, 210T, 210W, 211I, 211L, 211R, 211V, 212A, 212P, 212R, 212S, 213C, 213E, 213L, 213N, 213P, 213Q, 213R/345G, 213S, 213T/271K, 213V, 214K, 214L, 214T, 214V, 215K, 215M, 215P, 215R, 215R/271R, 215W, 216P, 217G, 217L, 217P, 217R, 217R/231V, 217S, 217V, 217W, 224I/268S/372F, 249V/284P, 269N, 269V, 270I, 270I/470M, 270R, 271A, 271K, 271L, 271P, 271Q/416V, 271S, 271T, 276F, 277M, 278H, 278S, 279C, 279E, 279G, 279L/280G/282M, 279V, 280E, 280G, 280S, 281P, 281V, 281Y/374N, 282A, 282C, 282Q, 282R, 282S, 282T, 282W, 283C, 283D, 283K, 283R/429V, 283T, 283V, 283Y, 284C, 284T, 284T/438T, 284V, 285L, 285M, 285P, 286V, 311I, 317C, 317P, 320A, 320F, 320G, 320G/323S, 320S, 320S/323S/372A, 320S/372A/376G, 320S/376G/377V, 320W, 321L, 321S, 323C, 323I, 323R, 323Y, 324A, 372A/376A, 372L, 373G, 376A, 376G, 376L, 376M, 377L, 377W, 377Y, 405D, 420G, 427A, 428V, and 429L, wherein the amino acid positions are numbered with reference to SEQ ID NO: 2. In some further embodiments, the polynucleotide sequences encode at least one engineered carboxyesterase comprising at least one substitution or substitution set selected from: T39M/F323I, R62H/P117G, P63A, P63R, P63T, P63Y, P64A, P64E, P64G, P64I, P64T, P64V, P64W, Y65G, Y65S, Y65T, Y65W, P66N, A68L, A68P, I69F, I69G, I69H, I69L, I69V, I69W, I69Y, G70L, G70R, G70T, G70W, A71F, A71G, A71H/Q263R, A71P, A71R, A71V, A71Y, F77S/E184G, W103P, W103R, W103T/P147S, I104P, I104Q/A429V, H105L, G107D/S185W, G107L, G107P, G107S, A108G, A108K, A108Q, A108R, A108S, A108W, F109G/P117M, T110A, T110H, T110P, T110S, N111L, N111M, N111R, N111S, N111V, N111W, S113P, G114A, G114H, G114Q, S115H, S115T, S115V, P117A, P117F, V118G/A349V, V118I, V118N, V118N/A269T, Y119G, Y119P, Y119S, R126C, R153H/N215P, R153L, W164R/W271T, G174D/L282V, G183P, E184F, E184G, E184P, E184S/A249T, E184Y, S185A, S185T, A186C, A186G, A186P, A186R, A186T, G187P, A188E, A188G, S190H, S190K, S190L, S190M, S190Q, S190R, S190W, L209E, L209G, L209P, L209S, L209V, Q210P, Q210T, Q210W, S211I, S211L, S211R, S211V, G212A, G212P, G212R, G212S, A213C, A213E, A213L, A213N, A213P, A213Q, A213R/S345G, A213S, A213T/W271K, A213V, G214K, G214L, G214T, G214V, N215K, N215M, N215P, N215R, N215R/W271R, N215W, M216P, A217G, A217L, A217P, A217R, A217R/A231V, A217S, A217V, A217W, T224I/P268S/I372F, A249V/F284P, A269N, A269V, V270I, V270I/V470M, V270R, W271A, W271K, W271L, W271P, W271Q/A416V, W271S, W271T, A276F, G277M, G278H, G278S, S279C, S279E, S279G, S279L/V280G/L282M, S279V, V280E, V280G, V280S, L281P, L281V, L281Y/D374N, L282A, L282C, L282Q, L282R, L282S, L282T, L282W, P283C, P283D, P283K, P283R/A429V, P283T, P283V, P283Y, F284C, F284T, F284T/P438T, F284V, A285L, A285M, A285P, P286V, L311I, T317C, T317P, Y320A, Y320F, Y320G, Y320G/F323S, Y320S, Y320S/F323S/I372A, Y320S/I372A/V376G, Y320S/V376G/F377V, Y320W, R321L, R321S, F323C, F323I, F323R, F323Y, L324A, I372A/V376A, I372L, T373G, V376A, V376G, V376L, V376M, F377L, F377W, F377Y, P405D, P420G, D427A, R428V, and A429L, wherein the amino acids are numbered with reference to SEQ ID NO: 2. In some embodiments, the polynucleotide sequences encode at least one engineered carboxyesterase comprising a substitution at position 282, wherein the position is numbered with reference to SEQ ID NO: 2. In some further embodiments, the substitution at position 282 is aliphatic, non-polar, basic, polar, or aromatic. In yet some additional embodiments, the substitution is selected from X282T, X282G, X282A, X282V, X282M, X282C, X282W, X282Q, X282S, X282T, and X282R.

The present invention also provides polynucleotide sequences encoding at least one engineered carboxyesterase comprising a polypeptide sequence having at least 80%, 85%, 86%, 87%, 88%, 89%, 90%, 91%, 92%, 93%, 94%, 95%, 96%, 97%, 98%, 99%, or more sequence identity to SEQ ID NO: 8 or a functional fragment thereof, wherein the engineered carboxyesterase comprises at least one substitution or substitution set in its polypeptide sequence, wherein the amino acid positions of the polypeptide sequence are numbered with reference to SEQ ID NO: 8. In some embodiments, the polynucleotide sequences encode engineered carboxyesterases comprising at least one substitution or substitution set at positions selected from: 63, 63/65/108, 63/65/108/189, 63/65/108/377, 63/65/282/285/320/323, 63/65/320/323, 63/108, 63/108/282/285/377, 63/108/285/377, 63/108/320/323, 63/189, 63/212/215, 63/212/215/268/269/343, 63/215, 63/215/269, 63/215/270/271, 63/215/343, 63/268/269/270/429, 63/377, 65/69/70/281/372, 65/69/70/372, 65/69/372, 65/70/372, 65/320, 65/320/323, 68, 68/69/189/214, 68/69/189/214/215, 68/69/189/214/215/271, 68/69/189/214/215/271/281/282/343/381, 68/69/189/214/271/280, 68/69/189/214/372, 68/69/189/214/377/381, 68/69/189/271, 68/69/189/271/280/372/381, 68/69/189/280/281/282/372/377, 68/69/189/281/282/372/377/381, 68/69/189/343/381, 68/69/189/372, 68/69/189/381, 68/69/214/215/271, 68/69/214/343, 68/69/215, 68/69/271, 68/69/282/287, 68/69/343/372, 68/108/377, 68/184, 68/184/189, 68/189/271/372, 68/189/343, 68/214/215/271/281/282/372, 68/215/271/343/372/381, 68/215/377, 68/271/372, 68/377, 69, 69/70, 69/70/331/372, 69/70/372, 69/70/459, 69/108, 69/108/270/372/377, 69/108/281/285, 69/110/215/281, 69/189, 69/189/214/271/281/282/343, 69/189/214/343/372, 69/189/215/343, 69/189/271, 69/189/271/281/282, 69/189/271/343, 69/189/271/343/381, 69/189/280/282/343/372/381, 69/189/281/373, 69/189/282, 69/189/343/381, 69/189/372, 69/189/372/377, 69/189/377, 69/212/213/215/280/281, 69/214/215/271/372/377/381, 69/214/271/282, 69/214/271/343, 69/215, 69/215/269/270/377, 69/215/271/280/281/282, 69/215/271/282, 69/215/271/372, 69/215/285/317, 69/215/323, 69/215/343, 69/215/343/372/381, 69/271, 69/271/372, 69/282, 69/282/343/372, 69/285/373, 69/372, 70, 70/212, 108, 108/189, 108/189/282/285/320, 108/189/320, 108/189/377, 108/215, 108/215/377, 108/269/270, 108/270, 108/282/285/377, 108/285, 108/320/323, 108/377, 126, 126/184/213/280/281/285/320, 126/184/213/372, 126/189/285/372, 126/215, 126/372, 181/215, 189, 189/214, 189/214/215/271/282, 189/215, 189/215/249/277, 189/215/271/281/282/377, 189/215/343/372, 189/270/285, 189/270/372, 189/280/282, 189/320/377, 189/343, 189/343/377, 189/372/377, 189/377, 189/381, 213/215/320, 214/215/271, 214/215/271/377, 214/271, 214/280/282/343/377/381, 215, 215/249/280/281/285/372, 215/271/372, 215/280/281/285/372, 215/281/285/372, 215/281/285/373, 215/281/373, 215/285, 215/285/317, 215/285/346, 215/285/445, 215/320, 215/320/372, 215/323, 215/372, 215/372/377, 215/373, 215/377, 215/381, 249/377, 269/270/281/372/377, 270/377, 271, 271/343, 271/343/372, 271/343/372/381, 280/285/372, 281/372, 282/285/320/323, 285/323, 320, 343/372, 372, 372/377, 372/381, 373, and 377, wherein the amino acid positions are numbered with reference to SEQ ID NO: 8. In some further embodiments, the polynucleotide sequence encodes an engineered carboxyesterase comprising at least one substitution or substitution set selected from: 63A, 63A/189A, 63A/215R/343V, 63R, 63R/65G/108G, 63R/65G/108G/189L, 63R/65G/108G/377I, 63R/65G/282A/285L/320W/323I, 63R/65G/320W/323I, 63R/108G, 63R/108G/282A/285L/377L, 63R/108G/285L/377I, 63R/108G/320W/323C, 63R/377I, 63T/215R, 63Y, 63Y/189L, 63Y/212P/215R, 63Y/212P/215R/268A/269N/343V, 63Y/215P/269N, 63Y/215R, 63Y/215R/270I/271S, 63Y/268A/269N/270I/429V, 65G/320W, 65G/320W/323I, 65W/69L/372L, 65W/69M/70A/281P/372L, 65W/69W/70L/372L, 65W/70L/372M, 68P, 68P/69L/189E/214R/271Y/280G, 68P/69L/189E/214R/372L, 68P/69L/189I/214R/215P/271Y, 68P/69L/189I/281P/282C/372L/377Y/381L, 68P/69L/189Q/214R, 68P/69L/189Q/271Y/280G/372L/381L, 68P/69L/215P, 68P/69L/271Y, 68P/69L/282C/287I, 68P/69L/343V/372L, 68P/69W/189E/214R/215P/271Y/281P/282G/343V/381L, 68P/69W/189E/280G/281P/282A/372L/377Y, 68P/69W/189E/343V/381L, 68P/69W/189I/214R/215P, 68P/69W/189I/214R/377Y/381L, 68P/69W/189I/271Y, 68P/69W/189I/372L, 68P/69W/189I/381L, 68P/69W/214R/215P/271Y, 68P/69W/214R/343V, 68P/69W/215P, 68P/108G/377L, 68P/184S, 68P/184S/189E, 68P/189I/271Y/372L, 68P/189I/343V, 68P/214R/215P/271Y/281P/282A/372L, 68P/215P/271Y/343V/372L/381L, 68P/215P/377L, 68P/271Y/372L, 68P/377L, 69F/108G/270E/372L/377L, 69F/189L, 69F/215K, 69F/215K/269L/270I/377L, 69F/215R, 69F/285L/373G, 69L, 69L/70L/331Q/372M, 69L/189E/271Y/281P/282A, 69L/189I, 69L/189I/214R/271Y/281P/282A/343V, 69L/189I/271Y/343V/381L, 69L/189I/280G/282G/343V/372L/381L, 69L/189I/282A, 69L/189Q/377Y, 69L/215P/271Y/280G/281P/282C, 69L/215P/271Y/282A, 69L/215P/271Y/372L, 69L/215P/343V/372L/381L, 69L/215R/285P/317P, 69L/271Y, 69L/271Y/372L, 69L/282C/343V/372L, 69L/372L, 69M/70A/372M, 69W, 69W/70L, 69W/70L/372M, 69W/70L/459R, 69W/108S, 69W/189E/214R/343V/372L, 69W/189E/271Y/343V, 69W/189E/372L, 69W/189I, 69W/189I/215P/343V, 69W/189I/271Y, 69W/189I/343V/381L, 69W/189Q/372L/377Y, 69W/212A/213L/215R/280G/281P, 69W/214R/215P/271Y/372L/377Y/381L, 69W/214R/271Y/282A, 69W/214R/271Y/343V, 69W/215K/343V, 69W/215P, 69W/215R, 69W/215R/323Y, 69W/282A, 69W/372M, 69Y/108G/281P/285P, 69Y/110A/215R/281P, 69Y/189L/281P/373G, 70L, 70L/212P, 108G, 108G/189I/282A/285L/320W, 108G/189L, 108G/189L/320W, 108G/189L/377I, 108G/215K, 108G/215P/377L, 108G/269L/270E, 108G/270E, 108G/282A/285L/377L, 108G/285L, 108G/320W/323I, 108G/377I, 108G/377L, 126C, 126C/184S/213S/280G/281P/285L/320G, 126C/184S/213S/372L, 126C/189I/285L/372L, 126C/215P, 126C/372L, 181L/215P, 189E/372L/377Y, 189I, 189I/214R/215P/271Y/282G, 189I/215K, 189I/215P/343V/372L, 189I/215R/249T/277M, 189I/270E/285L, 189I/270E/372L, 189I/280G/282A, 189I/320W/377I, 189I/343V, 189I/377I, 189L, 189Q, 189Q/214R, 189Q/215P/271Y/281P/282C/377Y, 189Q/343V, 189Q/343V/377Y, 189Q/381L, 213S/215P/320G, 214R/215P/271Y, 214R/215P/271Y/377Y, 214R/271Y, 214R/280G/282A/343V/377Y/381L, 215K, 215K/281P/285L/372L, 215K/281P/373G, 215K/285L/317P, 215K/285L/445L, 215K/323Y, 215K/372L, 215K/372L/377L, 215K/373G, 215P, 215P/271Y/372L, 215P/320G, 215P/320G/372L, 215P/372L, 215P/372L/377L, 215P/377L, 215P/381L, 215R, 215R/249T/280G/281P/285L/372L, 215R/280G/281P/285L/372L, 215R/281P/285L/373G, 215R/285P, 215R/320G, 215R/372L, 215W, 215W/285L/346S, 215W/285P, 215W/373G, 249T/377L, 269L/270E/281P/372L/377L, 270E/377L, 271Y, 271Y/343V, 271Y/343V/372L, 271Y/343V/372L/381L, 280G/285L/372L, 281P/372L, 282A/285L/320W/323I, 285L/323I, 320W, 343V/372L, 372L, 372L/377L, 372L/381L, 372M, 373G, and 377L, wherein the amino acid positions are numbered with reference to SEQ ID NO: 8. In some further embodiments, the polynucleotide sequence encodes an engineered carboxyesterase comprising at least one substitution or substitution set selected from P63A, P63A/M189A, P63A/N215R/A343V, P63R, P63R/Y65G/A108G, P63R/Y65G/A108G/M189L, P63R/Y65G/A108G/F377I, P63R/Y65G/T282A/A285L/Y320W/F323I, P63R/Y65G/Y320W/F323I, P63R/A108G, P63R/A108G/T282A/A285L/F377L, P63R/A108G/A285L/F377I, P63R/A108G/Y320W/F323C, P63R/F377I, P63T/N215R, P63Y, P63Y/M189L, P63Y/G212P/N215R, P63Y/G212P/N215R/P268A/A269N/A343V, P63Y/N215P/A269N, P63Y/N215R, P63Y/N215R/V270I/W271S, P63Y/P268A/A269N/V270I/A429V, Y65G/Y320W, Y65G/Y320W/F323I, Y65W/I69L/I372L, Y65W/

I69M/G70A/L281P/I372L, Y65W/I69W/G70L/I372L, Y65W/G70L/I372M, A68P, A68P/I69L/M189E/G214R/W271Y/V280G, A68P/I69L/M189E/G214R/I372L, A68P/I69L/M189I/G214R/N215P/W271Y, A68P/I69L/M189I/L281P/T282C/I372L/F377Y/A381L, A68P/I69L/M189Q/G214R, A68P/I69L/M189Q/W271Y/V280G/I372L/A381L, A68P/I69L/N215P, A68P/I69L/W271Y, A68P/I69L/T282C/V287I, A68P/I69L/A343V/I372L, A68P/I69W/M189E/G214R/N215P/W271Y/L281P/T282G/A343V/A381L, A68P/I69W/M189E/V280G/L281P/T282A/I372L/F377Y, A68P/I69W/M189E/A343V/A381L, A68P/I69W/M189I/G214R/N215P, A68P/I69W/M189I/G214R/F377Y/A381L, A68P/I69W/M189I/W271Y, A68P/I69W/M189I/I372L, A68P/I69W/M189I/381L, A68P/I69W/G214R/N215P/W271Y, A68P/I69W/G214R/A343V, A68P/I69W/N215P, A68P/A108G/F377L, A68P/E184S, A68P/E184S/M189E, A68P/M189I/W271Y/I372L, A68P/M189I/A343V, A68P/G214R/N215P/W271Y/L281P/T282A/I372L, A68P/N215P/W271Y/A343V/I372L/A381L, A68P/N215P/F377L, A68P/W271Y/I372L, A68P/F377L, I69F/A108G/V270E/I372L/F377L, I69F/M189L, I69F/N215K, I69F/N215K/A269L/V270I/F377L, I69F/N215R, I69F/A285L/T373G, I69L, I69L/G70L/P331Q/I372M, I69L/M189E/W271Y/L281P/T282A, I69L/M189I, I69L/M189I/G214R/W271Y/L281P/T282A/A343V, I69L/M189I/W271Y/A343V/A381L, I69L/M189I/V280G/T282G/A343V/I372L/A381L, I69L/M189I/T282A, I69L/M189Q/F377Y, I69L/N215P/W271Y/V280G/L281P/T282C, I69L/N215P/W271Y/T282A, I69L/N215P/W271Y/I372L, I69L/N215P/A343V/I372L/A381L, I69L/N215R/A285P/T317P, I69L/W271Y, I69L/W271Y/I372L, I69L/T282C/A343V/I372L, I69L/I372L, I69M/G70A/I372M, I69W, I69W/G70L, I69W/G70L/I372M, I69W/G70L/G459R, I69W/A108S, I69W/M189E/G214R/A343V/I372L, I69W/M189E/W271Y/A343V, I69W/M189E/I372L, I69W/M189I, I69W/M189I/N215P/A343V, I69W/M189I/W271Y, I69W/M189I/A343V/A381L, I69W/M189Q/I372L/F377Y, I69W/G212A/A213L/N215R/V280G/L281P, I69W/G214R/N215P/W271Y/I372L/F377Y/A381L, I69W/G214R/W271Y/T282A, I69W/G214R/W271Y/A343V, I69W/N215K/A343V, I69W/N215P, I69W/N215R, I69W/N215R/F323Y, I69W/T282A, I69W/I372M, I69Y/A108G/L281P/A285P, I69Y/T110A/N215R/L281P, I69Y/M189L/L281P/T373G, G70L, G70L/G212P, A108G, A108G/M189I/T282A/A285L/Y320W, A108G/M189L, A108G/M189L/Y320W, A108G/M189L/F377I, A108G/N215K, A108G/N215P/F377L, A108G/A269L/V270E, A108G/V270E, A108G/T282A/A285L/F377L, A108G/A285L, A108G/Y320W/F323I, A108G/F377I, A108G/F377L, R126C, R126C/E184S/A213S/V280G/L281P/A285L/Y320G, R126C/E184S/A213S/I372L, R126C/M189I/A285L/I372L, R126C/N215P, R126C/I372L, V181L/N215P, M189E/I372L/F377Y, M189I, M189I/G214R/N215P/W271Y/T282G, M189I/N215K, M189I/N215P/A343V/I372L, M189I/N215R/A249T/G277M, M189I/V270E/A285L, M189I/V270E/I372L, M189I/V280G/T282A, M189I/Y320W/F377I, M189I/A343V, M189I/F377I, M189L, M189Q, M189Q/G214R, M189Q/N215P/W271Y/L281P/T282C/F377Y, M189Q/A343V, M189Q/A343V/F377Y, M189Q/A381L, A213S/N215P/Y320G, G214R/N215P/W271Y, G214R/N215P/W271Y/F377Y, G214R/W271Y, G214R/V280G/T282A/A343V/F377Y/A381L, N215K, N215K/L281P/A285L/I372L, N215K/L281P/T373G, N215K/A285L/T317P, N215K/A285L/V445L, N215K/F323Y, N215K/I372L, N215K/I372L/F377L, N215K/T373G, N215P, N215P/W271Y/I372L, N215P/Y320G, N215P/Y320G/I372L, N215P/I372L, N215P/I372L/F377L, N215P/F377L, N215P/A381L, N215R, N215R/A249T/V280G/L281P/A285L/I372L, N215R/V280G/L281P/A285L/I372L, N215R/L281P/A285L/T373G, N215R/A285P, N215R/Y320G, N215R/I372L, N215W, N215W/A285L/G346S, N215W/A285P, N215W/T373G, A249T/F377L, A269L/V270E/L281P/I372L/F377L, V270E/F377L, W271Y, W271Y/A343V, W271Y/A343V/I372L, W271Y/A343V/I372L/A381L, V280G/A285L/I372L, L281P/I372L, T282A/A285L/Y320W/F323I, A285L/F323I, Y320W, A343V/I372L, I372L, I372L/F377L, I372L/A381L, I372M, T373G, and F377L, wherein the amino acid positions are numbered with reference to SEQ ID NO: 8.

An isolated polynucleotide encoding an improved carboxyesterase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

For bacterial host cells, suitable promoters for directing transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See, e.g., Villa-Kamaroff et al., Proc. Natl. Acad. Sci. USA 75: 3727-3731 [1978]), as well as the tac promoter (See, e.g., DeBoer et al., Proc. Natl Acad. Sci. USA 80: 21-25 [1983]). Additional suitable promoters are known to those in the art.

For filamentous fungal host cells, suitable promoters for directing the transcription of the nucleic acid constructs of the present invention include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, as well as other useful promoters for yeast host cells (See, e.g., Romanos, et al., Yeast 8:423-488 [1992]).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase, as well as other useful terminators for yeast host cells known in the art (See, e.g., Romanos et al., supra).

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase., as well as additional useful polyadenylation sequences for yeast host cells known in the art (See, e.g., Guo et al., Mol. Cell. Biol., 15:5983-5990 [1995]).

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA—as well as additional signal peptides known in the art (See, e.g., Simonen et al., Microbiol. Rev., 57: 109-137 [1993]).

Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase, as well as additional useful signal peptide coding regions (See, e.g., Romanos et al., 1992, supra).

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the carboxyesterase polypeptide of the present invention would be operably linked with the regulatory sequence.

Thus, in some embodiments, the present invention is also directed to a recombinant expression vector comprising a polynucleotide encoding an engineered carboxyesterase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector (i.e., a vector that exists as an extrachromosomal entity), the replication of which is independent of chromosomal replication, (e.g., a plasmid, an extrachromosomal element, a minichromosome, or an artificial chromosome). The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus.*

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Non-limiting examples of bacterial origins of replication are P15A on or the origins of replication of plasmids pBR322, pUC19, pACYC177 (which plasmid has the P15A ori), or pACYC184 permitting replication in *E. coli*, and pUB110, pE194, or pTA1060, permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (See, e.g., Ehrlich, Proc. Natl. Acad. Sci. USA 75:1433 [1978]).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include, but are not limited to p3×FLAG™ expression vectors (Sigma-Aldrich), which include a CMV promoter and hGH polyadenylation site for expression in mammalian host cells and a pBR322 origin of replication and ampicillin resistance markers for amplification in *E. coli*. Other commercially available suitable expression vectors include but are not limited to the pBluescriptII SK(−) and pBK-CMV vectors (Stratagene), and plasmids derived from pBR322 (Gibco BRL), pUC (Gibco BRL), pREP4, pCEP4 (Invitrogen) or pPoly (See, Lathe et al., Gene 57:193-201 [1987]).

The skilled person will appreciate that, upon production of an enzyme, in particular, depending upon the cell line used and the particular amino acid sequence of the enzyme, post-translational modifications may occur. For example, such post-translational modifications may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of engineered carboxyesterase enzymes that have been subjected to, or have undergone, one or more post-translational modifications. Thus, the engineered carboxyesterases of the invention includes one which has undergone a post-translational modification, such as described herein.

Deamidation is an enzymatic reaction primarily converting asparagine (N) to iso-aspartic acid (iso-aspartate) and aspartic acid (aspartate) (D) at approximately 3:1 ratio. This deamidation reaction is, therefore, related to isomerization of aspartate (D) to iso-aspartate. The deamidation of asparagine and the isomerisation of aspartate, both involve the intermediate succinimide. To a much lesser degree, deamidation can occur with glutamine residues in a similar manner.

Oxidation can occur during production and storage (i.e., in the presence of oxidizing conditions) and results in a covalent modification of a protein, induced either directly by reactive oxygen species, or indirectly by reaction with secondary by-products of oxidative stress. Oxidation happens primarily with methionine residues, but may occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

N-terminal glutamine (Q) and glutamate (glutamic acid) (E) in the engineered carboxyesterases are likely to form pyroglutamate (pGlu) via cyclization. Most pGlu formation happens in manufacturing, but it can be formed non-enzymatically, depending upon pH and temperature of processing and storage conditions.

C-terminal lysine clipping is an enzymatic reaction catalyzed by carboxypeptidases, and is commonly observed in enzymes. Variants of this process include removal of lysine from the enzymes from the recombinant host cell.

In the present invention, the post-translational modifications and changes in primary amino acid sequence described above do not result in significant changes in the activity of the engineered xcarboxyesterase enzymes.

Host Cells for Expression of Carboxyesterase Polypeptides

In another aspect, the present invention provides a host cell comprising a polynucleotide encoding an improved carboxyesterase polypeptide of the present invention, the polynucleotide being operatively linked to one or more control sequences for expression of the carboxyesterase enzyme in the host cell. Host cells for use in expressing the carboxyesterase polypeptides encoded by the expression vectors of the present invention are well known in the art and include but are not limited to, bacterial cells, such as *E. coli, Geobacillus stearothermophilus, Lactobacillus kefir, Lactobacillus brevis, Lactobacillus minor, Mycobacterium tuberculosis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture media and growth conditions for the above-described host cells are well known in the art.

Polynucleotides for expression of the carboxyesterase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

*Escherichia coli* W3110 is a host strain that finds use in the present invention, although it is not intended that the present invention be limited to this specific host strain. The expression vector was created by operatively linking a polynucleotide encoding an improved carboxyesterase into the plasmid pCK110900 operatively linked to the lac promoter under control of the lad repressor. The expression vector also contained the P15a origin of replication and the chloramphenicol resistance gene. Cells containing the subject polynucleotide in *Escherichia coli* W3110 can be isolated by subjecting the cells to chloramphenicol selection.

Methods of Generating Engineered Carboxyesterase Polypeptides.

In some embodiments, to make the improved carboxyesterase polynucleotides and polypeptides of the present invention, the naturally-occurring carboxyesterase enzyme that catalyzes the amidation reaction is obtained (or derived) from *T. fusca*. In some embodiments, the parent polynucleotide sequence is codon optimized to enhance expression of the carboxyesterase in a specified host cell. As an illustration, the parental polynucleotide sequence encoding the wild-type carboxyesterase polypeptide of *T. fusca* was constructed from oligonucleotides prepared based upon the known polypeptide sequence of *T. fusca* carboxyesterase sequence available in Genbank database (Genbank accession no. WP_011292850.1). The parental polynucleotide sequence, designated as SEQ ID NO: 1, was codon optimized for expression in *E. coli* and the codon-optimized polynucleotide cloned into an expression vector, placing the expression of the carboxyesterase gene under the control of the lac promoter and lacI repressor gene. Clones expressing the active carboxyesterase in *E. coli* were identified and the genes sequenced to confirm their identity. The codon-optimized polynucleotide sequence designated SEQ ID NO: 1 was the parent sequence utilized as the starting point for most experiments and library construction of engineered carboxyesterases evolved from the original wild-type carboxyesterase.

In other embodiments, to make the improved carboxyesterase polynucleotides and polypeptides of the present invention, the naturally-occurring carboxyesterase enzyme that catalyzes the amidation reaction is obtained (or derived) from *G. stearothermophilus*. In some embodiments, the parent polynucleotide sequence is codon optimized to enhance expression of the carboxyesterase in a specified host cell. As an illustration, the parental polynucleotide sequence encoding the wild-type carboxyesterase polypeptide of *G. stearothermophilus* was constructed from oligonucleotides prepared based upon the known polypeptide sequence of *G. stearothermophilus* carboxyesterase sequence available in Genbank database (Genbank accession no. WP_033015113). The parental polynucleotide sequence, designated as SEQ ID NO: 137, was codon optimized for expression in *E. coli* and the codon-optimized polynucleotide cloned into an expression vector, placing the expression of the carboxyesterase gene under the control of the lac promoter and lad repressor gene. Clones expressing the active carboxyesterase in *E. coli* were identified and the genes sequenced to confirm their identity. The polynucleotide sequence designated SEQ ID NO: 137 was the parent sequence utilized as the starting point for most experiments and library construction of engineered carboxyesterases evolved from the original wild-type carboxyesterase.

In some embodiments, to make the improved carboxyesterase polynucleotides and polypeptides of the present invention, the naturally-occurring carboxyesterase enzyme that catalyzes the amidation reaction was obtained or derived from *M. tuberculosis*. In some embodiments, the parent polynucleotide sequence was codon optimized to enhance expression of the carboxyesterase in a specified host cell. As an illustration, the parental polynucleotide sequence encoding the wild-type carboxyesterase polypeptide of *M. tuberculosis* was constructed from oligonucleotides prepared based upon the known polypeptide sequence of *M. tuberculosis* carboxyesterase sequence available in Genbank database (Genbank accession no. WP_003407276). The parental polynucleotide sequence, designated as SEQ ID NO: 139, was codon optimized for expression in *E. coli* and the codon-optimized polynucleotide cloned into an expression vector, placing the expression of the carboxyesterase gene under the control of the lac promoter and lad repressor gene. Clones expressing the active carboxyesterase in *E. coli* were identified and the genes sequenced to confirm their identity. The codon-optimized polynucleotide sequence designated SEQ ID NO: 139, was the parent sequence utilized as the starting point for most experiments and library construction of engineered carboxyesterases evolved from the original wild-type carboxyesterase, as described herein.

In some embodiments, engineered carboxyesterases are obtained by subjecting the polynucleotide encoding the naturally occurring carboxyesterase or a codon-optimized version of the polynucleotide encoding naturally-occurring carboxyesterase to mutagenesis and/or directed evolution methods, as discussed above. Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See, e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, 9,665,694, 9,684,771, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336. It is not intended that the present invention be limited to any particular methods, as various methods find use in the art.

In some embodiments, where the improved enzyme property desired is thermal stability, enzyme activity may be measured after subjecting the enzyme preparations to a defined temperature and measuring the amount of enzyme activity remaining after heat treatments. Clones containing a polynucleotide encoding a carboxyesterase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods or polymerase mediated methods) to form any desired continuous sequence. For example, polynucleotides and oligonucleotides of the invention can be prepared by chemical synthesis (e.g., using the classical phosphoramidite method described by Beaucage et al., Tet. Lett., 22:1859-69 [1981], or the method described by Matthes et al., EMBO J., 3:801-05 [1984], as it is typically practiced in automated synthetic methods). According to the phosphoramidite method, oligonucleotides are synthesized (e.g., in an automatic DNA synthesizer), purified, annealed, ligated and cloned in appropriate vectors. In addition, essentially any nucleic acid can be obtained from any of a variety of commercial sources (e.g., The Midland Certified Reagent Company, Midland, Tex., The Great American Gene Company, Ramona, Calif., ExpressGen Inc. Chicago, Ill., Operon Technologies Inc., Alameda, Calif., and many others).

Engineered carboxyesterase enzymes expressed in a host cell can be recovered from the cells and or the culture medium using any one or more of the well-known techniques for protein purification, including, among others, lysozyme treatment, sonication, filtration, salting-out, ultracentrifugation, and chromatography. Suitable solutions for lysing and the high efficiency extraction of proteins from bacteria, such as *E. coli*, are commercially available under the trade name CelLytic B (Sigma-Aldrich).

Chromatographic techniques for isolation of the carboxyesterase polypeptide include, among others, reverse phase chromatography high performance liquid chromatography (HPLC), ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved carboxyesterase enzymes. For affinity chromatography purification, any antibody which specifically binds the carboxyesterase polypeptide may be used. For the production of antibodies, various host animals, including but not limited to rabbits, mice, rats, etc., may be immunized by injection with the carboxyesterase. The carboxyesterase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacillus* Calmette Guerin) and *Corynebacterium parvum.*

The carboxyesterases may be prepared and used in the form of cells expressing the enzymes, as crude extracts, or as isolated or purified preparations. The carboxyesterases may be prepared as lyophilizates, in powder form (e.g., acetone powders), or prepared as enzyme solutions. In some embodiments, the carboxyesterases can be in the form of substantially pure preparations.

In some embodiments, the carboxyesterase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

Methods of Using the Engineered Carboxyesterase Enzymes and Compounds Prepared Therewith Whole cells transformed with gene(s) encoding the engineered carboxyesterase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like), followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the amidation reaction will generally vary depending on the quantities of product desired, and concomitantly the amount of carboxyesterase substrate employed. The following guidelines can be used to determine the amounts of carboxyesterase, and/or amine. Generally, ester and amine substrates can be employed at a concentration of about 5 to 200 grams/liter using from about 50 mg to about 5 g of carboxyesterase.

Those having ordinary skill in the art will readily understand how to vary these quantities to tailor them to the desired level of productivity and scale of production.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the carboxyesterase and the carboxyesterase substrate may be added first to the solvent.

For improved mixing efficiency when an aqueous co-solvent system is used, the carboxyesterase and amine may be added and mixed into the aqueous phase first. The organic phase may then be added and mixed in, followed by addition of the carboxyesterase substrate. Alternatively, the carboxyesterase substrate may be premixed in the organic phase, prior to addition to the aqueous phase Suitable conditions for carrying out the carboxyesterase-catalyzed amidation reactions described herein include a wide variety of conditions which can be readily optimized by routine experimentation that includes, but is not limited to, contacting the engineered carboxyesterase enzyme and substrates at an experimental pH and temperature and detecting product, for example, using the methods described in the Examples provided herein.

The carboxyesterase catalyzed amidation is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The amidation reaction is generally allowed to proceed until essentially complete, or near complete, coupling of substrates is obtained. Amide formation (product) can be monitored using known methods by detecting substrates and/or product. Suitable methods include, but are not limited to, gas chromatography, HPLC, and the like. Conversion yields of the amide product generated in the reaction mixture are generally greater than about 50%, may also be greater than about 60%, may also be greater than about 70%, may also be greater than about 80%, may also be greater than 90%, and are often greater than about 97%.

EXAMPLES

Various features and embodiments of the present invention are illustrated in the following representative examples, which are intended to be illustrative, and not limiting.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and 1 (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); RT (room temperature); MWD (multiple wavelength detector); CDS (coding sequence); DNA (deoxyribonucleic acid); RNA (ribonucleic acid); RP-HPLC (reversed-phased high performance liquid chromatography); FIOP (fold improvement over positive control); HTP (high throughput); LB (Luria broth); TFA (trifluoroacetic acid); MeCN (acetonitrile); TEoA (triethanolamine); THF (tetrahydrofuran); Sigma-Aldrich (Sigma-Aldrich, St. Louis, Mo.); Millipore (Millipore, Corp., Billerica Mass.); Difco (Difco Laboratories, BD Diagnostic Systems, Detroit, Mich.); Daicel (Daicel, West Chester, PA); Genetix (Genetix USA, Inc., Beaverton, Oreg.); Molecular Devices (Molecular Devices, LLC, Sunnyvale, CA); Applied Biosystems (Applied Biosystems, part of Life Technologies, Corp., Grand Island, NY), Agilent (Agilent Technologies, Inc., Santa Clara, CA); Thermo Scientific (part of Thermo Fisher Scientific, Waltham, MA); Corning (Corning, Inc., Palo Alto, CA); and Bio-Rad (Bio-Rad Laboratories, Hercules, CA); Phenomenex (Phenomenex, Inc., Torrence, CA); Epicentre (Epicentre, Madison, WI).

Example 1

Wild-type Carboxyesterase Gene Acquisition and Construction of Expression Vectors This Example describes the acquisition of the codon optimized recombinant polynucleotides encoding wild-type carboxyesterases (SEQ ID NOs: 2, 138, and 140) from which genes encoding engineered carboxyesterases in the following examples were derived, and expression vectors and host cells suitable for such engineering.

The codon optimized versions of the wild-type genes (SEQ ID NO: 1, 137, and 139) encoding the wild-type carboxyesterases (SEQ ID NO: 2, 138, and 140) of *T. fusca*, *G. stearothermophilus*, and *M. tuberculosis*, respectively, were synthesized for expression in *E. coli*. The codon optimized gene was cloned into expression vector pCK11 0900 (See, e.g., U.S. Pat. No. 9,714,437 and U.S. Pat. Appln. Publn. No. 2006/0195947, both of which are incorporated herein by reference in their entireties and for all purposes), under the control of a lac promoter. The expression vector also contained the P15a origin of replication and the chloramphenicol resistance gene. These sequence-verified vectors were transformed into a *E. coli* W3110 strain for expression. The polynucleotides (odd numbered SEQ ID NOs: 1-135) encoding the engineered carboxyesterases (even numbered SEQ ID NOs: 2-136) of the present invention were likewise cloned into vector pCK11 0900 for expression in a derivative of *E. coli* W3110 strain. Directed evolution techniques generally known to those skilled in the art were used to generate the libraries of the engineered carboxyesterases.

Example 2

HTP Production and Analysis of Wild-Type Carboxyesterase Polypeptides

HTP lysates were prepared by taking the codon-optimized carboxyesterase genes (described in Example 1) which were then transformed into *E. coli* W3110 and plated on Luria-Bertani (LB) agar medium containing 1% glucose and 30 μg/mL chloramphenicol (CAM). After incubation for at least 16 h at 30° C., colonies were picked using a Q-botobotic colony picker (Genetix) into a 96-well shallow well microtiter plate containing 200 μL of LB, 1% glucose, and 30 μg/mL CAM. Cells were grown 18-20 h at 30° C., with shaking at 200 rpm. Then, 20 μL of these cultures were then transferred to 360 μL of Terrific Broth (TB) and 30 μg/mL CAM in a deep well plate. After incubation at 30° C. with shaking at 250 rpm for 2.5 h ($OD_{600}$ 0.6-0.8), recombinant gene expression was induced by adding isopropyl thioglycoside (IPTG) to a final concentration of 1 mM. The plates were then incubated at 30° C., with shaking at 250 rpm for 18-21 h.

Cell cultures were pelleted at 3500×g for 20 mM, and the media discarded. Cell pellets were lysed in 200 μL of 0.2 M TEoA, pH 7.5 with 1 g/L lysozyme, 0.5 g/L polymixin B sulfate, and 0.5 μL OmniCleave™ endonuclease (Epicentre) by shaking at RT for 2 h. Samples were centrifuged at 3500×g for 20 min to clarify cellular debris, and the supernatant was used to carry out the transformations described in Examples 3 and 4.

Example 3

Activity of Wild-Type Carboxyesterases on Substrate Set #1

The wild-type carboxyesterase polypeptides were generated as described in Example 2. To analyze for amidation activity on substrate set #1 (Table 3.1), 20 μL supernatant were added to a mixture of 10 μL aniline, 10 μL ethyl acetate, 100 μL of 0.1 M sodium phosphate buffer, pH 7.0. Reactions were incubated at 20° C. and shaken at 300 rpm for 18 h. Samples were quenched by diluting 2-fold in MeCN. Analysis of reactions was performed by RP-HPLC as described in Example 12.1.

TABLE 3.1

| Substrate Sets Used to Evaluate Carboxyesterase Amidation Activity |
|---|
| Set 1 |
| 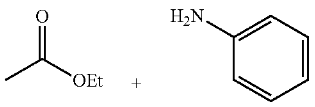 |
| Products |
| 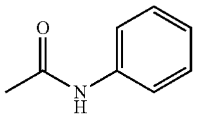 |
| 1 |
| Set 2 |
| 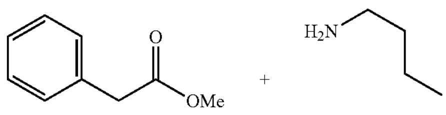 |
| 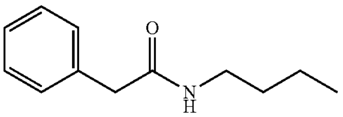 |
| 2 |
| Set 3 |
| 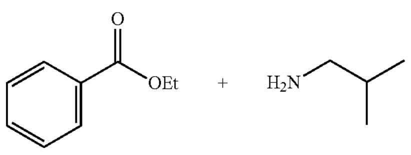 |
| 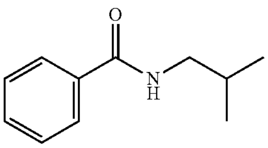 |
| 3 |

TABLE 3.1-continued
Substrate Sets Used to Evaluate Carboxyesterase Amidation Activity
Set 4
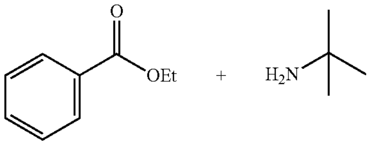
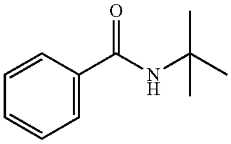
4
Set 5
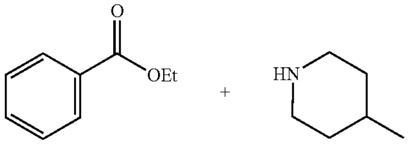
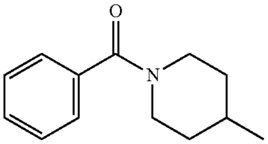
5
Set 6
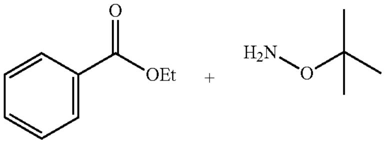
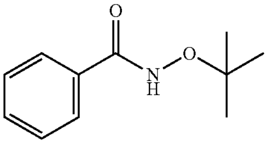
6
Set 7
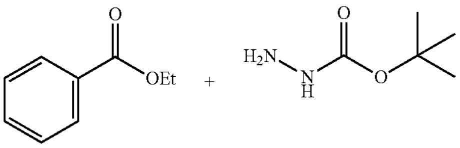
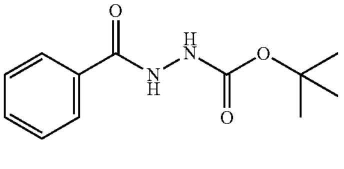 [SMILES: CC(C)(C)OC(=O)NNC(=O)c1ccccc1]
7
TABLE 3.1-continued
Substrate Sets Used to Evaluate Carboxyesterase Amidation Activity
Set 8
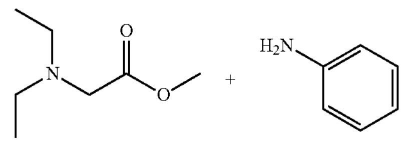
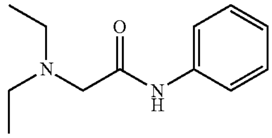
8
Set 9
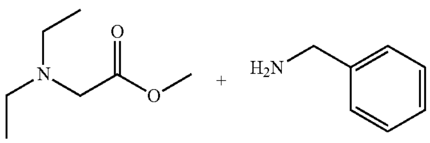
Products
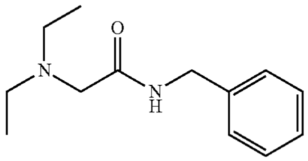 [SMILES: CCN(CC)CC(=O)NCc1ccccc1]
9
Set 10
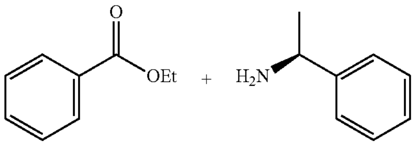
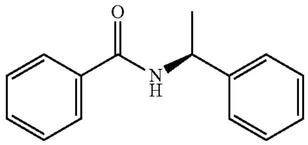 [SMILES: C[C@H](NC(=O)c1ccccc1)c1ccccc1]
10
Set 11
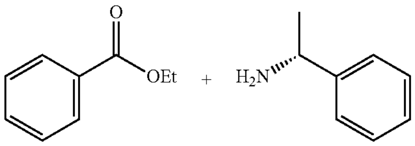

TABLE 3.1-continued

Substrate Sets Used to Evaluate Carboxyesterase Amidation Activity

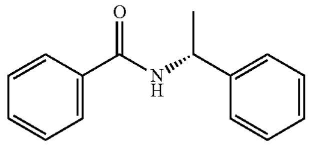 [SMILES: C[C@@H](NC(=O)c1ccccc1)c1ccccc1]

11

Set 12

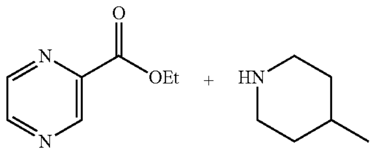

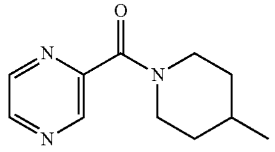

12

Set 13

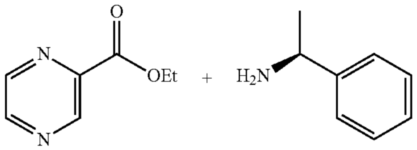

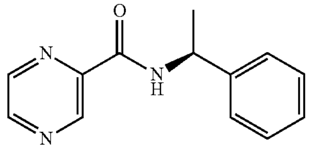 [SMILES: C[C@H](NC(=O)c1cnccn1)c1ccccc1]

13

Set 14

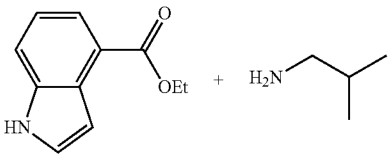

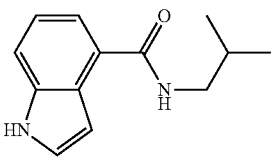 [SMILES: CC(C)CNC(=O)c1cccc2[nH]ccc12]

14

TABLE 3.1-continued

Substrate Sets Used to Evaluate Carboxyesterase Amidation Activity

Set 15

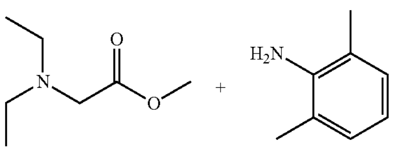

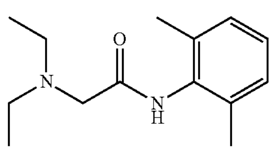 [SMILES: CCN(CC)CC(=O)Nc1c(C)cccc1C]

15

Example 4

Activity of Wild-Type Carboxyesterases on Substrate Sets #2-7

Wild-type carboxyesterase polypeptides were generated according to the methods described in Example 2. To analyze for amidation activity on substrate set #2 (See, Table 3.1), 100 μL supernatant was added to a mixture of 10 μL methyl phenylacetate, 10 μL n-butylamine, 10 μL dimethyl sulfoxide (DMSO), and 20 μL of 0.1 M sodium phosphate buffer, pH 7.0. Reactions were incubated at RT and shaken at 300 rpm for 18 h. Samples were quenched by diluting with an equal volume of MeCN. Analysis of substrates and products was performed by RP-HPLC using the methods described in Example 12.1.

To analyze for amidation activity on substrate sets #3-7 (See, Table 3.1), 120 μL of a mixture of 75-100 g/L amine and 15 g/L ethyl benzoate in 0.1 M potassium phosphate buffer, pH 7.5, with or without 50% isopropanol, were added to 100 μL supernatant, produced as described in Example 2. Reactions were incubated at 55° C. and shaken at 400 rpm for 18 h. Samples were quenched by diluting 3-fold in MeCN and then centrifuged for 5-8 min at 4000×g. The resultant supernatant was analyzed by RP-HPLC using the methods described in Example 12.2. In one experiment using substrate set #3, 120 μL of a mixture of 5 g/L isobutylamine and 15 g/L ethyl benzoate in 0.1 M potassium phosphate buffer, pH 7.5, was added to 100 μL supernatant, produced as described in Example 2. The results for all of these substrate sets are provided in Table 4.1 with the substrate sets indicated by "reaction" numbers (i.e., "R1," "R2," "R3," etc.).

TABLE 4.1

Solvent Tolerance and Substrate Scoping of Wild-type Carboxyesterases (SEQ ID NOs: 2, 138, and 140)[1]

| Conditions (KPi Buffer, pH 7.5) | R1 | R2 | R3 | R4 | R5 | R6 | R7 |
|---|---|---|---|---|---|---|---|
| *T. fusca* | ‡ | | † | | +++++ | +++ | +++ |
| *G. stearothermophilus* | ## | +++++ | # | + | | † | |
| *M. tuberculosis* | # | ++++ | + | +++ | | ++++ | |
| **Conditions (KPi Buffer, pH 7.5/IPA (50:50 v/v %))** | **R1** | **R2** | **R3** | **R4** | **R5** | **R6** | **R7** |
| *T. fusca* | | | † | | | | ++++ |
| *G. stearothermophilus* | | | ## | | | # | ++ |
| *M. tuberculosis* | | | ## | + | + | | +++ |

[1]Levels of increased activity were determined relative to the reference peak area of the negative control powder. In this Table, "+" = >0, <20; "++" = >20, <50; "+++" = >50, <100; "++++" = >100, <500; "+++++" = >500, <1000; "#" = >1000, <2000; "##" = >2000, <5000; "†" = >5000, <10000; "‡" = >10000, <15000.

Example 5

Production of Wild-Type Carboxyesterase Shake Flask Powders

The wild-type carboxyesterases (SEQ ID NOs: 2, 138, and 140) were produced in shake flasks for further characterization. The *E. coli* transformants containing the plasmid encoding WT carboxyesterases were grown on Luria-Bertani (LB) agar medium containing 1% glucose and 30 Kg/mL chloramphenicol (CAM). After incubation for at least 16 h at 30° C., single colonies were picked into 6 mL of LB, 1% glucose, and 30 μg/mL CAM. Cells were grown 18-20 h at 30° C., with shaking at 250 rpm. This culture was then transferred into Terrific Broth (TB) and 30 μg/mL CAM at a final $OD_{600}$ of 0.2 and a final volume of 250 mL. After incubation of the flasks at 25° C. or 30° C. with shaking at 250 rpm for 2.5 h ($OD_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed 3× in 30 mL ice cold 50 mM sodium phosphate pH 7.5, resuspended in 12 mL of the same buffer, and lysed using a cell disruptor at 18-20 kpsi. Lysates were clarified at 10000×g for 30 min, and clarified supernatants were lyophilized to an off-white powder.

TABLE 5.1

Wild-type Carboxyesterase (SEQ ID NO: 2, 138, and 140) Growth Evaluation

| Shake Flask | SEQ ID NO: | Growth $OD_{600}$[1] 25° C. 0 | Growth $OD_{600}$ 30° C. | Harvest $OD_{600}$ 25° C. | Harvest $OD_{600}$ 30° C. | [2]Pellet Mass 25° C. | Pellet Mass 30° C. | [3]Powder Mass 25° C. | Powder Mass 30° C. |
|---|---|---|---|---|---|---|---|---|---|
| Neg. Ctrl. | — | +++ | +++ | ++ | ++ | ++++ | +++ | + | ++ |
| *T. fusca* | 2 | ++++ | ++++ | +++ | ++++ | +++ | ++++ | ++ | ++ |
| *G. stearothermophilus* | 138 | ++++ | ++++ | + | N/A | ++ | N/A | ++ | N/A |
| *M. tuberculosis* | 140 | ++++ | ++++ | +++ | +++ | ++++ | ++++ | +++ | +++ |

[1]OD 600 rankings as follows ("+" = >10, <15: "++" = >15, <20: "+++" = >20, <25; "++++" = >25, <30);
[2]Mass pellet rankings as follows ("+" = >3 g, <4 g; "++" = >4 g, <5 g; "+++" = >5 g, <6 g; "++++" = >6 g, <7 g);
[3]Mass of powder ranking as follows ("+" = >0.2 g, <0.5 g; "++" = >0.5 g, <1.0 g; "+++" = >1.0 g, <1.5 g)

Example 6

Solvent Tolerance Evaluation of Wild-Type Carboxyesterase Polypeptides

In this Example, experiments conducted to determine the solvent tolerance of the wild-type carboxyesterases are described. In these experiments, the tolerance to organic solvent of the lyophilized shake flask powders prepared in Example 5 was determined, by testing activity on substrate sets #3 and #5. Reactions were conducted in a 96 well plate (reaction volume 220 μL) with 10 g/L enzyme powder, 30-34 g/L amine, 43 g/L ester, and 10% DMSO, or 50% isopropanol, or 15-25% MeCN or 25% THF in 0.1 M potassium phosphate buffer, pH 7.5. Reactions were heated to 50° C. with shaking at 400 rpm for 18-21 h. Reactions were quenched by diluting 3-fold in MeCN. Reaction samples were analyzed by RP-HPLC using methods described in Example 12.2.

TABLE 6.1

Solvent Tolerance Evaluation of Wild-type Carboxyesterases (SEQ ID NO: 2, 138, and 140)

| Substrate Set | Co-solvent | | *T. fusca* | *G. stearothermophilus* | *M. tuberculosis* |
|---|---|---|---|---|---|
| #3 | Buffer Only | | +++++ | ++ | ++ |
| | MeCN | 15% | ++ | ++ | ++ |
| | | 25% | ++ | ++ | ++ |
| | THF | 15% | ++ | − | ++ |
| | | 25% | ++ | ++ | ++ |
| | DMSO | 15% | ++++ | + | − |
| | | 25% | +++ | ++ | ++ |

TABLE 6.1-continued

| Solvent Tolerance Evaluation of Wild-type Carboxyesterases (SEQ ID NO: 2, 138, and 140) | | | | | |
|---|---|---|---|---|---|
| Substrate Set | Co-solvent | | *T. fusca* | *G. stearothermophilus* | *M. tuberculosis* |
| #5 | Buffer Only | | ++ | – | – |
| | MeCN | 15% | + | + | ++ |
| | | 25% | + | + | – |
| | THF | 15% | ++ | – | – |
| | | 25% | + | – | – |
| | DMSO | 15% | ++ | – | – |
| | | 25% | ++ | – | – |

[1] Levels of increased activity were determined relative to the reference negative control powder (Table 5.1) and defined as follows: "–" = no activity; "+" > 1-fold activity; "++" >1-fold activity, < 2-fold activity; "+++" > 2-fold, <3-fold activity; "++++" > 4-fold, <5-fold activity; "+++++" > than 5-fold activity.

Example 7

Production and Analysis of Engineered *T. fusca* Carboxyesterase Polypeptide Libraries Plasmid libraries containing evolved *T. fusca* carboxyesterase genes were transformed in *E. coli* according to the methods described in Example 1, and produced following the methods described in Example 2. The cell lysates were used to carry out the activity assessments described in Examples 8 and 9.

Example 8

Amidation Activity of Engineered *T. fusca* Carboxyesterase Polypeptides on Substrate Sets #3, 8-12

*T. fusca* carboxyesterase variants were generated according to Example 7. To analyze for amidation activity on substrate set #3 (See, Table 3.1), 20 μL of supernatant produced as described in Example 7, were added to a mixture of 25 μL MeCN with 3 M ethyl benzoate, 110 μL of 0.6 M isobutylamine in 0.2 M TEoA (pH adjusted to 9.5), and 65 μL 0.2 M TEoA, pH 8.5. Reactions were incubated at 50° C. and shaken at 300 rpm for 18 h. Samples were quenched by diluting 4-fold in MeCN. Analysis of reactions was performed by RP-HPLC using the methods described in Example 12.2.

To evaluate for amidation activity on substrate sets #3, 8-12 (See, Table 3.1), 20-50 μL supernatant produced as described in Example 7, were added to a mixture of 25 μL MeCN with 2-3.2 M amine, 110 μL of 0.4-0.6 M ester suspension in 0.2 M TEoA (pH adjusted to 8), and 35-65 μL 0.2 M TEoA, pH 8.5-9.0. Reactions were incubated at 50° C. and shaken at 300 rpm for 16-18 h. Samples were quenched by diluting 4-fold in MeCN. Analysis of reactions was performed by RP-HPLC, as described in Examples 13.3, 13.4, and 13.5. In one experiment using substrate set #8, 50 μL supernatant produced as described in Example 7, were added to a mixture of 25 μL MeCN with 3 M glycine methyl ester, 110 μL of 0.6 M aniline in 0.2 M TEoA (pH adjusted to 8), and 35 μL 0.2 M TEoA, pH 8.5. Reactions were incubated at 50° C. and shaken at 300 rpm for 18 h. Samples were quenched by diluting 4-fold in MeCN. Analysis of reactions was performed by RP-HPLC using the methods described in Example 12.3. The amino acid substitutions of these variants are indicated relative to SEQ ID NO: 2.

TABLE 8.1

| Amidation[1] by *T. fusca* Carboxyesterase Variants Relative to SEQ ID NO: 2 on Substrate Sets 3, 8, 9, 10, 11, and 12 | | | | | | | | |
|---|---|---|---|---|---|---|---|---|
| Variant No. | SEQ ID NO: (nt/aa) | Amino Acid Mutations | Set 3 | Set 8 | Set 9 | Set 10 | Set 11 | Set 12 |
| 1 | | A108W | *** | | | | | |
| 2 | 3/4 | L282Q | *** | | | | | |
| 3 | 5/6 | L282A | *** | * | | * | | |
| 4 | 7/8 | L282T | *** | | | * | ***** | |
| 5 | | A108K | *** | | | | | |
| 6 | 9/10 | A285L | ** | * | | | | |
| 7 | | I69F | ** | | | | | |
| 8 | 11/12 | L282C | ** | * | | | | |
| 9 | | L282W | ** | | | | | |
| 10 | | L282R | ** | | | | | |
| 11 | | F323Y | ** | | | | | |
| 12 | | I69W | * | | | | | |
| 13 | 13/14 | A108G | * | *** | | | | |
| 14 | | I69Y | * | | | | | |
| 15 | | T110A | * | | | | | |
| 16 | | A108Q | * | | | | | |
| 17 | | A285P | * | | | | | |
| 18 | | T373G | * | | | | | |
| 19 | 15/16 | N215R | * | * | | | | |
| 20 | | T317P | * | | | | | |
| 21 | | I69L | * | | | | | |
| 22 | | N215K | * | * | | | | |
| 23 | | A108R | * | | | | | |
| 24 | 17/18 | L281P | * | | | | ***** | |
| 25 | 19/20 | N215W | * | | | | | * |
| 26 | | L209P | * | | | | | |
| 27 | | P283K | * | | | | | |
| 28 | | F377Y | * | | | | | |
| 29 | | A213P | * | | | | | |

TABLE 8.1-continued

Amidation[1] by *T. fusca* Carboxyesterase Variants Relative to SEQ ID NO: 2 on Substrate Sets 3, 8, 9, 10, 11, and 12

| Variant No. | SEQ ID NO: (nt/aa) | Amino Acid Mutations | Set 3 | Set 8 | Set 9 | Set 10 | Set 11 | Set 12 |
|---|---|---|---|---|---|---|---|---|
| 30 | | G70W | * | | | | | |
| 31 | | A249V/F284P | * | | | | | |
| 32 | 21/22 | G212P | * | * | | | | |
| 33 | | A186G | * | | | | | |
| 34 | | I372A/V376A | * | | | | | |
| 35 | | A71R | * | * | | | | |
| 36 | | Y320S | * | | | | | |
| 37 | 135/136 | I372L | * | | | | | |
| 38 | | A71Y | * | | | | | |
| 39 | | A108S | * | | | | | |
| 40 | | S115T | * | | | | | |
| 41 | | A71G | * | | | | | |
| 42 | | A71F | * | | | | | |
| 43 | | S190H | * | | | | | |
| 44 | 23/24 | V280G | * | | | | ***** | |
| 45 | | P64W | * | | | | | |
| 46 | | I69V | * | | | | | |
| 47 | | L209E | * | | | | | |
| 48 | | P117A | * | | | | | |
| 49 | | A68L | * | | | | | |
| 50 | | P64I | * | | | | | |
| 51 | | L209S | * | | | | | |
| 52 | | Y65W | * | | | | | |
| 53 | 25/26 | N215P | * | * | | | | |
| 54 | | P63A | * | | | | | |
| 55 | | S279L/V280G/L282M | * | | | | | |
| 56 | | T110S | * | | | | | |
| 57 | | S115H | * | | | | | |
| 58 | | V376M | * | | | | | |
| 59 | | V376L | * | | | | | |
| 60 | | G70L | * | | | | | |
| 61 | | G214T | * | | | | | |
| 62 | | G212A | * | | | | | |
| 63 | | V376A | * | | | | | |
| 64 | | F284T | * | | | | | |
| 65 | | P405D | * | | | | | |
| 66 | | S185T | * | | | | | |
| 67 | | G70R | * | | | | | |
| 68 | | V280E | * | | | | | |
| 69 | 27/28 | P283D | * | | | | ***** | |
| 70 | | Y320S/I372A/V376G | * | | | | | |
| 71 | | G70T | * | | | | | |
| 72 | | P64E | * | | | | | |
| 73 | | Y320F | * | | | | | |
| 74 | | R428V | * | | | | | |
| 75 | | Y320A | * | | | | | |
| 76 | | R321S | * | | | | | |
| 77 | | W271K | * | | | | | |
| 78 | | W271P | * | | | | | |
| 79 | | Y65T | * | | | | | |
| 80 | | V376G | * | | | | | |
| 81 | | F377W | * | | | | | |
| 82 | | V118I | * | | | | | |
| 83 | | F323R | * | | | | | |
| 84 | | A217W | * | | | | | |
| 85 | | G214K | * | | | | | |
| 86 | | A429L | * | | | | | |
| 87 | | T110H | * | | | | | |
| 88 | | T110P | * | | | | | |
| 89 | | R153L | * | | | | | |
| 90 | 29/30 | Y320G | * | | | | *** | |
| 91 | | Y320S/V376G/F377V | * | | | | | |
| 92 | | G114H | * | | | | | |
| 93 | | V280S | * | | | | | |
| 94 | 31/32 | R321L | * | | | | *** | |
| 95 | | Y320S/F323S/I372A | * | | | | | |
| 96 | | T224I/P268S/1372F | * | | | | | |
| 97 | | V118N | | | | | | |
| 98 | | A217V | * | | | | | |

TABLE 8.1-continued

Amidation[1] by *T. fusca* Carboxyesterase Variants Relative to SEQ ID NO: 2 on Substrate Sets 3, 8, 9, 10, 11, and 12

| Variant No. | SEQ ID NO: (nt/aa) | Amino Acid Mutations | Set 3 | Set 8 | Set 9 | Set 10 | Set 11 | Set 12 |
|---|---|---|---|---|---|---|---|---|
| 99 | | A71P | * | | | | | |
| 100 | | L209V | * | | | | | |
| 101 | | Y320G/F323S | * | | | | | |
| 102 | | W271L | * | | | | | |
| 103 | | P420G | * | | | | | |
| 104 | 33/34 | W271T | * | | | | | * |
| 105 | | P283C | * | | | | | |
| 106 | 35/36 | P63R | * | * | | | | |
| 107 | 37/38 | Y320W | * | * | | | | |
| 108 | 39/40 | S190K | * | | | | | * |
| 109 | | R126C | | | | | **** | |
| 110 | | L282S | | | | | | * |
| 111 | | F284C | | | | | ***** | |
| 112 | | F284V | | | | | | * |
| 113 | | A269N | | * | | | | |
| 114 | | W271A | | | | | ** | |
| 115 | | P283T | | | | | **** | |
| 116 | | A71H/Q263R | | | | | * | |
| 117 | 41/42 | N215R/W271R | | | * | | * | |
| 118 | | A217G | | * | | | | |
| 119 | | A213S | | | | | ** | |
| 120 | | G277M | | | | | *** | |
| 121 | | L281V | | | | | *** | |
| 122 | 43/44 | P283V | | | | | **** | |
| 123 | | D427A | | | | | * | |
| 124 | | P63Y | | * | | | | |
| 125 | | V270I/V470M | | | * | | | |
| 126 | | A269V | | | | | * | |
| 127 | | S279G | | | | | **** | |
| 128 | | A217S | | | | | * | |
| 129 | 45/46 | A68P | | | | * | * | |
| 130 | | P63T | | * | | | | |
| 131 | | A285M | | * | | | | * |
| 132 | 47/48 | P283Y | | | | | ***** | |
| 133 | | L311I | | * | | | | |
| 134 | | S279C | | | | | **** | |
| 135 | | V270I | | * | | | | |
| 136 | | V270R | | | | | ** | |
| 137 | | T317C | | | | | ** | |
| 138 | | W271S | | * | | | * | |
| 139 | | S279V | | | | | **** | |
| 140 | | A217R | | | * | | | |
| 141 | | S190L | | | | | * | |
| 142 | | P64A | | | | | * | |
| 143 | | A71V | | | | | * | |
| 144 | | P117F | | | | | * | |
| 145 | 49/50 | E184S/A249T | | | | | ***** | |
| 146 | 51/52 | F284T/P438T | | | | | ***** | |
| 147 | | L209G | | | | | * | |
| 148 | | G278H | | | | | *** | |
| 149 | | L324A | | | | | **** | |
| 150 | | S190M | | | | | * | |
| 151 | | P64G | | | | | * | |
| 152 | | A276F | | | | | **** | |
| 153 | | P64V | | | | | * | |
| 154 | | P64T | | | | | * | |
| 155 | | P66N | | | | | * | |
| 156 | | A217L | | | | | * | |
| 157 | | I69H | | | | | * | |
| 158 | | M216P | | | | | * | |
| 159 | | A213N | | | | | * | |
| 160 | | A217R/A231V | | | | | * | |
| 161 | | A213T/W271K | | | | | * | |
| 162 | | V118G/A349V | | | | | * | |
| 163 | | N215M | | | | | * | |
| 164 | | A188G | | | | | * | |
| 165 | | S190Q | | | | | * | |
| 166 | | T39M/F323I | | * | | | | |
| 167 | | G278S | | | | | **** | |
| 168 | | V118N/A269T | | | | | * | |
| 169 | | A213C | | | | | * | |
| 170 | | Y65S | | | | | * | |
| 171 | | P283R/A429V | | | | | | * |
| 172 | | A213V | | | | | * | |

TABLE 8.1-continued

Amidation[1] by *T. fusca* Carboxyesterase Variants Relative to SEQ ID NO: 2 on Substrate Sets 3, 8, 9, 10, 11, and 12

| Variant No. | SEQ ID NO: (nt/aa) | Amino Acid Mutations | Set 3 | Set 8 | Set 9 | Set 10 | Set 11 | Set 12 |
|---|---|---|---|---|---|---|---|---|
| 173 | 53/54 | A213L | | | * | | * | |
| 174 | | A186C | | | | | * | |
| 175 | | E184F | | | * | | | |
| 176 | | A213Q | | | | | * | |
| 177 | | I104Q/A429V | | | | | * | |
| 178 | | A217P | | | | | * | |
| 179 | | N111W | | | | | * | |
| 180 | 55/56 | F377L | | ** | | | | |
| 181 | 57/58 | E184G | | | * | | ***** | |
| 182 | | G214V | | | | | * | |
| 183 | | F323C | | * | | | | |
| 184 | 59/60 | R153H/N215P | | | * | | | |
| 185 | | W164R/W271T | | | | | ** | |
| 186 | | G212R | | | | | * | |
| 187 | | P286V | | | | | ** | |
| 188 | | F323I | | * | | | | |
| 189 | | N111M | | | | | * | |
| 190 | | I69G | | | | | * | |
| 191 | 61/62 | G214L | | | | | * | |
| 192 | | G212S | | | | | * | |
| 193 | | W271Q/A416V | | | | | * | |
| 194 | 63/64 | S190W | | | * | | * | |
| 195 | | Q210T | | | * | | | |
| 196 | | G114Q | | | | | * | |
| 197 | | N111V | | | | | * | |
| 198 | | Y119S | | | | | * | |
| 199 | | N111L | | | | | * | |
| 200 | | A213E | | | | | * | |
| 201 | | S211I | | | | | | * |
| 202 | | A186T | | | | | * | |
| 203 | | F109G/P117M | | | | | * | |
| 204 | | Y119G | | | | | * | |
| 205 | | S211V | | | | | * | |
| 206 | | L281Y/D374N | | | | | * | |
| 207 | | E184P | | | | | ***** | |
| 208 | | Y119P | | | | | * | |
| 209 | | A213R/S345G | | | | | * | |
| 210 | | W103T/P147S | | | | | * | |
| 211 | | W103R | | | | | | * |
| 212 | | N111S | | | | | * | |
| 213 | | W103P | | | | | * | |
| 214 | | Q210W | | | | | * | |
| 215 | | I104P | | | | | * | |
| 216 | | S211L | | | | | * | |
| 217 | | S190R | | | | | * | |
| 218 | | G183P | | | | | * | |
| 219 | | Q210P | | | | | * | |
| 220 | | A188E | | | | | * | |
| 221 | | H105L | | | | | * | |
| 222 | | G107P | | | | | * | |
| 223 | | S113P | | | | | * | |
| 224 | | G114A | | | | | * | |
| 225 | 65/66 | F77S/E184G | | | | | ***** | |
| 226 | | S279E | | | | | **** | |
| 227 | | G107D/S185W | | | | | ** | |
| 228 | | S211R | | | | | * | |
| 229 | | S185A | | | | | * | |
| 230 | | A186R | | | | | * | |
| 231 | | G187P | | | | | * | |
| 232 | | A186P | | | | | * | |
| 233 | | R62H/P117G | | | | | * | |
| 234 | | N111R | | | | | * | |
| 235 | | S115V | | | | | * | |
| 236 | | G107L | | | * | | | |
| 237 | | G107S | | | * | | | |
| 238 | | Y65G | | * | | | | |
| 239 | | E184Y | | | | | | * |
| 240 | | G174D/L282V | | | | | | * |

[1]Levels of increased activity were determined relative to the reference polypeptide and defined as follows: <1.5x; "*" = >1.5x, <3.5x; "" = >3.5x, <5.5x; "*" = >5.5x, <7.5x; "**" = >7.5x, <9.5x; "***" = >9.5x, <10.5x.

Example 9

Evaluation of Shake Flask Powders of Engineered *T. fusca* Carboxyesterase Polypeptides Powders of evolved *T. fusca* carboxyesterases were prepared in shake flask scale quantities following the methods described in Example 5. The amidation activity of the lyophilized shake flask powders was assessed by testing their activity on substrate set #3. First, 1.0 mL reaction mixtures were prepared with 10 g/L enzyme powder, 0.3 M isobutylamine, 0.3 M ethyl benzoate in toluene, followed by addition of 20 μL of 0.2 M TEoA buffer, pH 8.5. Reactions were heated to 50° C. with shaking at 500 rpm for 60 h. Reactions were quenched by diluting 100 μL reaction mixture into 1.4 mL acetone. Reaction samples were analyzed by RP-HPLC using the methods provided in Table 12.2.

TABLE 9.1

Amide Formation by *T. fusca* Carboxyesterase Variants

| Variant No.: | Amide Formation (FIOP)[1] Relative to SEQ ID NO: 2 |
|---|---|
| 4 | ++++ |
| 3 | ++++ |
| 12 | +++ |
| 31 | +++ |
| 28 | ++ |
| 24 | ++ |
| 37 | ++ |

[1]Levels of increased activity or selectivity were determined relative to the reference polypeptide of SEQ ID NO: 2 and defined as follows: "++" > than 1.2-fold but less than 2.5-fold increase; "+++" > than 2.5-fold but less than 5-fold; "++++" > than 5-fold but less than 10-fold.

Example 10

Production and Analysis of Combinatorial *T. fusca* Carboxyesterase Libraries Plasmid libraries obtained through combinatorial shuffling on a *T. fusca* carboxyesterase variant (SEQ ID NO: 8) were transformed in to *E. coli* W3110 according to the methods described in Example 1. The HTP lysates produced according to the methods described in Example 2, were used to carry out the activity assessments described in Example 11.

Example 11

Activity of Engineered *T. fusca* Carboxyesterase Polypeptides on Selected Substrate Sets 3, 5, 8, 12-15

*T. fusca* carboxyesterase variants generated from combinatorial libraries were analyzed for amidation activity on substrate sets #3, 5, 8, and 12-15 (See, Table 3.1). To analyze for amidation activity on substrate set #3 (See, Table 3.1), 10 μL supernatant produced as described in Example 7, and were added to a mixture of 25 μL MeCN with 3 M ethyl benzoate, 110 μL of 0.6 M isobutylamine in 0.2 M TEoA (pH adjusted to 8), and 75 μL 0.2 M TEoA, pH 8.5. Reactions were incubated at 50° C. and shaken at 300 rpm for 18 h. Samples were quenched by diluting 4-fold in MeCN. To analyze for amidation activity on substrate sets #5, 8, and 12-15, 20-50 μL supernatant were produced as described in Example 7, and added to a mixture of 25 μL MeCN with 2-3.2 M amine, 110 μL of 0.4-0.6 M ester suspension in 0.2 M TEoA (pH adjusted to 8), and 35-65 μL 0.2 M TEoA, pH 8.5-9. Reactions were incubated at 50° C. and shaken at 300 rpm for 16-18 h. Samples were quenched by diluting 4-fold in MeCN. Analysis of reactions was performed by RP-HPLC, using the methods described in Examples 12.2 (Set 3), 12.3 (Set 8), 12.5 (Set 12, and 13), 12.6 (Set 14), and 12.7 (Set 5 and 15). In one experiment using substrate set #8, 20 μL supernatant produced as described in Example 7 were added to a mixture of 25 μL MeCN with 3 M glycine methyl ester, 110 μL of 0.6 M aniline in 0.2 M TEoA (pH adjusted to 9.5), and 65 μL 0.2 M TEoA, pH 8.5. Reactions were incubated at 50° C. and shaken at 300 rpm for 18 h. Samples were quenched by diluting 4-fold in MeCN. Analysis of reactions was performed by RP-HPLC, using the methods describe in Example 12.3.

TABLE 11.1

Amidation[1] by *T. fusca* Carboxyesterase Variants Relative to SEQ ID NO: 8 on Substrate Sets 3, 5, 8, and 12-15

| Variant No. | SEQ ID NO: (nt/aa) | Amino Acid Mutations | Set 3 | Set 5 | Set 8 | Set 12 | Set 13 | Set 14 | Set 15 |
|---|---|---|---|---|---|---|---|---|---|
| 241 | 67/68 | Y65W/I69L/I372L | **** | | | | | | |
| 242 | | Y65W/I69W/G70L/I372L | *** | | | | | | |
| 243 | | I69W/G70L/G459R | *** | | | | | | |
| 244 | | I69W/G70L | *** | | | | | | |
| 245 | | G70L | ** | | | | | | |
| 246 | 69/70 | A68P/I69L/A343V/I372L | * | | * | | | * | |
| 247 | | I69L/G70L/P331Q/I372M | * | | * | | | | |
| 248 | 71/72 | I69L/W271Y/I372L | * | | * | | | | |
| 249 | 73/74 | I372L | * | * | * | * | | | |
| 250 | 75/76 | P63R/A108G | * | | | | | * | * |
| 251 | | R126C/I372L | * | | | | | | |
| 252 | | Y320W | * | | | | | | * |
| 253 | | I69L/I372L | * | | | | | | |
| 254 | | I69W/G212A/A213L/N215R/ V280G/L281P | * | | | | | | |
| 255 | | I69W/G70L/I372M | * | | | | | | |
| 256 | 77/78 | Y65W/I69M/G70A/L281P/ I372L | * | | * | * | | | |
| 257 | | A108G | * | | | | | * | * |
| 258 | | R126C | * | | | | | | |

TABLE 11.1-continued

Amidation[1] by *T. fusca* Carboxyesterase Variants Relative to SEQ ID NO: 8 on Substrate Sets 3, 5, 8, and 12-15

| Variant No. | SEQ ID NO: (nt/aa) | Amino Acid Mutations | Set 3 | Set 5 | Set 8 | Set 12 | Set 13 | Set 14 | Set 15 |
|---|---|---|---|---|---|---|---|---|---|
| 259 | 79/80 | I69W/I372M | * | * | ** | | | * | |
| 260 | | I69M/G70A/I372M | * | | * | | | | * |
| 261 | | I69L/T282C/A343V/I372L | * | | | | | | |
| 262 | | P63R | * | | | | | | * |
| 263 | 81/82 | V280G/A285L/I372L | * | | | * | | | * |
| 264 | | A68P/I69L/W271Y | * | | * | | | | |
| 265 | 83/84 | W271Y/A343V/1372L | * | * | | * | * | | |
| 266 | 85/86 | I69L | * | | * | | * | | * |
| 267 | 87/88 | L281P/I372L | * | * | * | | | * | |
| 268 | | I69L/W271Y | | | * | | | | |
| 269 | | I372M | | * | * | | | | |
| 270 | 89/90 | P63R/Y65G/A108G | | | | | | * | *** |
| 271 | | A343V/I372L | | | * | | | | |
| 272 | 91/92 | A68P/W271Y/I372L | | ** | | | | | ** |
| 273 | 93/94 | A108G/A285L | | | | | | * | ** |
| 274 | | Y65W/G70L/I372M | | * | | * | | | |
| 275 | | I372L/A381L | | * | | | | | ** |
| 276 | | I69W/N215P | | | | | | | *** |
| 277 | | I69W | | ***** | * | | | | |
| 278 | | A108G/V270E | | | | | | * | * |
| 279 | | W271Y/A343V/I372L/A381L | | ***** | | | | | |
| 280 | | P63Y | | | | * | | | |
| 281 | | A108G/F377I | | | | | | | **** |
| 282 | | P63A | | | | | | * | |
| 283 | | A68P/I69L/T282C/V287I | | | | | | | * |
| 284 | | T373G | | | | * | | | * |
| 285 | | I69W/T282A | | | * | | | | |
| 286 | 95/96 | A108G/N215K | | | | * | | | ***** |
| 287 | | N215P/I372L | | | | * | | | * |
| 288 | | Y65G/Y320W | | | | | | | * |
| 289 | | I69Y/A108G/L281P/A285P | | | | | | * | |
| 290 | | P63R/A108G/Y320W/F323C | | | | | | | * |
| 291 | | I69L/N215P/W271Y/I372L | | | | ** | | | |
| 292 | 97/98 | A68P | | ** | | | * | | * |
| 293 | | P63Y/P268A/A269N/V270I/ A429V | | * | | * | | | |
| 294 | | W271Y | | * | | | | | |
| 295 | | W271Y/A343V | | ***** | | | | | |
| 296 | | A68P/I69W/N215P | | | | | | | ***** |
| 297 | | R126C/E184S/A213S/I372L | | | | * | | | |
| 298 | | A108G/M189L/Y320W | | | | | | | *** |
| 299 | | I69F/A108G/V270E/I372L/ F377L | | | | | | | ***** |
| 300 | | I69L/N215P/W271Y/V280G/ L281P/T282C | | | | | | | *** |
| 301 | 99/100 | N215R/I372L | | | | * | | | ** |
| 302 | | P63R/F377I | | | | | | | **** |
| 303 | | A108G/Y320W/F323I | | | | | | | * |
| 304 | | I372L/F377L | | | | | | | ***** |
| 305 | | N215P/W271Y/I372L | | | | | | | *** |
| 306 | | I69L/N215P/A343V/I372L/ A381L | | | | * | | | |
| 307 | | R126C/N215P | | | | | | | * |
| 308 | 101/102 | N215K/L281P/A285L/I372L | | | | ** | | | ** |
| 309 | | A68P/F377L | | | | | | | ** |
| 310 | | A68P/I69W/G214R/N215P/ W271Y | | | | * | * | | |
| 311 | | A68P/A108G/F377L | | | | | | | ***** |
| 312 | | F377L | | | | | | | ** |
| 313 | 103/104 | P63T/N215R | | | | * | * | | ** |
| 314 | | A68P/I69W/M1891/A381L | | | | | ** | | |
| 315 | | A68P/E184S | | | | * | | | |
| 316 | 105/106 | I69W/N215R | | | | * | | | ***** |
| 317 | | I69L/N215P/W271Y/T282A | | | | | | | ** |
| 318 | | I69W/A108S | | | * | | | | |
| 319 | | N215P/Y320G | | | | * | | | * |
| 320 | | N215R/V280G/L281P/A285L/ I372L | | | | * | | | * |
| 321 | | V181L/N215P | | | | | | | * |
| 322 | 107/108 | P63A/N215R/A343V | | | | * | * | | *** |
| 323 | | N215P/Y320G/I372L | | | | * | | | |
| 324 | | M189I/F377I | | | | | | | *** |
| 325 | 109/110 | P63Y/G212P/N215R | | | | * | * | | ** |

TABLE 11.1-continued

Amidation[1] by *T. fusca* Carboxyesterase Variants Relative to SEQ ID NO: 8 on Substrate Sets 3, 5, 8, and 12-15

| Variant No. | SEQ ID NO: (nt/aa) | Amino Acid Mutations | Set 3 | Set 5 | Set 8 | Set 12 | Set 13 | Set 14 | Set 15 |
|---|---|---|---|---|---|---|---|---|---|
| 326 | | A108G/F377L | | | | | | | *** |
| 327 | | P63Y/N215P/A269N | | | | * | * | | |
| 328 | | I69W/N215K/A343V | | | | | * | | |
| 329 | | A68P/I69W/M189E/G214R/N215P/W271Y/L281P/T282G/A343V/A381L | | * | | | | | |
| 330 | 111/112 | P63Y/G212P/N215R/P268A/A269N/A343V | | | | * | | | ** |
| 331 | | I69F/N215K | | | | * | | | ***** |
| 332 | | G214R/N215P/W271Y | | | | | | | *** |
| 333 | | I69F/A285L/T373G | | | | * | | | * |
| 334 | | N215R/A249T/V280G/L281P/A285L/I372L | | | | * | | | * |
| 335 | | A68P/I69L/N215P | | | | | * | | |
| 336 | | A68P/I69W/M189I/I372L | | | | | ** | | |
| 337 | | R126C/M1891/A285L/I372L | | | | | | | ** |
| 338 | | N215P | | | | * | | | ** |
| 339 | | A249T/F377L | | | | | | | * |
| 340 | | N215K/A285L/V445L | | | | * | | | *** |
| 341 | 113/114 | P63Y/N215R | | | | * | * | | * |
| 342 | | P63A/M189A | | | | | | | * |
| 343 | | N215K | | | | * | | | *** |
| 344 | | N215K/F323Y | | | | * | | | * |
| 345 | | A285L/F323I | | | | | | | * |
| 346 | | A68P/I69W/M189I/W271Y | | | | | * | | |
| 347 | | I69W/M189I/A343V/A381L | | * | | | | | |
| 348 | | P63Y/N215R/V270I/W271S | | | | | | | * |
| 349 | | N215R | | | | * | * | | * |
| 350 | | I69W/M189E/1372L | | * | | | | | |
| 351 | | N215P/I372L/F377L | | | | * | | | ***** |
| 352 | | A68P/N215P/W271Y/A343V/I372L/A381L | | | | * | * | | |
| 353 | | N215R/Y320G | | | | * | | | *** |
| 354 | | I69W/M189I/W271Y | | | | | | | *** |
| 355 | | I69L/M189I/V280G/T282G/A343V/I372L/A381L | | ***** | | | | | |
| 356 | | P63R/A108G/A285L/F377I | | | | | | | ***** |
| 357 | | I69W/M189E/W271Y/A343V | | * | | | | | |
| 358 | | I69W/M189I | | | | | * | | |
| 359 | | A68P/G214R/N215P/W271Y/L281P/T282A/I372L | | | | | | | * |
| 360 | | M189I/Y320W/F377I | | | | | | | **** |
| 361 | | N215K/L281P/T373G | | | | * | | | * |
| 362 | | N215R/A285P | | | | | | | **** |
| 363 | | M189I/V270E/A285L | | | | | | | ** |
| 364 | | P63R/Y65G/A108G/F377I | | | | | | | ***** |
| 365 | | I69W/N215R/F323Y | | | | * | | | * |
| 366 | | M189Q | | ***** | | | | | |
| 367 | | M189I/N215P/A343V/I372L | | | | * | | | |
| 368 | | M189Q/A343V | | ***** | | | | | |
| 369 | | P63R/Y65G/Y320W/F323I | | | | | | | ** |
| 370 | | I69W/G214R/N215P/W271Y/I372L/F377Y/A381L | | ***** | | | | | |
| 371 | | A108G/T282A/A285L/F377L | | | | | | | ***** |
| 372 | | N215P/A381L | | | | * | * | | |
| 373 | | A108G/M189I/T282A/A285L/Y320W | | | | | | | ** |
| 374 | | T282A/A285L/Y320W/F323I | | | | | | | ** |
| 375 | | P63R/A108G/T282A/A285L/F377L | | | | | | | ***** |
| 376 | | I69W/G214R/W271Y/T282A | | | | | | | ** |
| 377 | | M189Q/A381L | | **** | | | | | |
| 378 | 115/116 | A68P/169W/M189I/G214R/N215P | | ***** | | * | * | | |
| 379 | | Y65G/Y320W/F323I | | | | | | | *** |
| 380 | 117/118 | N215K/T373G | | | | * | | | **** |
| 381 | | I69W/M189Q/1372L/F377Y | | ***** | | | | | |
| 382 | | M189E/I372L/F377Y | | ***** | | | | | |
| 383 | | A108G/M189L | | | | | | | ** |
| 384 | | A68P/I69W/M189E/A343V/A381L | | | | | * | | |
| 385 | | I69W/M189E/G214R/A343V/I372L | | ***** | | | | | |

TABLE 11.1-continued

Amidation[1] by *T. fusca* Carboxyesterase Variants Relative to SEQ ID NO: 8 on Substrate Sets 3, 5, 8, and 12-15

| Variant No. | SEQ ID NO: (nt/aa) | Amino Acid Mutations | Set 3 | Set 5 | Set 8 | Set 12 | Set 13 | Set 14 | Set 15 |
|---|---|---|---|---|---|---|---|---|---|
| 386 | | I69L/M189I/T282A | | | | | * | | |
| 387 | | A68P/M189I/W271Y/I372L | | | | | * | | |
| 388 | | G214R/N215P/W271Y/F377Y | | | | * | | | |
| 389 | 119/120 | N215K/I372L/F377L | | | | * | | | ***** |
| 390 | 121/122 | M189I/A343V | | ***** | | | * | | |
| 391 | 123/124 | N215R/L281P/A285L/T373G | | | | *** | | | * |
| 392 | 125/126 | N215W/A285L/G346S | | | | * | | | ** |
| 393 | | G214R/W271Y | | | | | | | * |
| 394 | | R126C/E184S/A213S/V280G/L281P/A285L/Y320G | | | | ** | | | |
| 395 | | A68P/I69L/M189I/L281P/T282C/I372L/F377Y/A381L | | | | *** | | | |
| 396 | | A68P/M189I/A343V | | | | | * | | |
| 397 | | I69L/M189I/W271Y/A343V/A381L | | | | | ** | | |
| 398 | | M189L | | | | | | | ** |
| 399 | | P63Y/M189L | | | | | | | * |
| 400 | | I69L/M189I | | | | | ** | | |
| 401 | | A68P/169W/G214R/A343V | | | | | * | | |
| 402 | | N215W | | | | * | | | * |
| 403 | | M189I/V280G/T282A | | | | | * | | |
| 404 | | N215W/A285P | | | | | | | ** |
| 405 | | M189I/N215K | | | | | | | * |
| 406 | | A68P/I69L/M189I/G214R/N215P/W271Y | | | | | * | | |
| 407 | | A68P/I69L/M189Q/W271Y/V280G/I372L/A381L | | ** | | | | | |
| 408 | 127/128 | M189I | | ** | | | * | | * |
| 409 | | P63R/Y65G/T282A/A285L/Y320W/F323I | | | | | | | * |
| 410 | | I69W/M189I/N215P/A343V | | | | | * | | |
| 411 | | A108G/M189L/F377I | | | | | | | ** |
| 412 | | I69F/M189L | | | | | | | ** |
| 413 | | N215K/A285L/T317P | | | | * | | | * |
| 414 | | I69Y/T110A/N215R/L281P | | | | * | | | |
| 415 | | I69L/N215R/A285P/T317P | | | | | | | * |
| 416 | | I69W/G214R/W271Y/A343V | | | | | * | | |
| 417 | | A213S/N215P/Y320G | | | | * | | | |
| 418 | | I69Y/M189L/L281P/T373G | | | | | | | * |
| 419 | | N215W/T373G | | | | * | | | * |
| 420 | | M189I/G214R/N215P/W271Y/T282G | | | | | * | | |
| 421 | | P63R/Y65G/A108G/M189L | | | | | | | * |
| 422 | 129/130 | I69F/N215K/A269L/V270I/F377L | | | | | | | ***** |
| 423 | | A68P/N215P/F377L | | | | | | | **** |
| 424 | | N215P/F377L | | | | | | | **** |
| 425 | | I69L/M189I/G214R/W271Y/L281P/T282A/A343V | | | | | | | ** |
| 426 | | M189I/N215R/A249T/G277M | | | | | | | * |
| 427 | | G70L/G212P | | | | | | | * |
| 428 | | A68P/E184S/M189E | | | | ** | | | |
| 429 | | M189Q/G214R | | ***** | | | | | |
| 430 | | M189Q/A343V/F377Y | | ***** | | | | | |
| 431 | 131/132 | M189Q/N215P/W271Y/L281P/T282C/F377Y | | ***** | | | | | |
| 432 | | G214R/V280G/T282A/A343V/F377Y/A381L | | ** | | | | | |
| 433 | | A68P/I69L/M189E/G214R/W271Y/V280G | | ** | | | | | |
| 434 | | A68P/I69W/M189E/V280G/L281P/T282A/I372L/F377Y | | ** | | | | | |
| 435 | | A68P/I69L/M189E/G214R/I372L | | * | | | | | |
| 436 | | I69L/M189E/W271Y/L281P/T282A | | * | | | | | |
| 437 | | I69L/M189Q/F377Y | | * | | | | | |
| 438 | | A68P/I69L/M189Q/G214R | | * | | | | | |
| 439 | | A68P/I69W/M189I/G214R/F377Y/A381L | | * | | | | | |
| 440 | 133/134 | A108G/N215P/F377L | | | | | | | ***** |
| 441 | | I69F/N215R | | | | * | | | *** |
| 442 | | N215K/1372L | | | | * | | | *** |

TABLE 11.1-continued

| Variant No. | SEQ ID NO: (nt/aa) | Amino Acid Mutations | Set 3 | Set 5 | Set 8 | Set 12 | Set 13 | Set 14 | Set 15 |
|---|---|---|---|---|---|---|---|---|---|
| Amidation[1] by *T. fusca* Carboxyesterase Variants Relative to SEQ ID NO: 8 on Substrate Sets 3, 5, 8, and 12-15 | | | | | | | | | |
| 443 | | V270E/F377L | | | | | | | * |
| 444 | | A269L/V270E/L281P/I372L/F377L | | | | | | | * |
| 445 | | M189I/V270E/I372L | | | | | | | * |
| 446 | | A108G/A269L/V270E | | | | | | * | |

[1]Levels of increased activity were determined relative to the reference polypeptide and defined as follows: <1.5x; "*" = >1.5x, <3.5x; "" = >3.5x, <5.5x; "*" = >5.5x, <7.5x; "**" = >7.5x, <9.5x; "***" = >9.5x, <10.5x.

Example 12

Analytical Detection of Produced Amides and Precursor Substrates

Data described in the above Examples were collected using analytical methods in Tables 12.1 through 12.7. The methods provided herein all find use in analyzing the products from the *T. fusca* carboxyesterase variants produced using the present invention. However, it is not intended that the present invention be limited to the methods described herein for the analysis of the products provided herein and/or produced using the methods provided herein. Indeed, any suitable method finds use in the present invention. Product peak elution was confirmed either by confirmation with a commercially available standard or by LC/MS/MS analysis.

TABLE 12.1

| Analytical Method | |
|---|---|
| Instrument | Agilent 1100 Series HPLC |
| Column | Agilent XDB C-18, 4.6 x 100 mm, 5 μm |
| Mobile Phase | Gradient I (20% Methanol; 80% Water)<br>Isocratic Gradient |
| Flow Rate | 1.000 mL/min |
| Run Time | 10.0 min |
| Elution order | Substrate Set #1 -<br>Aniline, acetanilide (1)<br>Substrate Set #2 -<br>amide (2), methyl phenylacetate |
| Column Temperature | RT |
| Injection Volume | 10 μL |
| Detection | UV 254 nm; Detector: MWD |

TABLE 12.2

| Analytical Method | | |
|---|---|---|
| Instrument | Agilent 1100 Series HPLC | |
| Column | Phenomenex Luna, C-18 4.6 x 150 mm, 5 μm | |
| Mobile Phase | Gradient I (A = 0.1% TFA in water,<br>B = 0.1% TFA in MeCN) | |
| | Time(min) | % A |
| | 0.000 | 100 |
| | 7.000 | 5 |
| Flow Rate | 1.5 mL/min | |
| Run Time | 8.000 min | |
| Elution order | Substrate Set #3 -<br>isobutylbenzamide (3), ethyl benzoate<br>Substrate Set #4 -<br>t-butylbenzamide (4), ethyl benzoate<br>Substrate Set #6 - | |

TABLE 12.2-continued

| Analytical Method | |
|---|---|
| | t-butoxy-benzamide (6), ethyl benzoate<br>Substrate Set #7 -<br>N'-t-butoxycarbonyl-benzhydrazide (7),<br>ethyl benzoate |
| Column Temperature | 25° C. |
| Injection Volume | 10 μL |
| Detection | UV 254 nm; Detector: MWD |

TABLE 12.3

| Analytical Method | | |
|---|---|---|
| Instrument | Agilent 1100 Series HPLC | |
| Column | Phenomenex Luna, C-18 4.6 x 150 mm, 5 μm | |
| Mobile Phase | Gradient I (A = 0.1% TFA in water,<br>B = 0.1% TFA in MeCN) | |
| | Time(min) | % A |
| | 0.000 | 90 |
| | 2.750 | 45 |
| | 3.150 | 5 |
| Flow Rate | 1.5 mL/min | |
| Run Time | 5.000 min | |
| Elution order | Substrate Set #8 - aniline, (amide 8) | |
| Column Temperature | 30° C. | |
| Injection Volume | 10 μL | |
| Detection | UV 220 and 260 nm; Detector: MWD | |

TABLE 12.4

| Analytical Method | | |
|---|---|---|
| Instrument | Agilent 1100 Series HPLC | |
| Column | Phenomenex Luna, C-18 4.6 x 150 mm, 5 μm | |
| Mobile Phase | Gradient I (A = 0.1% TFA in water,<br>B = 0.1% TFA in MeCN) | |
| | Time(min) | % A |
| | 0.000 | 90 |
| | 2.750 | 30 |
| | 3.150 | 5 |
| Flow Rate | 1.5 mL/min | |
| Run Time | 5.000 min | |
| Elution order | Substrate Set #9 - benzylamine, (amide 9) | |
| Column Temperature | 30° C. | |
| Injection Volume | 10 μL | |
| Detection | UV 230 and 260 nm; Detector: MWD | |

TABLE 12.5

| Analytical Method | | |
|---|---|---|
| Instrument | Agilent 1100 Series HPLC | |
| Column | Phenomenex Luna, C-18 4.6 x 150 mm, 5 μm | |
| Mobile Phase | Gradient I (A = 0.1% TFA in water, B = 0.1% TFA in MeCN) | |
| | Time(min) | % A |
| | 0.000 | 95 |
| | 1.100 | 75 |
| | 5.900 | 30 |
| Flow Rate | 1.5 mL/min | |
| Run Time | 8.000 min | |
| Elution order | Substrate Set #10 - S-phenylethylamine, (amide 10), ethyl benzoate<br>Substrate Set #11 - R-phenylethylamine, (amide 11), ethyl benzoate<br>Substrate Set #12 - 4-methylpiperidine, pyrazine ethyl ester, (amide 12)<br>Substrate Set #13 - S-phenylethylamine, pyrazine ethylester, (amide 13) | |
| Column Temperature | 25° C. | |
| Injection Volume | 10 μL | |
| Detection | UV 230 and 260 nm; Detector: MWD | |

TABLE 12.6

| Analytical Method | | |
|---|---|---|
| Instrument | Agilent 1100 Series HPLC | |
| Column | Phenomenex Luna, C-18 4.6 x 150 mm, 5 μm | |
| Mobile Phase | Gradient I (A = 0.1% TFA in water, B = 0.1% TFA in MeCN) | |
| | Time(min) | % A |
| | 0.000 | 70 |
| | 2.750 | 5 |
| | 3.750 | 5 |
| Flow Rate | 1.5 mL/min | |
| Run Time | 5.800 min | |
| Elution order | Substrate Set #14 - (amide 14), ethyl-4-indole ester | |
| Column Temperature | 25° C. | |
| Injection Volume | 10 μL | |
| Detection | UV 230 and 260 nm; Detector: MWD | |

TABLE 12.7

| Analytical Method | | |
|---|---|---|
| Instrument | Agilent 1200 Series HPLC with CTC-PAL Autosampler; AB Sciex 4000 Q-Trap MS | |
| Column | Agilent Eclipse, C-18 4.6 x 50 mm, 1.6 μm | |
| Mobile Phase | Gradient I (A: 0.1% formic acid in water; B: 0.1% formic acid in MeCN) | |
| | Time(min) | % A |
| | 0.000 | 90 |
| | 1.000 | 90 |
| | 3.000 | 5 |
| | 4.000 | 5 |
| Flow Rate | 0.6 mL/min | |
| Run Time | 5.000 min | |
| MRM Target Mass | MRM: 204.3 → 105.4; (amide 5)<br>MRM: 235.4 → 86.4; (amide 15) | |
| Column Temperature | RT | |
| Injection Volume | 10 μL (Samples were quenched by 2-fold dilution in 1:1 MeCN:water) | |
| Detection Parameters | LC/MS/MS analysis<br>Source dependent parameters:<br>CUR: 40; IS: 5500; TEM: 550° C.; GS1: 40; GS2: 40; DP: 120; EP: 10; CE: 27; CXP: 14. | |

While various specific embodiments have been illustrated and described, it will be appreciated that various changes can be made without departing from the spirit and scope of the invention(s).

The invention claimed is:

1. A polynucleotide sequence encoding an engineered carboxyesterase comprising a polypeptide sequence having at least 80% sequence identity to SEQ ID NO: 2, wherein said engineered carboxyesterase comprises a replacement of leucine at position 282 with another amino acid, wherein the amino acid positions of said polypeptide sequence are numbered with reference to SEQ ID NO: 2.

2. The polynucleotide sequence of claim 1, wherein said encoded engineered carboxyesterase further comprises at least one substitution or substitution set at positions selected from: 39, 39/323, 62, 62/117, 63, 64, 65, 66, 68, 69, 70, 71, 71/263, 77, 77/184, 103, 103/147, 104, 104/429, 105, 107, 107/185, 108, 109, 109/117, 110, 111, 113, 114, 115, 117, 118, 118/269, 118/349, 119, 126, 147, 153, 153/215, 164, 164/271, 174, 174/282, 183, 184, 184/249, 185, 186, 187, 188, 190, 209, 210, 211, 212, 213, 213/271, 213/345, 214, 215, 215/271, 216, 217, 217/231, 224, 224/268/372, 231, 249, 249/284, 263, 268, 269, 270, 270/470, 271, 271/416, 276, 277, 278, 279, 279/280, 280, 281, 281/374, 283, 283/429, 284, 284/438, 285, 286, 311, 317, 320, 320/323, 320/323/372, 320/372/376, 320/376/377, 321, 323, 324, 345, 349, 372, 372/376, 373, 374, 376, 377, 405, 416, 420, 427, 428, 429, 438, and 470, wherein the amino acid positions of said polypeptide sequence are numbered with reference to SEQ ID NO: 2.

3. A polynucleotide sequence encoding an engineered carboxyesterase comprising a polypeptide sequence having at least 80% sequence identity to SEQ ID NO: 8, wherein said engineered carboxyesterase comprises an amino acid residue selected from glutamine, serine, and threonine in said polypeptide sequence at position 282, wherein the amino acid positions of said polypeptide sequence are numbered with reference to SEQ ID NO: 8.

4. The polynucleotide sequence of claim 3, wherein said encoded engineered carboxyesterase further comprises at least one substitution or substitution set in said polypeptide sequence at positions selected from: 63, 63/65/108, 63/65/108/189, 63/65/108/377, 63/65/285/320/323, 63/65/320/323, 63/108, 63/108/285/377, 63/108/285/377, 63/108/320/323, 63/189, 63/212/215, 63/212/215/268/269/343, 63/215, 63/215/269, 63/215/270/271, 63/215/343, 63/268/269/270/429, 63/377, 65/69/70/281/372, 65/69/70/372, 65/69/372, 65/70/372, 65/320, 65/320/323, 68, 68/69/189/214, 68/69/189/214/215, 68/69/189/214/215/271, 68/69/189/214/215/271/281/343/381, 68/69/189/214/271/280, 68/69/189/214/372, 68/69/189/214/377/381, 68/69/189/271, 68/69/189/271/280/372/381, 68/69/189/280/281/372/377, 68/69/189/281/372/377/381, 68/69/189/343/381, 68/69/189/372, 68/69/189/381, 68/69/214/215/271, 68/69/214/343, 68/69/215, 68/69/271, 68/69/287, 68/69/343/372, 68/108/377, 68/184, 68/184/189, 68/189/271/372, 68/189/343, 68/214/215/271/281/372, 68/215/271/343/372/381, 68/215/377, 68/271/372, 68/377, 69, 69/70, 69/70/331/372, 69/70/372, 69/70/459, 69/108, 69/108/270/372/377, 69/108/281/285, 69/110/215/281, 69/189, 69/189/214/271/281/343, 69/189/214/343/372, 69/189/215/343, 69/189/271, 69/189/271/281, 69/189/271/343, 69/189/271/343/381, 69/189/280/343/372/381, 69/189/281/373, 69/189, 69/189/343/381, 69/189/372, 69/189/372/377, 69/189/377, 69/212/213/215/280/281, 69/214/215/271/372/377/381, 69/214/271/282, 69/214/271/343, 69/215, 69/215/269/270/377, 69/215/271/280/281, 69/215/271, 69/215/271/372, 69/215/285/317, 69/215/323, 69/215/343, 69/215/343/372/381, 69/271, 69/271/372, 69/343/372, 69/285/373, 69/372, 70, 70/212, 108, 108/189, 108/189/285/320, 108/189/320, 108/189/377, 108/215, 108/215/377, 108/269/270, 108/270, 108/285/377, 108/285, 108/320/323, 108/377, 126, 126/184/213/280/281/285/320, 126/184/213/372, 126/189/285/372, 126/215, 126/372, 181/215, 189, 189/214, 189/214/215/271, 189/215, 189/215/249/277, 189/215/271/281/377, 189/215/343/372, 189/270/285, 189/270/372, 189/280, 189/320/377, 189/343, 189/343/377, 189/372/377, 189/377, 189/381, 213/215/320, 214/215/271, 214/215/271/377, 214/271, 214/280/343/377/381, 215, 215/249/280/281/285/372, 215/271/372, 215/280/281/285/372, 215/281/285/372, 215/281/285/373, 215/281/373, 215/285, 215/285/317, 215/285/346, 215/285/445, 215/320, 215/320/372, 215/323, 215/372, 215/372/377, 215/373, 215/377, 215/381, 249/377, 269/270/281/372/377, 270/377, 271, 271/343, 271/343/372, 271/343/372/381, 280/285/372, 281/372, 285/320/323, 285/323, 320, 343/372, 372, 372/377, 372/381, 373, and 377, wherein the amino acid positions of said polypeptide sequence are numbered with reference to SEQ ID NO: 8.

5. A polynucleotide sequence encoding at least one engineered carboxyesterase, said polynucleotide sequence comprising at least 85% sequence identity to SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and/or 139.

6. The polynucleotide sequence of claim 1, wherein said polynucleotide sequence is operably linked to a control sequence.

7. The polynucleotide sequence of claim 1, wherein said polynucleotide sequence is codon optimized.

8. An expression vector comprising at least one polynucleotide sequence of claim 1.

9. A host cell comprising at least one expression vector of claim 8.

10. A host cell comprising at least one polynucleotide sequence of claim 1.

11. The host cell of claim 9, wherein said host cell is *E. coli*.

12. A method of producing an engineered carboxyesterase in a host cell, comprising culturing a host cell comprising at least one polynucleotide of claim 1, under suitable conditions, such that at least one engineered carboxyesterase is produced.

13. The method of claim 12, further comprising recovering at least one engineered carboxyesterase from the culture and/or host cell.

14. The method of claim 13, further comprising the step of purifying said at least one engineered carboxyesterase.

15. The polynucleotide sequence of claim 1, wherein the substitution at position 282 is a polar amino acid.

16. The polynucleotide sequence of claim 1, wherein the substitution at position 282 is selected from: L282Q, L282S, and L282T.

17. The polynucleotide sequence of claim 1, wherein said polynucleotide sequence has at least 85% sequence identity to a sequence selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and 139.

18. The polynucleotide sequence of claim 3, wherein said polynucleotide sequence has at least 85% sequence identity to a sequence selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, and 139.

* * * * *

SEQUENCE LISTING

<160> NUMBER OF SEQ ID NOS: 140

<210> SEQ ID NO 1
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 1

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660
```

```
gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 2
<211> LENGTH: 497
<212> TYPE: PRT
<213> ORGANISM: Thermobifida fusca

<400> SEQUENCE: 2

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220
```

-continued

```
Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 3
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 3

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480
```

```
gcactggaat gggttcgcga caacattgca cgctttgggg gtgacccagg taatgtgacc    540
gtgtttggcg aaagtgcggg cgcgatgagc gtgtgcaccc tgatggcaac cccgcgtgca    600
cgtggtctgt ttcgtcgtgc tatcttacag agcggcgcag gcaacatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtg    840
ctgcagccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tgggctgctg ccgttcatca caggggacta tgttaccact   1020
cacttagcca agagcggttt agatgcagat gcggccaaag cgtataccgc ggaaggtcgt   1080
ggtgaagaac cgggcgacat cttggccagc atcatcaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g            1491
```

<210> SEQ ID NO 4
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 4

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190
```

```
Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Gln Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 5
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 5

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300
```

```
atggtgtgga ttcatggtgg tgcctttact aacggtagtg gtagcgaacc ggtgtatgac    360
ggtgcagcat ttgcacgtga tggtgtggtg tttgtgagct tcaactatcg tctgggcatc    420
attggctttg cagatctgcc agatgcacca agtaatcgcg gcctgttaga tcaaatcgcc    480
gcactggaat gggttcgcga caacattgca cgctttgggg gtgacccagg taatgtgacc    540
gtgtttggcg aaagtgcggg cgcgatgagc gtgtgcaccc tgatggcaac cccgcgtgca    600
cgtggtctgt ttcgtcgtgc tatcttacag agcggcgcag gcaacatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtg    840
ctggctccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tggctgctg ccgttcatca caggggacta tgttaccact   1020
cacttagcca agagcggttt agatgcagat gcggccaaag cgtataccgc ggaaggtcgt   1080
ggtgaagaac cgggcgacat cttggccagc atcatcaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g           1491
```

<210> SEQ ID NO 6
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 6

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
```

```
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Ala Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 7
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 7

atggagatcg tgattcgcac gggcagcgga gatgtgcgtg gtagtaaaga gaacggcatt     60
```

```
gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 8
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 8

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110
```

```
Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 9
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 9

```
atggagatcg tgattcgcac gggcagcgga gatgtgcgtg gtagtaaaga gaacggcatt      60
gcagtgtttc gtggcatccc ctatgcggaa ccaccggttg gcgctcaccg ctttacggcg     120
ccacgtccac cacgtccatg ggatggtgtt cgtgacgcta ctgaattctc ggcgactgca     180
ccacgtccac catatccaga ggcaattggt gcgttgctga tcgaacgctt cattcctggc     240
gacgattacc tgaccctgaa cgtatggact ccggacccga atgcagttgg tctgccagtc     300
atggtgtgga ttcatggtgg tgcctttact aacggtagtg gtagcgaacc ggtgtatgac     360
ggtgcagcat ttgcacgtga tggtgtggtg tttgtgagct tcaactatcg tctgggcatc     420
attggctttg cagatctgcc agatgcacca agtaatcgcg gcctgttaga tcaaatcgcc     480
gcactggaat gggttcgcga caacattgca cgctttgggg gtgacccagg taatgtgacc     540
gtgtttggcg aaagtgcggg cgcgatgagc gtgtgcaccc tgatggcaac cccgcgtgca     600
cgtggtctgt ttcgtcgtgc tatcttacag agcggcgcag gcaacatggc agtcgctgca     660
gaagatgcta ccacaatcgc agctgtgatt gcccatcgtt taggtgttga gccaactgca     720
gcagcattag cgcatgttcc agttgcacag ttactggatg ttcagcagca agttgcccaa     780
gagattcaag gcgcgccaga tccagcagtt tggggtgaac gtattgcggg cggcagtgtg     840
ctgctgccat ttctgcccgt cattgatggg gaactgctga gccaacgtcc agcggaagcc     900
attgcgggcg gcgcaggtca tgatgtagac ctcttgtttg gcactaccac cgatgaatac     960
cgtctgtttc tggcaccaac tggctgctg ccgttcatca caggggacta tgttaccact    1020
cacttagcca agagcggttt agatgcagat gcggccaaag cgtataccgc ggaaggtcgt    1080
ggtgaagaac cgggcgacat cttggccagc atcatcaccg accaggtgtt tcgtattccg    1140
gcgctgcgta ttgcagaatc ccgtgttgat gcgcctgcac gtacctttgg ctacgaattc    1200
gcgtggcgta cgccacaatt ggacggcatt ctgggtgctt gtcatgcggt ggaacttccg    1260
ttcgtgtttc gcaccttaga ccgtgcggca tcgctggtgg gcacaaaccc gccagaagaa    1320
ctggcagaaa ccgtacacaa tgcctgggtg cgcttcgcga catcaggtga tccagggtgg    1380
ccggcgtgga atccggaaac ccgcagcgtg atgcgctttg atcacccggt ttccgagatg    1440
gttaccgacc cgtacccggc gacccgtgca ctgtgggatg gtgtgccatt g            1491
```

<210> SEQ ID NO 10
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 10

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80
```

-continued

```
Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495
```

-continued

Leu

<210> SEQ ID NO 11
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 11

```
atggagatcg tgattcgcac gggcagcgga gatgtgcgtg gtagtaaaga gaacggcatt     60
gcagtgtttc gtggcatccc ctatgcggaa ccaccggttg gcgctcaccg ctttacggcg    120
ccacgtccac cacgtccatg ggatggtgtt cgtgacgcta ctgaattctc ggcgactgca    180
ccacgtccac catatccaga ggcaattggt gcgttgctga tcgaacgctt cattcctggc    240
gacgattacc tgaccctgaa cgtatggact ccggacccga atgcagttgg tctgccagtc    300
atggtgtgga ttcatggtgg tgcctttact aacggtagtg gtagcgaacc ggtgtatgac    360
ggtgcagcat ttgcacgtga tggtgtggtg tttgtgagct tcaactatcg tctgggcatc    420
attggctttg cagatctgcc agatgcacca agtaatcgcg gcctgttaga tcaaatcgcc    480
gcactggaat gggttcgcga caacattgca cgctttgggg gtgacccagg taatgtgacc    540
gtgtttggcg aaagtgcggg cgcgatgagc gtgtgcaccc tgatggcaac cccgcgtgca    600
cgtggtctgt ttcgtcgtgc tatcttacag agcggcgcag gcaacatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtg    840
ctgtgtccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tgggctgctg ccgttcatca caggggacta tgttaccact   1020
cacttagcca agagcggttt agatgcagat gcggccaaag cgtataccgc ggaaggtcgt   1080
ggtgaagaac cgggcgacat cttggccagc atcatcaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g            1491
```

<210> SEQ ID NO 12
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 12

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
```

-continued

```
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Cys Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460
```

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 13
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 13
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgggtttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 14
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 14

-continued

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
```

```
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 15
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 15

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaggatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 16
<211> LENGTH: 497
```

```
<212> TYPE: PRT
<213> ORGANISM: Artificial Sequence
<220> FEATURE:
<223> OTHER INFORMATION: variant of esterase from Thermobifida fusca

<400> SEQUENCE: 16

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380
```

-continued

Ala Glu Ser Arg Val Asp Ala Pro Ala Arg Thr Phe Gly Tyr Glu Phe
385 390 395 400

Ala Trp Arg Thr Pro Gln Leu Asp Gly Ile Leu Gly Ala Cys His Ala
405 410 415

Val Glu Leu Pro Phe Val Phe Arg Thr Leu Asp Arg Ala Ala Ser Leu
420 425 430

Val Gly Thr Asn Pro Pro Glu Glu Leu Ala Glu Thr Val His Asn Ala
435 440 445

Trp Val Arg Phe Ala Thr Ser Gly Asp Pro Gly Trp Pro Ala Trp Asn
450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 17
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 17
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
cctctgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380

```
ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 18
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 18

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Pro Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350
```

```
Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 19
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 19

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gctggatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200
```

-continued

```
gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 20
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 20

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Trp Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
```

-continued

```
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 21
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 21

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agccctgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960
```

-continued

```
cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 22
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 22

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Pro Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270
```

```
Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 23
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 23

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780
```

```
gagattcaag gcgcgccaga tccagcagtt tggggtgaac gtattgcggg cggcagtggg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 24
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 24

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240
```

```
Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Gly Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 25
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 25

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540
```

-continued

```
gtgtttggcg aaagtgcggg cgcgatgagc gtgtgcaccc tgatggcaac cccgcgtgca    600

cgtggtctgt ttcgtcgtgc tatcttacag agcggcgcag gcccgatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g             1491
```

```
<210> SEQ ID NO 26
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 26

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
```

-continued

```
        195                 200                 205

Leu Gln Ser Gly Ala Gly Pro Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 27
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 27

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360
```

-continued

```
ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctggatt ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 28
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 28

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160
```

-continued

```
Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Asp Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 29
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 29

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120
```

-continued ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaaggt 960
cgtctgtttc tggcaccaac tggggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 30
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 30

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

```
Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Gly
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 31
<211> LENGTH: 1491
<212> TYPE: DNA
<213> ORGANISM: Artificial Sequence
<220> FEATURE:
<223> OTHER INFORMATION: variant of esterase from Thermobifida fusca -continued

<400> SEQUENCE: 31
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaatac 960
ttgctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccagc gacccgtgca ctgtgggatg gtgtgccatt g 1491

<210> SEQ ID NO 32
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 32

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val

-continued

```
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Leu Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 33
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 33

```
atggagatcg tgattcgcac gggcagcgga gatgtgcgtg gtagtaaaga gaacggcatt     60

gcagtgtttc gtggcatccc ctatgcggaa ccaccggttg gtgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt actggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 34
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 34

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45
```

-continued

```
Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Thr Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
```

-continued 465 470 475 480

Val Thr Asp Pro Tyr Pro Ala Thr Arg Ala Leu Trp Asp Gly Val Pro
485 490 495

Leu

<210> SEQ ID NO 35
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 35
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtcggc catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 36
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 36

Met Glu Ile Val Ile Arg Thr Gly Ser Gly Asp Val Arg Gly Ser Lys
1 5 10 15

-continued

```
Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Arg Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430
```

```
Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 37
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 37

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatgg    960

cgtctgtttc tggcaccaac tggctgctg ccgttcatca caggggacta tgttaccact    1020

cacttagcca agagcggttt agatgcagat gcggccaaag cgtataccgc ggaaggtcgt    1080

ggtgaagaac cgggcgacat cttggccagc atcatcaccg accaggtgtt tcgtattccg    1140

gcgctgcgta ttgcagaatc ccgtgttgat gcgcctgcac gtacctttgg ctacgaattc    1200

gcgtggcgta cgccacaatt ggacggcatt ctgggtgctt gtcatgcggt ggaacttccg    1260

ttcgtgtttc gcaccttaga ccgtgcggca tcgctggtgg gcacaaaccc gccagaagaa    1320

ctggcagaaa ccgtacacaa tgcctgggtg cgcttcgcga catcaggtga tccagggtgg    1380

ccggcgtgga atccggaaac ccgcagcgtg atgcgctttg atcacccggt ttccgagatg    1440

gttaccgacc cgtacccggc gacccgtgca ctgtgggatg gtgtgccatt g             1491


<210> SEQ ID NO 38
<211> LENGTH: 497
<212> TYPE: PRT
<213> ORGANISM: Artificial Sequence
```

```
<220> FEATURE:
<223> OTHER INFORMATION: variant of esterase from Thermobifida fusca

<400> SEQUENCE: 38

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Trp
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400
```

```
Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 39
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 39

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgaag gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440
```

gttaccgacc cgtacccggc gacccgtgca ctgtgggatg gtgtgccatt g 1491

<210> SEQ ID NO 40
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 40

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Lys Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
```

-continued

```
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 41
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 41

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaggatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt aggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260
```

```
ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 42
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 42

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Arg Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320
```

```
Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 43
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 43

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgctggttt ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020
```

-continued cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 44
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 44

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Asn Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Trp Gly
260 265 270

Glu Arg Ile Ala Gly Gly Ser Val Leu Leu Val Phe Ala Pro Val Ile
275 280 285

-continued

```
Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 45
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 45

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga gcctattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840
```

```
ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 46
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 46

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Pro Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
```

-continued

```
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 47
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 47

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600
```

-continued

```
cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgtatt ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 48
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 48

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205
```

```
Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Tyr Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 49
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 49

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420
```

```
attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggct ctagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttacacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g             1491
```

<210> SEQ ID NO 50
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 50

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175
```

-continued

```
Gly Asn Val Thr Val Phe Gly Ser Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Thr Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 51
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 51

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180
```

ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccaa ctgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gacagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 52
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 52

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala

-continued

```
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Thr Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Thr Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 53
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 53

```
atggagatcg tgattcgcac gggcagcgga gatgtgcgtg gtagtaaaga gaacggcatt     60
gcagtgtttc gtggcatccc ctatgcggaa ccaccggttg gcgctcaccg ctttacggcg    120
ccacgtccac cacgtccatg ggatggtgtt cgtgacgcta ctgaattctc ggcgactgca    180
ccacgtccac catatccaga ggcaattggt gcgttgctga tcgaacgctt cattcctggc    240
gacgattacc tgaccctgaa cgtatggact ccggacccga atgcagttgg tctgccagtc    300
atggtgtgga ttcatggtgg tgcctttact aacggtagtg gtagcgaacc ggtgtatgac    360
ggtgcagcat ttgcacgtga tggtgtggtg tttgtgagct tcaactatcg tctgggcatc    420
attggctttg cagatctgcc agatgcacca agtaatcgcg gcctgttaga tcaaatcgcc    480
gcactggaat gggttcgcga caacattgca cgctttgggg gtgacccagg taatgtgacc    540
gtgtttggcg aaagtgcggg cgcgatgagc gtgtgcaccc tgatggcaac cccgcgtgca    600
cgtggtctgt ttcgtcgtgc tatcttacag agcggcctgg gcaacatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtg    840
ctgctgccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tggctgctg ccgttcatca caggggacta tgttaccact    1020
cacttagcca agagcggttt agatgcagat gcggccaaag cgtataccgc ggaaggtcgt   1080
ggtgaagaac cgggcgacat cttggccagc atcatcaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g             1491
```

<210> SEQ ID NO 54
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 54

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95
```

-continued

```
Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Leu Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 55

<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 55
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgct tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 56
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 56

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

```
Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Leu Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480
```

-continued

Val Thr Asp Pro Tyr Pro Ala Thr Arg Ala Leu Trp Asp Gly Val Pro
485 490 495

Leu

<210> SEQ ID NO 57
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 57
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg ggagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgctgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 58
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 58

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro

```
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Gly Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445
```

```
Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 59
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 59

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcacg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gccctatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgctgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagcca agagcggttt agatgcagat gcggccaaag cgtataccgc ggaaggtcgt    1080

ggtgaagaac cgggcgacat cttggccagc atcatcaccg accaggtgtt tcgtattccg    1140

gcgctgcgta ttgcagaatc ccgtgttgat gcgcctgcac gtacctttgg ctacgaattc    1200

gcgtggcgta cgccacaatt ggacggcatt ctgggtgctt gtcatgcggt ggaacttccg    1260

ttcgtgtttc gcaccttaga ccgtgcggca tcgctggtgg gcacaaaccc gccagaagaa    1320

ctggcagaaa ccgtacacaa tgcctgggtg cgcttcgcga catcaggtga tccagggtgg    1380

ccggcgtgga atccggaaac ccgcagcgtg atgcgctttg atcacccggt ttccgagatg    1440

gttaccgacc cgtacccggc gacccgtgca ctgtgggatg gtgtgccatt g             1491


<210> SEQ ID NO 60
<211> LENGTH: 497
<212> TYPE: PRT
<213> ORGANISM: Artificial Sequence
<220> FEATURE:
<223> OTHER INFORMATION: variant of esterase from Thermobifida fusca
```

<400> SEQUENCE: 60

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn His Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Pro Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala

```
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 61
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 61

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcac ttaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 62
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 62

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Leu Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365
```

```
Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 63
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 63

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgtgg gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgctgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagcca agagcggttt agatgcagat gcggccaaag cgtataccgc ggaaggtcgt    1080

ggtgaagaac cgggcgacat cttggccagc atcatcaccg accaggtgtt tcgtattccg    1140

gcgctgcgta ttgcagaatc ccgtgttgat gcgcctgcac gtacctttgg ctacgaattc    1200

gcgtggcgta cgccacaatt ggacggcatt ctgggtgctt gtcatgcggt ggaacttccg    1260

ttcgtgtttc gcaccttaga ccgtgcggca tcgctggtgg gcacaaaccc gccagaagaa    1320
```

-continued

```
ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 64
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 64

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Trp Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335
```

```
Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 65
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 65

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctc cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg ggagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgctgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagcca agagcggttt agatgcagat gcggccaaag cgtataccgc ggaaggtcgt    1080
```

-continued ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcaccccggt ttccgagatg 1440 gttaccgacc cgtacccggc gacccgtgca ctgtgggatg gtgtgccatt g 1491

<210> SEQ ID NO 66
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 66

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Ser Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Gly Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Asn Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Trp Gly
260 265 270

Glu Arg Ile Ala Gly Gly Ser Val Leu Leu Pro Phe Ala Pro Val Ile
275 280 285

Asp Gly Glu Leu Leu Ser Gln Arg Pro Ala Glu Ala Ile Ala Gly Gly

-continued

```
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 67
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 67

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catggccaga ggcacttggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900
```

```
attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcctgaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 68
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 68

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Trp Pro Glu Ala Leu Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255
```

```
Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 69
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 69

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga gccgctgggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660
```

-continued gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tggctgctg ccgttcatca caggggacta tgttaccact 1020
cacttagtga agagcggttt agatgcagat gcggccaaag cgtataccgc ggaaggtcgt 1080
ggtgaagaac cgggcgacat cttggccagc atcctgaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 70
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 70

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Pro Leu Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Asn Met Ala Val Ala Ala Glu Asp Ala Thr
210 215 220

```
Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Val Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 71
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 71

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcactgggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480
```

```
gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tatggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcctgaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 72
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 72

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Leu Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
```

-continued

```
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Tyr Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 73
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 73

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240
```

-continued

```
gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atccttaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 74
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 74

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140
```

```
Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 75
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 75

```
atggagatcg tgattcgcac gggcagcgga gatgtgcgtg gtagtaaaga gaacggcatt      60
```

```
gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtcggc catacccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tggctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g             1491
```

<210> SEQ ID NO 76
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 76

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Arg Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110
```

```
Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 77
<211> LENGTH: 1491
<212> TYPE: DNA

<213> ORGANISM: Artificial Sequence
<220> FEATURE:
<223> OTHER INFORMATION: variant of esterase from Thermobifida fusca

<400> SEQUENCE: 77

```
atggagatcg tgattcgcac gggcagcgga gatgtgcgtg gtagtaaaga gaacggcatt     60
gcagtgtttc gtggcatccc ctatgcggaa ccaccggttg gcgctcaccg ctttacggcg    120
ccacgtccac cacgtccatg ggatggtgtt cgtgacgcta ctgaattctc ggcgactgca    180
ccacgtccac catggccaga ggcaatggct gcgttgctga tcgaacgctt cattcctggc    240
gacgattacc tgaccctgaa cgtatggact ccggacccga atgcagttgg tctgccagtc    300
atggtgtgga ttcatggtgg tgcctttact aacggtagtg gtagcgaacc ggtgtatgac    360
ggtgcagcat ttgcacgtga tggtgtggtg tttgtgagct tcaactatcg tctgggcatc    420
attggctttg cagatctgcc agatgcacca agtaatcgcg gcctgttaga tcaaatcgcc    480
gcactggaat gggttcgcga caacattgca cgctttgggg gtgacccagg taatgtgacc    540
gtgtttggcg aaagtgcggg cgcgatgtca gtgtgcaccc tgatggcaac cccgcgtgca    600
cgtggtctgt ttcgtcgtgc tatcttacag agcggcgcag gcaacatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtt    840
ccgacgccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tggctgctg ccgttcatca caggggacta tgttaccact   1020
cacttagcca agagcggttt agatgcagat gcggccaaag cgtataccgc ggaaggtcgt   1080
ggtgaagaac cgggcgacat cttggccagc atccttaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g             1491
```

<210> SEQ ID NO 78
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 78

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Trp Pro Glu Ala Met Ala Ala Leu Leu Ile Glu Arg Phe Ile Pro Gly
```

-continued

```
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Pro Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495
```

Leu

<210> SEQ ID NO 79
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 79
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcatggggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatgaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 80
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 80

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

-continued

```
Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Trp Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Met Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
```

-continued 450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 81
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 81
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgcga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcccag ttactggatg ttcagcagca agttgcccaa 780
gagattcaag gcgcgccaga tccagcagtt tggggtgaac gtattgcggg cggcagtggt 840
ctgacgccat ttctgcccgt cattgatggg gaactgctga gccaacgtcc agcggaagcc 900
attgcgggcg gcgcaggtca tgatgtagac ctcttgtttg gcactaccac cgatgaatat 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atccttaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 82
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 82

-continued

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Gly Leu Thr Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415
```

```
Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 83
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 83

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tatggtgaac gtattgcggg cggcagtgtg     840

ctgacgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagtga agagcggttt agatgcagat gcggccaaag cgtataccgc ggaaggtcgt    1080

ggtgaagaac cgggcgacat cttggccagc atcctgaccg accaggtgtt tcgtattccg    1140

gcgctgcgta ttgcagaatc ccgtgttgat gcgcctgcac gtacctttgg ctacgaattc    1200

gcgtggcgta cgccacaatt ggacggcatt ctgggtgctt gtcatgcggt ggaacttccg    1260

ttcgtgtttc gcaccttaga ccgtgcggca tcgctggtgg gcacaaaccc gccagaagaa    1320

ctggcagaaa ccgtacacaa tgcctgggtg cgcttcgcga catcaggtga tccagggtgg    1380

ccggcgtgga atccggaaac ccgcagcgtg atgcgctttg atcacccggt ttccgagatg    1440

gttaccgacc cgtacccggc gacccgtgca ctgtgggatg gtgtgccatt g             1491


<210> SEQ ID NO 84
```

<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 84

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Tyr Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Val Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380
```

```
Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 85
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 85

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcactgggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380
```

ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 86
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 86

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Leu Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Asn Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Trp Gly
260 265 270

Glu Arg Ile Ala Gly Gly Ser Val Leu Thr Pro Phe Ala Pro Val Ile
275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp
325 330 335

Tyr Val Thr Thr His Leu Ala Lys Ser Gly Leu Asp Ala Asp Ala Ala

-continued

```
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 87
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 87

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtt    840

ccgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcctgaccg accaggtgtt tcgtattccg   1140
```

-continued

```
gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 88
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 88

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Pro Thr Pro Phe Ala Pro Val Ile
        275                 280                 285

Asp Gly Glu Leu Leu Ser Gln Arg Pro Ala Glu Ala Ile Ala Gly Gly
    290                 295                 300
```

```
Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 89
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 89

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtcggc caggaccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tggctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcaacatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgacgccat ttgctcccgt cattgatggg gaactgctga gccaacgtcc agcggaagcc     900

attgcgggcg gcgcaggtca tgatgtagac ctcttgtttg gcactaccac cgatgaatac     960
```

```
cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 90
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 90

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Arg Pro
    50                  55                  60

Gly Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270
```

Glu Arg Ile Ala Gly Gly Ser Val Leu Thr Pro Phe Ala Pro Val Ile
275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp
325 330 335

Tyr Val Thr Thr His Leu Ala Lys Ser Gly Leu Asp Ala Asp Ala Ala
340 345 350

Lys Ala Tyr Thr Ala Glu Gly Arg Gly Glu Glu Pro Gly Asp Ile Leu
355 360 365

Ala Ser Ile Ile Thr Asp Gln Val Phe Arg Ile Pro Ala Leu Arg Ile
370 375 380

Ala Glu Ser Arg Val Asp Ala Pro Ala Arg Thr Phe Gly Tyr Glu Phe
385 390 395 400

Ala Trp Arg Thr Pro Gln Leu Asp Gly Ile Leu Gly Ala Cys His Ala
405 410 415

Val Glu Leu Pro Phe Val Phe Arg Thr Leu Asp Arg Ala Ala Ser Leu
420 425 430

Val Gly Thr Asn Pro Pro Glu Glu Leu Ala Glu Thr Val His Asn Ala
435 440 445

Trp Val Arg Phe Ala Thr Ser Gly Asp Pro Gly Trp Pro Ala Trp Asn
450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 91
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 91
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga gccgattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720

```
gcagcattag cgcatgttcc agttgcacag ttactggatg ttcagcagca agttgcccaa    780

gagattcaag gcgcgccaga tccagcagtt tatggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcctgaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 92
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 92

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Pro Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
```

-continued

```
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Tyr Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 93
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 93

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccgc catacccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tggctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540
```

```
gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgaccccat tttacccgt cattgatggg gaactgctga gccaacgtcc agcggaagcc     900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 94
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 94

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190
```

-continued

```
Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 95
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 95

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300
```

-continued

```
atggtgtgga ttcatggtgg tgggtttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaagatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 96
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 96

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160
```

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Lys Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Trp Gly
260 265 270

Glu Arg Ile Ala Gly Gly Ser Val Leu Thr Pro Phe Ala Pro Val Ile
275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp
325 330 335

Tyr Val Thr Thr His Leu Ala Lys Ser Gly Leu Asp Ala Asp Ala Ala
340 345 350

Lys Ala Tyr Thr Ala Glu Gly Arg Gly Glu Glu Pro Gly Asp Ile Leu
355 360 365

Ala Ser Ile Ile Thr Asp Gln Val Phe Arg Ile Pro Ala Leu Arg Ile
370 375 380

Ala Glu Ser Arg Val Asp Ala Pro Ala Arg Thr Phe Gly Tyr Glu Phe
385 390 395 400

Ala Trp Arg Thr Pro Gln Leu Asp Gly Ile Leu Gly Ala Cys His Ala
405 410 415

Val Glu Leu Pro Phe Val Phe Arg Thr Leu Asp Arg Ala Ala Ser Leu
420 425 430

Val Gly Thr Asn Pro Pro Glu Glu Leu Ala Glu Thr Val His Asn Ala
435 440 445

Trp Val Arg Phe Ala Thr Ser Gly Asp Pro Gly Trp Pro Ala Trp Asn
450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 97
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 97
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120

```
ccacgtccac cacgtccatg ggatggtgtt cgtgacgcta ctgaattctc ggcgactgca    180

ccacgtccac catatccaga gccgattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaacatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 98
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 98

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Pro Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
```

```
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 99
<211> LENGTH: 1491
<212> TYPE: DNA
<213> ORGANISM: Artificial Sequence
<220> FEATURE:

<223> OTHER INFORMATION: variant of esterase from Thermobifida fusca

<400> SEQUENCE: 99

```
atggagatcg tgattcgcac gggcagcgga gatgtgcgtg gtagtaaaga gaacggcatt     60
gcagtgtttc gtggcatccc ctatgcggaa ccaccggttg gcgctcaccg ctttacggcg    120
ccacgtccac cacgtccatg ggatggtgtt cgtgacgcta ctgaattctc ggcgactgca    180
ccacgtccac catatccaga ggcaattggt gcgttgctga tcgaacgctt cattcctggc    240
gacgattacc tgaccctgaa cgtatggact ccggacccga atgcagttgg tctgccagtc    300
atggtgtgga ttcatggtgg tgcctttact aacggtagtg gtagcgaacc ggtgtatgac    360
ggtgcagcat ttgcacgcga tggtgtggtg tttgtgagct tcaactatcg tctgggcatc    420
attggctttg cagatctgcc agatgcacca agtaatcgcg gcctgttaga tcaaatcgcc    480
gcactggaat gggttcgcga caacattgca cgctttgggg gtgacccagg taatgtgacc    540
gtgtttggcg aaagtgcggg cgcgatgagc gtgtgcaccc tgatggcaac cccgcgtgca    600
cgtggtctgt ttcgtcgtgc tatcttacag agcggcgcgg gccgaatggc agtcgctgca    660
gaagatgcta ccacaatcgc agctgtgatt gcccatcgtt taggtgttga gccaactgca    720
gcagcattag cgcatgttcc agttgcacag ttactggatg ttcagcagca agttgcccaa    780
gagattcaag gcgcgccaga tccagcagtt tggggtgaac gtattgcggg cggcagtgtg    840
ctgacgccat ttgctcccgt cattgatggg gaactgctga gccaacgtcc agcggaagcc    900
attgcgggcg gcgcaggtca tgatgtagac ctcttgtttg gcactaccac cgatgaatac    960
cgtctgtttc tggcaccaac tgggctgctg ccgttcatca caggggacta tgttaccact   1020
cacttagcca agagcggttt agatgcagat gcggccaaag cgtataccgc ggaaggtcgt   1080
ggtgaagaac cgggcgacat cttggccagc atccttaccg accaggtgtt tcgtattccg   1140
gcgctgcgta ttgcagaatc ccgtgttgat gcgcctgcac gtacctttgg ctacgaattc   1200
gcgtggcgta cgccacaatt ggacggcatt ctgggtgctt gtcatgcggt ggaacttccg   1260
ttcgtgtttc gcaccttaga ccgtgcggca tcgctggtgg gcacaaaccc gccagaagaa   1320
ctggcagaaa ccgtacacaa tgcctgggtg cgcttcgcga catcaggtga tccagggtgg   1380
ccggcgtgga atccggaaac ccgcagcgtg atgcgctttg atcacccggt ttccgagatg   1440
gttaccgacc cgtacccggc gacccgtgca ctgtgggatg gtgtgccatt g            1491
```

<210> SEQ ID NO 100
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 100

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80
```

```
Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 101
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 101
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcatttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaagatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ccgacgccat ttttacccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atccttaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 102
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 102

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

-continued

```
Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Lys Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Pro Thr Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460
```

-continued

```
Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 103
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 103

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtacgc catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggagcag gccgcatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgacgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagcca agagcggttt agatgcagat gcggccaaag cgtataccgc ggaaggtcgt    1080

ggtgaagaac cgggcgacat cttggccagc atcatcaccg accaggtgtt tcgtattccg    1140

gcgctgcgta ttgcagaatc ccgtgttgat gcgcctgcac gtacctttgg ctacgaattc    1200

gcgtggcgta cgccacaatt ggacggcatt ctgggtgctt gtcatgcggt ggaacttccg    1260

ttcgtgtttc gcaccttaga ccgtgcggca tcgctggtgg gcacaaaccc gccagaagaa    1320

ctggcagaaa ccgtacacaa tgcctgggtg cgcttcgcga catcaggtga tccagggtgg    1380

ccggcgtgga atccggaaac ccgcagcgtg atgcgctttg atcacccggt ttccgagatg    1440

gttaccgacc cgtacccggc gacccgtgca ctgtgggatg gtgtgccatt g             1491


<210> SEQ ID NO 104
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 104

Met Glu Ile Val Ile Arg Thr Gly Ser Gly Asp Val Arg Gly Ser Lys
```

-continued

```
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Thr Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430
```

```
Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 105
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 105

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcatggggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaggatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 106
<211> LENGTH: 497
<212> TYPE: PRT
```

```
<213> ORGANISM: Artificial Sequence
<220> FEATURE:
<223> OTHER INFORMATION: variant of esterase from Thermobifida fusca

<400> SEQUENCE: 106

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Trp Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
```

-continued

```
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 107
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 107

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtgcgc catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggagcag gccgcatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccggcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagtga agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440
```

```
gttaccgacc cgtacccggc gacccgtgca ctgtgggatg gtgtgccatt g           1491


<210> SEQ ID NO 108
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 108

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Ala Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Val Lys Ser Gly Leu Asp Ala Asp Ala Ala
            340                 345                 350
```

```
Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 109
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 109

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgttatc catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agccccgcag gccgcatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccggcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200
```

-continued

```
gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 110
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 110

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Tyr Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Pro Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320
```

```
Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 111
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 111

```
atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgttatc catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agccccgcag gccgcatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tgcgaatgtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020
```

```
cacttagtga agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 112
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 112

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Tyr Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Pro Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Ala Asn Val Trp Gly
            260                 265                 270

Glu Arg Ile Ala Gly Gly Ser Val Leu Thr Pro Phe Ala Pro Val Ile
```

275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp
325 330 335

Tyr Val Thr Thr His Leu Val Lys Ser Gly Leu Asp Ala Asp Ala Ala
340 345 350

Lys Ala Tyr Thr Ala Glu Gly Arg Gly Glu Glu Pro Gly Asp Ile Leu
355 360 365

Ala Ser Ile Ile Thr Asp Gln Val Phe Arg Ile Pro Ala Leu Arg Ile
370 375 380

Ala Glu Ser Arg Val Asp Ala Pro Ala Arg Thr Phe Gly Tyr Glu Phe
385 390 395 400

Ala Trp Arg Thr Pro Gln Leu Asp Gly Ile Leu Gly Ala Cys His Ala
405 410 415

Val Glu Leu Pro Phe Val Phe Arg Thr Leu Asp Arg Ala Ala Ser Leu
420 425 430

Val Gly Thr Asn Pro Pro Glu Glu Leu Ala Glu Thr Val His Asn Ala
435 440 445

Trp Val Arg Phe Ala Thr Ser Gly Asp Pro Gly Trp Pro Ala Trp Asn
450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 113
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 113
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgttatc catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggagcag gccgcatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcga agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 114
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 114

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Tyr Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Met Ser Val Cys
180 185 190

Thr Leu Met Ala Thr Pro Arg Ala Arg Gly Leu Phe Arg Arg Ala Ile
195 200 205

Leu Gln Ser Gly Ala Gly Arg Met Ala Val Ala Ala Glu Asp Ala Thr
210 215 220

Thr Ile Ala Ala Val Ile Ala His Arg Leu Gly Val Glu Pro Thr Ala
225 230 235 240

```
Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 115
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 115

```
atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga gccgtggggt gcgttgctga tcgaacgctt cattcctggc     240

gacgattacc tgaccctgaa cgtatggact ccggacccga atgcagttgg tctgccagtc     300

atggtgtgga ttcatggtgg tgcctttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgattagc gtgtgcaccc tgatggcaac cccgcgtgca     600
```

```
cgtggtctgt ttcgtcgtgc tatcttacag agcggcgcac gtccgatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 116
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 116

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Pro Trp Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Ile Ser Val Cys
            180                 185                 190

Thr Leu Met Ala Thr Pro Arg Ala Arg Gly Leu Phe Arg Arg Ala Ile
        195                 200                 205
```

Leu Gln Ser Gly Ala Arg Pro Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu

<210> SEQ ID NO 117
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 117
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360

-continued

```
ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaaaatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac ggatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcgggg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

```
<210> SEQ ID NO 118
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 118

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
```

```
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Lys Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Gly Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

```
<210> SEQ ID NO 119
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 119

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180
```

```
ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaagatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atccttaccg accaggtgtt gcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 120
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 120

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125
```

```
Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Lys Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Leu Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 121
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 121
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgattagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagtga agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 122
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 122

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

```
Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Ile Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Val Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

```
<210> SEQ ID NO 123
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 123

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcaattggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaggatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccagcagtt tggggtgaac gtattgcggg cggcagtgtg    840

ccgacgccat ttctgcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcatcgggg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491


<210> SEQ ID NO 124
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 124

Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
```

-continued

```
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Arg Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Pro Thr Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Gly Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480
```

Val Thr Asp Pro Tyr Pro Ala Thr Arg Ala Leu Trp Asp Gly Val Pro
485 490 495

Leu

<210> SEQ ID NO 125
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 125
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gctggatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttctgcccgt cattgatggg gaactgctga gccaacgtcc agcggaagcc 900
attgcgggcg gcgcaggtca tgatgtagac ctcttgtttg gcactaccac ggatgaatac 960
cgtctgtttc tggcaccaac tgggctgctg ccgttcatca caggggacta tgttaccact 1020
cacttagcca agagcagttt agatgcagat gcggccaaag cgtataccgc ggaaggtcgt 1080
ggtgaagaac cgggcgacat cttggccagc atcatcactg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 126
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 126

Met Glu Ile Val Ile Arg Thr Gly Ser Gly Asp Val Arg Gly Ser Lys
1 5 10 15

-continued

```
Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Trp Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Leu Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Ser Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
```

435 440 445

Trp Val Arg Phe Ala Thr Ser Gly Asp Pro Gly Trp Pro Ala Trp Asn
450 455 460

Pro Glu Thr Arg Ser Val Met Arg Phe Asp His Pro Val Ser Glu Met
465 470 475 480

Val Thr Asp Pro Tyr Pro Ala Thr Arg Ala Leu Trp Asp Gly Val Pro
485 490 495

Leu

<210> SEQ ID NO 127
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 127
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgattagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840
ctgacgccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgtt tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260
ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 128
<211> LENGTH: 497
<212> TYPE: PRT
<213> ORGANISM: Artificial Sequence
<220> FEATURE:

<223> OTHER INFORMATION: variant of esterase from Thermobifida fusca

<400> SEQUENCE: 128

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Ile Ser Val Cys
180 185 190

Thr Leu Met Ala Thr Pro Arg Ala Arg Gly Leu Phe Arg Arg Ala Ile
195 200 205

Leu Gln Ser Gly Ala Gly Asn Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Trp Gly
260 265 270

Glu Arg Ile Ala Gly Gly Ser Val Leu Thr Pro Phe Ala Pro Val Ile
275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp
325 330 335

Tyr Val Thr Thr His Leu Ala Lys Ser Gly Leu Asp Ala Asp Ala Ala
340 345 350

Lys Ala Tyr Thr Ala Glu Gly Arg Gly Glu Glu Pro Gly Asp Ile Leu
355 360 365

Ala Ser Ile Ile Thr Asp Gln Val Phe Arg Ile Pro Ala Leu Arg Ile
370 375 380

Ala Glu Ser Arg Val Asp Ala Pro Ala Arg Thr Phe Gly Tyr Glu Phe
385 390 395 400

```
Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 129
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 129

atggagatcg tgattcgcac gggcagcgga gatgtgcgtg gtagtaaaga gaacggcatt     60

gcagtgtttc gtggcatccc ctatgcggaa ccaccggttg gcgctcaccg ctttacggcg    120

ccacgtccac cacgtccatg ggatggtgtt cgtgacgcta ctgaattctc ggcgactgca    180

ccacgtccac catatccaga ggcatttggt gcgttgctga tcgaacgctt cattcctggc    240

gacgattacc tgaccctgaa cgtatggact ccggacccga atgcagttgg tctgccagtc    300

atggtgtgga ttcatggtgg tgcctttact aacggtagtg gtagcgaacc ggtgtatgac    360

ggtgcagcat ttgcacgtga tggtgtggtg tttgtgagct tcaactatcg tctgggcatc    420

attggctttg cagatctgcc agatgcacca agtaatcgcg gcctgttaga tcaaatcgcc    480

gcactggaat gggttcgcga caacattgca cgctttgggg gtgacccagg taatgtgacc    540

gtgtttggcg aaagtgcggg cgcgatgagc gtgtgcaccc tgatggcaac cccgcgtgca    600

cgtggtctgt ttcgtcgtgc tatcttacag agcggcgcag gcaagatggc agtcgctgca    660

gaagatgcta ccacaatcgc agctgtgatt gcccatcgtt taggtgttga gccaactgca    720

gcagcattag cgcatgttcc agttgcacag ttactggatg ttcagcagca agttgcccaa    780

gagattcaag gcgcgccaga tccattaatc tggggtgaac gtattgcggg cggcagtgtg    840

ctgacgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tgggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atcattaccg accaggtgtt gcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 130
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 130

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Phe Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Lys Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Leu Ile Trp Gly
            260                 265                 270

Glu Arg Ile Ala Gly Gly Ser Val Leu Thr Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365
```

Ala Ser Ile Ile Thr Asp Gln Val Leu Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu

<210> SEQ ID NO 131
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 131
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgcagagc gtgtgcaccc tgatggcaac cccgcgtgca 600
cgtggtctgt ttcgtcgtgc tatcttacag agcggcgcag gcccgatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tatggtgaac gtattgcggg cggcagtgtg 840
ccgtgcccat ttgctcccgt cattgatggg gaactgctga gccaacgtcc agcggaagcc 900
attgcgggcg gcgcaggtca tgatgtagac ctcttgtttg gcactaccac cgatgaatac 960
cgtctgtttc tggcaccaac tgggctgctg ccgttcatca caggggacta tgttaccact 1020
cacttagcca agagcggttt agatgcagat gcggccaaag cgtataccgc ggaaggtcgt 1080
ggtgaagaac cgggcgacat cttggccagc atcatcaccg accaggtgta tcgtattccg 1140
gcgctgcgta ttgcagaatc ccgtgttgat gcgcctgcac gtacctttgg ctacgaattc 1200
gcgtggcgta cgccacaatt ggacggcatt ctgggtgctt gtcatgcggt ggaacttccg 1260

-continued ttcgtgtttc gcaccttaga ccgtgcggca tcgctggtgg gcacaaaccc gccagaagaa 1320
ctggcagaaa ccgtacacaa tgcctgggtg cgcttcgcga catcaggtga tccagggtgg 1380
ccggcgtgga atccggaaac ccgcagcgtg atgcgctttg atcacccggt ttccgagatg 1440
gttaccgacc cgtacccggc gacccgtgca ctgtgggatg gtgtgccatt g 1491

<210> SEQ ID NO 132
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 132

Met Glu Ile Val Ile Arg Thr Gly Ser Gly Asp Val Arg Gly Ser Lys
1 5 10 15

Glu Asn Gly Ile Ala Val Phe Arg Gly Ile Pro Tyr Ala Glu Pro Pro
20 25 30

Val Gly Ala His Arg Phe Thr Ala Pro Arg Pro Pro Arg Pro Trp Asp
35 40 45

Gly Val Arg Asp Ala Thr Glu Phe Ser Ala Thr Ala Pro Arg Pro Pro
50 55 60

Tyr Pro Glu Ala Ile Gly Ala Leu Leu Ile Glu Arg Phe Ile Pro Gly
65 70 75 80

Asp Asp Tyr Leu Thr Leu Asn Val Trp Thr Pro Asp Pro Asn Ala Val
85 90 95

Gly Leu Pro Val Met Val Trp Ile His Gly Gly Ala Phe Thr Asn Gly
100 105 110

Ser Gly Ser Glu Pro Val Tyr Asp Gly Ala Ala Phe Ala Arg Asp Gly
115 120 125

Val Val Phe Val Ser Phe Asn Tyr Arg Leu Gly Ile Ile Gly Phe Ala
130 135 140

Asp Leu Pro Asp Ala Pro Ser Asn Arg Gly Leu Leu Asp Gln Ile Ala
145 150 155 160

Ala Leu Glu Trp Val Arg Asp Asn Ile Ala Arg Phe Gly Gly Asp Pro
165 170 175

Gly Asn Val Thr Val Phe Gly Glu Ser Ala Gly Ala Gln Ser Val Cys
180 185 190

Thr Leu Met Ala Thr Pro Arg Ala Arg Gly Leu Phe Arg Arg Ala Ile
195 200 205

Leu Gln Ser Gly Ala Gly Pro Met Ala Val Ala Ala Glu Asp Ala Thr
210 215 220

Thr Ile Ala Ala Val Ile Ala His Arg Leu Gly Val Glu Pro Thr Ala
225 230 235 240

Ala Ala Leu Ala His Val Pro Val Ala Gln Leu Leu Asp Val Gln Gln
245 250 255

Gln Val Ala Gln Glu Ile Gln Gly Ala Pro Asp Pro Ala Val Tyr Gly
260 265 270

Glu Arg Ile Ala Gly Gly Ser Val Pro Cys Pro Phe Ala Pro Val Ile
275 280 285

Asp Gly Glu Leu Leu Ser Gln Arg Pro Ala Glu Ala Ile Ala Gly Gly
290 295 300

Ala Gly His Asp Val Asp Leu Leu Phe Gly Thr Thr Thr Asp Glu Tyr
305 310 315 320

Arg Leu Phe Leu Ala Pro Thr Gly Leu Leu Pro Phe Ile Thr Gly Asp

```
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Tyr Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu


<210> SEQ ID NO 133
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 133

atggagatcg tgattcgcac gggcagcgga gatgtgcgtg gtagtaaaga gaacggcatt      60

gcagtgtttc gtggcatccc ctatgcggaa ccaccggttg gcgctcaccg ctttacggcg     120

ccacgtccac cacgtccatg ggatggtgtt cgtgacgcta ctgaattctc ggcgactgca     180

ccacgtccac catatccaga ggcaattggt gcgttgctga tcgaacgctt cattcctggc     240

gacgattacc tgaccctgaa cgtatggact ccggacccga atgcagttgg tctgccagtc     300

atggtgtgga ttcatggtgg tgggtttact aacggtagtg gtagcgaacc ggtgtatgac     360

ggtgcagcat ttgcacgtga tggtgtggtg tttgtgagct tcaactatcg tctgggcatc     420

attggctttg cagatctgcc agatgcacca agtaatcgcg gcctgttaga tcaaatcgcc     480

gcactggaat gggttcgcga caacattgca cgctttgggg gtgacccagg taatgtgacc     540

gtgtttggcg aaagtgcggg cgcgatgagc gtgtgcaccc tgatggcaac cccgcgtgca     600

cgtggtctgt ttcgtcgtgc tatcttacag agcggcgcag gcccgatggc agtcgctgca     660

gaagatgcta ccacaatcgc agctgtgatt gcccatcgtt taggtgttga gccaactgca     720

gcagcattag cgcatgttcc agttgcacag ttactggatg ttcagcagca agttgcccaa     780

gagattcaag gcgcgccaga tccagcagtt tggggtgaac gtattgcggg cggcagtgtg     840

ctgacgccat ttgctcccgt cattgatggg gaactgctga gccaacgtcc agcggaagcc     900

attgcgggcg gcgcaggtca tgatgtagac ctcttgtttg gcactaccac cgatgaatac     960

cgtctgtttc tggcaccaac tgggctgctg ccgttcatca caggggacta tgttaccact    1020

cacttagcca agagcggttt agatgcagat gcggccaaag cgtataccgc ggaaggtcgt    1080
```

```
ggtgaagaac cgggcgacat cttggccagc atcattaccg accaggtgtt gcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g            1491
```

<210> SEQ ID NO 134
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 134

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Gly Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Pro Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255

Gln Val Ala Gln Glu Ile Gln Gly Ala Pro Asp Pro Ala Val Trp Gly
            260                 265                 270

Glu Arg Ile Ala Gly Gly Ser Val Leu Thr Pro Phe Ala Pro Val Ile
        275                 280                 285
```

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Ile Thr Asp Gln Val Leu Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu

<210> SEQ ID NO 135
<211> LENGTH: 1491
<212> TYPE: DNA
<213> ORGANISM: Artificial Sequence
<220> FEATURE:
<223> OTHER INFORMATION: variant of esterase from Thermobifida fusca

<400> SEQUENCE: 135
atggagatcg tgattcgcac gggcagcgga gatgtgcgtg gtagtaaaga gaacggcatt 60
gcagtgtttc gtggcatccc ctatgcggaa ccaccggttg gcgctcaccg ctttacggcg 120
ccacgtccac cacgtccatg ggatggtgtt cgtgacgcta ctgaattctc ggcgactgca 180
ccacgtccac catatccaga ggcaattggt gcgttgctga tcgaacgctt cattcctggc 240
gacgattacc tgaccctgaa cgtatggact ccggacccga atgcagttgg tctgccagtc 300
atggtgtgga ttcatggtgg tgcctttact aacggtagtg gtagcgaacc ggtgtatgac 360
ggtgcagcat ttgcacgtga tggtgtggtg tttgtgagct tcaactatcg tctgggcatc 420
attggctttg cagatctgcc agatgcacca agtaatcgcg gcctgttaga tcaaatcgcc 480
gcactggaat gggttcgcga caacattgca cgctttgggg gtgacccagg taatgtgacc 540
gtgtttggcg aaagtgcggg cgcgatgagc gtgtgcaccc tgatggcaac cccgcgtgca 600
cgtggtctgt ttcgtcgtgc tatcttacag agcggcgcag gcaacatggc agtcgctgca 660
gaagatgcta ccacaatcgc agctgtgatt gcccatcgtt taggtgttga gccaactgca 720
gcagcattag cgcatgttcc agttgcacag ttactggatg ttcagcagca agttgcccaa 780
gagattcaag gcgcgccaga tccagcagtt tggggtgaac gtattgcggg cggcagtgtg 840

```
ctgctgccat ttgctcccgt cattgatggg gaactgctga gccaacgtcc agcggaagcc    900

attgcgggcg gcgcaggtca tgatgtagac ctcttgtttg gcactaccac cgatgaatac    960

cgtctgtttc tggcaccaac tggggctgctg ccgttcatca caggggacta tgttaccact   1020

cacttagcca agagcggttt agatgcagat gcggccaaag cgtataccgc ggaaggtcgt   1080

ggtgaagaac cgggcgacat cttggccagc atccttaccg accaggtgtt tcgtattccg   1140

gcgctgcgta ttgcagaatc ccgtgttgat gcgcctgcac gtacctttgg ctacgaattc   1200

gcgtggcgta cgccacaatt ggacggcatt ctgggtgctt gtcatgcggt ggaacttccg   1260

ttcgtgtttc gcaccttaga ccgtgcggca tcgctggtgg gcacaaaccc gccagaagaa   1320

ctggcagaaa ccgtacacaa tgcctgggtg cgcttcgcga catcaggtga tccagggtgg   1380

ccggcgtgga atccggaaac ccgcagcgtg atgcgctttg atcacccggt ttccgagatg   1440

gttaccgacc cgtacccggc gacccgtgca ctgtgggatg gtgtgccatt g             1491
```

<210> SEQ ID NO 136
<211> LENGTH: 497
<212> TYPE: PRT
<213> ORGANISM: Artificial Sequence
<220> FEATURE:
<223> OTHER INFORMATION: variant of esterase from Thermobifida fusca

<400> SEQUENCE: 136

```
Met Glu Ile Val Ile Arg Thr Gly Ser Gly Asp Val Arg Gly Ser Lys
1               5                   10                  15

Glu Asn Gly Ile Ala Val Phe Arg Gly Ile Pro Tyr Ala Glu Pro Pro
            20                  25                  30

Val Gly Ala His Arg Phe Thr Ala Pro Arg Pro Pro Arg Pro Trp Asp
        35                  40                  45

Gly Val Arg Asp Ala Thr Glu Phe Ser Ala Thr Ala Pro Arg Pro Pro
    50                  55                  60

Tyr Pro Glu Ala Ile Gly Ala Leu Leu Ile Glu Arg Phe Ile Pro Gly
65                  70                  75                  80

Asp Asp Tyr Leu Thr Leu Asn Val Trp Thr Pro Asp Pro Asn Ala Val
                85                  90                  95

Gly Leu Pro Val Met Val Trp Ile His Gly Gly Ala Phe Thr Asn Gly
            100                 105                 110

Ser Gly Ser Glu Pro Val Tyr Asp Gly Ala Ala Phe Ala Arg Asp Gly
        115                 120                 125

Val Val Phe Val Ser Phe Asn Tyr Arg Leu Gly Ile Ile Gly Phe Ala
    130                 135                 140

Asp Leu Pro Asp Ala Pro Ser Asn Arg Gly Leu Leu Asp Gln Ile Ala
145                 150                 155                 160

Ala Leu Glu Trp Val Arg Asp Asn Ile Ala Arg Phe Gly Gly Asp Pro
                165                 170                 175

Gly Asn Val Thr Val Phe Gly Glu Ser Ala Gly Ala Met Ser Val Cys
            180                 185                 190

Thr Leu Met Ala Thr Pro Arg Ala Arg Gly Leu Phe Arg Arg Ala Ile
        195                 200                 205

Leu Gln Ser Gly Ala Gly Asn Met Ala Val Ala Ala Glu Asp Ala Thr
    210                 215                 220

Thr Ile Ala Ala Val Ile Ala His Arg Leu Gly Val Glu Pro Thr Ala
225                 230                 235                 240

Ala Ala Leu Ala His Val Pro Val Ala Gln Leu Leu Asp Val Gln Gln
                245                 250                 255
```

```
Gln Val Ala Gln Glu Ile Gln Gly Ala Pro Asp Pro Ala Val Trp Gly
            260                 265                 270

Glu Arg Ile Ala Gly Gly Ser Val Leu Leu Pro Phe Ala Pro Val Ile
        275                 280                 285

Asp Gly Glu Leu Leu Ser Gln Arg Pro Ala Glu Ala Ile Ala Gly Gly
    290                 295                 300

Ala Gly His Asp Val Asp Leu Leu Phe Gly Thr Thr Thr Asp Glu Tyr
305                 310                 315                 320

Arg Leu Phe Leu Ala Pro Thr Gly Leu Leu Pro Phe Ile Thr Gly Asp
                325                 330                 335

Tyr Val Thr Thr His Leu Ala Lys Ser Gly Leu Asp Ala Asp Ala Ala
            340                 345                 350

Lys Ala Tyr Thr Ala Glu Gly Arg Gly Glu Glu Pro Gly Asp Ile Leu
        355                 360                 365

Ala Ser Ile Leu Thr Asp Gln Val Phe Arg Ile Pro Ala Leu Arg Ile
    370                 375                 380

Ala Glu Ser Arg Val Asp Ala Pro Ala Arg Thr Phe Gly Tyr Glu Phe
385                 390                 395                 400

Ala Trp Arg Thr Pro Gln Leu Asp Gly Ile Leu Gly Ala Cys His Ala
                405                 410                 415

Val Glu Leu Pro Phe Val Phe Arg Thr Leu Asp Arg Ala Ala Ser Leu
            420                 425                 430

Val Gly Thr Asn Pro Pro Glu Glu Leu Ala Glu Thr Val His Asn Ala
        435                 440                 445

Trp Val Arg Phe Ala Thr Ser Gly Asp Pro Gly Trp Pro Ala Trp Asn
    450                 455                 460

Pro Glu Thr Arg Ser Val Met Arg Phe Asp His Pro Val Ser Glu Met
465                 470                 475                 480

Val Thr Asp Pro Tyr Pro Ala Thr Arg Ala Leu Trp Asp Gly Val Pro
                485                 490                 495

Leu
```

<210> SEQ ID NO 137
<211> LENGTH: 1494
<212> TYPE: DNA
<213> ORGANISM: Artificial Sequence
<220> FEATURE:
<223> OTHER INFORMATION: variant of esterase from Thermobifida fusca

<400> SEQUENCE: 137

```
atggaacgta cggttgtgga aactcgttat ggtcgtttac gcggagaaat gaatgaaggt     60

gtgtttgtct ggaaaggtat tccttacgct aaagcccctg taggagagcg tcgctttctg    120

ccaccagaac caccagatgc atgggatggt gttcgtgagg cgaccagctt tggtccagtt    180

gttatgcagc cgagtgatcc aatcttcagc ggtctgttag gtcgcatgtc cgaagcgcca    240

agtgaagatg gtctgtacct gaacatttgg agcccagcgg cagatggtaa gaaacgtcca    300

gtactgttct ggattcatgg tggtgcgttc ctgttcggta gtggtagtag tccatggtac    360

gatggtactg cgtttgccaa acacggtgat gttgtggtgg tgacgatcaa ctatcgtatg    420

aacgtattcg gctttctgca tttgggggat tctttcggag aagcgtatgc gcaagccggc    480

aacctgggta ttctggatca ggtggcagca ttacgctggg tgaaggagaa cattgccgca    540

ttcggaggcg acccggacaa catcacaatc ttcggcgagt cagcgggcgc ggcatcggtt    600

ggtgttcttc tgagtttacc agaagcaagt ggtctgtttc gtcgtgcaat gttgcaaagc    660
```

ggtagtggta gtctgttact gcgttcgccg gagactgcga tggcaatgac cgagcgtatt 720
ctggacaaag caggtattcg tccaggtgat cgtgaacgtc tgcttagtat tccggcggaa 780
gagctcttgc gtgcagcgtt gagtttaggt ccaggcgtta tgtatggtcc ggttgttgat 840
ggtcgtgtgc tgcgccgtca tccaattgaa gcactccgtt atggtgccgc aagtggcatt 900
cccattctga ttggcgtgac caaggacgag tacaatctgt ttaccttaac tgacccgagt 960
tggactaagc tgggtgagaa agaactgctg gaccgcatca atcgcgaagt tggtccagtt 1020
ccagaggaag caatccgcta ctacaaggaa accgcggaac caagtgcacc aacttggcag 1080
acttggctgc gcatcatgac ctatcgtgtc tttgtggagg gtatgttgcg taccgcggat 1140
gcacaggcag cacaaggagc cgatgtgtac atgtaccgct tcgactacga aacgccagtg 1200
tttggcggcc aattgaaagc ttgtcatgca ttggaactgc cgtttgtgtt ccacaacctg 1260
catcaacctg gagtggctaa cttcgttggt aatcgccctg agcgtgaagc gattgcaaac 1320
gagatgcatt acgcgtggtt gagctttgcg cgcaccggtg acccgaatgg tgctcatctg 1380
ccggaagcat ggccggcata caccaatgaa cgtaaagcag cgtttgtgtt tagcgcggcc 1440
tctcatgttg aagacgatcc ctttgggcgc gaacgtgcgg cgtggcaagg tcgc 1494

<210> SEQ ID NO 138
<211> LENGTH: 498
<212> TYPE: PRT
<213> ORGANISM: Geobacillus stearothermophilus

<400> SEQUENCE: 138

Met Glu Arg Thr Val Val Glu Thr Arg Tyr Gly Arg Leu Arg Gly Glu
1 5 10 15

Met Asn Glu Gly Val Phe Val Trp Lys Gly Ile Pro Tyr Ala Lys Ala
20 25 30

Pro Val Gly Glu Arg Arg Phe Leu Pro Pro Glu Pro Pro Asp Ala Trp
35 40 45

Asp Gly Val Arg Glu Ala Thr Ser Phe Gly Pro Val Val Met Gln Pro
50 55 60

Ser Asp Pro Ile Phe Ser Gly Leu Leu Gly Arg Met Ser Glu Ala Pro
65 70 75 80

Ser Glu Asp Gly Leu Tyr Leu Asn Ile Trp Ser Pro Ala Ala Asp Gly
85 90 95

Lys Lys Arg Pro Val Leu Phe Trp Ile His Gly Gly Ala Phe Leu Phe
100 105 110

Gly Ser Gly Ser Ser Pro Trp Tyr Asp Gly Thr Ala Phe Ala Lys His
115 120 125

Gly Asp Val Val Val Val Thr Ile Asn Tyr Arg Met Asn Val Phe Gly
130 135 140

Phe Leu His Leu Gly Asp Ser Phe Gly Glu Ala Tyr Ala Gln Ala Gly
145 150 155 160

Asn Leu Gly Ile Leu Asp Gln Val Ala Ala Leu Arg Trp Val Lys Glu
165 170 175

Asn Ile Ala Ala Phe Gly Gly Asp Pro Asp Asn Ile Thr Ile Phe Gly
180 185 190

Glu Ser Ala Gly Ala Ala Ser Val Gly Val Leu Leu Ser Leu Pro Glu
195 200 205

Ala Ser Gly Leu Phe Arg Arg Ala Met Leu Gln Ser Gly Ser Gly Ser
210 215 220

Leu Leu Leu Arg Ser Pro Glu Thr Ala Met Ala Met Thr Glu Arg Ile
225 230 235 240

Leu Asp Lys Ala Gly Ile Arg Pro Gly Asp Arg Glu Arg Leu Leu Ser
245 250 255

Ile Pro Ala Glu Glu Leu Leu Arg Ala Ala Leu Ser Leu Gly Pro Gly
260 265 270

Val Met Tyr Gly Pro Val Val Asp Gly Arg Val Leu Arg Arg His Pro
275 280 285

Ile Glu Ala Leu Arg Tyr Gly Ala Ala Ser Gly Ile Pro Ile Leu Ile
290 295 300

Gly Val Thr Lys Asp Glu Tyr Asn Leu Phe Thr Leu Thr Asp Pro Ser
305 310 315 320

Trp Thr Lys Leu Gly Glu Lys Glu Leu Leu Asp Arg Ile Asn Arg Glu
325 330 335

Val Gly Pro Val Pro Glu Glu Ala Ile Arg Tyr Tyr Lys Glu Thr Ala
340 345 350

Glu Pro Ser Ala Pro Thr Trp Gln Thr Trp Leu Arg Ile Met Thr Tyr
355 360 365

Arg Val Phe Val Glu Gly Met Leu Arg Thr Ala Asp Ala Gln Ala Ala
370 375 380

Gln Gly Ala Asp Val Tyr Met Tyr Arg Phe Asp Tyr Glu Thr Pro Val
385 390 395 400

Phe Gly Gly Gln Leu Lys Ala Cys His Ala Leu Glu Leu Pro Phe Val
405 410 415

Phe His Asn Leu His Gln Pro Gly Val Ala Asn Phe Val Gly Asn Arg
420 425 430

Pro Glu Arg Glu Ala Ile Ala Asn Glu Met His Tyr Ala Trp Leu Ser
435 440 445

Phe Ala Arg Thr Gly Asp Pro Asn Gly Ala His Leu Pro Glu Ala Trp
450 455 460

Pro Ala Tyr Thr Asn Glu Arg Lys Ala Ala Phe Val Phe Ser Ala Ala
465 470 475 480

Ser His Val Glu Asp Asp Pro Phe Gly Arg Glu Arg Ala Ala Trp Gln
485 490 495

Gly Arg

<210> SEQ ID NO 139
<211> LENGTH: 957
<212> TYPE: DNA
<213> ORGANISM: Artificial Sequence
<220> FEATURE:
<223> OTHER INFORMATION: variant of esterase from Thermobifida fusca

<400> SEQUENCE: 139
atgaccgaac caaccgtggc acgtcccgac attgatcctg tcctcaagat gctcctggat 60
acctttcccg ttacctttac cgctgcagat ggtgttgaag tagcccgcgc acgcttacgt 120
cagcttaaga cccctcctga attgctgccg gaactgcgca tcgaagaacg cactgtgggg 180
tatgatggac tgactgacat tccagttcgt gtgtactggc caccagttgt tcgtgataac 240
ctgccggtcg ttgtttacta tcacgggggt ggttggagtt taggcggctt agatacccat 300
gacccagttg cacgtgcaca cgctgtaggc gcacaagcga tcgtcgtgtc ggtggactac 360
cgcctggcac cggaacatcc gtatccagcc ggcattgatg attcttgggc ggcactgcgt 420
tgggttggtg agaacgcagc ggaattgggt ggtgatccga gtcgtattgc agttgcgggc 480

-continued

```
gatagtgcgg gcggcaacat ttccgctgtg atggcacagc tggcacgtga tgttggtggt    540

ccgccactgg tgtttcaact gctctggtat ccaacgacta tggctgattt gtcgctgccg    600

agctttaccg agaatgctga tgcaccaatc ctggatcgtg atgtgattga cgcgtttctc    660

gcgtggtatg tacctggctt ggacatctcc gatcatacga tgctgcctac tactttggcc    720

cctggcaatg cggatctgag cggtttaccg ccagcgttca ttggtaccgc tgaacatgac    780

cctttacgcg acgacggagc gtgttatgcg gagttgctga ccgcagctgg tgtgagcgtc    840

gaactctcaa atgaacccac catggttcat ggctatgtga actttgcctt agtggttccg    900

gcggcggcag aagcaaccgg acgtggactg gccgccctga aacgtgcgct gcacgct       957


<210> SEQ ID NO 140
<211> LENGTH: 319
<212> TYPE: PRT
<213> ORGANISM: Mycobacterium tuberculosis

<400> SEQUENCE: 140

Met Thr Glu Pro Thr Val Ala Arg Pro Asp Ile Asp Pro Val Leu Lys
1               5                   10                  15

Met Leu Leu Asp Thr Phe Pro Val Thr Phe Thr Ala Ala Asp Gly Val
            20                  25                  30

Glu Val Ala Arg Ala Arg Leu Arg Gln Leu Lys Thr Pro Pro Glu Leu
        35                  40                  45

Leu Pro Glu Leu Arg Ile Glu Glu Arg Thr Val Gly Tyr Asp Gly Leu
    50                  55                  60

Thr Asp Ile Pro Val Arg Val Tyr Trp Pro Pro Val Val Arg Asp Asn
65                  70                  75                  80

Leu Pro Val Val Val Tyr Tyr His Gly Gly Gly Trp Ser Leu Gly Gly
                85                  90                  95

Leu Asp Thr His Asp Pro Val Ala Arg Ala His Ala Val Gly Ala Gln
            100                 105                 110

Ala Ile Val Val Ser Val Asp Tyr Arg Leu Ala Pro Glu His Pro Tyr
        115                 120                 125

Pro Ala Gly Ile Asp Asp Ser Trp Ala Ala Leu Arg Trp Val Gly Glu
    130                 135                 140

Asn Ala Ala Glu Leu Gly Gly Asp Pro Ser Arg Ile Ala Val Ala Gly
145                 150                 155                 160

Asp Ser Ala Gly Gly Asn Ile Ser Ala Val Met Ala Gln Leu Ala Arg
                165                 170                 175

Asp Val Gly Gly Pro Pro Leu Val Phe Gln Leu Leu Trp Tyr Pro Thr
            180                 185                 190

Thr Met Ala Asp Leu Ser Leu Pro Ser Phe Thr Glu Asn Ala Asp Ala
        195                 200                 205

Pro Ile Leu Asp Arg Asp Val Ile Asp Ala Phe Leu Ala Trp Tyr Val
    210                 215                 220

Pro Gly Leu Asp Ile Ser Asp His Thr Met Leu Pro Thr Thr Leu Ala
225                 230                 235                 240

Pro Gly Asn Ala Asp Leu Ser Gly Leu Pro Pro Ala Phe Ile Gly Thr
                245                 250                 255

Ala Glu His Asp Pro Leu Arg Asp Asp Gly Ala Cys Tyr Ala Glu Leu
            260                 265                 270

Leu Thr Ala Ala Gly Val Ser Val Glu Leu Ser Asn Glu Pro Thr Met
        275                 280                 285

Val His Gly Tyr Val Asn Phe Ala Leu Val Val Pro Ala Ala Ala Glu
```

-continued

```
    290                 295                 300

Ala Thr Gly Arg Gly Leu Ala Ala Leu Lys Arg Ala Leu His Ala
305                 310                 315
```